(12) United States Patent
Adey et al.

(10) Patent No.: US 11,535,883 B2
(45) Date of Patent: *Dec. 27, 2022

(54) SINGLE CELL WHOLE GENOME LIBRARIES AND COMBINATORIAL INDEXING METHODS OF MAKING THEREOF

(71) Applicants: Illumina, Inc., San Diego, CA (US); Oregon Health & Science University, Portland, OR (US)

(72) Inventors: Andrew C. Adey, Portland, OR (US); Sarah A. Vitak, Portland, OR (US); Frank J. Steemers, San Diego, CA (US)

(73) Assignees: Illumina, Inc., San Diego, CA (US); Oregon Health & Science University, Portland, OR (US)

( * ) Notice: Subject to any disclaimer, the term of this patent is extended or adjusted under 35 U.S.C. 154(b) by 193 days.

This patent is subject to a terminal disclaimer.

(21) Appl. No.: 15/656,947

(22) Filed: Jul. 21, 2017

(65) Prior Publication Data

US 2018/0023119 A1 Jan. 25, 2018

Related U.S. Application Data

(60) Provisional application No. 62/365,916, filed on Jul. 22, 2016, provisional application No. 62/451,305, filed on Jan. 27, 2017.

(51) Int. Cl.

| C40B 50/00 | (2006.01) |
| C12Q 1/6806 | (2018.01) |
| C12Q 1/6874 | (2018.01) |
| C12N 15/10 | (2006.01) |
| C12Q 1/6869 | (2018.01) |

(52) U.S. Cl.
CPC ....... *C12Q 1/6806* (2013.01); *C12N 15/1065* (2013.01); *C12N 15/1093* (2013.01); *C12Q 1/6869* (2013.01); *C12Q 1/6874* (2013.01)

(58) Field of Classification Search
CPC .................................................... C12Q 1/68
See application file for complete search history.

(56) References Cited

U.S. PATENT DOCUMENTS

| 4,683,195 A | 7/1987 | Mullis et al. |
| 4,683,202 A | 7/1987 | Mullis |
| 5,130,238 A | 7/1992 | Malek et al. |
| 5,185,243 A | 2/1993 | Ullman et al. |
| 5,223,414 A | 6/1993 | Zarling et al. |
| 5,455,166 A | 10/1995 | Walker |
| 5,573,907 A | 11/1996 | Carrino et al. |
| 5,679,524 A | 10/1997 | Nikiforov et al. |
| 6,172,218 B1 | 1/2001 | Brenner |
| 6,210,891 B1 | 4/2001 | Nyren et al. |
| 6,214,587 B1 | 4/2001 | Dattagupta et al. |
| 6,245,974 B1 * | 6/2001 | Michalowski ..... C12N 15/8216 435/320.1 |
| 6,258,568 B1 | 7/2001 | Nyren |
| 6,274,320 B1 | 8/2001 | Rothberg et al. |
| 6,306,597 B1 | 10/2001 | Macevicz |
| 6,969,488 B2 | 11/2005 | Bridgham et al. |
| 7,001,792 B2 | 2/2006 | Sauer et al. |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,399,590 B2 | 7/2008 | Piepenburg et al. |
| 7,405,281 B2 | 7/2008 | Xu et al. |
| 7,427,673 B2 | 9/2008 | Balasubramanian et al. |
| 7,582,420 B2 | 9/2009 | Oliphant et al. |
| 7,611,869 B2 | 11/2009 | Fan |
| 7,741,463 B2 | 6/2010 | Gormley et al. |
| 7,829,284 B2 | 11/2010 | Kong et al. |
| 8,003,354 B2 | 8/2011 | Shen et al. |
| 8,053,192 B2 | 11/2011 | Bignell et al. |
| 8,563,477 B2 | 10/2013 | Smith et al. |
| 8,778,848 B2 | 7/2014 | Lin et al. |
| 8,778,849 B2 | 7/2014 | Bowen et al. |
| 8,895,249 B2 | 11/2014 | Shen et al. |
| 8,951,781 B2 | 2/2015 | Reed et al. |

(Continued)

FOREIGN PATENT DOCUMENTS

| EP | 0320308 B1 | 11/1993 |
| EP | 0336731 B1 | 5/1994 |

(Continued)

OTHER PUBLICATIONS

Vitak et al., Construction of Thousands of Single Cell Genome Sequencing Libraries Using Combinatorial Indexing, bioRxiv Pre-Print, 2016, 1-18. (Year: 2016).*

Cusanovich et al., Multiplex Single-Cell Profiling of Chromatin Accessibility by Combinatorial Cellular Indexing, Science, 2015, 348(6237, 910-914. (Year: 2015).*

Buenrostro et al., Transposition of Native Chromatin for Fast and Sensitive Epigenomic Profiling of Open Chromatin, DNA-Binding Proteins and Nucleosome Position, Nature Methods, 2013, 10(12), 1213-1220. (Year: 2013).*

Arrigoni et al., Standardizing Chromatin Research: A Simple and Universal Method for ChIP-Seq, Nucleic Acids Reasearch, 2015, 44(7), 1-13. (Year: 2015).*

(Continued)

*Primary Examiner* — Amy M Bunker
(74) *Attorney, Agent, or Firm* — Mueting Raasch Group

(57) ABSTRACT

Provided herein are methods for preparing a sequencing library that includes nucleic acids from a plurality of single cells. In one embodiment, the sequencing library includes whole genome nucleic acids from the plurality of single cells. In one embodiment, the method includes generating nucleosome-depleted nuclei by chemical treatment while maintaining integrity of the nuclei. Also provided herein are compositions, such as compositions that include chemically treated nucleosome-depleted isolated nuclei.

14 Claims, 44 Drawing Sheets

Specification includes a Sequence Listing.

(56) References Cited

U.S. PATENT DOCUMENTS

| | | | |
|---|---|---|---|
| 9,079,148 B2 | 7/2015 | Rigatti et al. | |
| 9,169,513 B2 | 10/2015 | Shen et al. | |
| 9,309,502 B2 | 4/2016 | Pipenburg et al. | |
| 2005/0079516 A1 | 4/2005 | Maniotis et al. | |
| 2005/0100900 A1 | 5/2005 | Kawashima et al. | |
| 2006/0188901 A1 | 8/2006 | Barnes et al. | |
| 2006/0240439 A1 | 10/2006 | Smith et al. | |
| 2006/0281109 A1 | 12/2006 | Barr et al. | |
| 2007/0166705 A1 | 7/2007 | Milton et al. | |
| 2008/0009420 A1 | 1/2008 | Schroth et al. | |
| 2008/0108082 A1 | 5/2008 | Rank et al. | |
| 2009/0026082 A1 | 1/2009 | Rothberg et al. | |
| 2009/0127589 A1 | 5/2009 | Rothberg et al. | |
| 2010/0111768 A1 | 5/2010 | Banerjee et al. | |
| 2010/0120098 A1 | 5/2010 | Grunenwald et al. | |
| 2010/0137143 A1 | 6/2010 | Rothberg et al. | |
| 2010/0282617 A1 | 11/2010 | Rothberg et al. | |
| 2011/0287435 A1 | 11/2011 | Grunenwald et al. | |
| 2012/0208705 A1 | 8/2012 | Steemers et al. | |
| 2012/0208724 A1 | 8/2012 | Steemers et al. | |
| 2012/0270305 A1 | 10/2012 | Reed et al. | |
| 2013/0079232 A1 | 3/2013 | Kain et al. | |
| 2013/0184796 A1 | 7/2013 | Marzano et al. | |
| 2013/0196860 A1 | 8/2013 | Grunenwald et al. | |
| 2013/0260372 A1 | 10/2013 | Buermann et al. | |
| 2013/0338042 A1 | 12/2013 | Shen et al. | |
| 2014/0194313 A1* | 7/2014 | Craighead | C12N 15/1017 506/9 |
| 2014/0194324 A1 | 7/2014 | Gormley et al. | |
| 2014/0243224 A1 | 8/2014 | Barnard et al. | |
| 2016/0060691 A1* | 3/2016 | Giresi | G16H 50/20 506/2 |
| 2019/0071656 A1* | 3/2019 | Chang | C12Q 1/6806 |

FOREIGN PATENT DOCUMENTS

| | | |
|---|---|---|
| EP | 0439182 B1 | 4/1996 |
| JP | H8-239400 A | 9/1996 |
| JP | 2007526743 A | 9/2007 |
| WO | WO 87/03910 A1 | 7/1987 |
| WO | WO 89/09835 A1 | 10/1989 |
| WO | WO 89/12696 A1 | 12/1989 |
| WO | WO 90/01069 A1 | 2/1990 |
| WO | WO 91/06678 A1 | 5/1991 |
| WO | WO 95/23875 A1 | 9/1995 |
| WO | WO 98/044151 A1 | 10/1998 |
| WO | WO 00/18957 A1 | 4/2000 |
| WO | WO 02/46456 A1 | 6/2002 |
| WO | WO 2004/018497 A2 | 3/2004 |
| WO | WO 2005/065814 A1 | 7/2005 |
| WO | WO 2006/064199 A1 | 6/2006 |
| WO | WO 2007/010251 A2 | 1/2007 |
| WO | WO 2007/123744 A2 | 11/2007 |
| WO | WO 2012/061832 A1 | 5/2012 |
| WO | WO 2014/142850 A1 | 9/2014 |
| WO | WO 2014/189957 A2 | 11/2014 |
| WO | WO 2015/002813 A1 | 1/2015 |
| WO | WO 2015/106941 A1 | 7/2015 |
| WO | WO 2016/003814 A1 | 1/2016 |
| WO | WO 2016/066586 A1 | 5/2016 |
| WO | WO 2016/083823 A1 | 6/2016 |
| WO | WO 2016/130704 A2 | 8/2016 |

OTHER PUBLICATIONS

Cusanovich et al., Supplementary Materials, Multiplex Single-Cell Profiling of Chromatin Accessibility by Combinatorial Cellular Indexing, Science, 2015, 1-34. (Year: 2015).*

White et al., The Impact of Detergents on the Tissue Decellularization Process: A ToF-SIMS Study, Acta Biomaterialia, 2017, 50, 207-219. (Year: 2017).*

Amini et al., Haplotype-Resolved Whole-Genome Sequencing by Contiguity-Preserving Transposition and Combinatorial Indexing, Nature Genetics, 2014, 46(12), 1343-1351. (Year: 2014).*

Kustatscher et al., Chromatin Enrichment for Proteomics, Nature Protocols, 2014, 9(9), 2090-2099. (Year: 2014).*

Sigma, Detergents and Solubilization Reagents, BioFiles for Life Science Research, Sigma-Aldrich, 2008, 1-36. (Year: 2008).*

Goldenberger et al., A Simple "Universal" DNA Extraction Procedure Using SDS and Proteinase K Is Compatible with Direct PCR Amplification, PCR Methods and Applications, 1995, 4, 368-370. (Year: 1995).*

Buenrostro et al., Transposition of Native Chromatin for Fast and Sensitive Epigenomic Profiling of Open Chromatin, DNA-Binding Proteins and Nucelosome Position, Nature Methods, 2013, 10(12), 1213-1220. (Year: 2013).*

Krishnaswami et al., Using Nuclei for RNA-Seq to Capture the Transcriptome of Postmortem Neurons, Nature Protocol, 2016, 11(3), 499-524. (Year: 2016).*

Nextera, Nextera XT Library Prep: Tips and Troubleshooting, Illumina, 2015, 1-6. (Year: 2015).*

Borrell et al., The Action of Triton X-100 and Sodium Dodecyl Sulphate on Lipid Layers. Effect on Monolayers and Liposomes, Journal of Microencapsulation, 1990, 7(2), 255-259 (Year: 1990).*

Kawashima et al., Efficient Extraction of Proteins From Formalin-Fixed Paraffin-Embedded Tissues Requires Higher Concentration of Tris(hydroxymethyl)aminomethane, Clinical Proteomics, 2014, 11(4), 1-6. (Year: 2014).*

Wilson et al., Improved Immunodetection of Nuclear Antigens After Sodium Dodecyl Sulfate Treatment of Formaldehyde-Fixed Cells, Journal of Histochemistry & Cytochemistry, 1999, 47(8), 1095-1100. (Year: 1999).*

Nickerson et al., The Nuclear Matrix Revealed by Eluting Chromatin From a Cross-linked Nucleus, Proc. Natl. Acad. Sci., 1997, 94, 4446-4450. (Year: 1997).*

Adey et al., "Rapid, low-input, low-bias construction of shotgun fragment libraries by high-density in vitro transposition," *Genome Biol.*, 2010; 11:R119, 1-17.

Adey et al., "The haplotype-resolved genome and epigenome of the aneuploid HeLa cancer cell line," *Nature*, Aug. 2013; 500(7461):207-211.

Adey et al., "In vitro, long-range sequence information for de novo genome assembly via transposase contiguity," *Genome Res.*, Oct. 2014; 24:2041-2049.

Amini et al., "Haplotype-resolved whole-genome sequencing by contiguity-preserving transposition and combinatorial indexing," *Nat. Genet.*, Dec. 2014; 46(12):1343-9.

Bailey et al., "Genomic analyses identify molecular subtypes of pancreatic cancer," *Nature*, Mar. 2016; 531(7592):47-52.

Baslan et al., "Optimizing sparse sequencing of single cells for highly multiplex copy number profiling," *Genome Res.*, Apr. 2015; 25:714-724.

Beitel et al., "Strain- and plasmid-level deconvolution of a synthetic metagenome by sequencing proximity ligation products," *PeerJ.*, May 2014; 2:e415.

Bentley et al., "Accurate whole genome sequencing using reversible terminator chemistry," *Nature*, Nov. 2008; 456(7218):53-59.

Boeke et al., "Transcription and reverse transcription of retrotransposons," *Annu Rev Microbiol.*, 1989; 43:403-34.

Brown et al., "Retroviral integration: structure of the initial covalent product and its precursor, and a role for the viral IN protein," *Proc Natl Acad Sci USA*, Apr. 1989; 86(8):2525-9.

Buenrostro et al., "Transposition of native chromatin for fast and sensitive epigenomic profiling of open chromatin, DNA-binding proteins and nucleosome position, Supplemental Material" *Nat. Methods*, Dec. 2013; 10(12):1213-8; 22 pp.

Burton et al., "Species-level deconvolution of metagenome assemblies with Hi-C-based contact probability maps," *G3 (Bethesda).* May 2014; 4(7):1339-46.

Cai et al. "Single-Cell, Genome-wide Sequencing Identifies Clonal Somatic Copy-Number Variation in the Human Brain," *Cell Rep.*, Sep. 2014; 8:1280-1289.

Callaway, "'Platinum' genome takes on disease," *Nat. News*, Nov. 2014; 515(7527):323.

(56) References Cited

OTHER PUBLICATIONS

Cockroft et al., "A single-molecule nanopore device detects DNA polymerase activity with single-nucleotide resolution," *J. Am. Chem. Soc.*, Jan. 2008; 130(3):818-820.
Colegio et al., "In vitro transposition system for efficient generation of random mutants of Campylobacter jejuni," *J. Bacteriol.*, Apr. 2001; 183(7):23 84-8.
Craig, "V(D)J recombination and transposition: closer than expected," *Science*, Mar. 1996; 271(5255):1512.
Craig, "Transposon Tn7," *Curr Top Microbiol. Immunol.*, 1996; 204:27-48.
Cusanovich et al., "Multiplex single-cell profiling of chromatin accessibility by combinatorial cellular indexing," *Science*, May 2015; 348:910-4.
De Kouchkovsky et al., "Acute myeloid leukemia: a comprehensive review and 2016 update," *Blood Cancer J.*, Jul. 2016; 6(7):e441.
Deamer et al., "Nanopores and nucleic acids: prospects for ultrapid sequencing," *Trends Biotechnol.*, Apr. 2000; 18(4):147-151.
Deamer et al., "Characterization of nucleic acids by nanopore analysis," *Acc. Chem. Res.*, Oct. 2002; 35(10):817-825.
Dean et al., "Comprehensive human genome amplification using multiple displacement amplification," *Proc. Natl. Acad. Sci. USA*, Apr. 2002; 99(8):5261-66.
Devine and Boeke, "Efficient integration of artificial transposons into plasmid targets in vitro: a useful tool for DNA mapping, sequencing and genetic analysis," *Nucleic Acids Res.*, Sep. 1994; 22(18):3765-72.
Eirew et al., "Dynamics of genomic clones in breast cancer patient xenografts at single-cell resolution," *Nature*, Feb. 2015; 518:422-6.
Forbes et al. "COSMIC: Exploring the world's knowledge of somatic mutations in human cancer," *Nucleic Acids Res.*, Jan. 2015; 43:D805-D811.
Gao et al., "Punctuated copy number evolution and clonal stasis in triple-negative breast cancer," *Nat. Genet.*, Oct. 2016; 48(10):1119-1130.
Garvin et al., "Interactive analysis and quality assessment of single-cell copy-number variations," bioRxiv, Nov. 2014; 1-32. doi:10.1101/011346.
Gawad et al., "Dissecting the clonal origins of childhood acute lymphoblastic leukemia by single-cell genomics," *Proc. Natl. Acad. Sci. USA.*, Dec. 2014; 111(50):17947-52.
Gawad et al., "Single-cell genome sequencing: current state of the science," *Nat. Rev. Genet.*, Jan. 2016; 17:175-88.
Gloor, "Gene targeting in *Drosophila*," *Methods Mol. Biol.*, 2004; 260:97-114.
Goryshin et al., "Tn5/IS50 target recognition," *Proc. Natl. Acad. Sci. USA*, Sep. 1998; 95(18)10716-10721.
Goryshin and Reznikoff, "Tn5 in vitro transposition," *J. Biol Chem.*, Mar. 1998; 273(13):7367-74.
Grothues et al., "PCR amplification of megabase DNA with tagged random primers (T-PCR)," *Nucleic Acids Res.*, Mar. 1993; 21(5):1321-2.
Ha et al., "Integrative analysis of genome-wide loss of heterozygosity and monoallelic expression at nucleotide resolution reveals disrupted pathways in triple-negative breast cancer," *Genome Res.*, Oct. 2012; 22(10):1995-2007.
Healy, "Nanopore-based single-molecule DNA analysis," *Nanomedicine (Lond).*, Aug. 2007; 2(4):459-481.
Hoffman et al., "Formaldehyde Crosslinking: A Tool for the Study of Chomatin Complexes," *J. Biol. Chem.*, Oct. 2015; 290(44):26404-26411.
Ichikawa, "In vitro transposition of transposon Tn3," *J. Biol. Chem.*, Nov. 1990; 265(31):18829-32.
Kirby et al., "Cryptic plasmids of *Mycobacterium avium*: Tn552 to the rescue," *Mol. Microbiol.*, Jan. 2002; 43(1):173-86.
Kleckner et al., "Tn10 and IS10 transposition and chromosome rearrangements: mechanism and regulation in vivo and in vitro," *Curr Top Microbiol Immunol.*, 1996; 204:49-82.
Knouse et al., "Single cell sequencing reveals low levels of aneuploidy across mammalian tissues," *Proc Natl Acad Sci USA*, Sep. 2014; 111(37):13409-13414.
Knouse et al., "Assessment of megabase-scale somatic copy number variation using single cell sequencing," *Genome Res.*, Jan. 2016; doi:10.1101/gr.198937.115.
Korlach, J et al. "Selective aluminum passivation for targeted immobilization of single DNA polymerase molecules in zero-mode waveguide nanostructures." *Proc. Natl. Acad. Sci. USA*, Jan. 2008; 105(4):1176-1181.
Kumagai et al., "Epigenetic regulation and molecular characterization of C/EBPalpha in pancreatic cancer cells," *Int. J. Cancer*, Feb. 2009; 124(4):827-833.
Lage et al., "Whole genome analysis of genetic alterations in small DNA samples using hyperbranched strand displacement amplification and array-CGH," *Genome Res.*, Feb. 2003; 13(2):294-307.
Lampe et al., "A purified mariner transposase is sufficient to mediate transposition in vitro," *The EMBO Journal*, 1996; 15(19):5470-9.
Langmead et al., "Fast gapped-read alignment with Bowtie 2," *Nat Methods*, Mar. 2012; 9:357-359.
Levene et al. "Zero-mode waveguides for single-molecule analysis at high concentrations," *Science*, Jan. 2003; 299(5607):682-686.
Li et al., "DNA molecules and configurations in a solid-state nanopore microscope," *Nature Materials*, Aug. 2003; 2:611-615.
Lizardi et al., "Mutation detection and single-molecule counting using isothermal rolling-circle amplification," *Nat. Genet.*, Jul. 1998; 19(3):225-232.
Lundquist et al. "Parallel confocal detection of single molecules in real time," *Opt. Lett.*, May 2008; 33(9):1026-1028.
Macosko et al., "Highly Parallel Genome-wide Expression Profiling of Individual Cells Using Nanoliter Droplets," *Cell*, May 2015; 161(5):1202-1214.
McConnell et al., "Mosaic Copy Number Variation in Human Neurons," *Science*, Nov. 2013; 342(6158):632-637.
Metzker, "Emerging technologies in DNA sequencing," *Genome Res.*, Dec. 2005; 15(12):1767-1776.
Mirkovitch et al., "Organization of the higher-order chromatin loop: specific DNA attachment sites on nuclear scaffold," *Cell*, Nov. 1984; 39(1):223-232.
Mizuuchi, "In vitro transposition of bacteriophage Mu: a biochemical approach to a novel replication reaction," *Cell*, Dec. 1983; 35(3 Pt 2):785-94.
Nagano et al., "Single-cell Hi-C reveals cell-to-cell variability in chromosome structure," *Nature*, Oct. 2013; 502:59-64.
Navin et al., "Tumour evolution inferred by single-cell sequencing," *Nature*, Apr. 2011; 472(7341):90-94.
Ohtsubo and Sekine, "Bacterial insertion sequences," *Curr. Top. Microbiol. Immunol.*, 1996; 204:1-26.
Olshen et al., "Circular binary segmentation for the analysis of array-based DNA copy number data," *Biostatistics*, Oct. 2004; 5(4):557-572.
Perkins, "Integrating cell-signalling pathways with NF-kappaB and IKK function," *Nat. Rev. Mol. Cell Biol.*, Jan. 2007; 8(1):49-62.
Plasterk, "The Tc1/mariner transposon family," *Curr Topics Microbiol. Immunol.*, 1996; 204:125-43.
Rehen et al., "Chromosomal variation in neurons of the developing and adult mammalian nervous system," *Proc. Natl. Acad. Sci. USA.*, Nov. 2001; 98(23):13361-6.
Ronaghi et al., "Real-time DNA sequencing using detection of pyrophosphate release," *Analytical Biochemistry*, Nov. 1996; 242(1):84-9.
Ronaghi et al., "A sequencing method based on real-time pyrophosphate," *Science*, Jul. 1998; 281(5375):363, 365.
Ronaghi, "Pyrosequencing sheds light on DNA sequencing," *Genome Res.*, Jan. 2001; 11(1):3-11.
Rosenkrantz et al., "Investigating somatic aneuploidy in the brain: why we need a new model," *Chromosoma*, Jun. 2017; 126(3):337-350.
Ruparel et al., "Design and synthesis of a 3'-O-allyl photocleavable fluorescent nucleotide as a reversible terminator for DNA sequencing by synthesis," *Proc. Natl. Acad. Sci. USA*, Apr. 2005; 102(17):5932-7.

(56) References Cited

OTHER PUBLICATIONS

Savilahti et al., "The phage Mu transpososome core: DNA requirements for assembly and function," *EMBO J*, Oct. 1995; 14(19):4893-4903.

Soni and Meller, "Progress toward ultrafast DNA sequencing using solid-state nanopores," *Clin. Chem.*, Nov. 2007; 53(11):1996-2001.

Sos et al., "Characterization of chromatin accessibility with a transposome hypersensitive sites sequencing (THS-seq) assay," *Genome Biol.*, Feb. 2016; 17:20.

Stahley et al., "Desmosomes in acquired disease," *Cell Tissue Res.*, Jun. 2015; 360(3):439-56.

Stergachis et al., "Developmental fate and cellular maturity encoded in human regulatory DNA landscapes," *Cell*, Aug. 2013; 154(4):888-903.

The ENCODE Project Consortium, "An integrated encyclopedia of DNA elements in the human genome," *Nature*, Sep. 2012; 489(7414):57-74.

Tomschik et al., "Fast, long-range, reversible conformational fluctuations in nucleosomes revealed by single-pair fluorescence resonance energy transfer," *Proc. Natl. Acad. Sci. USA.*, Mar. 1, 2005; 102(9):3278-3283.

Vitak et al., "SCI-seq: Sequencing thousands of single-cell genomes with combinatorial indexing," *Nature Methods*, doi:10.1038/nmeth.4154; 41 pages.

Vitak et al., "Sequencing thousands of single-cell genomes with combinatorial indexing," *Nature Medthods*, Jan. 2017; 1-10. 302-308.

Waddell et al., "Whole genomes redefine the mutational landscape of pancreatic cancer," *Nature*, Feb. 2015; 518(7540):495-501.

Walker et al., "Strand displacement amplification—an isothermal, in vitro DNA amplification technique," *Nucl. Acids Res.*, Apr. 1992; 20(7):1691-96.

Wilson et al., "New transposon delivery plasmids for insertional mutagenesis in Bacillus anthracis," *J. Microbiol. Methods*, Dec. 2007; 71(3):332-5.

Zhang et al., "A Novel Mechanism of Transposon-Mediated Gene Activation," *PLoS Genet.*, Oct. 2009; 5(10):e1000689.

Zong et al., "Genome-Wide Detection of Single Nucleotide and Copy Number Variations of a Single Human Cell," *Science*, 2012; 338(6114):1622-1626.

International Search Report and Written Opinion for International Application No. PCT/US2017/043381, dated Nov. 15, 2017, 17 pages.

Alberts et al., Molecular Biology of the Cell, 4th ed., New York: Garland Science; 2002. Available online at <ncbi.nlm.nih.gov/books/NBK26834/#630>, obtained on Oct. 10, 2019; excerpt from section title "Nucleosomes Are the Basic Unit of Eucaryotic Chromosome Structure". 1 pg.

Illumina® Safety Data Sheet, NX#-TDE1 Tagment DNA Enzyme 1, Issued Jan. 15, 2018, Revised Jan. 22, 2020, Revision No. 1.1.

Illumina® Safety Data Sheet, NX#-TD, Tagment DNA Buffer, Issued Jun. 5, 2018, Revised Jan. 22, 2020, Revision No. 2.4.

Illumina® Safety Data Sheet, LP#-TSB, Tagment Stop Buffer, Issued Nov. 12, 2018, Revised Jan. 22, 2020, Revision No. 4.2.

Clyde, "Barcoding the nucleus", Nature Reviews Genetics, published online Feb. 13, 2017, doi: 10.1038/nrg.2017.11.

Shalek, "Baring cellular souls", Science Translational Medicine, Feb. 15, 2017, vol. 9, Issue 377.

* cited by examiner

FIG. 4A
FIG. 4B
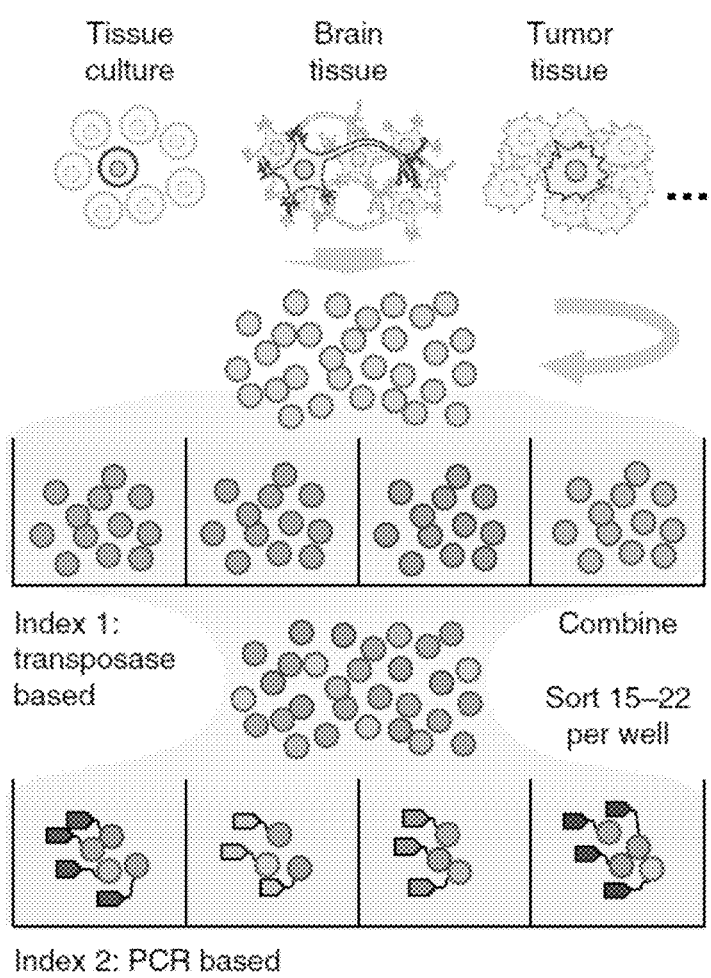
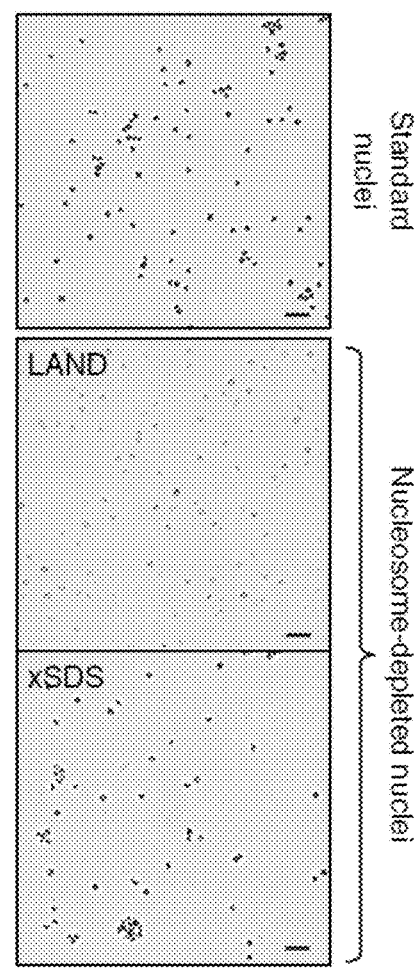

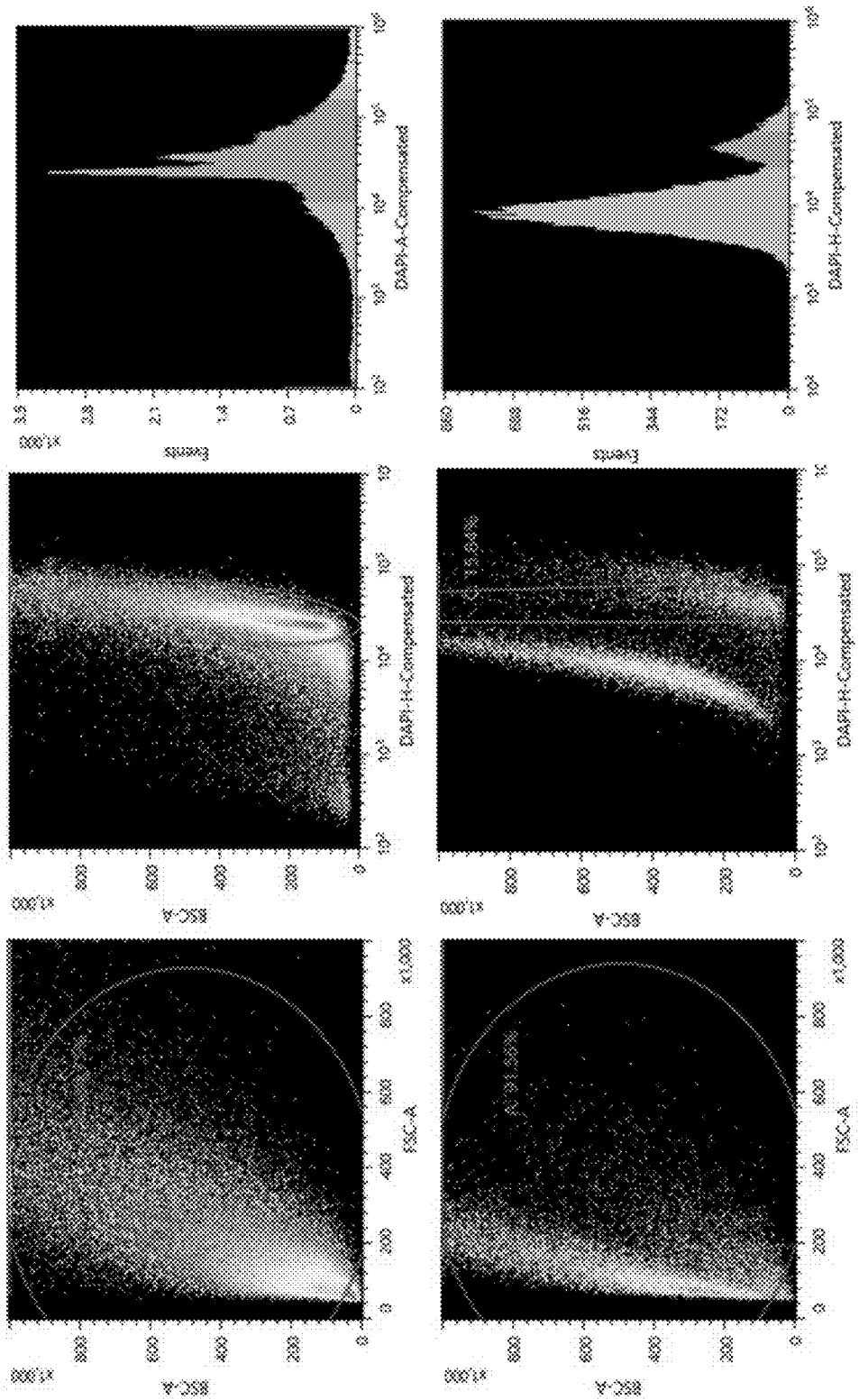

SEQUENCE LISTING

```
<160> NUMBER OF SEQ ID NOS: 145

<210> SEQ ID NO 1
<211> LENGTH: 19
<212> TYPE: DNA
<213> ORGANISM: Artificial
<220> FEATURE:
<223> OTHER INFORMATION: tagmentation oligonucleotide

<400> SEQUENCE: 1
ctgtctctta tacacatct                                               19

<210> SEQ ID NO 2
<211> LENGTH: 63
<212> TYPE: DNA
<213> ORGANISM: Artificial
<220> FEATURE:
<223> OTHER INFORMATION: tagmentation oligonucleotide

<400> SEQUENCE: 2
```
tcgtcggcag cgtctccacg ctatagcctg cgatcgagga cggcagatgt gtataagaga    60
cag                                                                63

<210> SEQ ID NO 3
<211> LENGTH: 63
<212> TYPE: DNA
<213> ORGANISM: Artificial
<220> FEATURE:
<223> OTHER INFORMATION: tagmentation oligonucleotide

<400> SEQUENCE: 3
tcgtcggcag cgtctccacg catagaggcg cgatcgagga cggcagatgt gtataagaga    60
cag                                                                63

<210> SEQ ID NO 4
<211> LENGTH: 63
<212> TYPE: DNA
<213> ORGANISM: Artificial
<220> FEATURE:
<223> OTHER INFORMATION: tagmentation oligonucleotide

<400> SEQUENCE: 4
tcgtcggcag cgtctccacg ccctatcctg cgatcgagga cggcagatgt gtataagaga    60
cag                                                                63

<210> SEQ ID NO 5
<211> LENGTH: 63
<212> TYPE: DNA
<213> ORGANISM: Artificial
<220> FEATURE:
<223> OTHER INFORMATION: tagmentation oligonucleotide

<400> SEQUENCE: 5
tcgtcggcag cgtctccacg cggctctgag cgatcgagga cggcagatgt gtataagaga    60
cag                                                                63

<210> SEQ ID NO 6
<211> LENGTH: 63
<212> TYPE: DNA
<213> ORGANISM: Artificial
<220> FEATURE:
<223> OTHER INFORMATION: tagmentation oligonucleotide

<400> SEQUENCE: 6
tcgtcggcag cgtctccacg caggcgaagg cgatcgagga cggcagatgt gtataagaga    60
cag                                                                63

<210> SEQ ID NO 7
<211> LENGTH: 63
<212> TYPE: DNA
<213> ORGANISM: Artificial
<220> FEATURE:
<223> OTHER INFORMATION: tagmentation oligonucleotide

<400> SEQUENCE: 7
tcgtcggcag cgtctccacg ctaatcttag cgatcgagga cggcagatgt gtataagaga    60
cag                                                                63

<210> SEQ ID NO 8
<211> LENGTH: 63
<212> TYPE: DNA
<213> ORGANISM: Artificial

```
<220> FEATURE:
<223> OTHER INFORMATION: tagmentation oligonucleotide

<400> SEQUENCE: 8
tcgtcggcag cgtctccacg ccaggacgtg cgatcgagga cggcagatgt gtataagaga    60
cag                                                                  63

<210> SEQ ID NO 9
<211> LENGTH: 63
<212> TYPE: DNA
<213> ORGANISM: Artificial
<220> FEATURE:
<223> OTHER INFORMATION: tagmentation oligonucleotide

<400> SEQUENCE: 9
tcgtcggcag cgtctccacg cgtactgacg cgatcgagga cggcagatgt gtataagaga    60
cag                                                                  63

<210> SEQ ID NO 10
<211> LENGTH: 69
<212> TYPE: DNA
<213> ORGANISM: Artificial
<220> FEATURE:
<223> OTHER INFORMATION: tagmentation oligonucleotide

<400> SEQUENCE: 10
gtctcgtggg ctcggctgtc cctgtcccga gtaatcaccg tctccgcctc agatgtgtat    60
aagagacag                                                            69

<210> SEQ ID NO 11
<211> LENGTH: 69
<212> TYPE: DNA
<213> ORGANISM: Artificial
<220> FEATURE:
<223> OTHER INFORMATION: tagmentation oligonucleotide

<400> SEQUENCE: 11
gtctcgtggg ctcggctgtc cctgtcctct ccggacaccg tctccgcctc agatgtgtat    60
aagagacag                                                            69

<210> SEQ ID NO 12
<211> LENGTH: 69
<212> TYPE: DNA
<213> ORGANISM: Artificial
<220> FEATURE:
<223> OTHER INFORMATION: tagmentation oligonucleotide

<400> SEQUENCE: 12
gtctcgtggg ctcggctgtc cctgtccaat gagcgcaccg tctccgcctc agatgtgtat    60
aagagacag                                                            69

<210> SEQ ID NO 13
<211> LENGTH: 69
<212> TYPE: DNA
<213> ORGANISM: Artificial
<220> FEATURE:
<223> OTHER INFORMATION: tagmentation oligonucleotide

<400> SEQUENCE: 13
gtctcgtggg ctcggctgtc cctgtccgga atctccaccg tctccgcctc agatgtgtat    60
aagagacag                                                            69
```

```
<210> SEQ ID NO 14
<211> LENGTH: 69
<212> TYPE: DNA
<213> ORGANISM: Artificial
<220> FEATURE:
<223> OTHER INFORMATION: tagmentation oligonucleotide

<400> SEQUENCE: 14
gtctcgtggg ctcggctgtc cctgtccttc tgaatcaccg tctccgcctc agatgtgtat      60
aagagacag                                                             69

<210> SEQ ID NO 15
<211> LENGTH: 69
<212> TYPE: DNA
<213> ORGANISM: Artificial
<220> FEATURE:
<223> OTHER INFORMATION: tagmentation oligonucleotide

<400> SEQUENCE: 15
gtctcgtggg ctcggctgtc cctgtccacg aattccaccg tctccgcctc agatgtgtat      60
aagagacag                                                             69

<210> SEQ ID NO 16
<211> LENGTH: 69
<212> TYPE: DNA
<213> ORGANISM: Artificial
<220> FEATURE:
<223> OTHER INFORMATION: tagmentation oligonucleotide

<400> SEQUENCE: 16
gtctcgtggg ctcggctgtc cctgtccagc ttcagcaccg tctccgcctc agatgtgtat      60
aagagacag                                                             69

<210> SEQ ID NO 17
<211> LENGTH: 69
<212> TYPE: DNA
<213> ORGANISM: Artificial
<220> FEATURE:
<223> OTHER INFORMATION: tagmentation oligonucleotide

<400> SEQUENCE: 17
gtctcgtggg ctcggctgtc cctgtccgcg cattacaccg tctccgcctc agatgtgtat      60
aagagacag                                                             69

<210> SEQ ID NO 18
<211> LENGTH: 69
<212> TYPE: DNA
<213> ORGANISM: Artificial
<220> FEATURE:
<223> OTHER INFORMATION: tagmentation oligonucleotide

<400> SEQUENCE: 18
gtctcgtggg ctcggctgtc cctgtcccat agccgcaccg tctccgcctc agatgtgtat      60
aagagacag                                                             69

<210> SEQ ID NO 19
<211> LENGTH: 69
<212> TYPE: DNA
<213> ORGANISM: Artificial
<220> FEATURE:
<223> OTHER INFORMATION: tagmentation oligonucleotide

<400> SEQUENCE: 19
```
gtctcgtggg ctcggctgtc cctgtccttc gcggacaccg tctccgcctc agatgtgtat        60
aagagacag                                                                69

<210> SEQ ID NO 20
<211> LENGTH: 69
<212> TYPE: DNA
<213> ORGANISM: Artificial
<220> FEATURE:
<223> OTHER INFORMATION: tagmentation oligonucleotide

<400> SEQUENCE: 20
gtctcgtggg ctcggctgtc cctgtccgcg cgagacaccg tctccgcctc agatgtgtat        60
aagagacag                                                                69

<210> SEQ ID NO 21
<211> LENGTH: 69
<212> TYPE: DNA
<213> ORGANISM: Artificial
<220> FEATURE:
<223> OTHER INFORMATION: tagmentation oligonucleotide

<400> SEQUENCE: 21
gtctcgtggg ctcggctgtc cctgtcccta tcgctcaccg tctccgcctc agatgtgtat        60
aagagacag                                                                69

<210> SEQ ID NO 22
<211> LENGTH: 49
<212> TYPE: DNA
<213> ORGANISM: Artificial
<220> FEATURE:
<223> OTHER INFORMATION: PCR primer

<400> SEQUENCE: 22
caagcagaag acggcatacg agataatgcc gcttgtctcg tgggctcgg                    49

<210> SEQ ID NO 23
<211> LENGTH: 49
<212> TYPE: DNA
<213> ORGANISM: Artificial
<220> FEATURE:
<223> OTHER INFORMATION: PCR primer

<400> SEQUENCE: 23
caagcagaag acggcatacg agattataga cgcagtctcg tgggctcgg                    49

<210> SEQ ID NO 24
<211> LENGTH: 49
<212> TYPE: DNA
<213> ORGANISM: Artificial
<220> FEATURE:
<223> OTHER INFORMATION: PCR primer

<400> SEQUENCE: 24
caagcagaag acggcatacg agattcaatc gcatgtctcg tgggctcgg                    49

<210> SEQ ID NO 25
<211> LENGTH: 49
<212> TYPE: DNA
<213> ORGANISM: Artificial
<220> FEATURE:
<223> OTHER INFORMATION: PCR primer

<400> SEQUENCE: 25
caagcagaag acggcatacg agatttctta ataagtctcg tgggctcgg    49

<210> SEQ ID NO 26
<211> LENGTH: 49
<212> TYPE: DNA
<213> ORGANISM: Artificial
<220> FEATURE:
<223> OTHER INFORMATION: PCR primer

<400> SEQUENCE: 26
caagcagaag acggcatacg agatgtccta gagggtctcg tgggctcgg    49

<210> SEQ ID NO 27
<211> LENGTH: 49
<212> TYPE: DNA
<213> ORGANISM: Artificial
<220> FEATURE:
<223> OTHER INFORMATION: PCR primer

<400> SEQUENCE: 27
caagcagaag acggcatacg agatatattg atacgtctcg tgggctcgg    49

<210> SEQ ID NO 28
<211> LENGTH: 49
<212> TYPE: DNA
<213> ORGANISM: Artificial
<220> FEATURE:
<223> OTHER INFORMATION: PCR primer

<400> SEQUENCE: 28
caagcagaag acggcatacg agatccgctg ccaggtctcg tgggctcgg    49

<210> SEQ ID NO 29
<211> LENGTH: 49
<212> TYPE: DNA
<213> ORGANISM: Artificial
<220> FEATURE:
<223> OTHER INFORMATION: PCR primer

<400> SEQUENCE: 29
caagcagaag acggcatacg agatcctagt acgtgtctcg tgggctcgg    49

<210> SEQ ID NO 30
<211> LENGTH: 49
<212> TYPE: DNA
<213> ORGANISM: Artificial
<220> FEATURE:
<223> OTHER INFORMATION: PCR primer

<400> SEQUENCE: 30
caagcagaag acggcatacg agatcaatta ccgtgtctcg tgggctcgg    49

<210> SEQ ID NO 31
<211> LENGTH: 49
<212> TYPE: DNA
<213> ORGANISM: Artificial
<220> FEATURE:
<223> OTHER INFORMATION: PCR primer

<400> SEQUENCE: 31
caagcagaag acggcatacg agatggccgt agtcgtctcg tgggctcgg    49

<210> SEQ ID NO 32
<211> LENGTH: 49
<212> TYPE: DNA
<213> ORGANISM: Artificial

<220> FEATURE:
<223> OTHER INFORMATION: PCR primer

<400> SEQUENCE: 32
caagcagaag acggcatacg agatcgatta cggcgtctcg tgggctcgg          49

<210> SEQ ID NO 33
<211> LENGTH: 49
<212> TYPE: DNA
<213> ORGANISM: Artificial
<220> FEATURE:
<223> OTHER INFORMATION: PCR primer

<400> SEQUENCE: 33
caagcagaag acggcatacg agattaatga acgagtctcg tgggctcgg          49

<210> SEQ ID NO 34
<211> LENGTH: 49
<212> TYPE: DNA
<213> ORGANISM: Artificial
<220> FEATURE:
<223> OTHER INFORMATION: PCR primer

<400> SEQUENCE: 34
caagcagaag acggcatacg agatccgttc cttagtctcg tgggctcgg          49

<210> SEQ ID NO 35
<211> LENGTH: 49
<212> TYPE: DNA
<213> ORGANISM: Artificial
<220> FEATURE:
<223> OTHER INFORMATION: PCR primer

<400> SEQUENCE: 35
caagcagaag acggcatacg agatggtacc atatgtctcg tgggctcgg          49

<210> SEQ ID NO 36
<211> LENGTH: 49
<212> TYPE: DNA
<213> ORGANISM: Artificial
<220> FEATURE:
<223> OTHER INFORMATION: PCR primer

<400> SEQUENCE: 36
caagcagaag acggcatacg agatccgatt cgcagtctcg tgggctcgg          49

<210> SEQ ID NO 37
<211> LENGTH: 49
<212> TYPE: DNA
<213> ORGANISM: Artificial
<220> FEATURE:
<223> OTHER INFORMATION: PCR primer

<400> SEQUENCE: 37
caagcagaag acggcatacg agatatggct ctgcgtctcg tgggctcgg          49

<210> SEQ ID NO 38
<211> LENGTH: 49
<212> TYPE: DNA
<213> ORGANISM: Artificial
<220> FEATURE:
<223> OTHER INFORMATION: PCR primer

<400> SEQUENCE: 38
caagcagaag acggcatacg agatgtataa tacggtctcg tgggctcgg          49

<210> SEQ ID NO 39
<211> LENGTH: 49
<212> TYPE: DNA
<213> ORGANISM: Artificial
<220> FEATURE:
<223> OTHER INFORMATION: PCR primer

<400> SEQUENCE: 39
caagcagaag acggcatacg agatatcagc aagtgtctcg tgggctcgg        49

<210> SEQ ID NO 40
<211> LENGTH: 49
<212> TYPE: DNA
<213> ORGANISM: Artificial
<220> FEATURE:
<223> OTHER INFORMATION: PCR primer

<400> SEQUENCE: 40
caagcagaag acggcatacg agatggcgaa ctcggtctcg tgggctcgg        49

<210> SEQ ID NO 41
<211> LENGTH: 49
<212> TYPE: DNA
<213> ORGANISM: Artificial
<220> FEATURE:
<223> OTHER INFORMATION: PCR primer

<400> SEQUENCE: 41
caagcagaag acggcatacg agatttaatt gaatgtctcg tgggctcgg        49

<210> SEQ ID NO 42
<211> LENGTH: 49
<212> TYPE: DNA
<213> ORGANISM: Artificial
<220> FEATURE:
<223> OTHER INFORMATION: PCR primer

<400> SEQUENCE: 42
caagcagaag acggcatacg agatttagga ccgggtctcg tgggctcgg        49

<210> SEQ ID NO 43
<211> LENGTH: 49
<212> TYPE: DNA
<213> ORGANISM: Artificial
<220> FEATURE:
<223> OTHER INFORMATION: PCR primer

<400> SEQUENCE: 43
caagcagaag acggcatacg agataagtaa gagcgtctcg tgggctcgg        49

<210> SEQ ID NO 44
<211> LENGTH: 49
<212> TYPE: DNA
<213> ORGANISM: Artificial
<220> FEATURE:
<223> OTHER INFORMATION: PCR primer

<400> SEQUENCE: 44
caagcagaag acggcatacg agatccttgg tccagtctcg tgggctcgg        49

<210> SEQ ID NO 45
<211> LENGTH: 49
<212> TYPE: DNA
<213> ORGANISM: Artificial
<220> FEATURE:
<223> OTHER INFORMATION: PCR primer -continued

```
<400> SEQUENCE: 45
caagcagaag acggcatacg agatcatcag aatggtctcg tgggctcgg        49

<210> SEQ ID NO 46
<211> LENGTH: 49
<212> TYPE: DNA
<213> ORGANISM: Artificial
<220> FEATURE:
<223> OTHER INFORMATION: PCR primer

<400> SEQUENCE: 46
caagcagaag acggcatacg agatttatag cagagtctcg tgggctcgg        49

<210> SEQ ID NO 47
<211> LENGTH: 49
<212> TYPE: DNA
<213> ORGANISM: Artificial
<220> FEATURE:
<223> OTHER INFORMATION: PCR primer

<400> SEQUENCE: 47
caagcagaag acggcatacg agatttactt ggaagtctcg tgggctcgg        49

<210> SEQ ID NO 48
<211> LENGTH: 49
<212> TYPE: DNA
<213> ORGANISM: Artificial
<220> FEATURE:
<223> OTHER INFORMATION: PCR primer

<400> SEQUENCE: 48
caagcagaag acggcatacg agatgctcag ccgggtctcg tgggctcgg        49

<210> SEQ ID NO 49
<211> LENGTH: 49
<212> TYPE: DNA
<213> ORGANISM: Artificial
<220> FEATURE:
<223> OTHER INFORMATION: PCR primer

<400> SEQUENCE: 49
caagcagaag acggcatacg agatacgtcc gcaggtctcg tgggctcgg        49

<210> SEQ ID NO 50
<211> LENGTH: 49
<212> TYPE: DNA
<213> ORGANISM: Artificial
<220> FEATURE:
<223> OTHER INFORMATION: PCR primer

<400> SEQUENCE: 50
caagcagaag acggcatacg agatttgact dacggtctcg tgggctcgg        49

<210> SEQ ID NO 51
<211> LENGTH: 49
<212> TYPE: DNA
<213> ORGANISM: Artificial
<220> FEATURE:
<223> OTHER INFORMATION: PCR primer

<400> SEQUENCE: 51
caagcagaag acggcatacg agatttgcga ggcagtctcg tgggctcgg        49

<210> SEQ ID NO 52
```

```
<211> LENGTH: 49
<212> TYPE: DNA
<213> ORGANISM: Artificial
<220> FEATURE:
<223> OTHER INFORMATION: PCR primer

<400> SEQUENCE: 52
caagcagaag acggcatacg agatttccaa ccgcgtctcg tgggctcgg          49

<210> SEQ ID NO 53
<211> LENGTH: 49
<212> TYPE: DNA
<213> ORGANISM: Artificial
<220> FEATURE:
<223> OTHER INFORMATION: PCR primer

<400> SEQUENCE: 53
caagcagaag acggcatacg agattaacct tcgggtctcg tgggctcgg          49

<210> SEQ ID NO 54
<211> LENGTH: 49
<212> TYPE: DNA
<213> ORGANISM: Artificial
<220> FEATURE:
<223> OTHER INFORMATION: PCR primer

<400> SEQUENCE: 54
caagcagaag acggcatacg agattcaagc cgatgtctcg tgggctcgg          49

<210> SEQ ID NO 55
<211> LENGTH: 49
<212> TYPE: DNA
<213> ORGANISM: Artificial
<220> FEATURE:
<223> OTHER INFORMATION: PCR primer

<400> SEQUENCE: 55
caagcagaag acggcatacg agatcttgca acctgtctcg tgggctcgg          49

<210> SEQ ID NO 56
<211> LENGTH: 49
<212> TYPE: DNA
<213> ORGANISM: Artificial
<220> FEATURE:
<223> OTHER INFORMATION: PCR primer

<400> SEQUENCE: 56
caagcagaag acggcatacg agatccatcg cgaagtctcg tgggctcgg          49

<210> SEQ ID NO 57
<211> LENGTH: 49
<212> TYPE: DNA
<213> ORGANISM: Artificial
<220> FEATURE:
<223> OTHER INFORMATION: PCR primer

<400> SEQUENCE: 57
caagcagaag acggcatacg agattagact tcttgtctcg tgggctcgg          49

<210> SEQ ID NO 58
<211> LENGTH: 49
<212> TYPE: DNA
<213> ORGANISM: Artificial
<220> FEATURE:
<223> OTHER INFORMATION: PCR primer

<400> SEQUENCE: 58
```
caagcagaag acggcatacg agattgcgcg atgcgtctcg tgggctcgg        49

<210> SEQ ID NO 59
<211> LENGTH: 49
<212> TYPE: DNA
<213> ORGANISM: Artificial
<220> FEATURE:
<223> OTHER INFORMATION: PCR primer

<400> SEQUENCE: 59
caagcagaag acggcatacg agatattgag attggtctcg tgggctcgg        49

<210> SEQ ID NO 60
<211> LENGTH: 49
<212> TYPE: DNA
<213> ORGANISM: Artificial
<220> FEATURE:
<223> OTHER INFORMATION: PCR primer

<400> SEQUENCE: 60
caagcagaag acggcatacg agatttgata tattgtctcg tgggctcgg        49

<210> SEQ ID NO 61
<211> LENGTH: 49
<212> TYPE: DNA
<213> ORGANISM: Artificial
<220> FEATURE:
<223> OTHER INFORMATION: PCR primer

<400> SEQUENCE: 61
caagcagaag acggcatacg agatcggtag gaatgtctcg tgggctcgg        49

<210> SEQ ID NO 62
<211> LENGTH: 49
<212> TYPE: DNA
<213> ORGANISM: Artificial
<220> FEATURE:
<223> OTHER INFORMATION: PCR primer

<400> SEQUENCE: 62
caagcagaag acggcatacg agataccagc gcaggtctcg tgggctcgg        49

<210> SEQ ID NO 63
<211> LENGTH: 49
<212> TYPE: DNA
<213> ORGANISM: Artificial
<220> FEATURE:
<223> OTHER INFORMATION: PCR primer

<400> SEQUENCE: 63
caagcagaag acggcatacg agatcgaatg agctgtctcg tgggctcgg        49

<210> SEQ ID NO 64
<211> LENGTH: 49
<212> TYPE: DNA
<213> ORGANISM: Artificial
<220> FEATURE:
<223> OTHER INFORMATION: PCR primer

<400> SEQUENCE: 64
caagcagaag acggcatacg agatagttcg agtagtctcg tgggctcgg        49

<210> SEQ ID NO 65
<211> LENGTH: 49
<212> TYPE: DNA

```
<213> ORGANISM: Artificial
<220> FEATURE:
<223> OTHER INFORMATION: PCR primer

<400> SEQUENCE: 65
caagcagaag acggcatacg agatttggac gctggtctcg tgggctcgg              49

<210> SEQ ID NO 66
<211> LENGTH: 49
<212> TYPE: DNA
<213> ORGANISM: Artificial
<220> FEATURE:
<223> OTHER INFORMATION: PCR primer

<400> SEQUENCE: 66
caagcagaag acggcatacg agatatagac tagggtctcg tgggctcgg              49

<210> SEQ ID NO 67
<211> LENGTH: 49
<212> TYPE: DNA
<213> ORGANISM: Artificial
<220> FEATURE:
<223> OTHER INFORMATION: PCR primer

<400> SEQUENCE: 67
caagcagaag acggcatacg agattatagt aagcgtctcg tgggctcgg              49

<210> SEQ ID NO 68
<211> LENGTH: 49
<212> TYPE: DNA
<213> ORGANISM: Artificial
<220> FEATURE:
<223> OTHER INFORMATION: PCR primer

<400> SEQUENCE: 68
caagcagaag acggcatacg agatcggtcg ttaagtctcg tgggctcgg              49

<210> SEQ ID NO 69
<211> LENGTH: 49
<212> TYPE: DNA
<213> ORGANISM: Artificial
<220> FEATURE:
<223> OTHER INFORMATION: PCR primer

<400> SEQUENCE: 69
caagcagaag acggcatacg agatatggcg gatcgtctcg tgggctcgg              49

<210> SEQ ID NO 70
<211> LENGTH: 49
<212> TYPE: DNA
<213> ORGANISM: Artificial
<220> FEATURE:
<223> OTHER INFORMATION: PCR primer

<400> SEQUENCE: 70
caagcagaag acggcatacg agatctctga tcaggtctcg tgggctcgg              49

<210> SEQ ID NO 71
<211> LENGTH: 49
<212> TYPE: DNA
<213> ORGANISM: Artificial
<220> FEATURE:
<223> OTHER INFORMATION: PCR primer

<400> SEQUENCE: 71
caagcagaag acggcatacg agatggccag tccggtctcg tgggctcgg              49
```

<210> SEQ ID NO 72
<211> LENGTH: 49
<212> TYPE: DNA
<213> ORGANISM: Artificial
<220> FEATURE:
<223> OTHER INFORMATION: PCR primer

<400> SEQUENCE: 72
caagcagaag acggcatacg agatcggaag atatgtctcg tgggctcgg         49

<210> SEQ ID NO 73
<211> LENGTH: 49
<212> TYPE: DNA
<213> ORGANISM: Artificial
<220> FEATURE:
<223> OTHER INFORMATION: PCR primer

<400> SEQUENCE: 73
caagcagaag acggcatacg agattggctg atgagtctcg tgggctcgg         49

<210> SEQ ID NO 74
<211> LENGTH: 49
<212> TYPE: DNA
<213> ORGANISM: Artificial
<220> FEATURE:
<223> OTHER INFORMATION: PCR primer

<400> SEQUENCE: 74
caagcagaag acggcatacg agatgaaggt tgccgtctcg tgggctcgg         49

<210> SEQ ID NO 75
<211> LENGTH: 49
<212> TYPE: DNA
<213> ORGANISM: Artificial
<220> FEATURE:
<223> OTHER INFORMATION: PCR primer

<400> SEQUENCE: 75
caagcagaag acggcatacg agatgttgaa ggatgtctcg tgggctcgg         49

<210> SEQ ID NO 76
<211> LENGTH: 49
<212> TYPE: DNA
<213> ORGANISM: Artificial
<220> FEATURE:
<223> OTHER INFORMATION: PCR primer

<400> SEQUENCE: 76
caagcagaag acggcatacg agatccattc gtaagtctcg tgggctcgg         49

<210> SEQ ID NO 77
<211> LENGTH: 49
<212> TYPE: DNA
<213> ORGANISM: Artificial
<220> FEATURE:
<223> OTHER INFORMATION: PCR primer

<400> SEQUENCE: 77
caagcagaag acggcatacg agattgcgcc agaagtctcg tgggctcgg         49

<210> SEQ ID NO 78
<211> LENGTH: 49
<212> TYPE: DNA
<213> ORGANISM: Artificial
<220> FEATURE:

<223> OTHER INFORMATION: PCR primer

<400> SEQUENCE: 78
caagcagaag acggcatacg agatcgaata attcgtctcg tgggctcgg    49

<210> SEQ ID NO 79
<211> LENGTH: 49
<212> TYPE: DNA
<213> ORGANISM: Artificial
<220> FEATURE:
<223> OTHER INFORMATION: PCR primer

<400> SEQUENCE: 79
caagcagaag acggcatacg agatgcgacg ccttgtctcg tgggctcgg    49

<210> SEQ ID NO 80
<211> LENGTH: 49
<212> TYPE: DNA
<213> ORGANISM: Artificial
<220> FEATURE:
<223> OTHER INFORMATION: PCR primer

<400> SEQUENCE: 80
caagcagaag acggcatacg agatatcaac gattgtctcg tgggctcgg    49

<210> SEQ ID NO 81
<211> LENGTH: 49
<212> TYPE: DNA
<213> ORGANISM: Artificial
<220> FEATURE:
<223> OTHER INFORMATION: PCR primer

<400> SEQUENCE: 81
caagcagaag acggcatacg agatgttctg aattgtctcg tgggctcgg    49

<210> SEQ ID NO 82
<211> LENGTH: 49
<212> TYPE: DNA
<213> ORGANISM: Artificial
<220> FEATURE:
<223> OTHER INFORMATION: PCR primer

<400> SEQUENCE: 82
caagcagaag acggcatacg agatgctaac ctcagtctcg tgggctcgg    49

<210> SEQ ID NO 83
<211> LENGTH: 49
<212> TYPE: DNA
<213> ORGANISM: Artificial
<220> FEATURE:
<223> OTHER INFORMATION: PCR primer

<400> SEQUENCE: 83
caagcagaag acggcatacg agatcaagca actggtctcg tgggctcgg    49

<210> SEQ ID NO 84
<211> LENGTH: 49
<212> TYPE: DNA
<213> ORGANISM: Artificial
<220> FEATURE:
<223> OTHER INFORMATION: PCR primer

<400> SEQUENCE: 84
caagcagaag acggcatacg agatggagcg gccggtctcg tgggctcgg    49

```
<210> SEQ ID NO 85
<211> LENGTH: 49
<212> TYPE: DNA
<213> ORGANISM: Artificial
<220> FEATURE:
<223> OTHER INFORMATION: PCR primer

<400> SEQUENCE: 85
caagcagaag acggcatacg agatcgcgta cgacgtctcg tgggctcgg        49

<210> SEQ ID NO 86
<211> LENGTH: 49
<212> TYPE: DNA
<213> ORGANISM: Artificial
<220> FEATURE:
<223> OTHER INFORMATION: PCR primer

<400> SEQUENCE: 86
caagcagaag acggcatacg agatcgatgg cgccgtctcg tgggctcgg        49

<210> SEQ ID NO 87
<211> LENGTH: 49
<212> TYPE: DNA
<213> ORGANISM: Artificial
<220> FEATURE:
<223> OTHER INFORMATION: PCR primer

<400> SEQUENCE: 87
caagcagaag acggcatacg agattggtat tcatgtctcg tgggctcgg       49

<210> SEQ ID NO 88
<211> LENGTH: 49
<212> TYPE: DNA
<213> ORGANISM: Artificial
<220> FEATURE:
<223> OTHER INFORMATION: PCR primer

<400> SEQUENCE: 88
caagcagaag acggcatacg agatgataag gcaagtctcg tgggctcgg       49

<210> SEQ ID NO 89
<211> LENGTH: 49
<212> TYPE: DNA
<213> ORGANISM: Artificial
<220> FEATURE:
<223> OTHER INFORMATION: PCR primer

<400> SEQUENCE: 89
caagcagaag acggcatacg agatgccggt cgaggtctcg tgggctcgg       49

<210> SEQ ID NO 90
<211> LENGTH: 49
<212> TYPE: DNA
<213> ORGANISM: Artificial
<220> FEATURE:
<223> OTHER INFORMATION: PCR primer

<400> SEQUENCE: 90
caagcagaag acggcatacg agattgcgcc atctgtctcg tgggctcgg       49

<210> SEQ ID NO 91
<211> LENGTH: 49
<212> TYPE: DNA
<213> ORGANISM: Artificial
<220> FEATURE:
<223> OTHER INFORMATION: PCR primer
```

```
<400> SEQUENCE: 91
caagcagaag acggcatacg agataagtct tccggtctcg tgggctcgg          49

<210> SEQ ID NO 92
<211> LENGTH: 49
<212> TYPE: DNA
<213> ORGANISM: Artificial
<220> FEATURE:
<223> OTHER INFORMATION: PCR primer

<400> SEQUENCE: 92
caagcagaag acggcatacg agatagactc aagcgtctcg tgggctcgg          49

<210> SEQ ID NO 93
<211> LENGTH: 49
<212> TYPE: DNA
<213> ORGANISM: Artificial
<220> FEATURE:
<223> OTHER INFORMATION: PCR primer

<400> SEQUENCE: 93
caagcagaag acggcatacg agatgcaggc gacggtctcg tgggctcgg          49

<210> SEQ ID NO 94
<211> LENGTH: 53
<212> TYPE: DNA
<213> ORGANISM: Artificial
<220> FEATURE:
<223> OTHER INFORMATION: PCR primer

<400> SEQUENCE: 94
aatgatacgg cgaccaccga gatctacacg tccttaagat cgtcggcagc gtc     53

<210> SEQ ID NO 95
<211> LENGTH: 53
<212> TYPE: DNA
<213> ORGANISM: Artificial
<220> FEATURE:
<223> OTHER INFORMATION: PCR primer

<400> SEQUENCE: 95
aatgatacgg cgaccaccga gatctacaca gtaacggtct cgtcggcagc gtc     53

<210> SEQ ID NO 96
<211> LENGTH: 53
<212> TYPE: DNA
<213> ORGANISM: Artificial
<220> FEATURE:
<223> OTHER INFORMATION: PCR primer

<400> SEQUENCE: 96
aatgatacgg cgaccaccga gatctacacg ttcgtcagat cgtcggcagc gtc     53

<210> SEQ ID NO 97
<211> LENGTH: 53
<212> TYPE: DNA
<213> ORGANISM: Artificial
<220> FEATURE:
<223> OTHER INFORMATION: PCR primer

<400> SEQUENCE: 97
aatgatacgg cgaccaccga gatctacacc gcctaatgct cgtcggcagc gtc     53

<210> SEQ ID NO 98
<211> LENGTH: 53
```

```
<212> TYPE: DNA
<213> ORGANISM: Artificial
<220> FEATURE:
<223> OTHER INFORMATION: PCR primer

<400> SEQUENCE: 98
aatgatacgg cgaccaccga gatctacaca ccggaattat cgtcggcagc gtc        53

<210> SEQ ID NO 99
<211> LENGTH: 53
<212> TYPE: DNA
<213> ORGANISM: Artificial
<220> FEATURE:
<223> OTHER INFORMATION: PCR primer

<400> SEQUENCE: 99
aatgatacgg cgaccaccga gatctacact aggccatagt cgtcggcagc gtc        53

<210> SEQ ID NO 100
<211> LENGTH: 53
<212> TYPE: DNA
<213> ORGANISM: Artificial
<220> FEATURE:
<223> OTHER INFORMATION: PCR primer

<400> SEQUENCE: 100
aatgatacgg cgaccaccga gatctacact aactcttagt cgtcggcagc gtc        53

<210> SEQ ID NO 101
<211> LENGTH: 53
<212> TYPE: DNA
<213> ORGANISM: Artificial
<220> FEATURE:
<223> OTHER INFORMATION: PCR primer

<400> SEQUENCE: 101
aatgatacgg cgaccaccga gatctacact atgagttaat cgtcggcagc gtc        53

<210> SEQ ID NO 102
<211> LENGTH: 53
<212> TYPE: DNA
<213> ORGANISM: Artificial
<220> FEATURE:
<223> OTHER INFORMATION: PCR primer

<400> SEQUENCE: 102
aatgatacgg cgaccaccga gatctacact atcatgatct cgtcggcagc gtc        53

<210> SEQ ID NO 103
<211> LENGTH: 53
<212> TYPE: DNA
<213> ORGANISM: Artificial
<220> FEATURE:
<223> OTHER INFORMATION: PCR primer

<400> SEQUENCE: 103
aatgatacgg cgaccaccga gatctacacg agcatatggt cgtcggcagc gtc        53

<210> SEQ ID NO 104
<211> LENGTH: 53
<212> TYPE: DNA
<213> ORGANISM: Artificial
<220> FEATURE:
<223> OTHER INFORMATION: PCR primer

<400> SEQUENCE: 104
```
aatgatacgg cgaccaccga gatctacact aacgatccat cgtcggcagc gtc    53

<210> SEQ ID NO 105
<211> LENGTH: 53
<212> TYPE: DNA
<213> ORGANISM: Artificial
<220> FEATURE:
<223> OTHER INFORMATION: PCR primer

<400> SEQUENCE: 105
aatgatacgg cgaccaccga gatctacacc ggcgtaactt cgtcggcagc gtc    53

<210> SEQ ID NO 106
<211> LENGTH: 53
<212> TYPE: DNA
<213> ORGANISM: Artificial
<220> FEATURE:
<223> OTHER INFORMATION: PCR primer

<400> SEQUENCE: 106
aatgatacgg cgaccaccga gatctacacc gtcgcagcct cgtcggcagc gtc    53

<210> SEQ ID NO 107
<211> LENGTH: 53
<212> TYPE: DNA
<213> ORGANISM: Artificial
<220> FEATURE:
<223> OTHER INFORMATION: PCR primer

<400> SEQUENCE: 107
aatgatacgg cgaccaccga gatctacacg tagctccatt cgtcggcagc gtc    53

<210> SEQ ID NO 108
<211> LENGTH: 53
<212> TYPE: DNA
<213> ORGANISM: Artificial
<220> FEATURE:
<223> OTHER INFORMATION: PCR primer

<400> SEQUENCE: 108
aatgatacgg cgaccaccga gatctacact tgccttggct cgtcggcagc gtc    53

<210> SEQ ID NO 109
<211> LENGTH: 53
<212> TYPE: DNA
<213> ORGANISM: Artificial
<220> FEATURE:
<223> OTHER INFORMATION: PCR primer

<400> SEQUENCE: 109
aatgatacgg cgaccaccga gatctacact gctaattctt cgtcggcagc gtc    53

<210> SEQ ID NO 110
<211> LENGTH: 53
<212> TYPE: DNA
<213> ORGANISM: Artificial
<220> FEATURE:
<223> OTHER INFORMATION: PCR primer

<400> SEQUENCE: 110
aatgatacgg cgaccaccga gatctacacg tcctacttgt cgtcggcagc gtc    53

<210> SEQ ID NO 111
<211> LENGTH: 53
<212> TYPE: DNA
<213> ORGANISM: Artificial

<220> FEATURE:
<223> OTHER INFORMATION: PCR primer

<400> SEQUENCE: 111
aatgatacgg cgaccaccga gatctacacg gtaggttagt cgtcggcagc gtc    53

<210> SEQ ID NO 112
<211> LENGTH: 53
<212> TYPE: DNA
<213> ORGANISM: Artificial
<220> FEATURE:
<223> OTHER INFORMATION: PCR primer

<400> SEQUENCE: 112
aatgatacgg cgaccaccga gatctacacg agcatcattt cgtcggcagc gtc    53

<210> SEQ ID NO 113
<211> LENGTH: 53
<212> TYPE: DNA
<213> ORGANISM: Artificial
<220> FEATURE:
<223> OTHER INFORMATION: PCR primer

<400> SEQUENCE: 113
aatgatacgg cgaccaccga gatctacacc cgctccggct cgtcggcagc gtc    53

<210> SEQ ID NO 114
<211> LENGTH: 53
<212> TYPE: DNA
<213> ORGANISM: Artificial
<220> FEATURE:
<223> OTHER INFORMATION: PCR primer

<400> SEQUENCE: 114
aatgatacgg cgaccaccga gatctacact tcttccggtt cgtcggcagc gtc    53

<210> SEQ ID NO 115
<211> LENGTH: 53
<212> TYPE: DNA
<213> ORGANISM: Artificial
<220> FEATURE:
<223> OTHER INFORMATION: PCR primer

<400> SEQUENCE: 115
aatgatacgg cgaccaccga gatctacaca ggagagaact cgtcggcagc gtc    53

<210> SEQ ID NO 116
<211> LENGTH: 53
<212> TYPE: DNA
<213> ORGANISM: Artificial
<220> FEATURE:
<223> OTHER INFORMATION: PCR primer

<400> SEQUENCE: 116
aatgatacgg cgaccaccga gatctacact aactcaattt cgtcggcagc gtc    53

<210> SEQ ID NO 117
<211> LENGTH: 53
<212> TYPE: DNA
<213> ORGANISM: Artificial
<220> FEATURE:
<223> OTHER INFORMATION: PCR primer

<400> SEQUENCE: 117
aatgatacgg cgaccaccga gatctacaca ctataggttt cgtcggcagc gtc    53

```
<210> SEQ ID NO 118
<211> LENGTH: 53
<212> TYPE: DNA
<213> ORGANISM: Artificial
<220> FEATURE:
<223> OTHER INFORMATION: PCR primer

<400> SEQUENCE: 118
aatgatacgg cgaccaccga gatctacact aacgaattgt cgtcggcagc gtc      53

<210> SEQ ID NO 119
<211> LENGTH: 53
<212> TYPE: DNA
<213> ORGANISM: Artificial
<220> FEATURE:
<223> OTHER INFORMATION: PCR primer

<400> SEQUENCE: 119
aatgatacgg cgaccaccga gatctacact gagaaccaat cgtcggcagc gtc      53

<210> SEQ ID NO 120
<211> LENGTH: 53
<212> TYPE: DNA
<213> ORGANISM: Artificial
<220> FEATURE:
<223> OTHER INFORMATION: PCR primer

<400> SEQUENCE: 120
aatgatacgg cgaccaccga gatctacact tattctgagt cgtcggcagc gtc      53

<210> SEQ ID NO 121
<211> LENGTH: 53
<212> TYPE: DNA
<213> ORGANISM: Artificial
<220> FEATURE:
<223> OTHER INFORMATION: PCR primer

<400> SEQUENCE: 121
aatgatacgg cgaccaccga gatctacact tattatggtt cgtcggcagc gtc      53

<210> SEQ ID NO 122
<211> LENGTH: 53
<212> TYPE: DNA
<213> ORGANISM: Artificial
<220> FEATURE:
<223> OTHER INFORMATION: PCR primer

<400> SEQUENCE: 122
aatgatacgg cgaccaccga gatctacaca tatgagccat cgtcggcagc gtc      53

<210> SEQ ID NO 123
<211> LENGTH: 53
<212> TYPE: DNA
<213> ORGANISM: Artificial
<220> FEATURE:
<223> OTHER INFORMATION: PCR primer

<400> SEQUENCE: 123
aatgatacgg cgaccaccga gatctacacc aaccagtact cgtcggcagc gtc      53

<210> SEQ ID NO 124
<211> LENGTH: 53
<212> TYPE: DNA
<213> ORGANISM: Artificial
<220> FEATURE:
<223> OTHER INFORMATION: PCR primer
```

<400> SEQUENCE: 124
aatgatacgg cgaccaccga gatctacacc atccgactat cgtcggcagc gtc      53

<210> SEQ ID NO 125
<211> LENGTH: 53
<212> TYPE: DNA
<213> ORGANISM: Artificial
<220> FEATURE:
<223> OTHER INFORMATION: PCR primer

<400> SEQUENCE: 125
aatgatacgg cgaccaccga gatctacaca tcatggctgt cgtcggcagc gtc      53

<210> SEQ ID NO 126
<211> LENGTH: 53
<212> TYPE: DNA
<213> ORGANISM: Artificial
<220> FEATURE:
<223> OTHER INFORMATION: PCR primer

<400> SEQUENCE: 126
aatgatacgg cgaccaccga gatctacacc cgcaagttct cgtcggcagc gtc      53

<210> SEQ ID NO 127
<211> LENGTH: 53
<212> TYPE: DNA
<213> ORGANISM: Artificial
<220> FEATURE:
<223> OTHER INFORMATION: PCR primer

<400> SEQUENCE: 127
aatgatacgg cgaccaccga gatctacacc ttctcattgt cgtcggcagc gtc      53

<210> SEQ ID NO 128
<211> LENGTH: 53
<212> TYPE: DNA
<213> ORGANISM: Artificial
<220> FEATURE:
<223> OTHER INFORMATION: PCR primer

<400> SEQUENCE: 128
aatgatacgg cgaccaccga gatctacacc aggaggagat cgtcggcagc gtc      53

<210> SEQ ID NO 129
<211> LENGTH: 53
<212> TYPE: DNA
<213> ORGANISM: Artificial
<220> FEATURE:
<223> OTHER INFORMATION: PCR primer

<400> SEQUENCE: 129
aatgatacgg cgaccaccga gatctacacg atatcggcgt cgtcggcagc gtc      53

<210> SEQ ID NO 130
<211> LENGTH: 53
<212> TYPE: DNA
<213> ORGANISM: Artificial
<220> FEATURE:
<223> OTHER INFORMATION: PCR primer

<400> SEQUENCE: 130
aatgatacgg cgaccaccga gatctacacc cagtcctctt cgtcggcagc gtc      53

<210> SEQ ID NO 131

-continued

```
<211> LENGTH: 53
<212> TYPE: DNA
<213> ORGANISM: Artificial
<220> FEATURE:
<223> OTHER INFORMATION: PCR primer

<400> SEQUENCE: 131
aatgatacgg cgaccaccga gatctacacc atagttcggt cgtcggcagc gtc         53

<210> SEQ ID NO 132
<211> LENGTH: 53
<212> TYPE: DNA
<213> ORGANISM: Artificial
<220> FEATURE:
<223> OTHER INFORMATION: PCR primer

<400> SEQUENCE: 132
aatgatacgg cgaccaccga gatctacacc gtaatgcagt cgtcggcagc gtc         53

<210> SEQ ID NO 133
<211> LENGTH: 53
<212> TYPE: DNA
<213> ORGANISM: Artificial
<220> FEATURE:
<223> OTHER INFORMATION: PCR primer

<400> SEQUENCE: 133
aatgatacgg cgaccaccga gatctacacc cgttcggatt cgtcggcagc gtc         53

<210> SEQ ID NO 134
<211> LENGTH: 53
<212> TYPE: DNA
<213> ORGANISM: Artificial
<220> FEATURE:
<223> OTHER INFORMATION: PCR primer

<400> SEQUENCE: 134
aatgatacgg cgaccaccga gatctacacc cataagtcct cgtcggcagc gtc         53

<210> SEQ ID NO 135
<211> LENGTH: 53
<212> TYPE: DNA
<213> ORGANISM: Artificial
<220> FEATURE:
<223> OTHER INFORMATION: PCR primer

<400> SEQUENCE: 135
aatgatacgg cgaccaccga gatctacacg gcaatgagat cgtcggcagc gtc         53

<210> SEQ ID NO 136
<211> LENGTH: 53
<212> TYPE: DNA
<213> ORGANISM: Artificial
<220> FEATURE:
<223> OTHER INFORMATION: PCR primer

<400> SEQUENCE: 136
aatgatacgg cgaccaccga gatctacacc ggttatgcct cgtcggcagc gtc         53

<210> SEQ ID NO 137
<211> LENGTH: 53
<212> TYPE: DNA
<213> ORGANISM: Artificial
<220> FEATURE:
<223> OTHER INFORMATION: PCR primer

<400> SEQUENCE: 137
```

-continued aatgatacgg cgaccaccga gatctacact ggccggcctt cgtcggcagc gtc      53

<210> SEQ ID NO 138
<211> LENGTH: 53
<212> TYPE: DNA
<213> ORGANISM: Artificial
<220> FEATURE:
<223> OTHER INFORMATION: PCR primer

<400> SEQUENCE: 138
aatgatacgg cgaccaccga gatctacaca gctgcaatat cgtcggcagc gtc      53

<210> SEQ ID NO 139
<211> LENGTH: 53
<212> TYPE: DNA
<213> ORGANISM: Artificial
<220> FEATURE:
<223> OTHER INFORMATION: PCR primer

<400> SEQUENCE: 139
aatgatacgg cgaccaccga gatctacact ggccatgcat cgtcggcagc gtc      53

<210> SEQ ID NO 140
<211> LENGTH: 53
<212> TYPE: DNA
<213> ORGANISM: Artificial
<220> FEATURE:
<223> OTHER INFORMATION: PCR primer

<400> SEQUENCE: 140
aatgatacgg cgaccaccga gatctacact gacgctccgt cgtcggcagc gtc      53

<210> SEQ ID NO 141
<211> LENGTH: 53
<212> TYPE: DNA
<213> ORGANISM: Artificial
<220> FEATURE:
<223> OTHER INFORMATION: PCR primer

<400> SEQUENCE: 141
aatgatacgg cgaccaccga gatctacaca actgctgcct cgtcggcagc gtc      53

<210> SEQ ID NO 142
<211> LENGTH: 34
<212> TYPE: DNA
<213> ORGANISM: Artificial
<220> FEATURE:
<223> OTHER INFORMATION: sequencing primer

<400> SEQUENCE: 142
gcgatcgagg acggcagatg tgtataagag acag      34

<210> SEQ ID NO 143
<211> LENGTH: 34
<212> TYPE: DNA
<213> ORGANISM: Artificial
<220> FEATURE:
<223> OTHER INFORMATION: sequencing primer

<400> SEQUENCE: 143
caccgtctcc gcctcagatg tgtataagag acag      34

<210> SEQ ID NO 144
<211> LENGTH: 34
<212> TYPE: DNA

```
<213> ORGANISM: Artificial
<220> FEATURE:
<223> OTHER INFORMATION: sequencing primer

<400> SEQUENCE: 144
ctgtctctta tacacatctg aggcggagac ggtg                              34

<210> SEQ ID NO 145
<211> LENGTH: 34
<212> TYPE: DNA
<213> ORGANISM: Artificial
<220> FEATURE:
<223> OTHER INFORMATION: sequencing primer

<400> SEQUENCE: 145
ctgtctctta tacacatctg ccgtcctcga tcgc                              34
```

SINGLE CELL WHOLE GENOME LIBRARIES AND COMBINATORIAL INDEXING METHODS OF MAKING THEREOF

CROSS-REFERENCE TO RELATED APPLICATIONS

This application claims the benefit of U.S. Provisional Application Ser. No. 62/365,916, filed Jul. 22, 2016, and U.S. Provisional Application Ser. No. 62/451,305, filed Jan. 27, 2017, each of which are incorporated by reference herein.

SEQUENCE LISTING

This application contains a Sequence Listing electronically submitted via EFS-Web to the United States Patent and Trademark Office as an ASCII text file entitled "1592 ST25" having a size of 28 kilobytes and created on Sep. 28, 2017. The information contained in the Sequence Listing is incorporated by reference herein.

FIELD

Embodiments of the present disclosure relate to sequencing nucleic acids. In particular, embodiments of the methods and compositions provided herein relate to producing indexed single-cell sequencing libraries and obtaining sequence data therefrom.

BACKGROUND

Single cell sequencing has uncovered the breadth of genomic heterogeneity between cells in a variety of contexts, including somatic aneuploidy in the mammalian brain (McConnell, M. J. et al. Science (80.). 342, 632-637 (2013), Cai, X. et al. Cell Rep. 8, 1280-1289 (2014), Knouse, K. A. et al., Proc Natl Acad Sci USA 111, 13409-13414 (2014), Rehen, S. K. et al. Proc. Natl. Acad. Sci. U.S.A 98, 13361-6 (2001)) and intra-tumor heterogeneity (Navin, N. et al. Nature 472, 90-94 (2011), Eirew, P. et al. Nature 518, 422-6 (2014), Gawad, C. et al. Proc. Natl. Acad. Sci. U.S.A 111, 17947-52 (2014), Gao, R. et al. Nat. Genet. 1-15 (2016). doi:10.1038/ng.3641). Studies have taken one of two approaches: high depth of sequencing per cell for single nucleotide variant detection (Cai, X. et al. Cell Rep. 8, 1280-1289 (2014), Zong, C. et al. Science (80-.). 338, 1622-1626 (2012)), or low-pass sequencing to identify copy number variants (CNVs) and aneuploidy (McConnell, M. J. et al. Science (80.). 342, 632-637 (2013), Baslan, T. et al. Genome Res. 125, 714-724 (2015), Knouse, K. A. et al. Genome Res. gr.198937.115-(2016). doi:10.1101/gr.198937.115). In the latter approach, the lack of an efficient, cost-effective method to produce large numbers of single cell libraries has made it difficult to quantify the frequency of CNV-harboring cells at population scale, or to provide a robust analysis of heterogeneity in the context of cancer (Gawad, C. et al. Nat. Rev. Genet. 17, 175-88 (2016)).

Recently, contiguity-preserving transposition (CPT-seq) was established, a method to produce thousands of individually barcoded libraries of linked sequence reads using a transposase-based combinatorial indexing strategy (Adey, A. et al. Genome Biol. 11, R119 (2010), Amini, S. et al. Nat. Genet. 46, 1343-9 (2014), Adey, A. et al. Genome Res. 24, 2041-2049 (2014)). We applied CPT-seq to the problem of genomic haplotype resolution ( )Amini, S. et al. Nat. Genet. 46, 1343-9 (2014)) and de novo genome assembly (Adey, A. et al. Genome Res. 24, 2041-2049 (2014)). This concept was then integrated into the chromatin accessibility assay, ATAC-seq (Buenrostro, J. D. et al. Nat. Methods 10, 1213-8 (2013), to produce profiles of active regulatory elements in thousands of single cells (Cusanovich, D. a et al. Science 348, 910-4 (2015)) (sciATAC-seq, FIG. 4a). In combinatorial indexing, nuclei are first barcoded by the incorporation of one of 96 indexed sequencing adaptors via transposase. The 96 reactions are then combined and 15-25 of these randomly indexed nuclei are deposited into each well of a PCR plate by Fluorescence Activated Nuclei Sorting (FANS, FIG. 5). The probability of any two nuclei having the same transposase barcode is therefore low (6-11%) (Cusanovich, D. a et al. Science 348, 910-4 (2015)). Each PCR well is then uniquely barcoded using indexed primers. At the end of this process, each sequence read contains two indexes: Index 1 from the transposase plate, and Index 2 from the PCR plate, which facilitate single cell discrimination. As proof of principle, Cusanovich and colleagues produced over 15,000 sciATAC-seq profiles and used them to separate a mix of two cell types by their accessible chromatin landscapes (Cusanovich, D. a et al. Science 348, 910-4 (2015)).

Although high cell count single-cell sequencing has shown its efficacy in separation of populations within complex tissues via transcriptomes, chromatin-accessibility, and mutational differences, it has not been possible until now to obtain sequence information that includes the whole genome of single cells.

SUMMARY OF THE APPLICATION

Provided herein are methods for preparing a sequencing library that includes nucleic acids from a plurality of single cells. In one embodiment, the method includes providing isolated nuclei from a plurality of cells; subjecting the isolated nuclei to a chemical treatment to generate nucleosome-depleted nuclei while maintaining integrity of the isolated nuclei; distributing subsets of the nucleosome-depleted nuclei into a first plurality of compartments and contacting each subset with a transposome complex, where the transposome complex in each compartment includes a transposase and a first index sequence that is different from first index sequences in the other compartments; fragmenting nucleic acids in the subsets of nucleosome-depleted nuclei into a plurality of nucleic acid fragments and incorporating the first index sequences into at least one strand of the nucleic acid fragments to generate indexed nuclei that include indexed nucleic acid fragments, where the indexed nucleic acid fragments remain attached to the transposases; combining the indexed nuclei to generate pooled indexed nuclei; distributing subsets of the pooled indexed nuclei into a second plurality of compartments; incorporating into the indexed nucleic acid fragments in each compartment a second index sequence to generate dual-index fragments, where the second index sequence in each compartment is different from second index sequences in the other compartments; and combining the dual-index fragments, thereby producing a sequencing library that includes whole genome nucleic acids from the plurality of single cells.

In one embodiment, the chemical treatment includes a treatment with a chaotropic agent capable of disrupting nucleic acid-protein interactions, such as lithium 3,5-diiodosalicylic acid. In one embodiment, the chemical treatment includes a treatment with a detergent capable of disrupting nucleic acid-protein interactions, such as sodium dodecyl sulfate (SDS).

In one embodiment, the nuclei are treated with a cross-linking agent before subjecting the isolated nuclei to the chemical treatment, such as formaldehyde. The cross-linking agent can be at a concentration from about 0.2% to about 2%, and in one embodiment is about 1.5%. In one embodiment, the cross-linking by formaldehyde is reversed after distributing subsets of the pooled indexed nuclei and before incorporating into the indexed nucleic acid fragments in each compartment a second index sequence. In one embodiment, the reversal of the cross-linking includes incubation at about 55° C. to about 72° C. In one embodiment, the transposases are disassociated from the indexed nucleic acid fragments prior to the reversal of the cross-linking. In one embodiment, the transposases are disassociated from the indexed nucleic acid fragments using sodium dodecyl sulfate (SDS).

In one embodiment, the nuclei are treated with a restriction enzyme prior to fragmenting nucleic acids in the subsets of nucleosome-depleted nuclei into a plurality of nucleic acid fragments and incorporating the first index sequences. In one embodiment, the nuclei are treated with a ligase after treatment with the restriction enzyme.

In one embodiment, the distributing subsets of the nucleosome-depleted nuclei, the distributing subsets of the pooled indexed nuclei, or the combination thereof, is performed by fluorescence-activated nuclei sorting. In one embodiment, the subsets of the nucleosome-depleted nuclei include approximately equal numbers of nuclei, and in one embodiment, the subsets of the nucleosome-depleted nuclei include from 1 to about 2000 nuclei. In one embodiment, the subsets of the pooled indexed nuclei include approximately equal numbers of nuclei, and in one embodiment, the subsets of the pooled indexed nuclei include from 1 to about 25 nuclei. In one embodiment, the subsets of the pooled indexed nuclei include at least 10 times fewer nuclei than the subsets of the nucleosome-depleted nuclei, or at least 100 times fewer nuclei than the subsets of the nucleosome-depleted nuclei.

In one embodiment, the first plurality of compartments, the second plurality of compartments, or the combination thereof, is a multi-well plate, such as a 96-well plate or a 384-well plate.

In one embodiment, the transposome complex is added to the compartments after the subsets of nucleosome-depleted nuclei are distributed into the compartments. In one embodiment, each of the transposome complexes includes a transposon, and each of the transposons includes a transferred strand. In one embodiment, the transferred strand includes the first index sequence and a first universal sequence.

In one embodiment, the incorporation of the second index sequence into the indexed nucleic acid fragments includes contacting the indexed nucleic acid fragments in each compartment with a first universal primer and a second universal primer, each including an index sequence and each including a sequence identical to or complementary to a portion of the first universal sequence, and performing an exponential amplification reaction. In one embodiment, the exponential amplification reaction can be a polymerase chain reaction (PCR), and in one embodiment, the PCR can include 15 to 30 cycles. In one embodiment, the index sequence of the first universal primer is the reverse complement of the index sequence of the second universal primer, and in another embodiment, the index sequence of the first universal primer is different from the reverse complement of the index sequence of the second universal primer. In one embodiment, the first universal primer further includes a first capture sequence and a first anchor sequence complementary to a universal sequence at the 3' end of the dual-index fragments, and in one embodiment, the first capture sequence includes the P5 primer sequence. In one embodiment, the second universal primer further includes a second capture sequence and a second anchor sequence complementary to a universal sequence at the 5' end of the dual-index fragments, and in one embodiment, the second capture sequence includes the reverse complement of the P7 primer sequence.

The method can also include an enrichment of dual-index fragments using a plurality of capture oligonucleotides having specificity for the dual-index fragments. In one embodiment, the capture oligonucleotides are immobilized on a surface of a solid substrate, and in one embodiment, the capture oligonucleotides include a first member of a universal binding pair and a second member of the binding pair is immobilized on a surface of a solid substrate.

The method can also include sequencing of the dual-index fragments to determine the nucleotide sequence of nucleic acids from the plurality of single cells. In one embodiment, the method can include providing a surface that includes a plurality of amplification sites, where the amplification sites include at least two populations of attached single stranded capture oligonucleotides having a free 3' end, and contacting the surface that includes amplification sites with the dual-index fragments under conditions suitable to produce a plurality of amplification sites that each include a clonal population of amplicons from an individual dual-index fragment. In one embodiment, the number of the dual-index fragments exceeds the number of amplification sites, where the dual-index fragments have fluidic access to the amplification sites, and where each of the amplification sites includes a capacity for several dual-index fragments in the sequencing library. In one embodiment, the contacting includes simultaneously (i) transporting the dual-index fragments to the amplification sites at an average transport rate, and (ii) amplifying the dual-index fragments that are at the amplification sites at an average amplification rate, where the average amplification rate exceeds the average transport rate.

Also provided herein are compositions. In one embodiment, a composition includes chemically treated nucleosome-depleted isolated nuclei, where the isolated nuclei include indexed nucleic acid fragments. In one embodiment, the isolated nuclei include non-natural cross-links. In one embodiment, the composition includes indexed nucleic acid fragments that terminate in a cleaved restriction site including an overhang. In one embodiment, the isolated nuclei include rearranged genomic DNA. In another embodiment, a composition includes a multi-well plate, where a well of the multi-well plate includes chemically treated nucleosome-depleted isolated nuclei, where the isolated nuclei include indexed nucleic acid fragments.

BRIEF DESCRIPTION OF THE FIGURES

The following detailed description of illustrative embodiments of the present disclosure may be best understood when read in conjunction with the following drawings.

FIG. 4 shows single cell combinatorial indexing with nucleosome depletion. (FIG. 4a) Single cell combinatorial indexing workflow. (FIG. 4b) Phase contrast images of intact nuclei generated by standard isolation followed by nucleosome depletion using Lithium Assisted Nucleosome Depletion (LAND) or crosslinking and SDS treatment (xSDS). Scale bar: 100 µm.

(FIG. 7a) Complexity for one of six LAND SCI-seq preparations on GM12878. Right, histogram showing distribution of read counts. Dashed line represents single-cell read cutoff. (FIG. 7b) As in FIG. 7a but for xSDS nucleosome depletion for one of three PCR plates. (FIG. 7c) Left, model built on downsampled reads for the GM12878 xSDS preparation and used to predict the full depth of coverage. Right, projections for one of the LAND preparations and the full xSDS preparation. Shading represents s.d. over multiple models. Points represent actual depth of sequencing. (FIG. 7d) Coverage uniformity scores for SCI-seq using LAND or xSDS and for quasi-random priming (QRP) and degenerate oligonucleotide PCR (DOP). (FIG. 7e) Summary of the percentage of cells showing aneuploidy at the chromosome-arm level across all preparations with and without the imposition of a variance filter. (FIG. 7f) Karyotyping results of 50 GM12878 cells. (FIG. 7g, FIG. 7h) Summary of windowed copy-number calls and clustering of single GM12878 cells produced using LAND (FIG. 7g) or xSDS (FIG. 7h). In each panel top represents a chromosome-arm-scale summary of gain or loss frequency for all cells; bottom is the clustered profile for cells that contain at least one CNV call.

FIGS. 8-1 to 8-3 show SCI-seq library complexity and index read count distributions for all preparations. For each preparation two plots are shown. Left: each point represents a unique index combination, x-axis is the fraction of unique reads assigned to that index combination, y-axis is the log 10 unique read count for the index combination. Contour lines represent point density. Right: A histogram of the log 10 unique read counts for each of the index combinations. We expect the majority of potential index combinations not to represent a single cell library and therefore containing very few unique reads (leftmost distribution), with the single cell libraries having far greater read counts (right distribution, or tail in lower performance libraries). Since the plot is on a log 10 scale, the noise distribution actually only takes up a minority of the total read counts.

(FIG. 9a,b) LAND nucleosome depletion on Human (GM12878) and Mouse (3T3), (FIG. 9c,d) LAND nucleosome depletion on Human (HeLa S3) and Mouse (3T3), (FIG. 9e) xSDS nucleosome depletion on Human (HeLa S3) and Mouse (3T3).

(FIG. 11a) Diagram of how the 9 bp copying occurs from the transposition event. (FIG. 11b) Representative single cells showing the size of all amplicon overlaps with a dashed line at 9 bp.

FIGS. 14-1 and 14-2 show variance by window size and read count cutoff across all methods. Plots showing the change in MAD or MAPD score as a function of window size and read counts per cell.

FIGS. 15-1 and 15-2 show GM12878 aneuploidy rates across variance score cutoffs. Each point is the aneuploidy rate for the population of cells (y-axis), scaled by the number of cells included at a given score cutoff (x-axis).

(FIG. 16a) Ginkgo Calls, (FIG. 16b) CBS calls, (FIG. 16c) HMM calls, (FIG. 16d) Intersection of all three, and (FIG. 16e) Intersection of just CBS and HMM.

(FIG. 17a) Ginkgo Calls, (FIG. 17b) CBS calls, (FIG. 17c) HMM calls, (FIG. 17d) Intersection of all three, and (FIG. 17e) Intersection of just CBS and HMM.

(FIG. 18a) Ginkgo Calls, (FIG. 18b) CBS calls, (FIG. 18c) HMM calls, (FIG. 18d) Intersection of all three, and (FIG. 18e) Intersection of just CBS and HMM.

(FIG. 19a) Ginkgo Calls, (FIG. 19b) CBS calls, (FIG. 19c) HMM calls, (FIG. 19d) Intersection of all three, and (FIG. 19e) Intersection of just CBS and HMM.

(FIG. 20a) Three single-cell examples showing copy number variants, and one representative euploid cell for the SCI-seq preparation (HMM). (FIG. 20b) Frequency of aneuploidy as determined by each of the methods with and without filtering.

FIGS. 22-1 and 22-2 show Rhesus aneuploidy rates across variance score cutoffs. Each point is the aneuploidy rate for the population of cells (y-axis), scaled by the number of cells included at a given score cutoff (x-axis).

(FIG. 23a) Ginkgo Calls, (FIG. 23b) CBS calls, (FIG. 23c) HMM calls, (FIG. 23d) Intersection of all three, and (FIG. 23e) Intersection of just CBS and HMM.

(FIG. 24a) SCI-seq library complexity. Right panel, histogram showing distribution of read counts. Dashed line represents single cell read cutoff. (FIG. 24b) Breakpoint calls (top) and breakpoint window matrix of log 2 sequence depth ratio. (FIG. 24c) Principle component analysis and k-means clustering on breakpoint matrix. (FIG. 24d) 100 kbp resolution CNV calling on aggregated cells from each cluster. (FIG. 24e) Cluster specific CNVs and CEBPA amplification present in all clusters (k4 shown).

FIGS. 25-1 and 25-2 show SCI-seq using xSDS-based nucleosome depletion on pancreatic ductal adenocarcinoma. Copy number call summary for 2.5 Mbp windows for the three methods of copy number calling used in the analysis: (FIG. 25a) Ginkgo, (FIG. 25b) CBS, and (FIG. 25c) HMM.

(FIG. 30a) Breakpoints identified in the HeLa cell line from an HMM analysis using 2.5 Mbp windows. (FIG. 30b) Log 2 matrix of HeLa breakpoint windows for cells normalized to GM12878.

Figure 1:
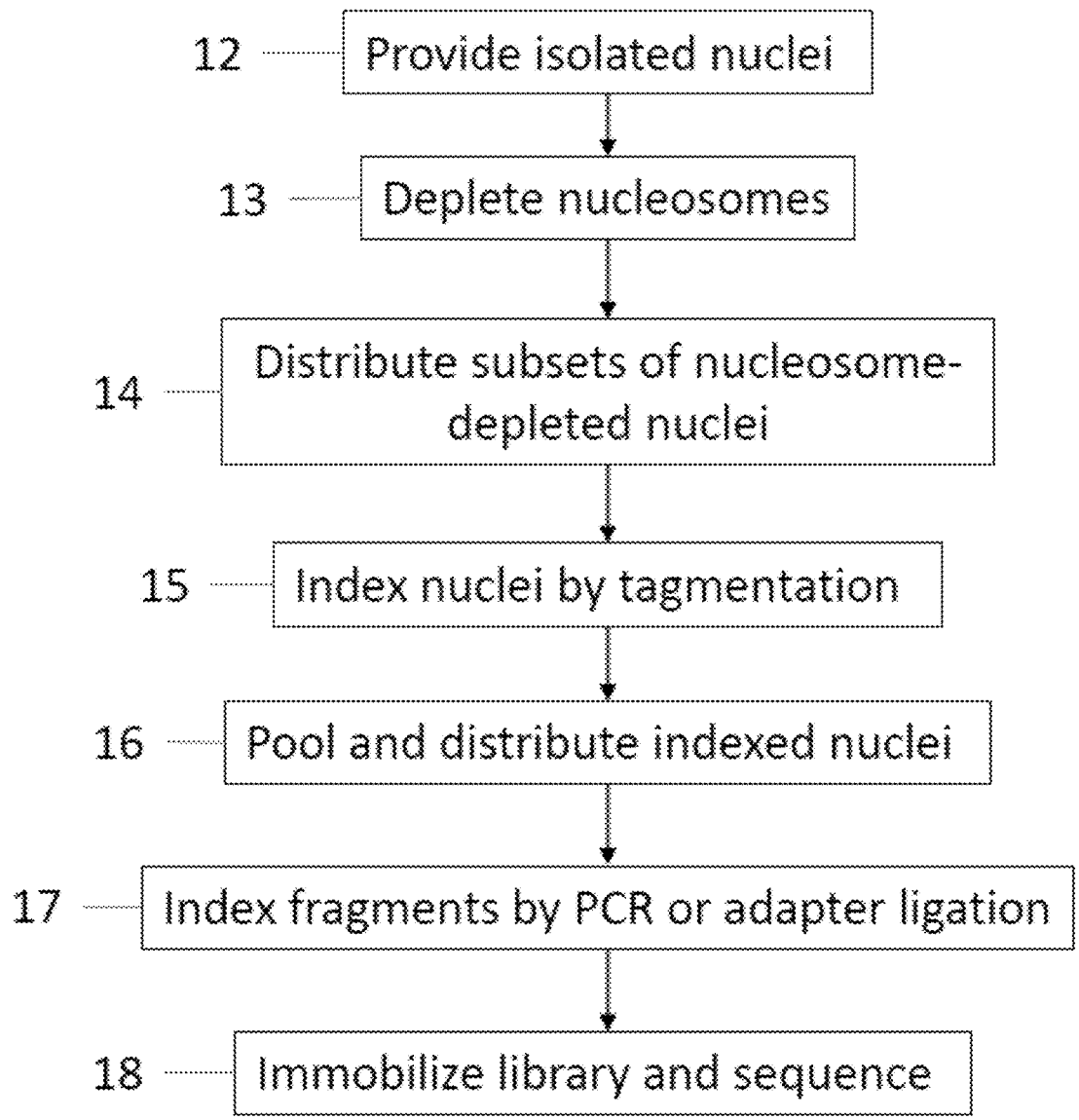
FIG. 1 shows a general block diagram of a general illustrative method for single-cell combinatorial indexing according to the present disclosure.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION OF ILLUSTRATIVE EMBODIMENTS

As used herein, the terms "organism," "subject," are used interchangeably and refer to animals and plants. An example of an animal is a mammal, such as a human.

As used herein, the term "cell type" is intended to identify cells based on morphology, phenotype, developmental origin or other known or recognizable distinguishing cellular characteristic. A variety of different cell types can be obtained from a single organism (or from the same species of organism). Exemplary cell types include, but are not limited to, urinary bladder, pancreatic epithelial, pancreatic alpha, pancreatic beta, pancreatic endothelial, bone marrow lymphoblast, bone marrow B lymphoblast, bone marrow macrophage, bone marrow erythroblast, bone marrow dendritic, bone marrow adipocyte, bone marrow osteocyte, bone marrow chondrocyte, promyeloblast, bone marrow megakaryoblast, bladder, brain B lymphocyte, brain glial, neuron, brain astrocyte, neuroectoderm, brain macrophage, brain microglia, brain epithelial, cortical neuron, brain fibroblast, breast epithelial, colon epithelial, colon B lymphocyte, mammary epithelial, mammary myoepithelial, mammary fibroblast, colon enterocyte, cervix epithelial, ovary epithelial, ovary fibroblast, breast duct epithelial, tongue epithelial, tonsil dendritic, tonsil B lymphocyte, peripheral blood lymphoblast, peripheral blood T lymphoblast, peripheral blood cutaneous T lymphocyte, peripheral blood natural killer, peripheral blood B lymphoblast, peripheral blood monocyte, peripheral blood myeloblast, peripheral blood monoblast, peripheral blood promyeloblast, peripheral blood macrophage, peripheral blood basophil, liver endothelial, liver mast, liver epithelial, liver B lymphocyte, spleen endothelial, spleen epithelial, spleen B lymphocyte, liver hepatocyte, liver fibroblast, lung epithelial, bronchus epithelial, lung fibroblast, lung B lymphocyte, lung Schwann, lung squamous, lung macrophage, lung osteoblast, neuroendocrine, lung alveolar, stomach epithelial, and stomach fibroblast.

As used herein, the term "tissue" is intended to mean a collection or aggregation of cells that act together to perform one or more specific functions in an organism. The cells can optionally be morphologically similar. Exemplary tissues include, but are not limited to, eye, muscle, skin, tendon, vein, artery, blood, heart, spleen, lymph node, bone, bone marrow, lung, bronchi, trachea, gut, small intestine, large intestine, colon, rectum, salivary gland, tongue, gall bladder, appendix, liver, pancreas, brain, stomach, skin, kidney, ureter, bladder, urethra, gonad, testicle, ovary, uterus, fallopian tube, thymus, pituitary, thyroid, adrenal, or parathyroid. Tissue can be derived from any of a variety of organs of a human or other organism. A tissue can be a healthy tissue or an unhealthy tissue. Examples of unhealthy tissues include, but are not limited to, malignancies in lung, breast, colorectum, prostate, nasopharynx, stomach, testes, skin, nervous system, bone, ovary, liver, hematologic tissues, pancreas, uterus, kidney, lymphoid tissues, etc. The malignancies may be of a variety of histological subtypes, for example, carcinoma, adenocarcinoma, sarcoma, fibroadenocarcinoma, neuroendocrine, or undifferentiated.

As used herein, the term "nucleosome" refers to the basic repeating unit of chromatin. The human genome consists of several meters of DNA compacted within the nucleus of a cell having an average diameter of ~10 µm. In the eukaryote nucleus, DNA is packaged into a nucleoprotein complex known as chromatin. The nucleosome (the basic repeating unit of chromatin) typically includes ~146 base pairs of DNA wrapped approximately 1.7 times around a core histone octamer. The histone octamer consists of two copies of each of the histones H2A, H2B, H3 and H4. Nucleosomes are regularly spaced along the DNA in the manner of beads on a string.

As used herein, the term "compartment" is intended to mean an area or volume that separates or isolates something from other things. Exemplary compartments include, but are not limited to, vials, tubes, wells, droplets, boluses, beads, vessels, surface features, or areas or volumes separated by physical forces such as fluid flow, magnetism, electrical current or the like. In one embodiment, a compartment is a well of a multi-well plate, such as a 96- or 384-well plate.

As used herein, a "transposome complex" refers to an integration enzyme and a nucleic acid including an integration recognition site. A "transposome complex" is a functional complex formed by a transposase and a transposase recognition site that is capable of catalyzing a transposition reaction (see, for instance, Gunderson et al., WO 2016/130704). Examples of integration enzymes include, but are not limited to, an integrase or a transposase. Examples of integration recognition sites include, but are not limited to, a transposase recognition site.

As used herein, the term "nucleic acid" is intended to be consistent with its use in the art and includes naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of adenine, uracil, cytosine or guanine. Useful non-native bases that can be included in a nucleic acid are known in the art. Examples of non-native bases include a locked nucleic acid (LNA) and a bridged nucleic acid (BNA). LNA and BNA bases can be incorporated into a DNA oligonucleotide and increase oligonucleotide hybridization strength and specificity. LNA and BNA bases and the uses of such bases are known to the person skilled in the art and are routine.

As used herein, "nuclease" refers to any enzyme that cleaves nucleic acids. Nucleases belong to a class of enzymes called hydrolases and are usually specific in action, ribonucleases acting preferentially upon ribonucleic acids (RNA) and deoxyribonucleases acting preferentially upon deoxyribonucleic acids (DNA).

As used herein, the term "target," when used in reference to a nucleic acid, is intended as a semantic identifier for the nucleic acid in the context of a method or composition set forth herein and does not necessarily limit the structure or function of the nucleic acid beyond what is otherwise explicitly indicated. A target nucleic acid may be essentially any nucleic acid of known or unknown sequence. It may be, for example, a fragment of genomic DNA or cDNA. Sequencing may result in determination of the sequence of the whole, or a part of the target molecule. The targets can be derived from a primary nucleic acid sample, such as a nucleus. The targets can also be obtained from a primary RNA sample by reverse transcription into cDNA. In one embodiment, the targets can be processed into templates suitable for amplification by the placement of universal sequences at the ends of each target fragment.

As used herein, the term "universal," when used to describe a nucleotide sequence, refers to a region of sequence that is common to two or more nucleic acid molecules where the molecules also have regions of sequence that differ from each other. A universal sequence that is present in different members of a collection of molecules can allow capture of multiple different nucleic acids using a population of universal capture nucleic acids, e.g., capture oligonucleotides that are complementary to a portion of the universal sequence, e.g., a universal capture sequence. Non-limiting examples of universal capture sequences include sequences that are identical to or complementary to P5 and P7 primers. Similarly, a universal sequence present in different members of a collection of molecules can allow the amplification or replication (e.g., sequencing) of multiple different nucleic acids using a population of universal primers that are complementary to a portion of the universal sequence, e.g., a universal anchor sequence. A capture oligonucleotide or a universal primer therefore includes a sequence that can hybridize specifically to a universal sequence. Two universal sequences that hybridize are referred to as a universal binding pair. For instance, a capture oligonucleotide and a universal capture sequence that hybridize are a universal binding pair.

The terms "P5" and "P7" may be used when referring to a universal capture sequence or a capture oligonucleotide. The terms "P5'" (P5 prime) and "P7'" (P7 prime) refer to the complement of P5 and P7, respectively. It will be understood that any suitable universal capture sequence or a capture oligonucleotide can be used in the methods presented herein, and that the use of P5 and P7 are exemplary embodiments only. Uses of capture oligonucleotides such as P5 and P7 or their complements on flowcells are known in the art, as exemplified by the disclosures of WO 2007/010251, WO 2006/064199, WO 2005/065814, WO 2015/106941, WO 1998/044151, and WO 2000/018957. For example, any suitable forward amplification primer, whether immobilized or in solution, can be useful in the methods presented herein for hybridization to a complementary sequence and amplification of a sequence. Similarly, any suitable reverse amplification primer, whether immobilized or in solution, can be useful in the methods presented herein for hybridization to a complementary sequence and amplification of a sequence. One of skill in the art will understand how to design and use primer sequences that are suitable for capture and/or amplification of nucleic acids as presented herein.

As used herein, the term "primer" and its derivatives refer generally to any nucleic acid that can hybridize to a target sequence of interest. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer can include any combination of nucleotides or analogs thereof. In some embodiments, the primer is a single-stranded oligonucleotide or polynucleotide. The terms "polynucleotide" and "oligonucleotide" are used interchangeably herein to refer to a polymeric form of nucleotides of any length, and may include ribonucleotides, deoxyribonucleotides, analogs thereof, or mixtures thereof. The terms should be understood to include, as equivalents, analogs of either DNA or RNA made from nucleotide analogs and to be applicable to single stranded (such as sense or antisense) and double stranded polynucleotides. The term as used herein also encompasses cDNA, that is complementary or copy DNA produced from an RNA template, for example by the action of reverse transcriptase. This term refers only to the primary structure of the molecule. Thus, the term includes triple-, double- and single-stranded deoxyribonucleic acid ("DNA"), as well as triple-, double- and single-stranded ribonucleic acid ("RNA").

As used herein, the term "adapter" and its derivatives, e.g., universal adapter, refers generally to any linear oligonucleotide which can be ligated to a nucleic acid molecule of the disclosure. In some embodiments, the adapter is substantially non-complementary to the 3' end or the 5' end of any target sequence present in the sample. In some embodiments, suitable adapter lengths are in the range of about 10-100 nucleotides, about 12-60 nucleotides, or about 15-50 nucleotides in length. Generally, the adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a universal primer. In some embodiments, the adapter can include a barcode (also referred to herein as a tag or index) to assist with downstream error correction, identification, or sequencing. The terms "adaptor" and "adapter" are used interchangeably.

As used herein, the term "each," when used in reference to a collection of items, is intended to identify an individual item in the collection but does not necessarily refer to every item in the collection unless the context clearly dictates otherwise.

As used herein, the term "transport" refers to movement of a molecule through a fluid. The term can include passive transport such as movement of molecules along their concentration gradient (e.g. passive diffusion). The term can also include active transport whereby molecules can move along their concentration gradient or against their concentration gradient. Thus, transport can include applying energy to move one or more molecule in a desired direction or to a desired location such as an amplification site.

As used herein, "amplify", "amplifying" or "amplification reaction" and their derivatives, refer generally to any action or process whereby at least a portion of a nucleic acid molecule is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. Amplification optionally includes linear or exponential replication of a nucleic acid molecule. In some embodiments, such amplification can be performed using isothermal conditions; in other embodiments, such amplification can include thermocycling. In some embodiments, the amplification is a multiplex amplification that includes the simultaneous amplification of a plurality of target sequences in a single amplification reaction. In some embodiments, "amplification" includes amplification of at least some portion of DNA and RNA based nucleic acids alone, or in combination. The amplification reaction can include any of the amplification processes known to one of ordinary skill in the art. In some embodiments, the amplification reaction includes polymerase chain reaction (PCR).

As used herein, "amplification conditions" and its derivatives, generally refers to conditions suitable for amplifying one or more nucleic acid sequences. Such amplification can be linear or exponential. In some embodiments, the amplification conditions can include isothermal conditions or alternatively can include thermocycling conditions, or a combination of isothermal and thermocycling conditions. In some embodiments, the conditions suitable for amplifying one or more nucleic acid sequences include polymerase chain reaction (PCR) conditions. Typically, the amplification conditions refer to a reaction mixture that is sufficient to amplify nucleic acids such as one or more target sequences flanked by a universal sequence, or to amplify an amplified target sequence ligated to one or more adapters. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{2+}$ or $Mn^{2+}$ and can also include various modifiers of ionic strength.

As used herein, "re-amplification" and their derivatives refer generally to any process whereby at least a portion of an amplified nucleic acid molecule is further amplified via any suitable amplification process (referred to in some embodiments as a "secondary" amplification), thereby producing a reamplified nucleic acid molecule. The secondary amplification need not be identical to the original amplification process whereby the amplified nucleic acid molecule was produced; nor need the reamplified nucleic acid molecule be completely identical or completely complementary to the amplified nucleic acid molecule; all that is required is that the reamplified nucleic acid molecule include at least a portion of the amplified nucleic acid molecule or its complement. For example, the re-amplification can involve the use of different amplification conditions and/or different primers, including different target-specific primers than the primary amplification.

As used herein, the term "polymerase chain reaction" ("PCR") refers to the method of Mullis U.S. Pat. Nos. 4,683,195 and 4,683,202, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a series of thermal cycling in the presence of a DNA polymerase. The two primers are complementary to their respective strands of the double stranded polynucleotide of interest. The mixture is denatured at a higher temperature first and the primers are then annealed to complementary sequences within the polynucleotide of interest molecule. Following annealing, the primers are extended with a polymerase to form a new pair of complementary strands. The steps of denaturation, primer annealing and polymerase extension can be repeated many times (referred to as thermocycling) to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". In a modification to the method discussed above, the target nucleic acid molecules can be PCR amplified using a plurality of different primer pairs, in some cases, one or more primer pairs per target nucleic acid molecule of interest, thereby forming a multiplex PCR reaction.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy can be about 12-plex, 24-plex, 48-plex, 96-plex, 192-plex, 384-plex, 768-plex, 1536-plex, 3072-plex, 6144-plex or higher. It is also possible to detect the amplified target sequences by several different methodologies (e.g., gel electrophoresis followed by densitometry, quantitation with a bioanalyzer or quantitative PCR, hybridization with a labeled probe; incorporation of biotinylated primers followed by avidin-enzyme conjugate detection; incorporation of $^{32}$P-labeled deoxynucleotide triphosphates into the amplified target sequence).

As used herein, "amplified target sequences" and its derivatives, refers generally to a nucleic acid sequence produced by the amplifying the target sequences using target-specific primers and the methods provided herein. The amplified target sequences may be either of the same sense (i.e. the positive strand) or antisense (i.e., the negative strand) with respect to the target sequences.

As used herein, the terms "ligating", "ligation" and their derivatives refer generally to the process for covalently linking two or more molecules together, for example covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, the ligation can include forming a covalent bond between a 5' phosphate group of one nucleic acid and a 3' hydroxyl group of a second nucleic acid thereby forming a ligated nucleic acid molecule. Generally for the purposes of this disclosure, an amplified target sequence can be ligated to an adapter to generate an adapter-ligated amplified target sequence.

As used herein, "ligase" and its derivatives, refers generally to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but are not limited to, T4 DNA ligase, T4 RNA ligase, and $E.$ $coli$ DNA ligase.

As used herein, "ligation conditions" and its derivatives, generally refers to conditions suitable for ligating two molecules to each other. In some embodiments, the ligation conditions are suitable for sealing nicks or gaps between nucleic acids. As used herein, the term nick or gap is consistent with the use of the term in the art. Typically, a nick or gap can be ligated in the presence of an enzyme, such as ligase at an appropriate temperature and pH. In some embodiments, T4 DNA ligase can join a nick between nucleic acids at a temperature of about 70-72° C.

The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "amplification site" refers to a site in or on an array where one or more amplicons can be generated. An amplification site can be further configured to contain, hold or attach at least one amplicon that is generated at the site.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "capacity," when used in reference to a site and nucleic acid material, means the maximum amount of nucleic acid material that can occupy the site. For example, the term can refer to the total number of nucleic acid molecules that can occupy the site in a particular condition. Other measures can be used as well including, for example, the total mass of nucleic acid material or the total number of copies of a particular nucleotide sequence that can occupy the site in a particular condition. Typically, the capacity of a site for a target nucleic acid will be substantially equivalent to the capacity of the site for amplicons of the target nucleic acid.

As used herein, the term "capture agent" refers to a material, chemical, molecule or moiety thereof that is capable of attaching, retaining or binding to a target molecule (e.g. a target nucleic acid). Exemplary capture agents include, without limitation, a capture nucleic acid (also referred to herein as a capture oligonucleotide) that is complementary to at least a portion of a target nucleic acid, a member of a receptor-ligand binding pair (e.g. avidin, streptavidin, biotin, lectin, carbohydrate, nucleic acid binding protein, epitope, antibody, etc.) capable of binding to a target nucleic acid (or linking moiety attached thereto), or a chemical reagent capable of forming a covalent bond with a target nucleic acid (or linking moiety attached thereto).

As used herein, the term "clonal population" refers to a population of nucleic acids that is homogeneous with respect to a particular nucleotide sequence. The homogenous sequence is typically at least 10 nucleotides long, but can be even longer including for example, at least 50, 100, 250, 500 or 1000 nucleotides long. A clonal population can be derived from a single target nucleic acid or template nucleic acid. Typically, all of the nucleic acids in a clonal population will have the same nucleotide sequence. It will be understood that a small number of mutations (e.g. due to amplification artifacts) can occur in a clonal population without departing from clonality.

As used herein, "providing" in the context of a composition, an article, a nucleic acid, or a nucleus means making the composition, article, nucleic acid, or nucleus, purchasing the composition, article, nucleic acid, or nucleus, or otherwise obtaining the compound, composition, article, or nucleus.

The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

The method provided herein can be used to produce sequencing libraries that include the whole genomes of a plurality of single cells. In one embodiment, the method can be used to detect copy number variants (CNV, e.g., the number of copies of a particular sequence, such as a gene, in the genotype of a cell). For instance, the method can be used to quantify the frequency of CNV-harboring nuclei in a sample of somatic cells from an organism, or provide information on heterogeneity in the context of certain conditions, such as cancer.

Figure 34:
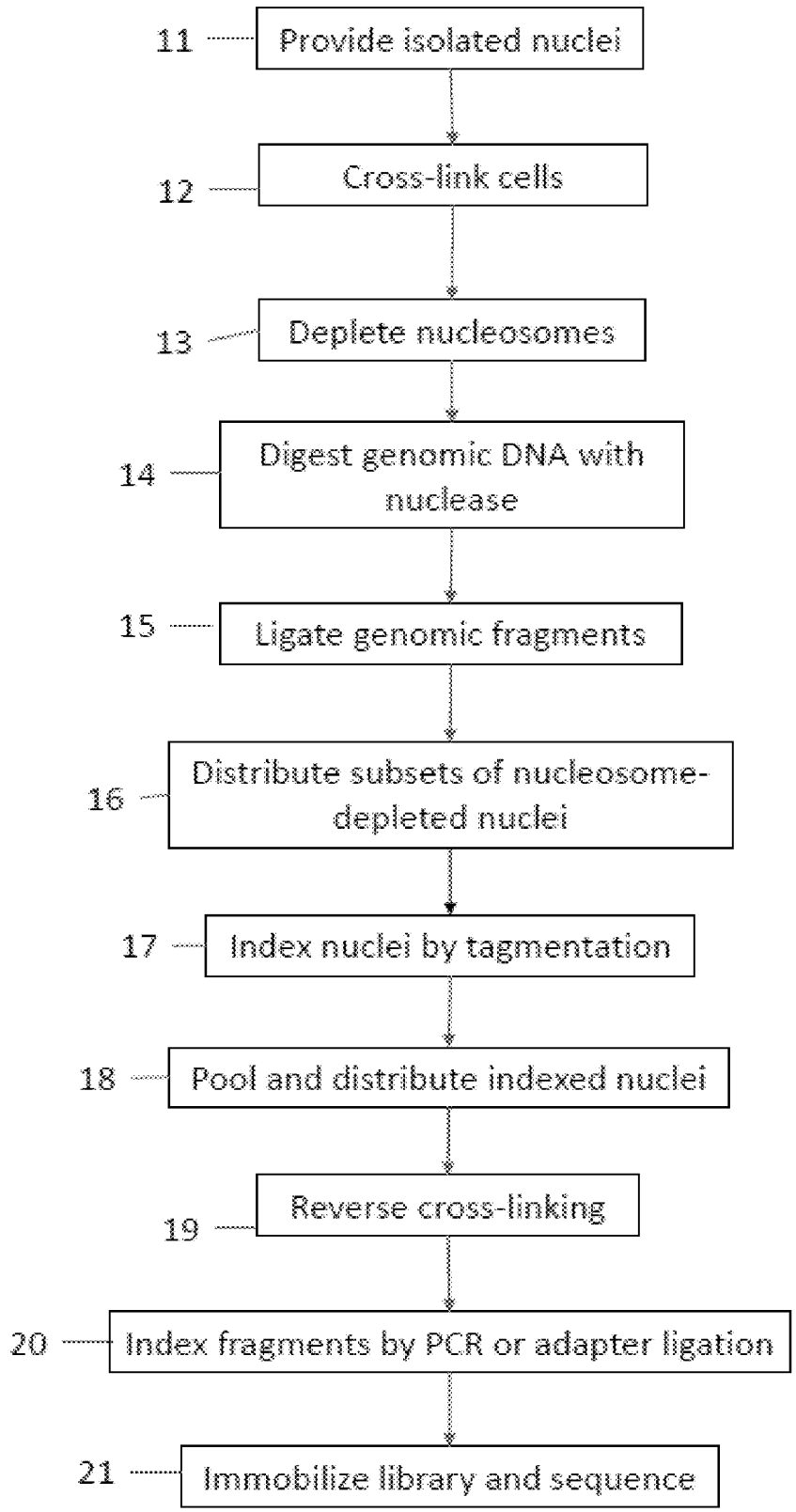
FIG. 34 shows a general block diagram of one embodiment of a general illustrative method for single-cell combinatorial indexing and genome and chromosome conformation according to the present disclosure.

The method provided herein includes providing isolated nuclei from a plurality of cells (FIG. 1, block 12; FIG. 34 block 12). The cells can be from any organism(s), and from any cell type or any tissue of the organism(s). The method can further include dissociating cells, and/or isolating the nuclei. Methods for isolating nuclei from cells are known to the person skilled in the art and are routine. The number of nuclei can be at least two. The upper limit is dependent on the practical limitations of equipment (e.g., multi-well plates) used in other steps of the method as described herein. For instance, in one embodiment the number of nuclei can be no greater than 1,000,000,000, no greater than 100,000, 000, no greater than 10,000,000, no greater than 1,000,000, no greater than 100,000, no greater than 10,000, or no greater than 1,000. The skilled person will recognize that the nucleic acid molecules in each nucleus represent the entire genetic complement of an organism (also referred to as the whole genome of an organism), and are genomic DNA molecules which include both intron and exon sequences, as well as non-coding regulatory sequences such as promoter and enhancer sequences.

The isolated nuclei can be nucleosome-free, or can be subjected to conditions that deplete the nuclei of nucleosomes, generating nucleosome-depleted nuclei (FIG. 1, block 13; FIG. 34 block 13). Nucleosome-depleted nuclei are useful in methods for determining the DNA sequence of the whole genome of a cell.

In one embodiment, the conditions used for nucleosome-depletion maintain the integrity of the isolated nuclei. Typically, nucleosome-depletion methods are used on a pellet or suspension of single cells, thus in those embodiments where an adherent cell culture or tissue is used as a source of the cells, the source is treated to obtain a pellet or suspension of single cells.

In one embodiment, the conditions for nucleosome-depletion include a chemical treatment with a chaotropic agent capable of disrupting nucleic acid-protein interactions. An example of a useful chaotropic agent includes, but is not limited to, 3,5-lithium diiodosalicylic acid. Conditions for using 3,5-lithium diiodosalicylic acid include adding it to a pellet of cells and incubating on ice.

In another embodiment, the conditions include a chemical treatment with a detergent capable of disrupting nucleic acid-protein interactions. An example of a useful detergent includes, but is not limited to, sodium dodecyl sulfate (SDS). Conditions for using SDS include adding it to a pellet of cells and incubating at an elevated temperature such as 42° C., and then adding a nonionic detergent such as Triton™ X-100 and incubating at an elevated temperature such as 42° C.

In some embodiments, when a detergent such as SDS is used, the nuclei are exposed to a cross-linking agent prior to the depletion of nucleosomes. In one embodiment, the nuclei are exposed to the cross-linking agent while inside cells (FIG. 34, block 11), and in another embodiment, isolated nuclei are exposed to the cross-linking agent. A useful example of a cross-linking agent includes, but is not limited to, formaldehyde (Hoffman et al., 2015, *J. Biol. Chem.*, 290:26404-26411). Treatment of cells with formaldehyde can include adding formaldehyde to a suspension of cells and incubating at room temperature. In one embodiment, the concentration of formaldehyde can be from 0.2% to 2%, such as greater than 0.2% and no greater than 1.5%. After the formaldehyde treatment, the nuclei can be exposed to glycine and a nonionic, non-denaturing detergent nonionic, non-denaturing detergent such as Igepal®. If cells are cross-linked before isolating the nuclei, the cross-linking can be, and typically is, reversed by incubation at 55° C. to 72° C., such as 68° C., for 30 minutes to 16 hours, such as 1 hour (FIG. 34, block 19). Reversal typically occurs later, after distributing subsets of pooled indexed nuclei into a second plurality of compartments (FIG. 34, block 18) and before generating dual-index fragments (FIG. 34, block 20). The distributing subsets and generating dual-index fragments is described herein.

In some embodiments where a cross-linking agent is used, the method can also include manipulations that provide information on chromosome structure within a nucleus, such as chromatin folding analysis and detection of genomic rearrangements such as, but not limited to, translocations. Such types of analyses are known in art as chromosome conformation capture (3C) and related methods (4C, 5C, and Hi-C). The manipulations typically include digestion of genomic DNA within a nucleus (FIG. 34, block 14) followed by ligation of the ends of genomic fragments that are in close proximity (FIG. 34, block 15). These steps result in chimeric fragments, where the chimeric fragments are likely nearby in physical proximity within the nucleus which are also typically near in sequence space (Nagano et al., 2013, Nature, 502:59-64). Typically, after nuclei are exposed to a cross-linking agent and before fragmenting nucleic acids, the genomic DNA present in the nuclei is digested with a nuclease, such as a restriction endonuclease (FIG. 34, block 14). Any restriction endonuclease can be used, and in one embodiment, the restriction endonuclease cleaves a nucleic acid to result in two overhangs, also known to the skilled person as sticky ends. After digestion of the genomic DNA with a restriction endonuclease, the nuclei are exposed to a ligase to join fragments of genomic DNA (FIG. 34, block 15).

During the process of depleting nucleosomes in the isolated nuclei (FIG. 1, block 13; FIG. 34 block 13), the integrity of the isolated nuclei is maintained. Whether nuclei remain intact after exposure to conditions for depleting nucleosomes can be determined by visualizing the status of the nuclei by routine methods such as phase-contrast imaging. In one embodiment, at least 100,000 nuclei are intact after nucleosome-depletion.

The method provided herein includes distributing subsets of the nucleosome-depleted nuclei into a first plurality of compartments (FIG. 1, block 14; FIG. 34, block 16). The number of nuclei present in a subset, and therefore in each compartment, can be at least 1. In one embodiment, the number of nuclei present in a subset is no greater than 1,000,000, no greater than 100,000, no greater than 10,000, no greater than 4,000, no greater than 3,000, no greater than 2,000, or no greater than 1,000. In one embodiment, the number of nuclei present in a subset can be 1 to 1,000, 1,000 to 10,000, 10,000 to 100,000, or 100,000 to 1,000,000. In one embodiment, the number of nuclei present each subset is approximately equal. Methods for distributing nuclei into subsets are known to the person skilled in the art and are routine. Examples include, but are not limited to, fluorescence-activated nuclei sorting (FANS).

Each compartment includes a transposome complex. The transposome complex can be added to each compartment before, after, or at the same time a subset of the nuclei is added to the compartment. The transposome complex, a transposase bound to a transposase recognition site, can insert the transposase recognition site into a target nucleic acid within a nucleus in a process sometimes termed "tagmentation." In some such insertion events, one strand of the transposase recognition site may be transferred into the target nucleic acid. Such a strand is referred to as a "transferred strand." In one embodiment, a transposome complex includes a dimeric transposase having two subunits, and two non-contiguous transposon sequences. In another embodiment, a transposase includes a dimeric transposase having two subunits, and a contiguous transposon sequence.

Some embodiments can include the use of a hyperactive Tn5 transposase and a Tn5-type transposase recognition site (Goryshin and Reznikoff, *J. Biol. Chem.*, 273:7367 (1998)), or MuA transposase and a Mu transposase recognition site comprising R1 and R2 end sequences (Mizuuchi, K., *Cell*, 35: 785, 1983; Savilahti, H, et al., *EMBO J.*, 14: 4893, 1995). Tn5 Mosaic End (ME) sequences can also be used as optimized by a skilled artisan.

More examples of transposition systems that can be used with certain embodiments of the compositions and methods provided herein include *Staphylococcus aureus* Tn552 (Colegio et al., *J. Bacteriol.*, 183: 2384-8, 2001; Kirby C et al., *Mol. Microbiol.*, 43: 173-86, 2002), Ty1 (Devine & Boeke, *Nucleic Acids Res.*, 22: 3765-72, 1994 and International Publication WO 95/23875), Transposon Tn7 (Craig, N L, *Science.* 271: 1512, 1996; Craig, N L, *Review in: Curr Top Microbiol Immunol.*, 204:27-48, 1996), Tn/O and IS10 (Kleckner N, et al., *Curr Top Microbiol Immunol.*, 204:49-82, 1996), Mariner transposase (Lampe D J, et al., *EMBO J.*, 15: 5470-9, 1996), Tc1 (Plasterk R H, *Curr. Topics Microbiol. Immunol.*, 204: 125-43, 1996), P Element (Gloor, G B, *Methods Mol. Biol.*, 260: 97-114, 2004), Tn3 (Ichikawa & Ohtsubo, *J Biol. Chem.* 265:18829-32, 1990), bacterial insertion sequences (Ohtsubo & Sekine, *Curr. Top. Microbiol. Immunol.* 204: 1-26, 1996), retroviruses (Brown, et al., *Proc Natl Acad Sci USA,* 86:2525-9, 1989), and retrotransposon of yeast (Boeke & Corces, *Annu Rev Microbiol.* 43:403-34, 1989). More examples include IS5, Tn10, Tn903, IS911, and engineered versions of transposase family enzymes (Zhang et al., (2009) *PLoS Genet.* 5:e1000689. Epub 2009 Oct. 16; Wilson C. et al (2007) *J. Microbiol. Methods* 71:332-5).

Other examples of integrases that may be used with the methods and compositions provided herein include retroviral integrases and integrase recognition sequences for such retroviral integrases, such as integrases from HIV-1, HIV-2, SIV, PFV-1, RSV.

Transposon sequences useful with the methods and compositions described herein are provided in U.S. Patent Application Pub. No. 2012/0208705, U.S. Patent Application Pub. No. 2012/0208724 and Int. Patent Application Pub. No. WO 2012/061832. In some embodiments, a transposon sequence includes a first transposase recognition site, a second transposase recognition site, and an index sequence present between the two transposase recognition sites.

Some transposome complexes useful herein include a transposase having two transposon sequences. In some such embodiments, the two transposon sequences are not linked to one another, in other words, the transposon sequences are non-contiguous with one another. Examples of such transposomes are known in the art (see, for instance, U.S. Patent Application Pub. No. 2010/0120098).

In some embodiments, a transposome complex includes a transposon sequence nucleic acid that binds two transposase subunits to form a "looped complex" or a "looped transposome." In one example, a transposome includes a dimeric transposase and a transposon sequence. Looped complexes can ensure that transposons are inserted into target DNA while maintaining ordering information of the original target DNA and without fragmenting the target DNA. As will be appreciated, looped structures may insert desired nucleic acid sequences, such as indexes, into a target nucleic acid, while maintaining physical connectivity of the target nucleic acid. In some embodiments, the transposon sequence of a looped transposome complex can include a fragmentation site such that the transposon sequence can be fragmented to create a transposome complex comprising two transposon sequences. Such transposome complexes are useful to ensuring that neighboring target DNA fragments, in which the transposons insert, receive code combinations that can be unambiguously assembled at a later stage of the assay.

A transposome complex also includes at least one index sequence, also referred to as a transposase index. The index sequence is present as part of the transposon sequence. In one embodiment, the index sequence can be present on a transferred strand, the strand of the transposase recognition site that is transferred into the target nucleic acid. An index sequence, also referred to as a tag or barcode, is useful as a marker characteristic of the compartment in which a particular target nucleic acid was present. The index sequence of a transposome complex is different for each compartment. Accordingly, in this embodiment, an index is a nucleic acid sequence tag which is attached to each of the target nucleic acids present in a particular compartment, the presence of which is indicative of, or is used to identify, the compartment in which a population of nuclei were present at this stage of the method.

An index sequence can be up to 20 nucleotides in length, e.g., 1, 2, 3, 4, 5, 6, 7, 8, 9, 10, 11, 12, 13, 14, 15, 16, 17, 18, 19, 20. A four nucleotide tag gives a possibility of multiplexing 256 samples on the same array, and a six base tag enables 4096 samples to be processed on the same array.

In one embodiment, the transferred strand can also include a universal sequence. Universal sequences are described herein. Thus, in some embodiments where the transferred strand is transferred to target nucleic acids, the target nucleic acids include a transposase index a universal sequence, or a combination thereof.

The method also includes generating indexed nuclei (FIG. 1, block 15; FIG. 34 block 17). In one embodiment, generating indexed nuclei includes fragmenting nucleic acids present in the subsets of nucleosome-depleted nuclei (e.g., the nuclei acids present in each compartment) into a plurality of nucleic acid fragments. After nucleic acids are fragmented, the transposase remains attached to the nucleic acid fragments, such that nucleic acid fragments derived from the same genomic DNA molecule remain physically linked (Adey et al., 2014, Genome Res., 24:2041-2049).

Figure 2:
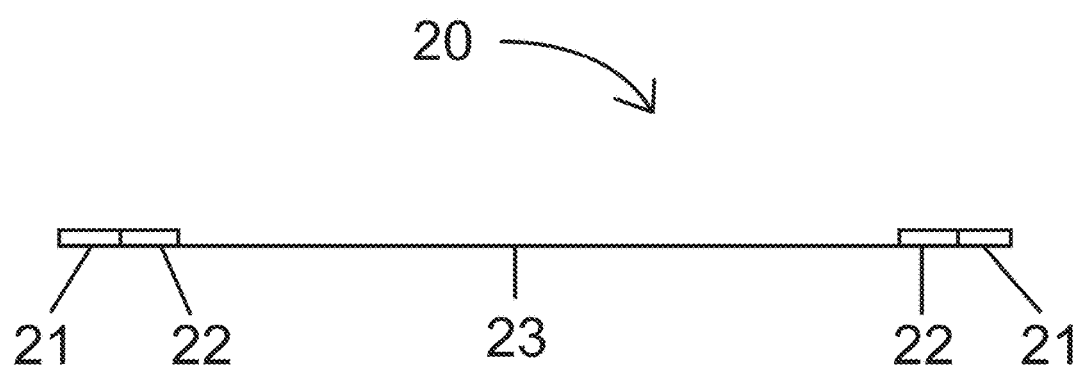
FIG. 2 shows a schematic drawing of an illustrative embodiment of an indexed nucleic acid fragment.

In one embodiment, fragmenting nucleic acids is accomplished by using a fragmentation site present in the nucleic acids. Typically, fragmentation sites are introduced into target nucleic acids by using a transposome complex. For instance, a looped transposome complex can include a fragmentation site. A fragmentation site can be used to cleave the physical, but not the informational association between index sequences that have been inserted into a target nucleic acid. Cleavage may be by biochemical, chemical or other means. In some embodiments, a fragmentation site can include a nucleotide or nucleotide sequence that may be fragmented by various means. Examples of fragmentation sites include, but are not limited to, a restriction endonuclease site, at least one ribonucleotide cleavable with an RNAse, nucleotide analogues cleavable in the presence of a certain chemical agent, a diol linkage cleavable by treatment with periodate, a disulfide group cleavable with a chemical reducing agent, a cleavable moiety that may be subject to photochemical cleavage, and a peptide cleavable by a peptidase enzyme or other suitable means (see, for instance, U.S. Patent Application Pub. No. 2012/0208705, U.S. Patent Application Pub. No. 2012/0208724 and WO 2012/061832. The result of the fragmenting is a population of indexed nuclei, where each nucleus contains indexed nucleic acid fragments. The indexed nucleic acid fragments can, and typically do, include on at least one strand the index sequence indicative of the particular compartment. An example of an indexed nucleic acid fragment is shown in FIG. 2. The single strand of the indexed nucleic acid fragment 20 includes nucleotides 21 and 22 originating from the transferred strand of the transposome complex, which includes a transposase index and a universal sequence that can be used for amplification and/or sequencing. The indexed nucleic acid fragment also includes the nucleotides originating from the genomic DNA of a nucleus 23.

The indexed nuclei from multiple compartments can be combined (FIG. 1, block 16; FIG. 34 block 18). For instance, the indexed nuclei from 2 to 96 compartments (when a 96-well plate is used), or from 2 to 384 compartments (when a 384-well plate is used) are combined. Subsets of these combined indexed nuclei, referred to herein as pooled indexed nuclei, are then distributed into a second plurality of compartments. The number of nuclei present in a subset, and therefor in each compartment, is based in part on the desire to reduce index collisions, which is the presence of two nuclei having the same transposase index ending up in the same compartment in this step of the method. The number of nuclei present in a subset in this embodiment can be from 2 to 30, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In one embodiment, the number of nuclei present in a subset is from 20 to 24, such as 22. In one embodiment, the number of nuclei present each subset is approximately equal. In one embodiment, the number of nuclei present each subset is at least 10 times fewer nuclei than the subsets of the nucleosome-depleted nuclei (FIG. 1, block 14; FIG. 34 block 16). In one embodiment, the number of nuclei present each subset is at least 100 times fewer nuclei than the subsets of the nucleosome-depleted nuclei (FIG. 1, block 14; FIG. 34 block 16). Methods for distributing nuclei into subsets are known to the person skilled in the art and are routine. Examples include, but are not limited to, fluorescence-activated nuclei sorting (FANS).

Distribution of nuclei into subsets is followed by incorporating into the indexed nucleic acid fragments in each compartment a second index sequence to generate dual-index fragments, where the second index sequence in each compartment is different from second index sequences in the other compartments. This results in the further indexing of the indexed nucleic acid fragments (FIG. 1, block 17; FIG. 34 block 20) prior to immobilizing and sequencing. In those embodiments where cells are cross-linked by a cross-linking agent, the transposases attached to the indexed nucleic acid fragments are dissociated from the indexed nucleic acid fragments. In one embodiment, the attached transposases are dissociated before the cross-linking is reversed (FIG. 34, block 19). A detergent can be used to dissociate the transposases, and in one embodiment the detergent is sodium dodecyl sulfate (SDS).

In one embodiment, the incorporation is typically by an exponential amplification reaction, such as a PCR. The universal sequences present at ends of the indexed nucleic acid fragment can be used for the binding of universal anchor sequences which can serve as primers and be extended in an amplification reaction. Typically, two different universal primers are used. One primer hybridizes with universal sequences at the 3' end of one strand of the indexed nucleic acid fragments, and a second primer hybridizes with universal sequences at the 3' end of the other strand of the indexed nucleic acid fragments. Thus, the anchor sequence of each primer can be different. Suitable primers can each include additional universal sequences, such as a universal capture sequence, and another index sequence. Because each primer can include an index, this step results in the addition of one or two index sequences, e.g., a second and an optional third index. Indexed nucleic acid fragments having the second and the optional third indexes are referred to as dual-index fragments. The second and third indexes can be the reverse complements of each other, or the second and third indexes can have sequences that are not the reverse complements of each other. This second index sequence and optional third index is unique for each compartment in which the distributed indexed nuclei were placed (FIG. 1, block 16; FIG. 34 block 18).

In one embodiment, the incorporation of the second index sequence includes contacting the indexed nucleic acid fragments in each compartment with a first universal primer and a second universal primer. The first universal primer includes a sequence identical to a portion of the first universal sequence, and the second universal primer includes a sequence complementary to a portion of the first universal sequence. Each primer includes an index sequence. In one embodiment, the index sequence of the first universal primer is the reverse complement of the index sequence of the second universal primer. In another embodiment, the index sequence of the first universal primer is different from the reverse complement of the index sequence of the second universal primer.

In one embodiment, the first universal primer also includes a first capture sequence and a first anchor sequence complementary to a universal sequence at the 3' end of the dual-index fragments. In one embodiment, the first capture sequence includes the P5 primer sequence. In one embodiment, the second universal primer also includes a second capture sequence and a second anchor sequence complementary to a universal sequence at the 5' end of the dual-index fragments. In one embodiment, the second capture sequence includes the reverse complement of the P7 primer sequence.

In another embodiment, the incorporation includes subjecting the indexed nucleic acid fragments to conditions that result in the ligation of additional sequences to both ends of the fragments. In one embodiment, blunt-ended ligation can be used. In another embodiment, the fragments are prepared with single overhanging nucleotides by, for example, activity of certain types of DNA polymerase such as Taq polymerase or Klenow exo minus polymerase which has a non-template-dependent terminal transferase activity that adds a single deoxynucleotide, for example, deoxyadenosine (A) to the 3' ends of the indexed nucleic acid fragments. Such enzymes can be used to add a single nucleotide 'A' to the blunt ended 3' terminus of each strand of the fragments. Thus, an 'A' could be added to the 3' terminus of each strand of the double-stranded target fragments by reaction with Taq or Klenow exo minus polymerase, while the additional sequences to be added to each end of the fragment can include a compatible 'T' overhang present on the 3' terminus of each region of double stranded nucleic acid to be added. This end modification also prevents self-ligation of the nucleic acids such that there is a bias towards formation of the indexed nucleic acid fragments flanked by the sequences that are added in this embodiment.

Fragmentation of nucleic acid molecules by the methods described herein can result in fragments with a heterogeneous mix of blunt and 3'- and 5'-overhanging ends. In some embodiments, it is therefore desirable to repair the fragment ends using methods or kits (such as the Lucigen DNA terminator End Repair Kit) known in the art to generate ends that are optimal for insertion, for example, into blunt sites of cloning vectors. In a particular embodiment, the fragment ends of the population of nucleic acids are blunt ended. More particularly, the fragment ends are blunt ended and phosphorylated. The phosphate moiety can be introduced via enzymatic treatment, for example, using polynucleotide kinase.

In one embodiment, the indexed nucleic acid fragments are treated by first ligating identical universal adapters (also referred to as 'mismatched adaptors,' the general features of which are described in Gormley et al., U.S. Pat. No. 7,741,463, and Bignell et al., U.S. Pat. No. 8,053,192,) to the 5' and 3' ends of the indexed nucleic acid fragments to form dual-index fragments. In one embodiment, the universal adaptor includes all sequences necessary for sequencing, including one or two index sequences and sequences for immobilizing the dual-index fragments on an array. Because the nucleic acids to be sequenced are from single cells, further amplification of the dual-index fragments is helpful to achieve a sufficient number of dual-index fragments for sequencing.

In one embodiment, the incorporation of the second index sequence includes ligating a universal adapter to the indexed nucleic acid fragments in each compartment. The universal adapter includes two nucleic acid strands, wherein each strand includes the second index sequence. In one embodiment, the second index sequence of one strand of the universal adapter is the reverse complement of the second index sequence of the second strand of the universal adapter. In other embodiment, the second index sequence of one strand of the universal adapter is different from the reverse complement of the second index sequence of the second strand of the universal adapter.

In one embodiment, the universal adapter also includes a first capture sequence and a first anchor sequence. In one embodiment, the first capture sequence includes the P5 primer sequence. In one embodiment, the universal adapter also includes a second capture sequence and a second anchor sequence. In one embodiment, the second capture sequence includes the reverse complement of the P7 primer sequence.

In another embodiment, when the universal adapter ligated to the indexed nucleic acid fragments does not include all sequences necessary for sequencing, then an exponential amplification step, such as PCR, can be used to further modify the universal adapters present in each indexed nucleic acid fragment prior to immobilizing and sequencing. For instance, an initial primer extension reaction is carried out using a universal anchor sequence complementary to a universal sequence present in the indexed nucleic acid fragment, in which extension products complementary to both strands of each individual indexed nucleic acid fragment are formed. Typically, the PCR adds additional universal sequences, such as a universal capture sequence, and another index sequence. Because each primer can include an index, this step results in the addition of one or two index sequences, e.g., a second and an optional third index, and indexing of the indexed nucleic acid fragment by adapter ligation (FIG. 1, block 17; FIG. 34 block 20).

Figure 3:
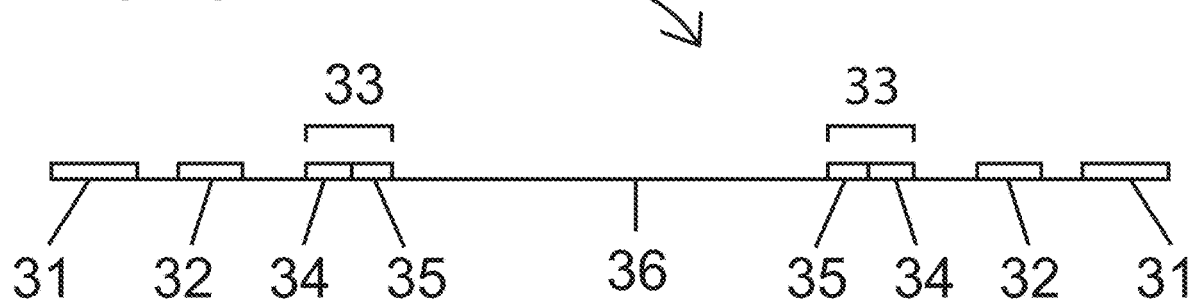
FIG. 3 shows a schematic drawing of an illustrative embodiment of a dual-index fragment.

After the universal adapters are added, either by a single step method of ligating a universal adaptor including all sequences necessary for sequencing, or by a two-step method of ligating a universal adapter and then an exponential amplification to further modify the universal adapter, the final dual-index fragments will include a universal capture sequence, a second index sequence, and an optional third index sequence. The second and third indexes can be the reverse complements of each other, or the second and third indexes can have sequences that are not the reverse complements of each other. These second and optional third index sequences are unique for each compartment in which the distributed indexed nuclei were placed (FIG. 1, block 17; FIG. 34 block 20) after the first index was added by tagmentation. The result of adding universal adapters to each end is a plurality or library of dual-index fragments having a structure similar or identical to the dual-index fragment 30 shown in FIG. 3. A single strand of the dual-index fragment 30 includes a capture sequence 31 and 38, also referred to as a 3' flowcell adapter (e.g., P5) and 5' flowcell adapter (e.g., P7'), respectively, and an index 32 and 37, such as i5 and i7. The dual-index fragment 30 also includes nucleotides originating from the transferred strand of the transposome complex 33, which includes a transposase index 34 and a universal sequence 35 that can be used for amplification and/or sequencing. The dual-index fragment also includes the nucleotides originating from the genomic DNA of a nucleus 36.

The resulting dual-index fragments collectively provide a library of nucleic acids that can be immobilized and then sequenced. The term library, also referred to herein as a sequencing library, refers to the collection of nucleic acid fragments from single cells containing known universal sequences at their 3' and 5' ends. The library includes whole genome nucleic acids from one or more of the isolated nuclei.

The dual-index fragments can be subjected to conditions that select for a predetermined size range, such as from 150 to 400 nucleotides in length, such as from 150 to 300 nucleotides. The resulting dual-index fragments are pooled, and optionally can be subjected to a clean-up process to enhance the purity to the DNA molecules by removing at least a portion of unincorporated universal adapters or primers. Any suitable clean-up process may be used, such as electrophoresis, size exclusion chromatography, or the like. In some embodiments, solid phase reversible immobilization paramagnetic beads may be employed to separate the desired DNA molecules from unattached universal adapters or primers, and to select nucleic acids based on size. Solid phase reversible immobilization paramagnetic beads are commercially available from Beckman Coulter (Agencourt AMPure XP), Thermofisher (MagJet), Omega Biotek (Mag-Bind), Promega Beads (Promega), and Kapa Biosystems (Kapa Pure Beads).

The plurality of dual-indexed fragments can be prepared for sequencing. After the dual-indexed fragments are pooled they are enriched, typically by immobilization and/or amplification, prior to sequencing (FIG. 1, block 18; FIG. 34 block 21). Methods for attaching dual-indexed fragments from one or more sources to a substrate are known in the art. In one embodiment, dual-index fragments are enriched using a plurality of capture oligonucleotides having specificity for the dual-index fragments, and the capture oligonucleotides can be immobilized on a surface of a solid substrate. For instance, capture oligonucleotides can include a first member of a universal binding pair, and wherein a second member of the binding pair is immobilized on a surface of a solid substrate. Likewise, methods for amplifying immobilized dual-indexed fragments include, but are not limited to, bridge amplification and kinetic exclusion. Methods for immobilizing and amplifying prior to sequencing are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

A pooled sample can be immobilized in preparation for sequencing. Sequencing can be performed as an array of single molecules, or can be amplified prior to sequencing. The amplification can be carried out using one or more immobilized primers. The immobilized primer(s) can be, for instance, a lawn on a planar surface, or on a pool of beads. The pool of beads can be isolated into an emulsion with a single bead in each "compartment" of the emulsion. At a concentration of only one template per "compartment," only a single template is amplified on each bead.

The term "solid-phase amplification" as used herein refers to any nucleic acid amplification reaction carried out on or in association with a solid support such that all or a portion of the amplified products are immobilized on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilized on the solid support. Solid phase PCR covers systems such as emulsions, wherein one primer is anchored to a bead and the other is in free solution, and colony formation in solid phase gel matrices wherein one primer is anchored to the surface, and one is in free solution.

In some embodiments, the solid support comprises a patterned surface. A "patterned surface" refers to an arrangement of different regions in or on an exposed layer of a solid support. For example, one or more of the regions can be features where one or more amplification primers are present. The features can be separated by interstitial regions where amplification primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. Exemplary patterned surfaces that can be used in the methods and compositions set forth herein are described in U.S. Pat. Nos. 8,778,848, 8,778,849 and 9,079,148, and US Pub. No. 2014/0243224.

In some embodiments, the solid support includes an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface can be wells in an array of wells (e.g. microwells or nanowells) on glass, silicon, plastic or other suitable solid supports with patterned, covalently-linked gel such as poly(N-(5-azidoacetamidylpentyl) acrylamide) (PAZAM, see, for example, US Pub. No. 2013/184796, WO 2016/066586, and WO 2015/002813). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However, in many embodiments the gel need not be covalently linked to the wells. For example, in some conditions silane free acrylamide (SFA, see, for example, U.S. Pat. No. 8,563,477) which is not covalently attached to any part of the structured substrate, can be used as the gel material.

In particular embodiments, a structured substrate can be made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of dual-index fragments can then be contacted with the polished substrate such that individual dual-index fragments will seed individual wells via interactions with primers attached to the gel material; however, the target nucleic acids will not occupy the interstitial regions due to absence or inactivity of the gel material. Amplification of the dual-index fragments will be confined to the wells since absence or inactivity of gel in the interstitial regions prevents outward migration of the growing nucleic acid colony. The process can be conveniently manufactured, being scalable and utilizing conventional micro- or nanofabrication methods.

Although the disclosure encompasses "solid-phase" amplification methods in which only one amplification primer is immobilized (the other primer usually being present in free solution), in one embodiment it is preferred for the solid support to be provided with both the forward and the reverse primers immobilized. In practice, there will be a 'plurality' of identical forward primers and/or a 'plurality' of identical reverse primers immobilized on the solid support, since the amplification process requires an excess of primers to sustain amplification. References herein to forward and reverse primers are to be interpreted accordingly as encompassing a 'plurality' of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may include template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the disclosure. Other embodiments may use forward and reverse primers which contain identical template-specific sequences but which differ in some other structural features. For example, one type of primer may contain a non-nucleotide modification which is not present in the other.

In all embodiments of the disclosure, primers for solid-phase amplification are preferably immobilized by single point covalent attachment to the solid support at or near the 5' end of the primer, leaving the template-specific portion of the primer free to anneal to its cognate template and the 3' hydroxyl group free for primer extension. Any suitable covalent attachment means known in the art may be used for this purpose. The chosen attachment chemistry will depend on the nature of the solid support, and any derivatization or functionalization applied to it. The primer itself may include a moiety, which may be a non-nucleotide chemical modification, to facilitate attachment. In a particular embodiment, the primer may include a sulphur-containing nucleophile, such as phosphorothioate or thiophosphate, at the 5' end. In the case of solid-supported polyacrylamide hydrogels, this nucleophile will bind to a bromoacetamide group present in the hydrogel. A more particular means of attaching primers and templates to a solid support is via 5' phosphorothioate attachment to a hydrogel comprised of polymerized acrylamide and N-(5-bromoacetamidylpentyl) acrylamide (BRAPA), as described in WO 05/065814.

Certain embodiments of the disclosure may make use of solid supports that include an inert substrate or matrix (e.g. glass slides, polymer beads, etc.) which has been "functionalized," for example by application of a layer or coating of an intermediate material including reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel), but the intermediate material may itself be non-covalently attached to the substrate or matrix (e.g. the glass substrate). The term "covalent attachment to a solid support" is to be interpreted accordingly as encompassing this type of arrangement.

The pooled samples may be amplified on beads wherein each bead contains a forward and reverse amplification primer. In a particular embodiment, the library of dual-index fragments is used to prepare clustered arrays of nucleic acid colonies, analogous to those described in U.S. Pub. No. 2005/0100900, U.S. Pat. No. 7,115,400, WO 00/18957 and WO 98/44151 by solid-phase amplification and more particularly solid phase isothermal amplification. The terms 'cluster' and 'colony' are used interchangeably herein to refer to a discrete site on a solid support including a plurality of identical immobilized nucleic acid strands and a plurality of identical immobilized complementary nucleic acid strands. The term "clustered array" refers to an array formed from such clusters or colonies. In this context, the term "array" is not to be understood as requiring an ordered arrangement of clusters.

The term "solid phase" or "surface" is used to mean either a planar array wherein primers are attached to a flat surface, for example, glass, silica or plastic microscope slides or similar flow cell devices; beads, wherein either one or two primers are attached to the beads and the beads are amplified; or an array of beads on a surface after the beads have been amplified.

Clustered arrays can be prepared using either a process of thermocycling, as described in WO 98/44151, or a process whereby the temperature is maintained as a constant, and the cycles of extension and denaturing are performed using changes of reagents. Such isothermal amplification methods are described in patent application numbers WO 02/46456 and U.S. Pub. No. 2008/0009420. Due to the lower temperatures useful in the isothermal process, this is particularly preferred in some embodiments.

It will be appreciated that any of the amplification methodologies described herein or generally known in the art may be used with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354. The above amplification methods may be employed to amplify one or more nucleic acids of interest. For example, PCR, including multiplex PCR, SDA, TMA, NASBA and the like may be utilized to amplify immobilized DNA fragments. In some embodiments, primers directed specifically to the polynucleotide of interest are included in the amplification reaction.

Other suitable methods for amplification of polynucleotides may include oligonucleotide extension and ligation, rolling circle amplification (RCA) (Lizardi et al., sNat. Genet. 19:225-232 (1998)) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835) technologies. It will be appreciated that these amplification methodologies may be designed to amplify immobilized DNA fragments. For example, in some embodiments, the amplification method may include ligation probe amplification or oligonucleotide ligation assay (OLA) reactions that contain primers directed specifically to the nucleic acid of interest. In some embodiments, the amplification method may include a primer extension-ligation reaction that contains primers directed specifically to the nucleic acid of interest. As a non-limiting example of primer extension and ligation primers that may be specifically designed to amplify a nucleic acid of interest, the amplification may include primers used for the GoldenGate assay (Illumina, Inc., San Diego, Calif.) as exemplified by U.S. Pat. Nos. 7,582,420 and 7,611,869.

Exemplary isothermal amplification methods that may be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587. Other non-PCR-based methods that may be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyper-branched strand displacement amplification which is described in, for example Lage et al., Genome Res. 13:294-307 (2003). Isothermal amplification methods may be used with, for instance, the strand-displacing Phi 29 polymerase or Bst DNA polymerase large fragment, 5'-→3' exo- for random primer amplification of genomic DNA. The use of these polymerases takes advantage of their high processivity and strand displacing activity. High processivity allows the polymerases to produce fragments that are 10-20 kb in length. As set forth above, smaller fragments may be produced under isothermal conditions using polymerases having low processivity and strand-displacing activity such as Klenow polymerase. Additional description of amplification reactions, conditions and components are set forth in detail in the disclosure of U.S. Pat. No. 7,670,810.

Another polynucleotide amplification method that is useful in the present disclosure is Tagged PCR which uses a population of two-domain primers having a constant 5' region followed by a random 3' region as described, for example, in Grothues et al. *Nucleic Acids Res.* 21(5):1321-2 (1993). The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers may be removed and further replication may take place using primers complementary to the constant 5' region.

In some embodiments, isothermal amplification can be performed using kinetic exclusion amplification (KEA), also referred to as exclusion amplification (ExAmp). A nucleic acid library of the present disclosure can be made using a method that includes a step of reacting an amplification reagent to produce a plurality of amplification sites that each includes a substantially clonal population of amplicons from an individual target nucleic acid that has seeded the site. In some embodiments, the amplification reaction proceeds until a sufficient number of amplicons are generated to fill the capacity of the respective amplification site. Filling an already seeded site to capacity in this way inhibits target nucleic acids from landing and amplifying at the site thereby producing a clonal population of amplicons at the site. In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example, in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

In some embodiments, amplification sites in an array can be, but need not be, entirely clonal. Rather, for some applications, an individual amplification site can be predominantly populated with amplicons from a first dual-indexed fragment and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons. It will be understood that in an array or other collection of sites, at least 50%, 75%, 80%, 85%, 90%, 95% or 99% or more of the sites can be clonal or apparently clonal.

In some embodiments, kinetic exclusion can occur when a process occurs at a sufficiently rapid rate to effectively exclude another event or process from occurring. Take for example the making of a nucleic acid array where sites of the array are randomly seeded with dual-indexed fragments from a solution and copies of the dual-indexed fragments are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of US Application Pub. No. 2013/0338042.

Kinetic exclusion can exploit a relatively slow rate for initiating amplification (e.g. a slow rate of making a first copy of a dual-index fragment) vs. a relatively rapid rate for making subsequent copies of the dual-indexed fragment (or of the first copy of the dual-indexed fragment). In the example of the previous paragraph, kinetic exclusion occurs due to the relatively slow rate of dual-indexed fragment seeding (e.g. relatively slow diffusion or transport) vs. the relatively rapid rate at which amplification occurs to fill the site with copies of the dual-indexed fragment seed. In another exemplary embodiment, kinetic exclusion can occur due to a delay in the formation of a first copy of a dual-indexed fragment that has seeded a site (e.g. delayed or slow activation) vs. the relatively rapid rate at which subsequent copies are made to fill the site. In this example, an individual site may have been seeded with several different dual-indexed fragments (e.g. several dual-indexed fragments can be present at each site prior to amplification). However, first copy formation for any given dual-indexed fragment can be activated randomly such that the average rate of first copy formation is relatively slow compared to the rate at which subsequent copies are generated. In this case, although an individual site may have been seeded with several different dual-indexed fragments, kinetic exclusion will allow only one of those dual-indexed fragments to be amplified. More specifically, once a first dual-indexed fragment has been activated for amplification, the site will rapidly fill to capacity with its copies, thereby preventing copies of a second dual-indexed fragment from being made at the site.

In one embodiment, the method is carried out to simultaneously (i) dual-index fragments to amplification sites at an average transport rate, and (ii) amplify the dual-index fragments that are at the amplification sites at an average amplification rate, wherein the average amplification rate exceeds the average transport rate (U.S. Pat. No. 9,169,513). Accordingly, kinetic exclusion can be achieved in such embodiments by using a relatively slow rate of transport. For example, a sufficiently low concentration of dual-index fragments can be selected to achieve a desired average transport rate, lower concentrations resulting in slower average rates of transport. Alternatively or additionally, a high viscosity solution and/or presence of molecular crowding reagents in the solution can be used to reduce transport rates. Examples of useful molecular crowding reagents include, but are not limited to, polyethylene glycol (PEG), ficoll, dextran, or polyvinyl alcohol. Exemplary molecular crowding reagents and formulations are set forth in U.S. Pat. No. 7,399,590, which is incorporated herein by reference. Another factor that can be adjusted to achieve a desired transport rate is the average size of the target nucleic acids.

An amplification reagent can include further components that facilitate amplicon formation and in some cases increase the rate of amplicon formation. An example is a recombinase. Recombinase can facilitate amplicon formation by allowing repeated invasion/extension. More specifically, recombinase can facilitate invasion of a dual-index fragment by the polymerase and extension of a primer by the polymerase using the dual-indexed fragment as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification.

Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, Mass.). Further, examples of useful formulations that include a helicase protein are described in U.S. Pat. Nos. 7,399,590 and 7,829,284.

Yet another example of a component that can be included in an amplification reagent to facilitate amplicon formation and in some cases increase the rate of amplicon formation is an origin binding protein.

Following attachment of dual-indexed fragments to a surface, the sequence of the immobilized and amplified dual-indexed fragments is determined. Sequencing can be carried out using any suitable sequencing technique, and methods for determining the sequence of immobilized and amplified dual-indexed fragments, including strand re-synthesis, are known in the art and are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a dual-index fragment can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

In one embodiment, a nucleotide monomer includes locked nucleic acids (LNAs) or bridged nucleic acids (BNAs). The use of LNAs or BNAs in a nucleotide monomer increases hybridization strength between a nucleotide monomer and a sequencing primer sequence present on an immobilized dual-index fragment.

SBS can use nucleotide monomers that have a terminator moiety or those that lack any terminator moieties. Methods using nucleotide monomers lacking terminators include, for example, pyrosequencing and sequencing using γ-phosphate-labeled nucleotides, as set forth in further detail herein. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can use nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments where two or more different nucleotides are present in a sequencing reagent, the different nucleotides can be distinguishable from each other, or alternatively the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320). In pyrosequencing, released PPi can be detected by being immediately converted to adenosine triphosphate (ATP) by ATP sulfurase, and the level of ATP generated is detected via luciferase-produced photons. The nucleic acids to be sequenced can be attached to features in an array and the array can be imaged to capture the chemiluminescent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026. This approach is being commercialized by Solexa (now Illumina Inc.), and is also described in WO 91/06678 and WO 07/123,744. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In some reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments, each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth herein.

In particular embodiments some or all of the nucleotide monomers can include reversible terminators. In such embodiments, reversible terminators/cleavable fluorophores can include fluorophores linked to the ribose moiety via a 3' ester linkage (Metzker, Genome Res. 15:1767-1776 (2005)). Other approaches have separated the terminator chemistry from the cleavage of the fluorescence label (Ruparel et al., Proc Natl Acad Sci USA 102: 5932-7 (2005)). Ruparel et al. described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluorophore and effectively reverses the termination. Examples of modified nucleotides are also described in U.S. Pat. Nos. 7,427,673, and 7,057,026.

Additional exemplary SBS systems and methods which can be utilized with the methods and systems described herein are described in U.S. Pub. Nos. 2007/0166705, 2006/0188901, 2006/0240439, 2006/0281109, 2012/0270305, and 2013/0260372, U.S. Pat. No. 7,057,026, PCT Publication No. WO 05/065814, U.S. Patent Application Publication No. 2005/0100900, and PCT Publication Nos. WO 06/064199 and WO 07/010,251.

Some embodiments can use detection of four different nucleotides using fewer than four different labels. For example, SBS can be performed using methods and systems described in the incorporated materials of U.S. Pub. No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can use sequencing by ligation techniques. Such techniques use DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597.

Some embodiments can use nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis", Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003)). In such embodiments, the dual-index fragment passes through a nanopore. The nanopore can be a synthetic pore or biological membrane protein, such as α-hemolysin. As the dual-index fragment passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008)). Data obtained from nanopore sequencing can be stored, processed and analyzed as set forth herein. In particular, the data can be treated as an image in accordance with the exemplary treatment of optical images and other images that is set forth herein.

Some embodiments can use methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414, or nucleotide incorporations can be detected with zero-mode waveguides as described, for example, in U.S. Pat. No. 7,315,019, and using fluorescent nucleotide analogs and engineered polymerases as described, for example, in U.S. Pat. No. 7,405,281 and U.S. Pub. No. 2008/0108082. The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008)). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Pub. Nos. 2009/0026082; 2009/0127589; 2010/0137143; and 2010/0282617. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different dual-index fragments are manipulated simultaneously. In particular embodiments, different dual-index fragments can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the dual-index fragments can be in an array format. In an array format, the dual-index fragments can be typically bound to a surface in a spatially distinguishable manner. The dual-index fragments can be bound by direct covalent attachment, attachment to a bead or other particle or binding to a polymerase or other molecule that is attached to the surface. The array can include a single copy of a dual-index fragment at each site (also referred to as a feature) or multiple copies having the same sequence can be present at each site or feature. Multiple copies can be produced by amplification methods such as, bridge amplification or emulsion PCR as described in further detail herein.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of cm$^2$, in parallel. Accordingly, the present disclosure provides integrated systems capable of preparing and detecting nucleic acids using techniques known in the art such as those exemplified herein. Thus, an integrated system of the present disclosure can include fluidic components capable of delivering amplification reagents and/or sequencing reagents to one or more immobilized dual-index fragments, the system including components such as pumps, valves, reservoirs, fluidic lines and the like. A flow cell can be configured and/or used in an integrated system for detection of target nucleic acids. Exemplary flow cells are described, for example, in U.S. Pub. No. 2010/0111768 and U.S. Ser. No. 13/273,666. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. Ser. No. 13/273,666.

Also provided herein are compositions. During the practice of the methods described herein various compositions can result. For example, a composition including chemically treated nucleosome-depleted isolated nuclei, where isolated nuclei include indexed nucleic acid fragments, can result. Also provided is a multi-well plate, wherein a well of the multi-well plate includes isolated nuclei having indexed nucleic acid fragments. In one embodiment, isolated nuclei can include non-natural cross-links, such as the type of cross-links formed by a cross-linking agent, e.g., formaldehyde. In one embodiment, indexed nucleic acid fragments terminate in a cleaved restriction site having an overhang. In one embodiment, the isolated nuclei comprise rearranged genomic DNA.

EMBODIMENTS

Embodiment 1

A method of preparing a sequencing library comprising nucleic acids from a plurality of single cells, the method comprising:
 (a) providing isolated nuclei from a plurality of cells;
 (b) subjecting the isolated nuclei to a chemical treatment to generate nucleosome-depleted nuclei, while maintaining integrity of the isolated nuclei;
 (c) distributing subsets of the nucleosome-depleted nuclei into a first plurality of compartments and contacting each subset with a transposome complex, wherein the transposome complex in each compartment comprises a transposase and a first index sequence that is different from first index sequences in the other compartments;
 (d) fragmenting nucleic acids in the subsets of nucleosome-depleted nuclei into a plurality of nucleic acid fragments and incorporating the first index sequences into at least one strand of the nucleic acid fragments to generate indexed nuclei comprising indexed nucleic acid fragments, wherein the indexed nucleic acid fragments remain attached to the transposases;
 (e) combining the indexed nuclei to generate pooled indexed nuclei;
 (f) distributing subsets of the pooled indexed nuclei into a second plurality of compartments;
 (g) incorporating into the indexed nucleic acid fragments in each compartment a second index sequence to generate dual-index fragments, wherein the second index sequence in each compartment is different from second index sequences in the other compartments;
 (h) combining the dual-index fragments, thereby producing a sequencing library comprising whole genome nucleic acids from the plurality of single cells.

Embodiment 2

The method of Embodiment 1, wherein the chemical treatment comprises a treatment with a chaotropic agent capable of disrupting nucleic acid-protein interactions.

Embodiment 3

The method of Embodiment 2 or 3, wherein the chaotropic agent comprises lithium 3,5-diiodosalicylic acid.

Embodiment 4

The method of any of Embodiments 1 to 3, wherein the chemical treatment comprises a treatment with a detergent capable of disrupting nucleic acid-protein interactions.

Embodiment 5

The method of any of Embodiments 1 to 4, wherein the detergent comprises sodium dodecyl sulfate (SDS).

Embodiment 6

The method of any of Embodiments 1 to 5, wherein the nuclei are treated with a cross-linking agent prior to step (b).

Embodiment 7

The method of any of Embodiments 1 to 6, wherein the cross-linking agent is formaldehyde.

Embodiment 8

The method of any of Embodiments 1 to 7, wherein the concentration of formaldehyde ranges from about 0.2% to about 2%.

Embodiment 9

The method of any of Embodiments 1 to 8, wherein the concentration of formaldehyde is no greater than about 1.5%.

Embodiment 10

The method of any of Embodiments 1 to 9, wherein the cross-linking by formaldehyde is reversed after step (f) and prior to step (g).

Embodiment 11

The method of any of Embodiments 1 to 10, wherein the reversal of the cross-linking comprises incubation at about 55° C. to about 72° C.

Embodiment 12

The method of any of Embodiments 1 to 11, wherein the transposases are disassociated from the indexed nucleic acid fragments prior to the reversal of the cross-linking.

Embodiment 13

The method of any of Embodiments 1 to 12, wherein the transposases are disassociated from the indexed nucleic acid fragments using sodium dodecyl sulfate (SDS).

Embodiment 14

The method of any of Embodiments 1 to 13, wherein the nuclei are treated with a restriction enzyme prior to step (d).

Embodiment 15

The method of any of Embodiments 1 to 14, wherein the nuclei are treated with a ligase after treatment with the restriction enzyme.

Embodiment 16

The method of any of Embodiments 1 to 15, wherein the distributing in steps (c) and (f) is performed by fluorescence-activated nuclei sorting.

Embodiment 17

The method of any of Embodiments 1 to 16, wherein the subsets of the nucleosome-depleted nuclei comprise approximately equal numbers of nuclei.

Embodiment 18

The method of any of Embodiments 1 to 17, wherein the subsets of the nucleosome-depleted nuclei comprise from 1 to about 2000 nuclei.

Embodiment 19

The method of any of Embodiments 1 to 18, wherein the first plurality of compartments is a multi-well plate.

Embodiment 20

The method of any of Embodiments 1 to 19, wherein the multi-well plate is a 96-well plate or a 384-well plate.

Embodiment 21

The method of any of Embodiments 1 to 20, wherein the subsets of the pooled indexed nuclei comprise approximately equal numbers of nuclei.

Embodiment 22

The method of any of Embodiments 1 to 21, wherein the subsets of the pooled indexed nuclei comprise from 1 to about 25 nuclei.

Embodiment 23

The method of any of Embodiments 1 to 22, wherein the subsets of the pooled indexed nuclei include at least 10 times fewer nuclei than the subsets of the nucleosome-depleted nuclei.

Embodiment 24

The method of any of Embodiments 1 to 23, wherein the subsets of the pooled indexed nuclei include at least 100 times fewer nuclei than the subsets of the nucleosome-depleted nuclei.

Embodiment 25

The method of any of Embodiments 1 to 24, wherein the second plurality of compartments is a multi-well plate.

Embodiment 26

The method of any of Embodiments 1 to 25, wherein the multi-well plate is a 96-well plate or a 384-well plate.

Embodiment 27

The method of any of Embodiments 1 to 26, wherein step (c) comprises adding the transposome complex to the compartments after the subsets of nucleosome-depleted nuclei are distributed.

Embodiment 28

The method of any of Embodiments 1 to 27, wherein each of the transposome complexes comprises a transposon, each of the transposons comprising a transferred strand.

Embodiment 29

The method of any of Embodiments 1 to 28, wherein the transferred strand comprises the first index sequence and a first universal sequence.

Embodiment 30

The method of any of Embodiments 1 to 29, wherein the incorporation of the second index sequence in step (g) comprises contacting the indexed nucleic acid fragments in each compartment with a first universal primer and a second universal primer, each comprising an index sequence and each comprising a sequence identical to or complementary to a portion of the first universal sequence, and performing an exponential amplification reaction.

Embodiment 31

The method of any of Embodiments 1 to 30, wherein the index sequence of the first universal primer is the reverse complement of the index sequence of the second universal primer.

Embodiment 32

The method of any of Embodiments 1 to 31, wherein the index sequence of the first universal primer is different from the reverse complement of the index sequence of the second universal primer.

Embodiment 33

The method of any of Embodiments 1 to 32, wherein the first universal primer further comprises a first capture sequence and a first anchor sequence complementary to a universal sequence at the 3' end of the dual-index fragments.

Embodiment 34

The method of any of Embodiments 1 to 33, wherein the first capture sequence comprises the P5 primer sequence.

Embodiment 35

The method of any of Embodiments 1 to 34, wherein the second universal primer further comprises a second capture sequence and a second anchor sequence complementary to a universal sequence at the 5' end of the dual-index fragments.

Embodiment 36

The method of any of Embodiments 1 to 35, wherein the second capture sequence comprises the reverse complement of the P7 primer sequence.

Embodiment 37

The method of any of Embodiments 1 to 36, wherein the exponential amplification reaction comprises a polymerase chain reaction (PCR).

Embodiment 38

The method of any of Embodiments 1 to 37, wherein the PCR comprises 15 to 30 cycles.

Embodiment 39

The method of any of Embodiments 1 to 38, further comprising an enrichment of dual-index fragments using a plurality of capture oligonucleotides having specificity for the dual-index fragments.

Embodiment 40

The method of any of Embodiments 1 to 39, wherein the capture oligonucleotides are immobilized on a surface of a solid substrate.

Embodiment 41

The method of any of Embodiments 1 to 40, wherein the capture oligonucleotides comprise a first member of a universal binding pair, and wherein a second member of the binding pair is immobilized on a surface of a solid substrate.

Embodiment 42

The method of any of Embodiments 1 to 42, further comprising sequencing of the dual-index fragments to determine the nucleotide sequence of nucleic acids from the plurality of single cells.

Embodiment 43

The method of any of Embodiments 1 to 42, further comprising:
providing a surface comprising a plurality of amplification sites, wherein the amplification sites comprise at least two populations of attached single stranded capture oligonucleotides having a free 3' end, and
contacting the surface comprising amplification sites with the dual-index fragments under conditions suitable to produce a plurality of amplification sites that each comprise a clonal population of amplicons from an individual dual-index fragment.

Embodiment 44

The method of any of Embodiments 1 to 43, wherein the number of the dual-index fragments exceeds the number of amplification sites, wherein the dual-index fragments have fluidic access to the amplification sites, and wherein each of the amplification sites comprises a capacity for several dual-index fragments in the sequencing library.

Embodiment 45

The method of any of Embodiments 1 to 44, wherein the contacting comprises simultaneously (i) transporting the dual-index fragments to the amplification sites at an average transport rate, and (ii) amplifying the dual-index fragments that are at the amplification sites at an average amplification rate, wherein the average amplification rate exceeds the average transport rate.

Embodiment 46

A composition comprising chemically treated nucleosome-depleted isolated nuclei, wherein the isolated nuclei comprise indexed nucleic acid fragments.

Embodiment 47

The composition of Embodiment 46, wherein the isolated nuclei comprise non-natural cross-links.

Embodiment 48

The composition of any of Embodiments 46 or 47, wherein the composition comprises indexed nucleic acid fragments that terminate in a cleaved restriction site comprising an overhang.

Embodiment 49

The composition of any of Embodiments 46 to 48, wherein the isolated nuclei comprise rearranged genomic DNA.

Embodiment 50

A multi-well plate, wherein a well of the multi-well plate comprises the composition of any of Embodiments 46-49.

The present disclosure is illustrated by the following examples. It is to be understood that the particular examples, materials, amounts, and procedures are to be interpreted broadly in accordance with the scope and spirit of the disclosure as set forth herein.

Example 1

Generating and Sequencing Thousands of Single-Cell Genomes with Combinatorial Indexing Single-cell genome sequencing has proven valuable for the detection of somatic variation, particularly in the context of tumor evolution. Current technologies suffer from high library construction costs which restrict the number of cells that can be assessed and thus impose limitations on the ability to measure heterogeneity within a tissue. Here, Single cell Combinatorial Indexed Sequencing (SCI-seq) is presented as a way of simultaneously generating thousands of low-pass single cell libraries for somatic copy number variant detection. Libraries for 16,698 single cells were constructed from a combination of cultured cell lines, primate frontal cortex tissue, and two human adenocarcinomas, including a detailed assessment of subclonal variation within a pancreatic tumor. This Example is also available as Vitak et al. (2017, Nature Methods, 14, 302-308, doi.10.1038/nmeth.4154)

Methods

Sample preparation and nuclei isolation.

Tissue culture cell lines were trypsinized then pelleted if adherent (HeLa S3, ATCC CCL-2.2; NIH/3T3, ATCC CRL-1658) or pelleted if grown in suspension (GM12878, Coriell; karyotyped at the OHSU Research Cytogenetics Laboratory), followed by one wash with ice cold PBS. They were then carried through crosslinking (for the xSDS method) or directly into nuclei preparation using Nuclei Isolation Buffer (NIB, 10 mM TrisHCl pH7.4, 10 mM NaCl, 3 mM MgCl2, 0.1% Igepal®, 1× protease inhibitors (Roche, Cat. 11873580001)) with or without nucleosome depletion. Tissue samples (RhesusFcx1, RhesusFcx2, PDAC, CRC) were dounce homogenized in NIB then passed through a 35 μm cell strainer prior to nucleosome depletion. The frozen Rhesus frontal cortex samples, RhesusFcx1 (4 yr. female) and RhesusFcx2 (9 yr. female), were obtained from the Oregon National Primate Research Center as a part of their aging nonhuman primate resource.

Standard Single Cell Library Construction

Single cell libraries constructed using quasi-random priming (QRP) and degenerate oligonucleotide primed PCR (DOP) were prepared from isolated nuclei without nucleosome depletion and brought up to 1 mL of NIB, stained with 5 piL of 5 mg/ml DAPI (Thermo Fisher, Cat. D1306) then FANS sorted on a Sony SH800 in single cell mode. One nucleus was deposited into each single well containing the respective sample buffers. QRP libraries were prepared using the PicoPlex DNA-seq Kit (Rubicon Genomics, Cat. R300381) according to the manufacturer's protocol and using the indexed PCR primers provided in the kit. DOP libraries were prepared using the SeqPlex DNA Amplification Kit (Sigma, Cat. SEQXE-50RXN) according to the manufacturer's protocol, but with the use of custom PCR indexing primers that contain 10 bp index sequences. To avoid over-amplification, all QRP and DOP libraries were amplified with the addition of 0.5 µL of 100×SYBR Green (FMC BioProducts, Cat. 50513) on a BioRad CFX thermocycler in order to monitor the amplification and pull reactions that have reached mid-exponential amplification.

Nucleosome Depletion

Lithium Assisted Nucleosome Depletion (LAND):

Prepared Nuclei were pelleted and resuspended in NIB supplemented with 200 µL of 12.5 mM lithium 3,5-diiodosalicylic acid (referred to as Lithium diiodosalicylate in main text, Sigma, Cat. D3635) for 5 minutes on ice prior to the addition of 800 lpL NIB and then taken directly into flow sorting.

Crosslinking and SDS Nucleosome Depletion (xSDS):

Crosslinking was achieved by incubating cells in 10 mL of media (cell culture) or nuclei in 10 mL of HEPES NIB (20 mM HEPES, 10 mM NaCl, 3 mM MgCl2, 0.1% igepal, 1× protease inhibitors (Roche, Cat. 11873580001)) (tissue samples) containing 1.5% formaldehyde at room for 10 minutes. The crosslinking reaction was neutralized by bringing the reaction to 200 mM Glycine (Sigma, Cat. G8898-500G) and incubating on ice for 5 minutes. Cell culture samples were crosslinked and then washed once with 10 ml ice cold 1×PBS and had nuclei isolated by incubating in NIB buffer on ice for 20 minutes and pelleted once again. Nuclei were then resuspended in 800 uL 1×NEBuffer 2.1 (NEB, Cat. B7202S) with 0.3% SDS (Sigma, Cat. L3771) and incubated at 42° C. with vigorous shaking for 30 minutes in a thermomixer (Eppendorf). SDS was then quenched by the addition of 200 µL of 10% Triton-X100 (Sigma, Cat. 9002-93-1) and incubated at 42° C. with vigorous shaking for 30 minutes.

Combinatorial Indexing Via Tagmentation and PCR

Nuclei were stained with 5 µL of 5 mg/ml DAPI (Thermo Fisher, Cat. D1306) and passed through a 35 jpm cell strainer. A 96 well plate was prepared with 10 piL of 1× Nextera® Tagment DNA (TD) buffer from the Nextera® DNA Sample Preparation Kit (Illumina, Cat. FC-121-1031) diluted with NIB in each well. A Sony SH800 flow sorter was used to sort 2,000 single nuclei into each well of the 96 well tagmentation plate in fast sort mode. Next, 1 µL of a uniquely indexed 2.5 µM transposase-adaptor complex (transposome) was added to each well. These complexes and associated sequences are described in Amini et. al. (Amini, S. et al. *Nat. Genet.* 46, 1343-9, 2014). Reactions were incubated at 55° C. for 15 minutes. After cooling to room temperature, all wells were pooled and stained with DAPI as previously described. A second 96 well plate, or set of 96 well plates, were prepared with each well containing 8.5 µL of a 0.058% SDS, 8.9 nM BSA solution and 2.5 µL of 2 uniquely barcoded primers at 10 µM. 22 post-tagmentation nuclei from the pool of 96 reactions were then flow sorted on the same instrument but in single cell sort mode into each well of the second plate and then incubated in the SDS solution at 55° C. for 5 minutes to disrupt the nuclear scaffold and disassociate the transposase enzyme. Crosslinks were reversed by incubating at 68° C. for an hour (xSDS). SDS was then diluted by the addition of 7.5 µL of Nextera® PCR Master mix (Illumina, Cat. FC-121-1031) as well as 0.5 µL of 100×SYBR Green (FMC BioProducts, Cat. 50513) and 4 µL of water. Real time PCR was then performed on a BioRad CFX thermocycler by first incubating reactions at 72° C. for 5 minutes, prior to 3 minutes at 98° C. and 15-20 cycles of [20 sec. at 98° C., 15 sec. at 63° C., and 25 sec. at 72° C.]. Reactions were monitored and stopped once exponential amplification was observed in a majority of wells. 5 µL of each well was then pooled and purified using a Qiaquick PCR Purification column (Qiagen, Cat. 28104) and eluted in 30 µL of EB.

Library Quantification and Sequencing

Libraries were quantified between the range of 200 bp and 1 kbp on a High Sensitivity Bioanalyzer kit (Agilent, Cat. 5067-4626). Libraries were sequenced on an Illumina NextSeq®500 loaded at 0.8 µM with a custom sequencing chemistry protocol (Read 1: 50 imaged cycles; Index Read 1: 8 imaged cycles, 27 dark cycles, 10 imaged cycles; Index Read 2: 8 imaged cycles, 21 dark cycles, 10 imaged cycles; Read 2: 50 imaged cycles) using custom sequencing primers described in Amini et. al. (Amini, S. et al. *Nat. Genet.* 46, 1343-9, 2014). QRP and DOP libraries were sequenced using standard primers on the NextSeq® 500 using high-capacity 75 cycle kits with dual-indexing. For QRP there is an additional challenge that the first 15 bp of the read are highly enriched for "G" bases, which are non-fluorescent with the NextSeq® 2-color chemistry and therefore cluster identification on the instrument fails. The libraries were therefore sequenced using a custom sequencing protocol that skips this region (Read 1: 15 dark cycles, 50 imaged cycles; Index Read 1: 10 imaged cycles; Index Read 2: 10 imaged cycles).

Sequence Read Processing

Software for processing SCI-seq raw reads is available on the World Wide Web at sci-seq.sourceforge.net. Sequence runs were processed using bcl2fastq (Illumina Inc., version 2.15.0) with the -create-fastq-for-index-reads and -with-failed-reads options to produce fastq files. Index reads were concatenated (36 bp total) and used as the read name with a unique read number appended to the end. These indexes were then matched to the corresponding index reference sets allowing for a hamming distance of two for each of the four index components (i7-Transposase (8 bp), i7-PCR (10 bp), i5-Transposase (8 bp), and i5-PCR (10 bp)), reads matching a quad-index combination were then renamed to the exact index (and retained the unique read number) which was subsequently used as the cell identifier. Reads were then adaptor trimmed, then paired and unpaired reads were aligned to reference genomes by Bowtie2 and merged. Human preparations were aligned to GRCh37, Rhesus preparations were aligned to RheMac8, and Human/Mouse mix preparations were aligned to a combined human (GRCh37) and mouse (mm10) reference. Aligned bam files were subjected to PCR duplicate removal using a custom script that removes reads with identical alignment coordinates on a per-barcode basis along with reads with an alignment score less than 10 as reported by Bowtie2.

Single Cell Discrimination

Figure 6:
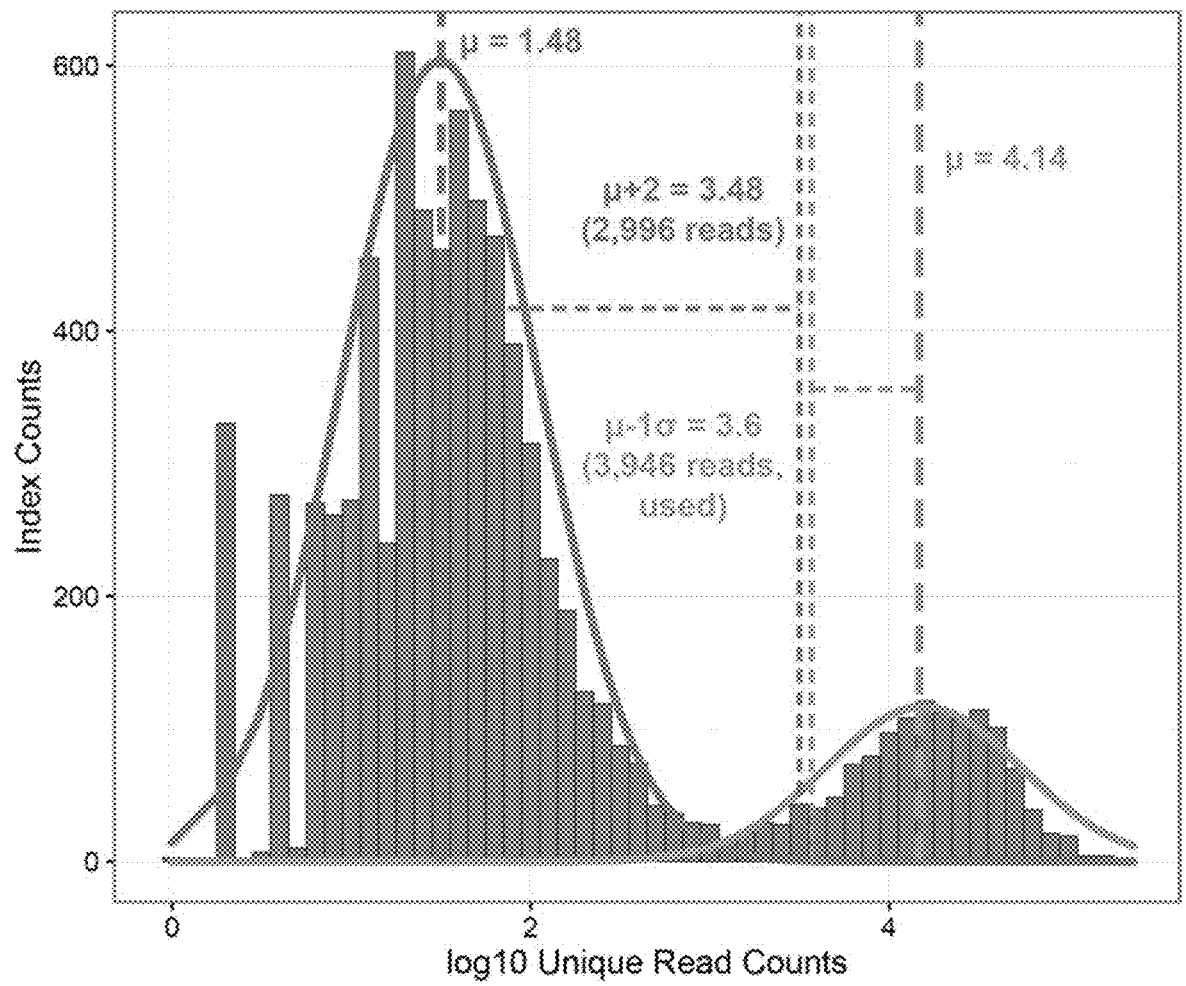
FIG. 6 shows SCI-seq single cell determination using a mixed model. HeLa.LAND3 shown. normalmixEM of the R package mixtools was used to identify each distribution: noise index combinations (left peak) and single cell libraries (right peak). The read count threshold to consider an index combination as a single cell library is the greater of either one standard deviation (in log 10 space) below the mean of the single cell distribution, or 2 greater (in log 10 space, thus 100 fold greater) than the mean of the noise distribution and at a minimum of 1,000. For the library shown, one standard deviation below the mean of the single cell component is greater and therefore used as the read count threshold.

For each PCR plate, a total of 9,216 unique index combinations are possible (12 i7-Transposase indexes×8 i5-Transposase indexes×12 i7-PCR indexes×8 i5-PCR indexes), for which only a minority should have a substantial read count, as the majority of index combinations should be absent—i.e. transposase index combinations of nuclei that were not sorted into a given PCR well. These "empty" indexes typically contain very few reads (1-3% of a run) with the majority of reads falling into bonafide single cell index combinations (97-99% of a run). The resulting histogram of $\log_{10}$ unique read counts for index combinations (FIG. 6) produces a mix of two normal distributions: a noise component and a single cell component. The R package "mixtools" was then used to fit a mixed model (normalmixEM) to identify the proportion ($\lambda$) mean ($\mu$) and standard deviation ($\sigma$) of each component. The read count threshold to qualify as a single cell library was taken to be the greater of either one standard deviation below the mean of the single cell component in $\log_{10}$ space, or 100 fold greater than the mean of the noise component (+2 in $\log_{10}$ space), and had to be a minimum of 1,000 unique reads.

Human-Mouse Mix Experiments

One of two approaches was taken to mix human (GM12878 or HeLa S3) and mouse (3T3) cells: i) mixing at the cell stage (HumMus.LAND1 and HumMus.LAND2) or ii) mixing at the nuclei stage (HumMus.LAND3, HumMus.LAND4, and HumMus.xSDS). The latter was employed to control for nuclei crosslinking or agglomerating together that could result in doublets. Libraries were constructed as described herein, for instances where two distinct DAPI-positive populations were observed during flow sorting, included both populations in the same gate so as not to skew proportions. Reads were processed as in other experiments, except reads were instead aligned to a reference comprised of GRCh37 (hg19) and mm10. The mapping quality 10 filter effectively removed reads that aligned to conserved regions in both genomes and then for each identified single cell, reads to each species were tallied and used to estimate collision frequency. For early LAND preparations 25 indexed nuclei were sorted per PCR well and produced total collision rates (i.e. twice the human-mouse collision rate) of 28.1% and 10.4%. For the second two LAND preparations we sorted 22 nuclei per PCR well, which produced a total collision rate of 4.3% for one preparation and no detectable collisions in another. We also tested two FANS sorting conditions for our xSDS preparation, one was permissive and allowed a broader range of DAPI fluorescence, and the other more restrictive, and carried out both preparations on separate sides of the same PCR plate. For the permissive gating we observed a total collision rate of 23.6% with a substantial reduction for the more restrictive gating at 8.1%. Based on these results we decided to continue sorting 22 nuclei per PCR well using the more restrictive FANS Library Depth Projections To estimate the performance of a library pool if, or when, it was sequenced to a greater depth, random reads were incrementally sampled from each SCI-seq preparation across all index combinations including unaligned and low quality reads without replacement at every one percent of the total raw reads. For each point we identified the total number reads that are aligned with high quality (MQ≥10) assigned to each single cell index and the fraction of those reads that are unique, non-PCR duplicates, as well as the corresponding fraction of total reads sampled that were assigned to that index. Using these points we fit both a nonlinear model and a Hanes-Woolfe transformed model to predict additional sequencing for each individual single cell library within the pool and projected out to a median unique read percentage across cells of 5%. To determine the accuracy of the models, we determined the number of downsampled raw reads of each library that would reach the point in which the median unique read percentage per cell was 90%, which is somewhat less than what was achieved for libraries that were sequenced at low coverage. We then subsampled the pre-determined number of reads for 30 iterations and built a new model for each cell at each iteration and then predicted the unique read counts for each cell out to the true sequencing depth that was achieved. The standard deviation of the true read count across all iterations for all cells was then calculated.

Genome Windowing

Genomic windows were determined on a per-library basis using custom tools. For each chromosome the size of the entire chromosome was divided by the target window size to produce the number of windows per chromosome. The total read count for the chromosome summarized over the pool of all single cells (GM12878 for all human samples where absolute copy number was determined, as well as for each pooled sample where amplifications or deletions relative to the mean copy number were determined) was then divided by the window count to determine the mean read count per window. The chromosome was then walked and aligned reads from the pool tallied and a window break was made once the target read count per window was reached. Windows at chromosome boundaries were only included if they contained more than 75% of the average reads per window limit for that chromosome. By using dynamic windows we accounted for biases, such as highly repetitive regions, centromeres and other complex regions that can lead to read dropout in the case of fixed size bins[22].

GC Bias Correction

Reads were placed into the variable sized bins and GC corrected based on individual read GC content instead of the GC content of the dynamic windows. We posit that the large bin sizes needed for single cell analysis average out smaller scale GC content changes. Furthermore, SCI-seq does not involve pre-amplification where large regions of the genome are amplified, therefore GC bias originates solely from the PCR and is amplicon-specific. To calculate correction weights for the reads we compared the fraction of all reads with a given GC to the fraction of total simulated reads with the average insert size at the same GC fraction. This weight was then used in lieu of read counts and summed across all reads in a given window. All regions present in DAC blacklisted regions were excluded from analysis for the human sample analyses (genome.ucsc.edu/cgi-bin/hgFileUi?db=hg19&g=wgEncodeMapability)[19]. Following GC correction, all reads were normalized by the average number of reads per bin across the genome. Finally, for each window we took the normalized read count of each cell and divided it by the pooled sample baseline to produce a ratio score.

Measures of Data Variation

To measure data quality, we calculated two different measures of coverage dispersion: the median absolute deviation (MAD), the median absolute pairwise difference (MAPD). For each score we calculated the median of the absolute values of all pairwise differences between neighboring bins that have been normalized by the mean bin count within the cell (log 2-normalized ratios for the MAPD scores). These scores measure the dispersion of normalized binned reads due to technical noise, rather than due copy number state changes, which are less frequent[2,22].

Copy Number Variant Calling

CNV calling was performed on the windowed, GC corrected and bulk sample normalized reads with two available R packages that employ two different segmentation strategies: a Hidden Markov Model approach (HMMcopy, version 3.3.0, Ha, G. et al., *Genome Res.* 22, 1995-2007, 2012) and Circular Binary Segmentation (DNAcopy, version 1.44.0, Olshen et al. *Biostatistics* 5, 557-572, 2004). Values were $Log_2$ transformed for input ($2*log_2$ for CBS) and copy number calls were made based on the optimized parameters from Knouse et al. 2016, Knouse et al., *Genome Res.* gr.198937.115, 2016, doi:10.1101/gr.198937.115). For optimal sensitivity and specificity to detect copy number calls with sizes≥5 Mb we set the probability of segment extension (E) to 0.995 for HMM and for CBS we chose the significance level to accept a copy number change (a) to be 0.0001. The $Log_2$ cutoffs for calling losses or gains were 0.4 and −0.35 for HMM and 1.32 and 0.6 for CBS. As an additional tool for CNV calling we used Ginkgo[22], which uses an alternative method for data normalization. We uploaded bed files for each cell and a bulk down sampled bed file, which we created with Picard Tools (we used a down sample probability of 0.1). For the analysis we chose to segment single cells with the down sampled bulk bed file and when ploidy was known for the samples we created FACS files to force Ginkgo to normalize to that ploidy. Calls for the three methods were intersected either on a per-window basis or were filtered to only include calls that span≥80% of a chromosome arm and then intersected for aneuploidy analysis.

Tumor Breakpoint Analysis

Unlike the assessment of sporadic aneuploidy, tumor structural variation is much more complex with a large portion of breakpoints within chromosomes. Further, sporadic aneuploidy within any given subclone of a tumor is less pertinent than an accurate profile of the subpopulations that are present. We therefore used the HMM and CBS segmented ratio score matrixes to identify breakpoints by tallying up the boundaries of segmented regions across cells. We then used the resulting distribution of shared chromosomal breakpoints across the genome to identify local maxima to account for variability in which specific window the call was made, and then retained those that are present in at least 5% of cells. We then merged all windows within each breakpoint span and calculated the new log 2 ratio of each aneuploid cell over the mean values of the euploid population. We then carried out principle components analysis prior to k-means clustering with a k value determined by Silhouette analysis. To minimize the effect of doublets which can account for ~10% of putative single cells and also to exclude low-performance cells, we retained only those in the close proximity to their respective centroids. We then merged sequence reads for all cells within each cluster and then carried out a higher resolution CNV analysis (target window size of 100 kbp) using an HMM strategy followed by absolute copy number state identification and the identification of focal amplifications and deletions using a sliding window outlier strategy[20]. Intra-tumoral clonal relationships are most accurately captured by shared breakpoints as opposed to the drift in copy number of a segment based on the assumption that structural changes involving breaks in the DNA as being more impactful on the cell. We therefore compared cells by assessing the proportion of segments between breakpoints that were identified using the high resolution (100 kbp) CNV analysis that overlapped by at least 90% (to account for noise in the exact window that was called as the copy number change) out of the total number of segments.

Results

Nucleosome Depletion for Uniform Genome Coverage

A hurdle to adapt combinatorial indexing to produce uniformly distributed sequence reads is the removal of nucleosomes bound to genomic DNA without compromising nuclear integrity. The sciATAC-seq method is carried out on native chromatin, which permits the conversion of DNA into library molecules only within regions of open chromatin (1-4% of the genome)s. This restriction is desirable for epigenetic characterization; however, for CNV detection, it results in biological bias and severely limited read counts (~3,000 per cell)[17]. We therefore developed two strategies to unbind nucleosomes from genomic DNA while retaining nuclear integrity for SCI-seq library construction. The first, Lithium Assisted Nucleosome Depletion (LAND), utilizes the chaotropic agent, Lithium diiodosalycylate, to disrupt DNA-protein interactions in the cell, therefore releasing DNA from histones. The second, crosslinking with SDS (xSDS), uses the detergent SDS to denature histone proteins and render them unable to bind DNA. However, SDS has a disruptive effect on nuclear integrity, thus necessitating a crosslinking step prior to denaturation in order to maintain intact nuclei.

Figure 4C:
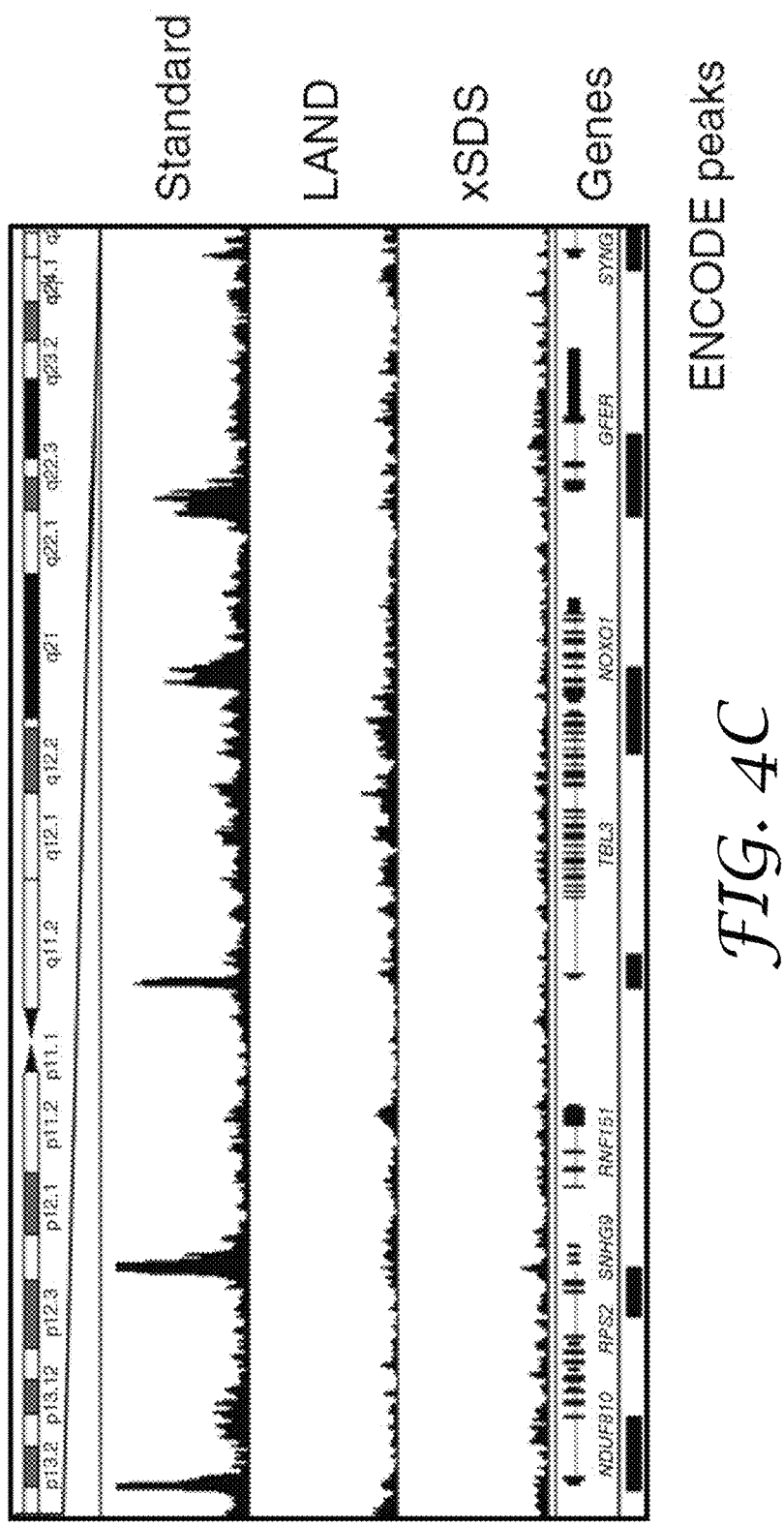
(FIG. 4c) Nucleosome depletion produces genome-wide uniform coverage that is not restricted to sites of chromatin accessibility.
Figures 5A, 5B:
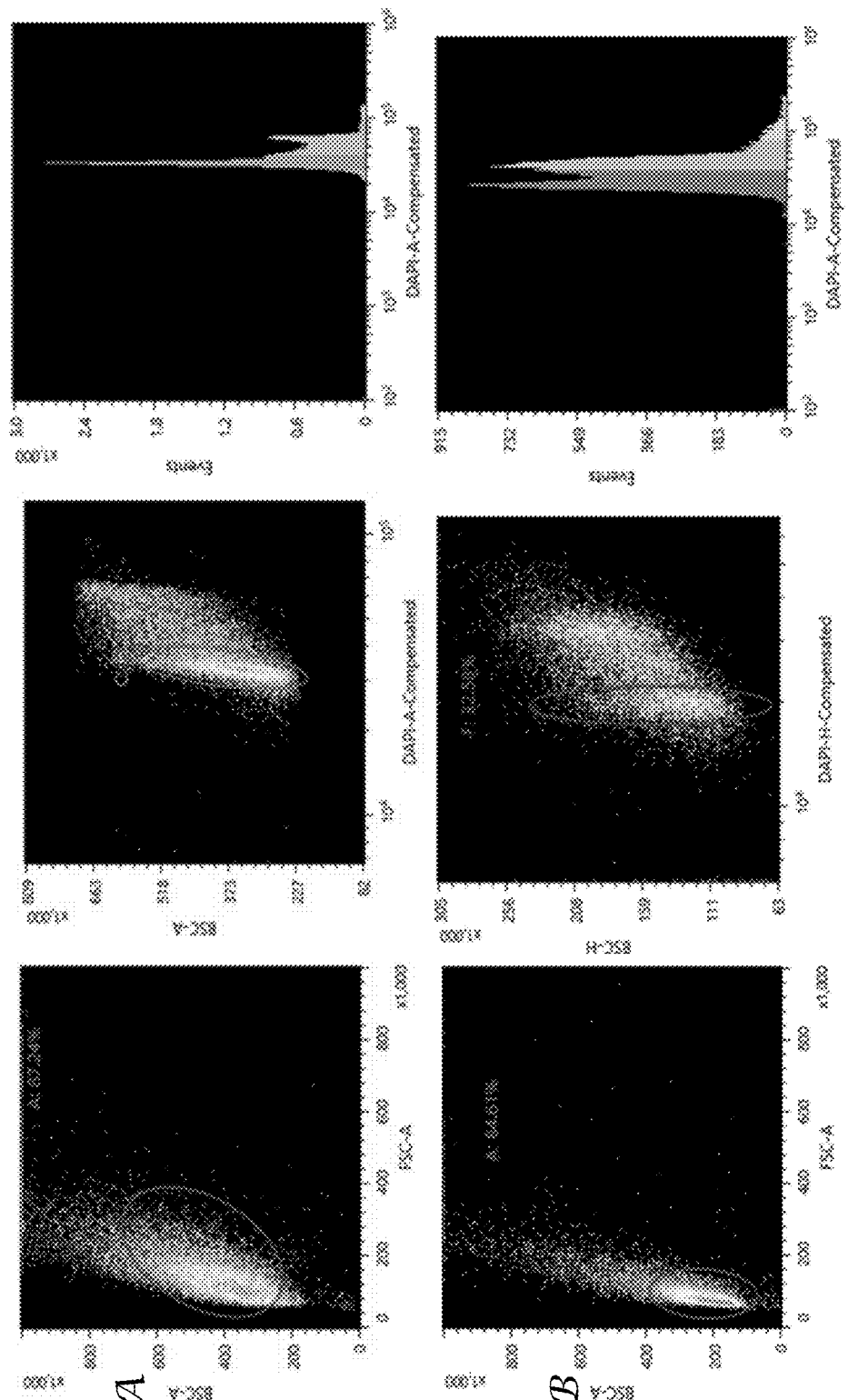
(FIG. 5a) ATAC-seq Nuclei (FIG. 5b) LAND (FIG. 5c) HeLa S3 and 3T3 (FIG. 5d) xSDS (FIG. 5e) PDAC Sort 1 Transposase Plate (FIG. 5f) PDAC Sort 2 PCR plate.
Figures 5C, 5D:
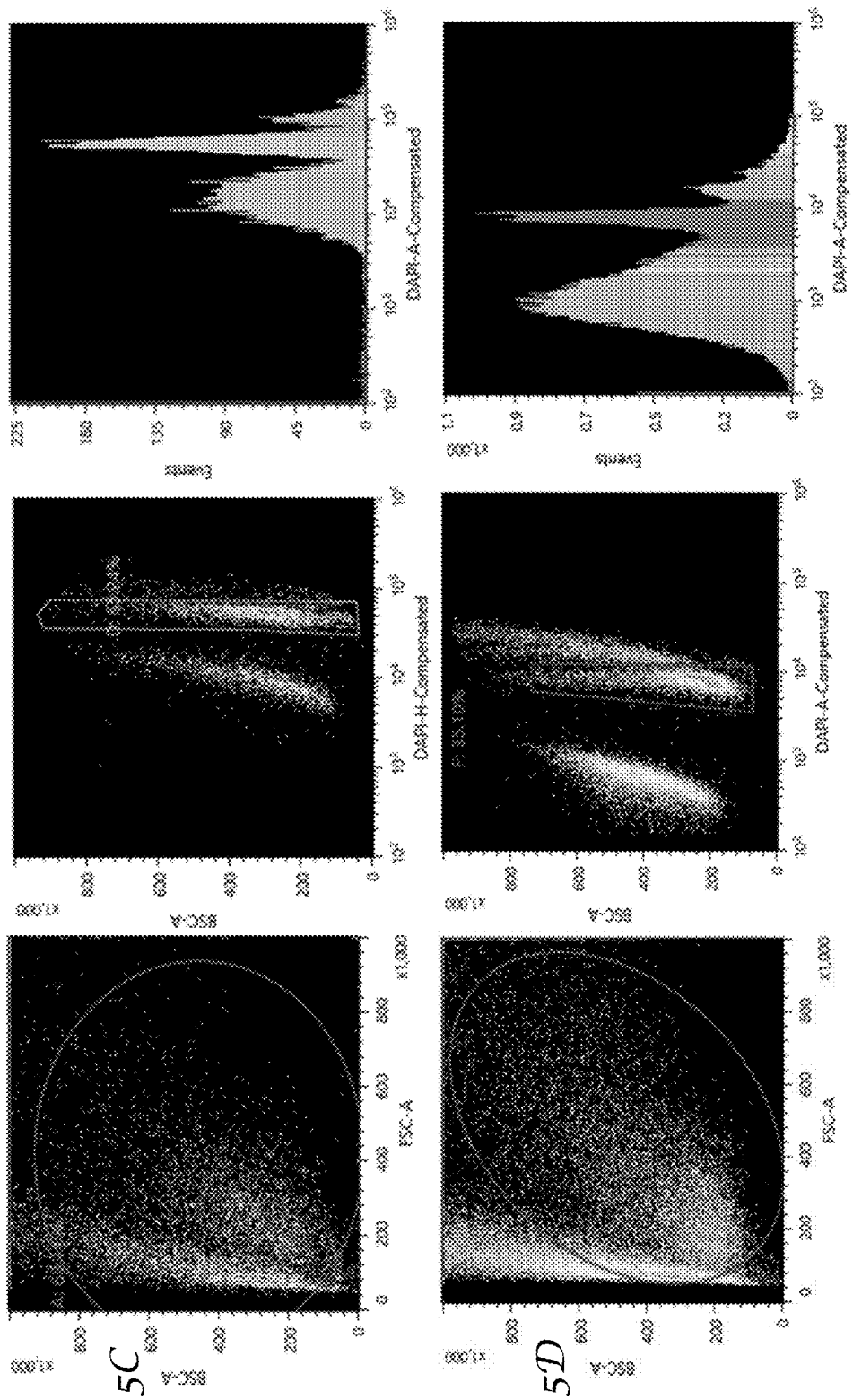
FIG. 5 shows Fluorescence Activated Nuclei Sorting (FANS). Representative plots from FANS sorting of single nuclei. All plots are from sorting the second (PCR) plate unless noted otherwise.

To test the viability of these strategies, we performed bulk (30,000 nuclei) preparations on the HeLa S3 cell line, for which chromatin accessibility and genome structure has been extensively profiled[19,20], and carried out LAND or xSDS treatments along with a standard control. In all three cases, nuclei remained intact—a key requirement for the SCI-seq workflow (FIG. 4b). Prepared nuclei were then carried through standard ATAC-seq library construction[16]. The library prepared from untreated nuclei produced the expected ATAC-seq signal with a 10.8 fold enrichment of sequence reads aligning to annotated HeLa S3 accessibility sites. Both the LAND and xSDS preparations had substantially lower enrichments of 2.8 and 2.2 fold respectively, close to the 1.4 fold observed for shotgun sequencing (FIG. 4c, Table 1). Furthermore, the projected number of unique sequence reads present in the LAND and xSDS preparations were 1.7 billion and 798 million respectively, much greater than for the standard library at 170 million, suggesting a larger proportion of the genome was converted into viable sequencing molecules.

TABLE 1

Bulk library statistics. Information on bulk cell libraries constructed to evaluate nucleosome depletion.

| Bulk Library | Duplication Rate | Reads MQ ≥10 | Reads in HeLa DHS sites | Percent in DHS sites | Fold Enrichment | Estimated Library Size |
|---|---|---|---|---|---|---|
| xSDS | 4.50% | 83,507,827 | 2,307,825 | 2.76% | 2.22 | 798,085,544 |
| LAND | 1.86% | 64,353,617 | 2,240,466 | 3.48% | 2.79 | 1,657,844,868 |

TABLE 1-continued

Bulk library statistics. Information on bulk cell libraries constructed to evaluate nucleosome depletion.

| Bulk Library | Duplication Rate | Reads MQ ≥10 | Reads in HeLa DHS sites | Percent in DHS sites | Fold Enrichment | Estimated Library Size |
|---|---|---|---|---|---|---|
| ATAC | 27.24% | 60,494,125 | 8,179,083 | 13.52% | 10.84 | 170,409,197 |
| SHOT* | NA | 60,000,000 | 1,031,310 | 1.72% | 1.38 | NA |

*SHOT library is a random sampling of 60M reads obtained from the HeLa dbGaP repository under accession: phs000640.v4.p1 (The ENCODE Project Consortium. An integrated encyclopedia of DNA elements in the human genome. *Nature* 489, 57-74 (2012).
Library size estimates were generated using Picard tools function "EstimateLibraryComplexity".
For shotgun sequencing, the read used were duplicate removed, and therefore duplication rate and library size estimates were not determined.

SCI-Seq with Nucleosome Depletion

To assess the performance of nucleosome depletion with our single cell combinatorial indexing workflow, we first focused on the deeply profiled, euploid lymphoblastoid cell line GM12878[14,15,19]. We produced a total of six SCI-seq libraries with a variety of LAND conditions, each using a single 96-well plate at the PCR indexing stage, and a single xSDS library with 3×96-well PCR plates. To serve as a comparison to existing methods, we prepared 42 single cell libraries using quasi-random priming (QRP, 40 passing QC) and 51 using degenerate oligonucleotide primed PCR (DOP, 45 passing QC). Finally, we karyotyped 50 cells to serve as a non-sequencing means of aneuploidy measurement (Table 2).

TABLE 2

SCI-seq library summary. Information on library construction and statistics on the actual depth obtained for each SCI-seq library preparation. (a) Details of library construction and the mixed model used to determine the read count threshold for single cell libraries. (b) Details on libraries for the actual sequence depth obtained in this study.

Table 2a

| Library | Sample | Nucleosome Depletion Method | PCR Wells | Nuc./well | λ (noise, single cell) | μ (noise, single cell) | σ |
|---|---|---|---|---|---|---|---|
| GM12878.LAND1 | Human (GM12878) | LAND (27.6 μM LIS) | 96 | 25 | 0.872007, 0.127993 | 1.080594, 3.841161 | 0.66137 |
| GM12878.LAND2 | Human (GM12878) | LAND (13.8 μM LIS) | 96 | 25 | 0.419749, 0.580251 | 0.291373, 1.982663 | 0.513341 |
| GM12878.NSTLAND | Human (GM12878) | LAND (13.8 μM LIS + 200 mM NaCl) | 96 | 22 | 0.752279, 0.247721 | 1.177030, 3.937951 | 0.736942 |
| GM12878.xLAND | Human (GM12878) | x-link + LAND (13.8 μM LIS) | 96 | 22 | 0.803801, 0.196199 | 0.814446, 3.409897 | 0.578019 |
| GM12878.LAND3 | Human (GM12878) | LAND (13.8 μM LIS) | 96 | 22 | 0.842110, 0.157890 | 1.307204, 4.047124 | 0.680607 |
| GM12878.LAND4 | Human (GM12878) | LAND (4.6 μM LIS) | 96 | 22 | 0.861427, 0.138573 | 1.184529, 3.689950 | 0.619864 |
| GM12878.arrLAND | Human (GM12878) | Arrested, LAND (4.6 μM LIS) | 96 | 22 | 0.970847, 0.0291532 | 1.280424, 4.3764043 | 0.526405 |
| HeLa.LAND1 | Human (HeLa S3) | LAND (4.6 μM LIS) | 96 | 22 | 0.884456, 0.115544 | 1.489698, 4.622590 | 0.740663 |
| HeLa.LAND2 | Human (HeLa S3) | LAND (4.6 μM LIS) | 96 | 22 | 0.849262, 0.150738 | 0.816437, 3.448150 | 0.496199 |
| HeLa.LAND3 | Human (HeLa S3) | LAND (4.6 μM LIS) | 96 | 22 | 0.838170, 0.161830 | 1.476571, 4.135318 | 0.539156 |
| HumMus.LAND1 | Human (HeLa S3), Mouse (3T3) | LAND (27.6 μM LIS) | 96 | 25 | 0.816623, 0.183377 | 0.826636, 2.662703 | 0.559918 |
| HumMus.LAND2 | Human (HeLa S3), Mouse (3T3) | LAND (113.8 μM LIS) | 96 | 25 | 0.784437, 0.215563 | 1.223024, 3.960925 | 0.716764 |
| HumMus.LAND3 | Human (GM12878), Mouse (3T3) | LAND (4.6 μM LIS) | 96 | 22 | 0.863399, 0.136601 | 1.473206, 4.590961 | 0.627049 |
| HumMus.LAND4 | Human (GM12878), Mouse (3T3) | LAND (4.6 μM LIS) | 96 | 22 | 0.973846, 0.0261538 | 1.448882, 5.0360715 | 0.712699 |
| RhesusInd1.LAND | Rhesus Individual 1 (frozen) | LAND (4.6 μM LIS) | 16 | 22 | 0.823777, 0.176223 | 1.774362, 4.301835 | 1.09558 |
| GM12878.xSDS | Human (GM12878) | xSDS | 288 | 22 | 0.871926, 0.128074 | 1.781897, 4.291739 | 0.764169 |
| HumMus.xSDS | Human (HeLa S3), Mouse (3T3) | xSDS | 96 | 22 | 0.868349, 0.131651 | 1.776006, 4.209856 | 0.878084 |
| CRC.xSDS | Stage 2 Colorectal Cancer (frozen) | xSDS | 16 | 22 | 0.911423, 0.0885767 | 1.423343, 4.7335258 | 0.83885 |
| PDAC.xSDS | Stage 3 Pancreatic Ductal Adenocarcinoma (fresh) | xSDS | 288 | 22 | 0.915855, 0.0841453 | 1.713041, 4.4984682 | 0.872799 |
| RhesusInd1.xSDS | Rhesus Individual 1 (frozen) | xSDS | 96 | 22 | 0.953348, 0.0466516 | 1.122175, 4.4798411 | 0.788582 |
| RhesusInd2.xSDS | Rhesus Individual 2 (frozen) | xSDS | 96 | 22 | 0.931090, 0.0689105 | 1.091425, 4.5055530 | 0.763775 |

TABLE 2-continued

SCI-seq library summary. Information on library construction and statistics on the actual depth obtained for each SCI-seq library preparation. (a) Details of library construction and the mixed model used to determine the read count threshold for single cell libraries. (b) Details on libraries for the actual sequence depth obtained in this study.

Table 2b

| | Sequenced Reads | | | | | |
|---|---|---|---|---|---|---|
| Library | Single Cell Read Cutoff | Single Cell Libraries | Median Unique MQ ≥10 Reads | Mean Unique MQ ≥10 Reads | Median Complexity | Cells ≥5e4 Reads |
| GM12878.LAND1 | 1,512 | 621 | 11,721 | 37,055 | 45.96 | 129 |
| GM12878.LAND2 | 1,000 | 113 | 2,091 | 3,434 | 90.79 | 0 |
| GM12878.NSTLAND | 1,588 | 1,060 | 13,734 | 52,244 | 71.33 | 313 |
| GM12878.xLAND | 1,000 | 1,212 | 6,384 | 14,148 | 58.80 | 72 |
| GM12878.LAND3 | 2,325 | 1,015 | 16,673 | 84,010 | 34.42 | 232 |
| GM12878.LAND4 | 1,529 | 616 | 7,151 | 32,614 | 87.55 | 68 |
| GM12878.arrLAND | 7,079 | 119 | 33,923 | 94,036 | 36.51 | 54 |
| HeLa.LAND1 | 7,619 | 573 | 67,077 | 100,016 | 91.01 | 338 |
| HeLa.LAND2 | 1,000 | 648 | 4,756 | 18,026 | 37.45 | 29 |
| HeLa.LAND3 | 3,946 | 1,140 | 18,695 | 25,501 | 97.73 | 120 |
| HumMus.LAND1 | 1,000 | 263 | 2,699 | 6,174 | 2.90 | 4 |
| HumMus.LAND2 | 1,754 | 1,346 | 13,876 | 51,952 | 71.31 | 388 |
| HumMus.LAND3 | 9,202 | 645 | 61,408 | 74,329 | 96.69 | 378 |
| HumMus.LAND4 | 21,055 | 115 | 119,428 | 359,175 | 95.84 | 99 |
| RhesusInd1.LAND | 5,947 | 340 | 141,449 | 165,453 | 88.21 | 248 |
| GM12878.xSDS | 6,051 | 3,123 | 29,550 | 64,986 | 53.08 | 1,056 |
| HumMus.xSDS | 5,970 | 1,331 | 44,699 | 64,659 | 87.89 | 605 |
| CRC.xSDS | 7,846 | 151 | 72,753 | 110,823 | 89.70 | 111 |
| PDAC.xSDS | 5,164 | 1,715 | 49,272 | 86,592 | 68.60 | 846 |
| RhesusInd1.xSDS | 4,912 | 171 | 55,142 | 120,769 | 24.36 | 92 |
| RhesusInd2.xSDS | 5,517 | 381 | 62,731 | 122,602 | 23.76 | 213 |
| | | 16,698 | | | | 5,395 |

Figure 7:
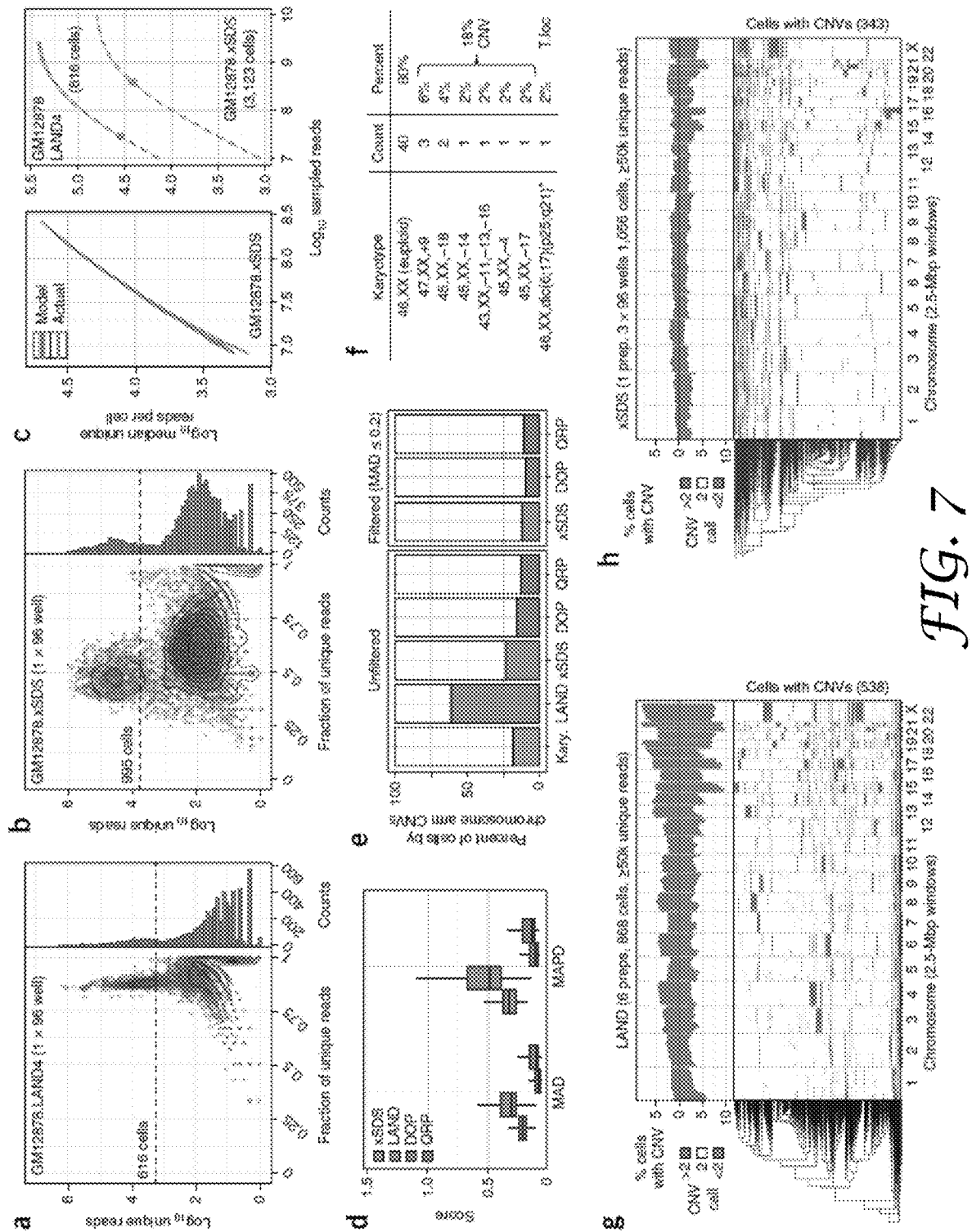
FIG. 7 shows comparison of LAND and xSDS nucleosome depletion methods with SCI-seq.
Figures 1, 8:
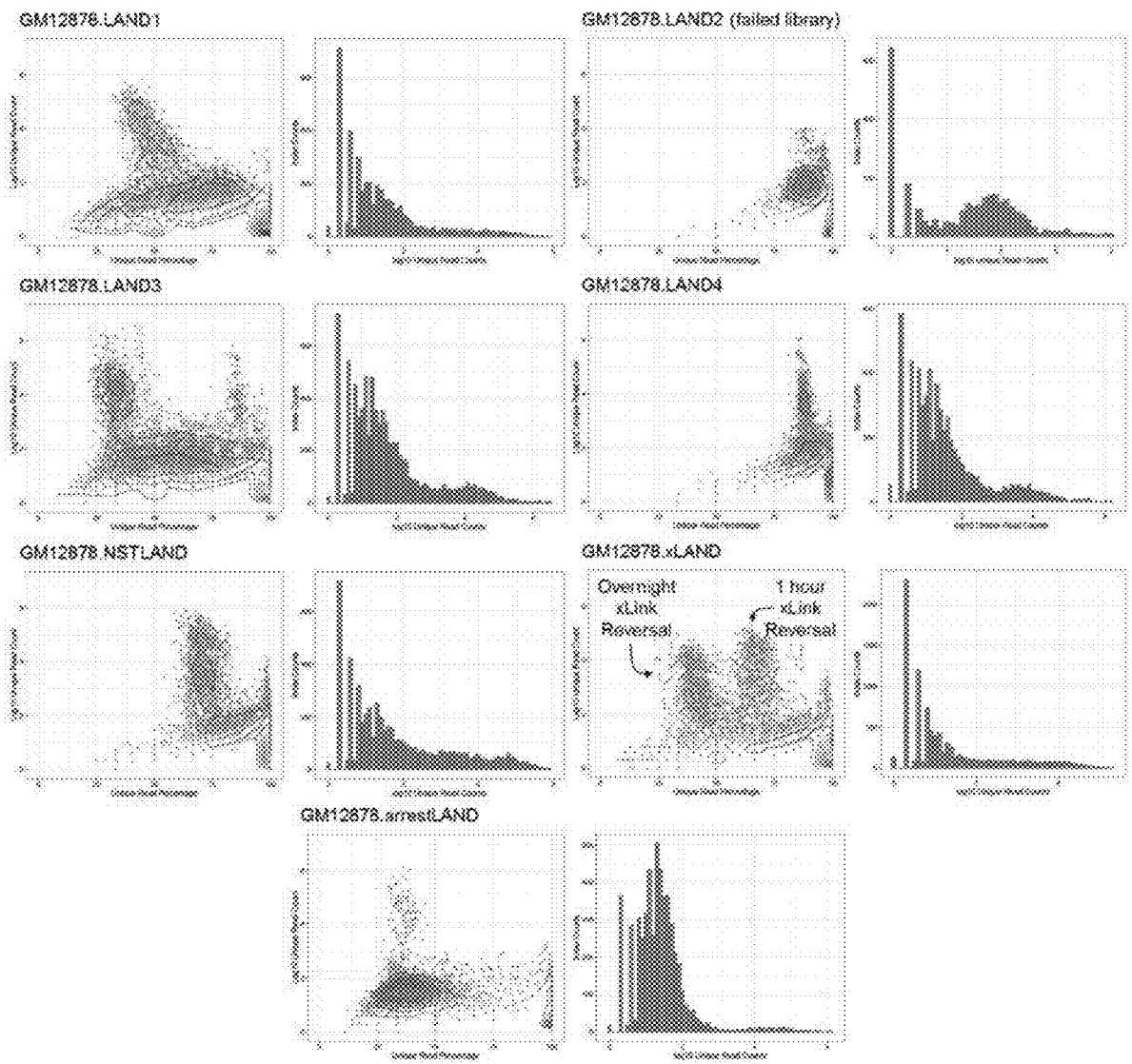
Figures 2, 8:
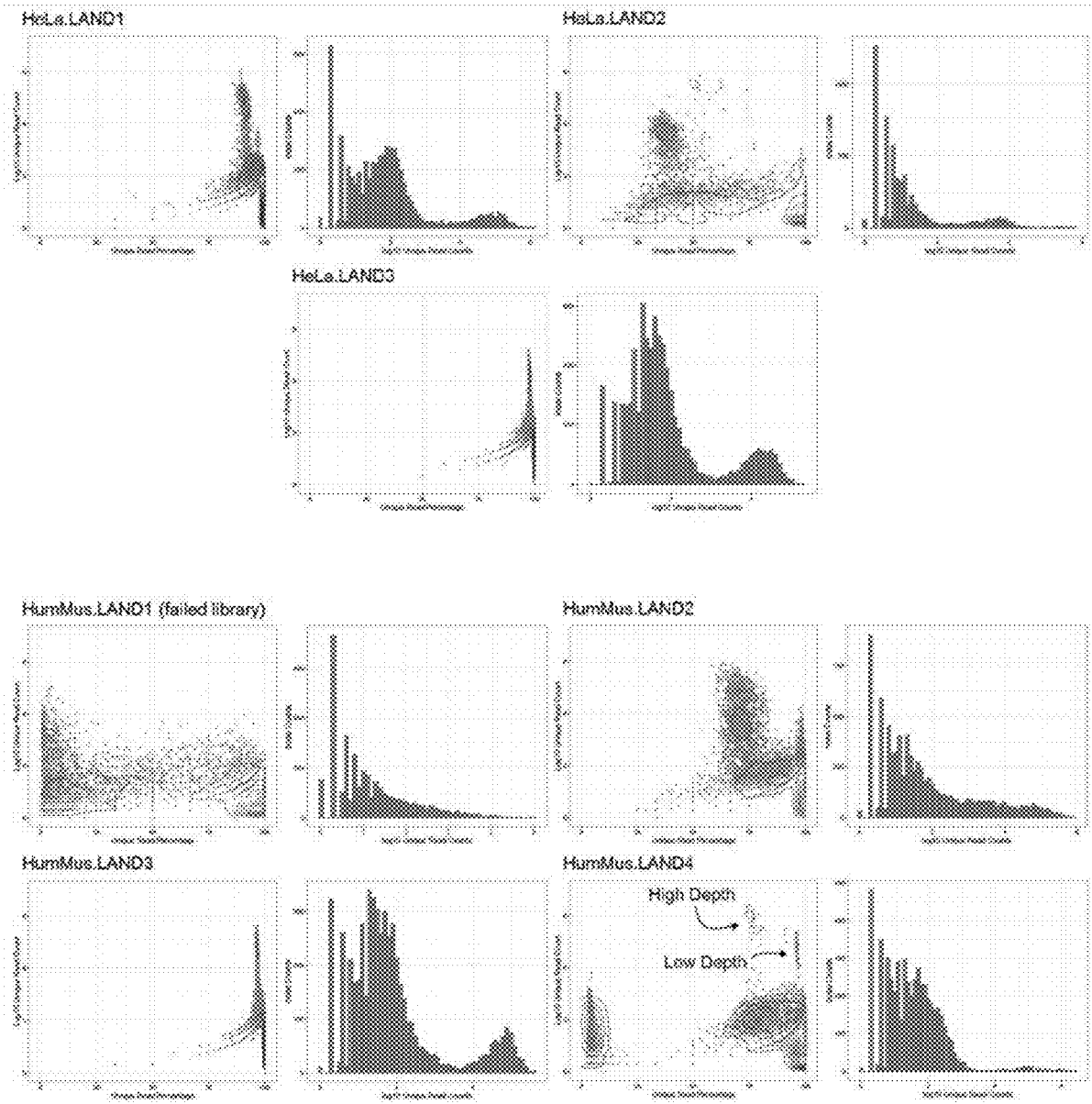
Figures 3, 8:
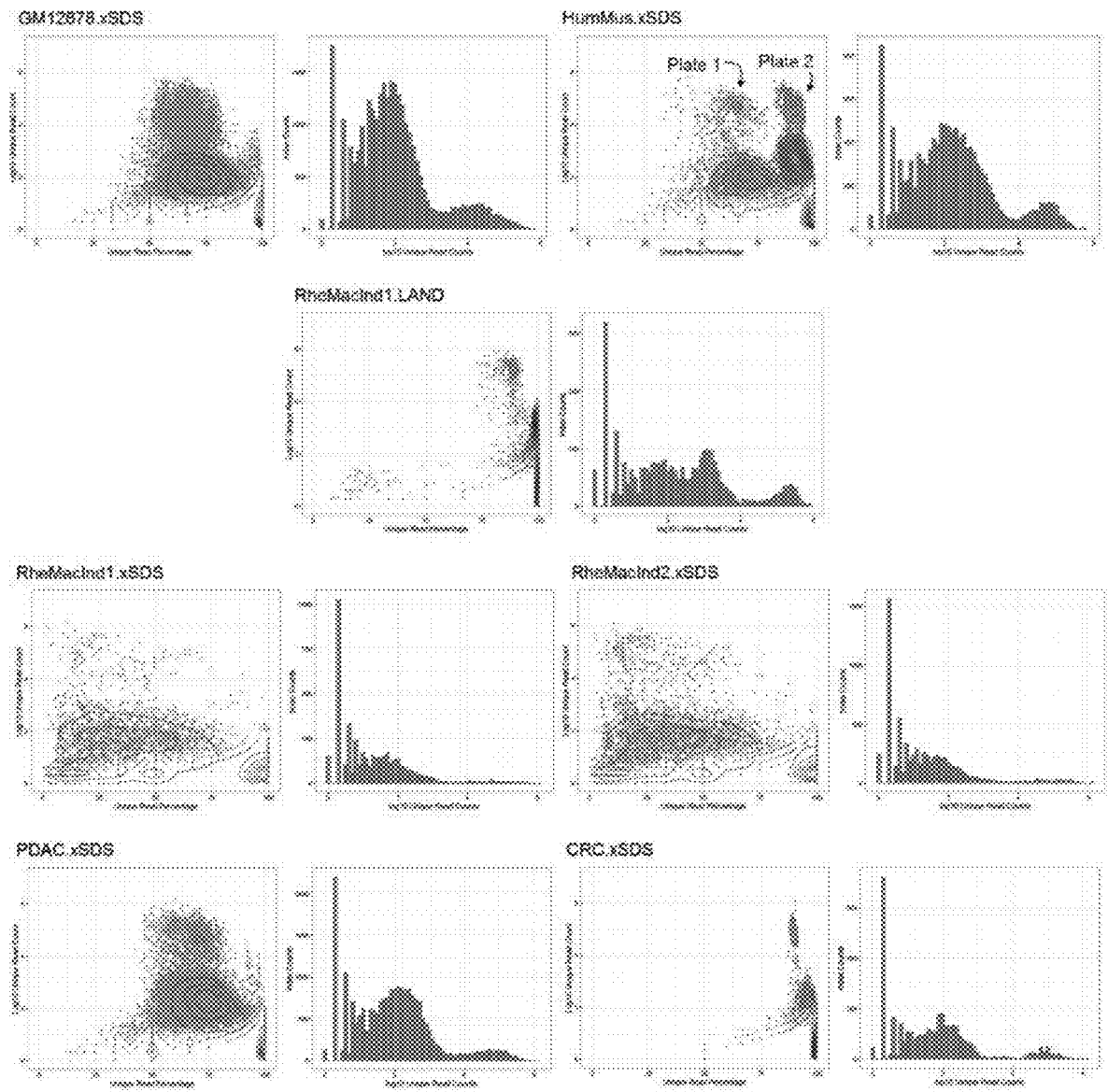

For each SCI-seq preparation, the number of potential index combinations is 96 (transposase indexing)×N (PCR indexing, 96 per plate); however, not all index combinations represent a single cell library, as each PCR well contains only 15-25 transposase-indexed nuclei. To identify non-empty index combinations, we generated a $\log_{10}$ transformed histogram of unique (i.e. non-PCR duplicate), high-quality (MQ≥10) aligned reads for each potential index combination. This resulted in a bimodal distribution comprised of a low-read-count, noise component centered between 50 and 200 reads, and a high-read-count, single cell component centered between 10,000 and 100,000 reads (FIG. 7a,b, FIG. 8). We then used a mixed model to identify indexes that fall in this high-read-count component (FIG. 6), which resulted in 4,643 single cell libraries across the six SCI-seq preparations that used LAND for nucleosome depletion and 3,123 for the xSDS preparation.

Figure 9:
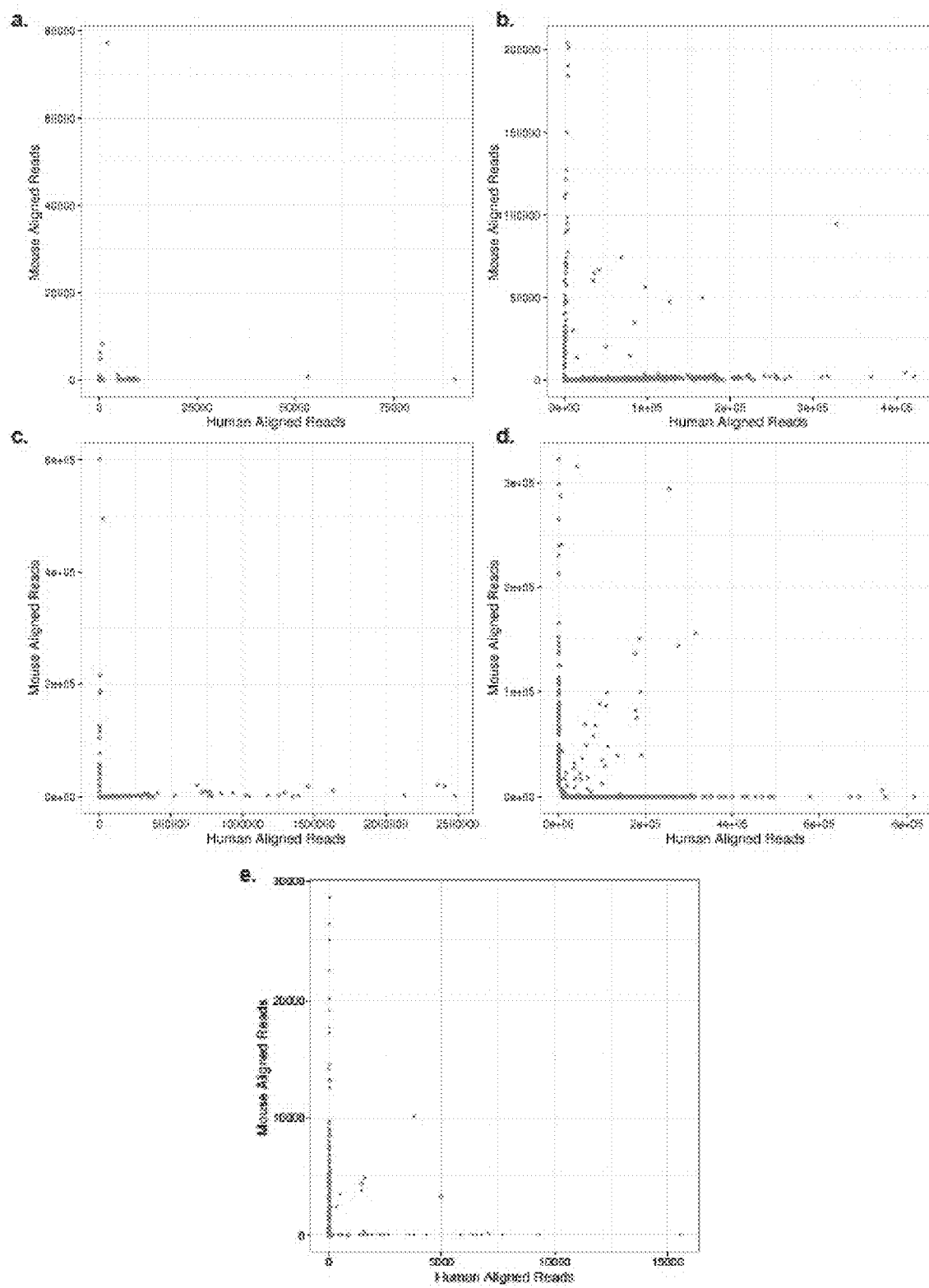
FIG. 9 shows SCI-seq on a mix of human and mouse cells. For all panels the number of reads for each index component are plotted based on the count aligning to the human reference genome, or the mouse reference genome.

To confirm that the majority of putative single cell libraries contain true single cells, we carried out four SCI-seq library preparations on a mix of human and mouse cells using LAND (2,369 total cells) with either 22 or 25 nuclei per PCR well, and one preparation using xSDS split between two FANS conditions (1,367 total cells; FIG. 9). For each experiment we analyzed the proportion of putative single cells with ≥90% of their reads that aligned exclusively to the human or mouse genome. The remaining cells represent human-mouse collisions (i.e. doublets) and make up approximately half of the total collision rate (the remaining half being human-human or mouse-mouse). The total collision rates varied between 0-23.6%, and were used to decide upon 22 nuclei per well with restrictive sorting conditions for a target doublet frequency of <10%, comparable to sciATAC-seq[17] or high throughput single cell RNA-seq technologies[21].

Figure 10:
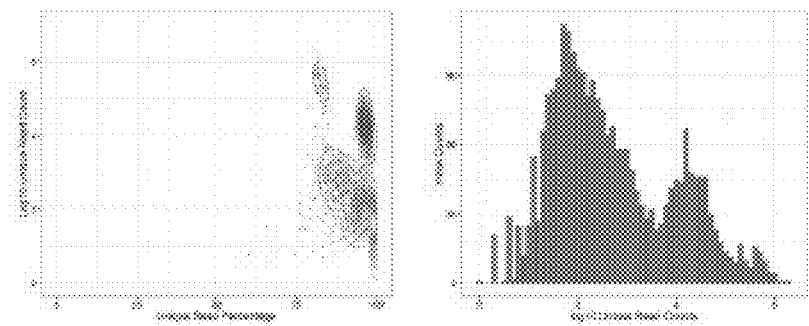
FIG. 10 shows SCI-seq library complexity and index read count distributions after deeper sequencing. For each preparation two plots are shown as in S2 the left plot shows fraction of unique reads versus unique read count for each index combination. While the right plot shows a histogram of read counts for each index combination. Cells from wells sequenced more deeply are shown along with the rest of the plate that those wells belong to. The population of cells with lower complexity (more to the left) is the population that has been sequenced more deeply.
Figure 10:
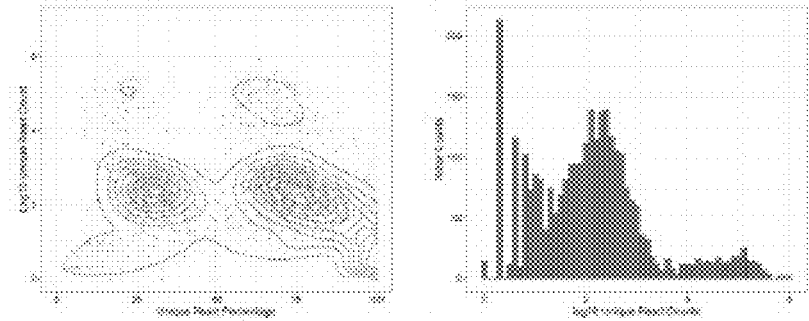
Figure 10:
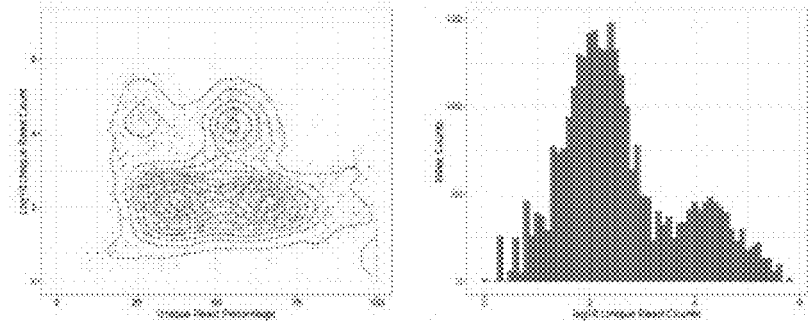
Figure 10:
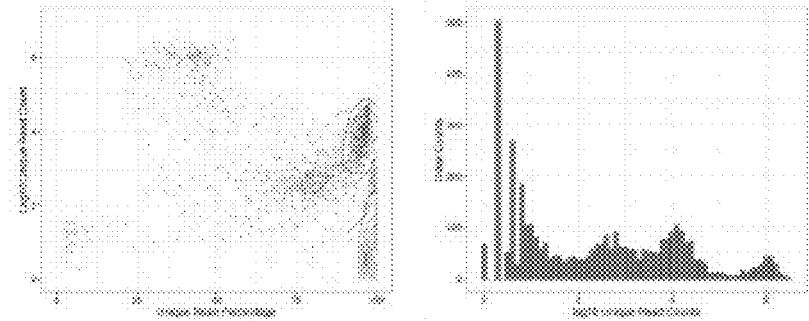

The unique read count produced for each library in a SCI-seq preparation is a function of library complexity and sequencing depth. Due to the inhibitive cost of deeply sequencing every preparation during development, we implemented a model to project the anticipated read count and PCR duplicate percentage that would be achieved with increased sequencing depth (FIG. 7c, Methods). As a means of quality assessment, we identified the depth at which a median of 50% of reads across cells are PCR duplicates (M50), representing the point at which additional sequencing becomes excessive (i.e. greater than 50% of additional reads provide no new information), along with several other metrics (Table 3). Model projections from a subset of the sequenced reads accurately predicted the actual median unique read count within a median of 0.02% (maximum 2.25%, mean 0.41%) across all libraries. As further confirmation, additional sequencing of a subset of PCR wells from several preparations produced unique reads counts for each cell that were within a median of 0.13% (maximum 3.56%, mean 0.72%) of what was predicted by our model (FIG. 10).

TABLE 3

SCI-seq library projection statistics. Information on projected statistics of each SCI-seq library if increased sequencing depth were obtained. Projections use the model described in the methods section. Libraries that either failed (GM12878.LAND2 and HeLa.LAND2), or were sequenced to saturation for which the projections do not apply (Rhesus.Ind1.xSDS and Rhesus.Ind2.xSDS) are not included. (a) Projections out to a given median complexity including the raw read count to reach that point. (b) The number of single cells meeting various read count thresholds are listed if libraries were sequenced to saturation (median complexity of 5%).

Table 3a
Library Projections

| Library | Projected to Median of 50% Complexity | | | Projected to Median of 25% Complexity | | | Projected to Median of 10% Complexity | | |
|---|---|---|---|---|---|---|---|---|---|
| | Median | Mean | Raw Reads | Median | Mean | Raw Reads | Median | Mean | Raw Reads |
| GM12878.LAND1 | 378,305 | 1,176,230 | 1,640,000,000 | 554,638 | 1,734,782 | 4,850,000,000 | 653,064 | 2,115,189 | 14,120,000,000 |
| GM12878.NSTLAND | 44,608 | 155,477 | 350,000,000 | 68,418 | 228,101 | 1,030,000,000 | 83,359 | 269,951 | 2,980,000,000 |
| GM12878.LAND3 | 218,132 | 1,318,212 | 2,430,000,000 | 323,878 | 2,133,376 | 7,220,000,000 | 399,607 | 2,718,203 | 21,050,000,000 |
| GM12878.LAND4 | 135,114 | 746,530 | 810,000,000 | 200,422 | 1,239,687 | 2,390,000,000 | 246,204 | 2,082,902 | 6,940,000,000 |
| GM12878.arrLAND | 1,490,817 | 3,684,539 | 910,000,000 | 2,141,086 | 5,687,397 | 2,710,000,000 | 2,792,344 | 7,024,499 | 7,900,000,000 |
| HeLa.LAND1 | 3,997,311 | 5,642,469 | 7,180,000,000 | 6,140,962 | 8,861,587 | 21,380,000,000 | 7,399,793 | 11,190,892 | 62,310,000,000 |
| HeLa.LAND3 | 736,813 | 901,740 | 2,350,000,000 | 1,107,204 | 1,415,747 | 6,970,000,000 | 1,337,941 | 1,806,880 | 20,320,000,000 |
| HumMus.LAND1 | 35,991 | 79,857 | 50,000,000 | 56,355 | 126,673 | 150,000,000 | 70,808 | 161,428 | 420,000,000 |
| HumMus.LAND2 | 44,393 | 154,148 | 440,000,000 | 67,957 | 226,139 | 1,290,000,000 | 82,696 | 277,161 | 3,760,000,000 |
| HumMus.LAND3 | 2,257,543 | 2,638,358 | 3,890,000,000 | 3,453,346 | 3,957,131 | 11,600,000,000 | 4,186,331 | 4,806,388 | 33,740,000,000 |
| HumMus.LAND4 | 4,305,319 | 11,479,621 | 3,260,000,000 | 6,126,707 | 16,880,151 | 9,710,000,000 | 7,474,417 | 20,732,681 | 28,290,000,000 |
| RhesusInd1.LAND | 454,681 | 514,445 | 530,000,000 | 685,354 | 756,326 | 1,570,000,000 | 823,686 | 902,566 | 4,570,000,000 |
| GM12878.xSDS | 26,791 | 63,223 | 580,000,000 | 39,666 | 94,153 | 1,710,000,000 | 48,089 | 113,352 | 4,980,000,000 |
| CRC.xSDS | 352,168 | 530,978 | 190,000,000 | 532,772 | 790,798 | 560,000,000 | 641,639 | 946,770 | 1,620,000,000 |
| PDAC.xSDS | 71,378 | 129,304 | 590,000,000 | 107,615 | 191,011 | 1,750,000,000 | 130,444 | 228,852 | 5,110,000,000 |

Table 3b

| | Number of Cells That Can Reach N Reads from Projections | | | | | | |
|---|---|---|---|---|---|---|---|
| Library | 5.00E+04 | 1.00E+05 | 1.50E+05 | 2.50E+05 | 5.00E+05 | 7.50E+05 | 1.00E+06 |
| GM12878.LAND1 | 619 | 604 | 579 | 504 | 373 | 308 | 268 |
| GM12878.NSTLAND | 662 | 504 | 439 | 340 | 183 | 112 | 78 |
| GM12878.LAND3 | 990 | 886 | 810 | 674 | 470 | 370 | 310 |
| GM12878.LAND4 | 574 | 474 | 403 | 319 | 211 | 167 | 137 |
| GM12878.arrLAND | 119 | 119 | 118 | 117 | 115 | 107 | 102 |
| HeLa.LAND1 | 573 | 573 | 573 | 572 | 557 | 547 | 541 |
| HeLa.LAND3 | 1,140 | 1,138 | 1,129 | 1,115 | 1,057 | 941 | 812 |
| HumMus.LAND1 | 167 | 113 | 76 | 40 | 19 | 11 | 6 |
| HumMus.LAND2 | 851 | 636 | 550 | 421 | 228 | 137 | 100 |
| HumMus.LAND3 | 645 | 645 | 645 | 641 | 634 | 610 | 593 |
| HumMus.LAND4 | 115 | 115 | 115 | 115 | 115 | 115 | 115 |
| RhesusInd1.LAND | 328 | 299 | 277 | 260 | 219 | 186 | 148 |
| GM12878.xSDS | 1,804 | 1,094 | 769 | 468 | 183 | 69 | 22 |
| CRC.xSDS | 151 | 147 | 144 | 137 | 107 | 70 | 43 |
| PDAC.xSDS | 1,356 | 1,080 | 874 | 601 | 242 | 98 | 54 |

Coverage uniformity was assessed using mean absolute deviation (MAD)[22] and mean absolute pairwise deviation (MAPD)[2], which indicated substantially better uniformity using xSDS over LAND (MAD: mean 1.57-fold improvement, $p=<1\times10^{-15}$; MAPD: 1.70-fold improvement, $p=<1\times10^{-15}$, Welch's t-test). The deviation using xSDS is similar to multiple displacement amplification methods, though still greater than for QRP and DOP (FIG. 7d)[22]. While LAND preparations had higher coverage bias, they also produced higher unique read counts per cell (e.g. M50 of 763,813 for one of three HeLa LAND preparations) when compared to xSDS (e.g. M50 of 63,223 for the GM12878 preparation).

Figure 11:
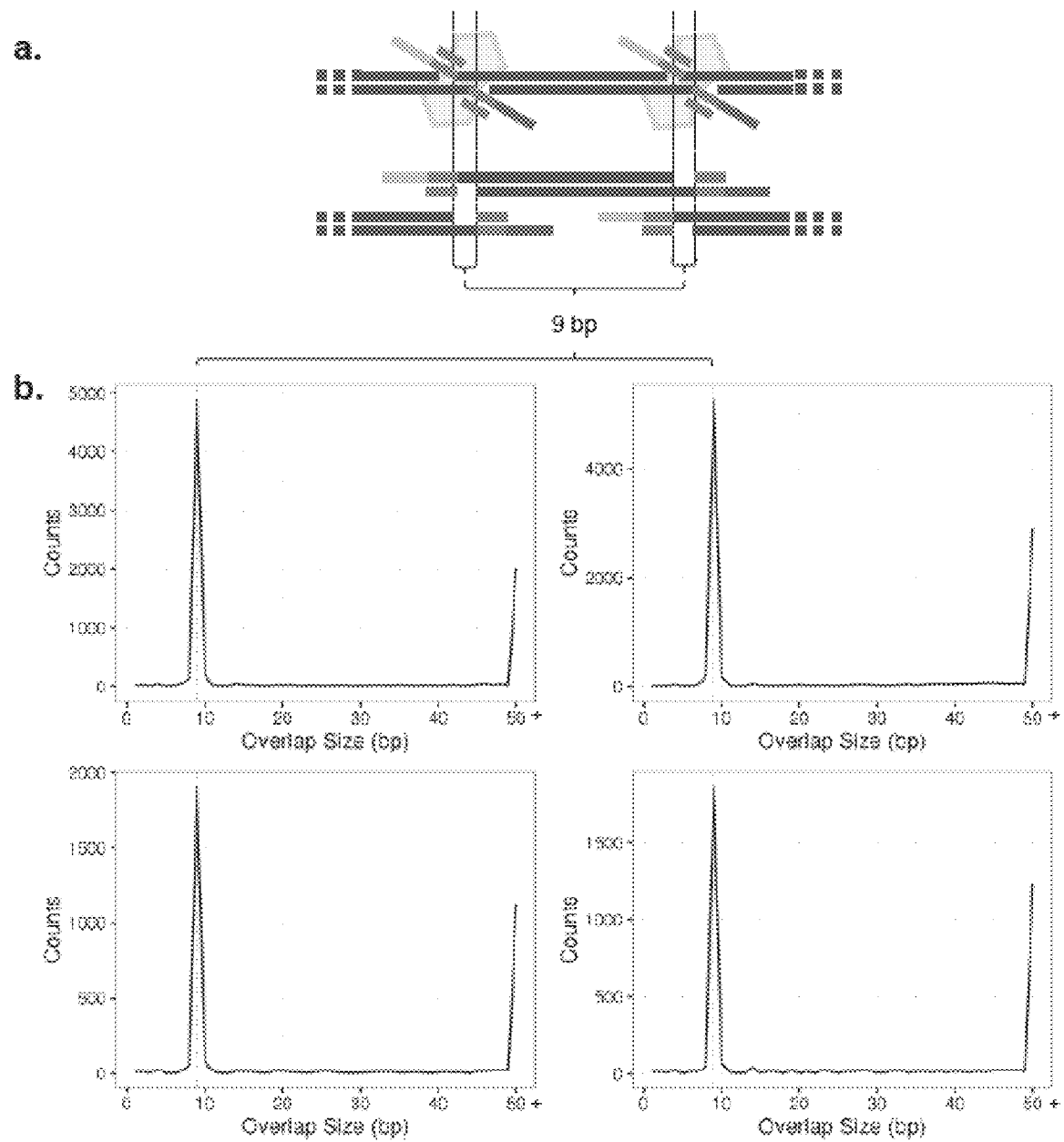
FIG. 11 shows 9 bp read overlaps observed from sequencing adjacent transposition events in the same single cell.

For all libraries, we observed the characteristic 9 basepair overlap of adjacent read pairs due to the mechanism of transposition[13,23], indicating we are able to sequence molecules on either side of a transposase insertion event (FIG. 11).

Copy Number Variant Calling Using SCI-Seq

Figure 12:
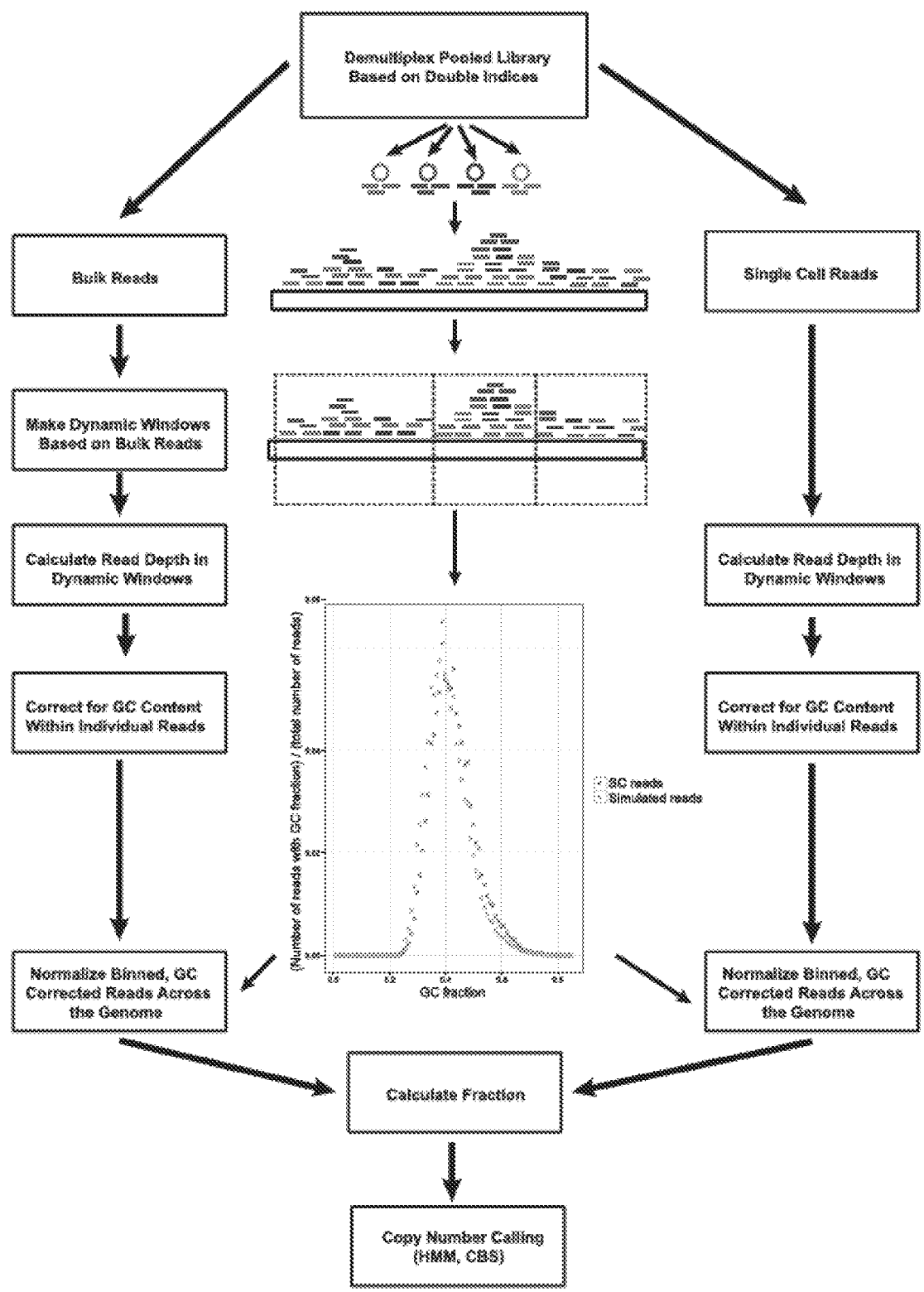
FIG. 12 shows copy number calling computational workflow for HMM and CBS. After calling, call sets for CBS and HMM were intersected together with Ginkgo and only calls present in all three sets were retained as the final call set.
Figure 13:
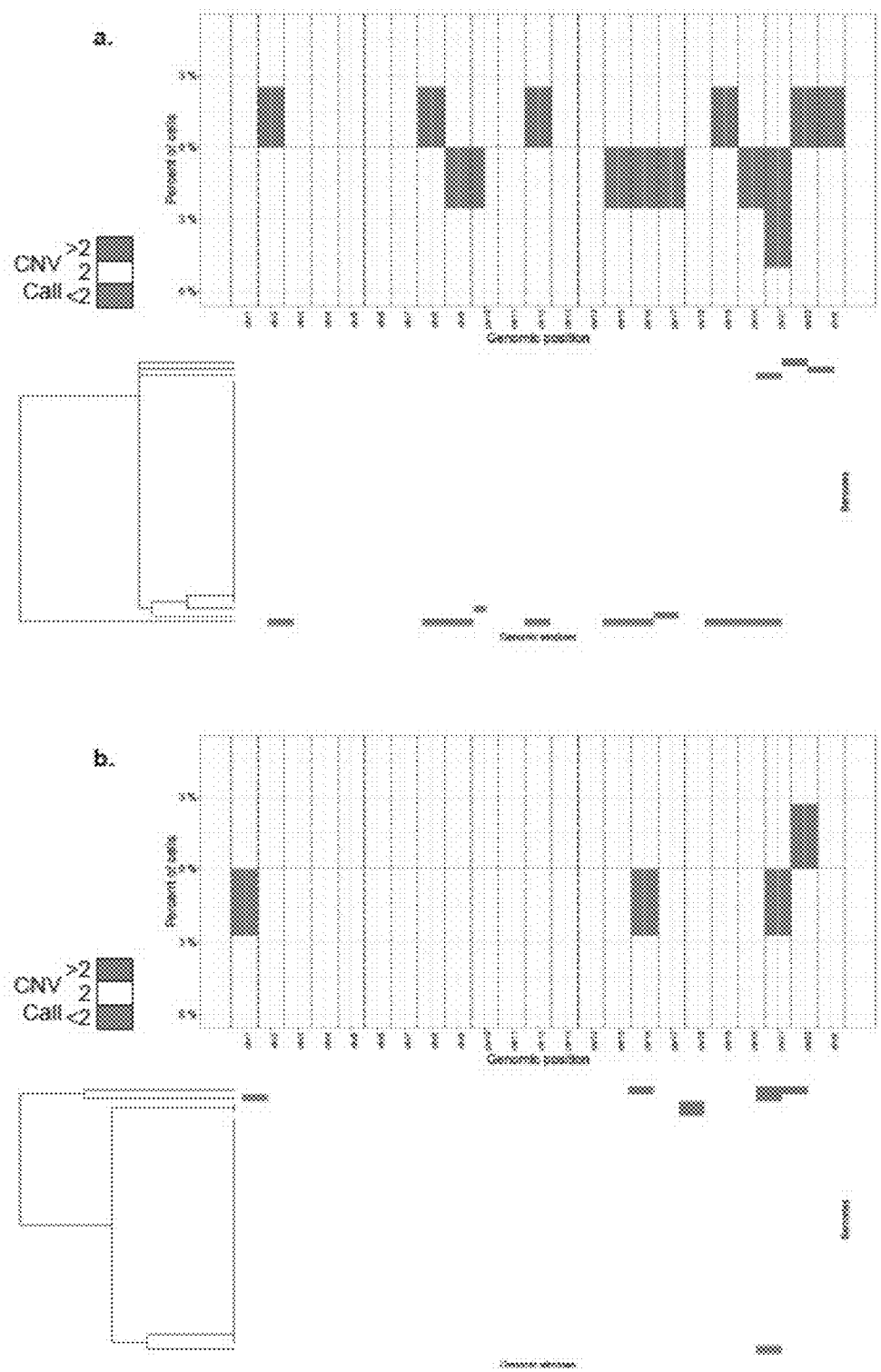
FIG. 13 shows CNV assessment using standard methods of single cell sequencing on GM12878. Top: Summary of chromosome arm amplifications and deletions, Bottom: hierarchical clustering of cells.

For any single cell genome sequencing study, determining how to filter out failed libraries without removing true aneuploid cells is a significant challenge. We initially proceeded with CNV calling on our SCI-seq preparations without any filtering in order to directly compare with other methods. For all preparations, we used cells with a minimum of 50,000 unique, high quality aligned reads (868 across all LAND libraries, 1,056 for the xSDS library), applied Ginkgo[22], Circular Binary Segmentation (CBS)[24], and a Hidden Markov Model (HMM)[25], with variable-sized genomic windows (target median of 2.5 million bp) for CNV calling (FIG. 12) and conservatively retained the intersection of all three methods. To compare our sequencing-based calls with karyotyped cells, we focused on chromosome-arm level events (FIG. 7$e,f$). Consistent with the coverage uniformity differences, our LAND SCI-seq preparations produced a high aneuploidy rate (61.9%), suggesting an abundance of false positives due to lack of coverage uniformity (FIG. 7$e,g$). However, the xSDS nucleosome depletion strategy with SCI-seq resulted in an aneuploidy frequency of 22.6%, much closer to the karyotyping results (FIG. 7$e,h$) as well as DOP and QRP (15.0% and 13.5%, respectively) (FIG. 13).

Figures 1, 14:
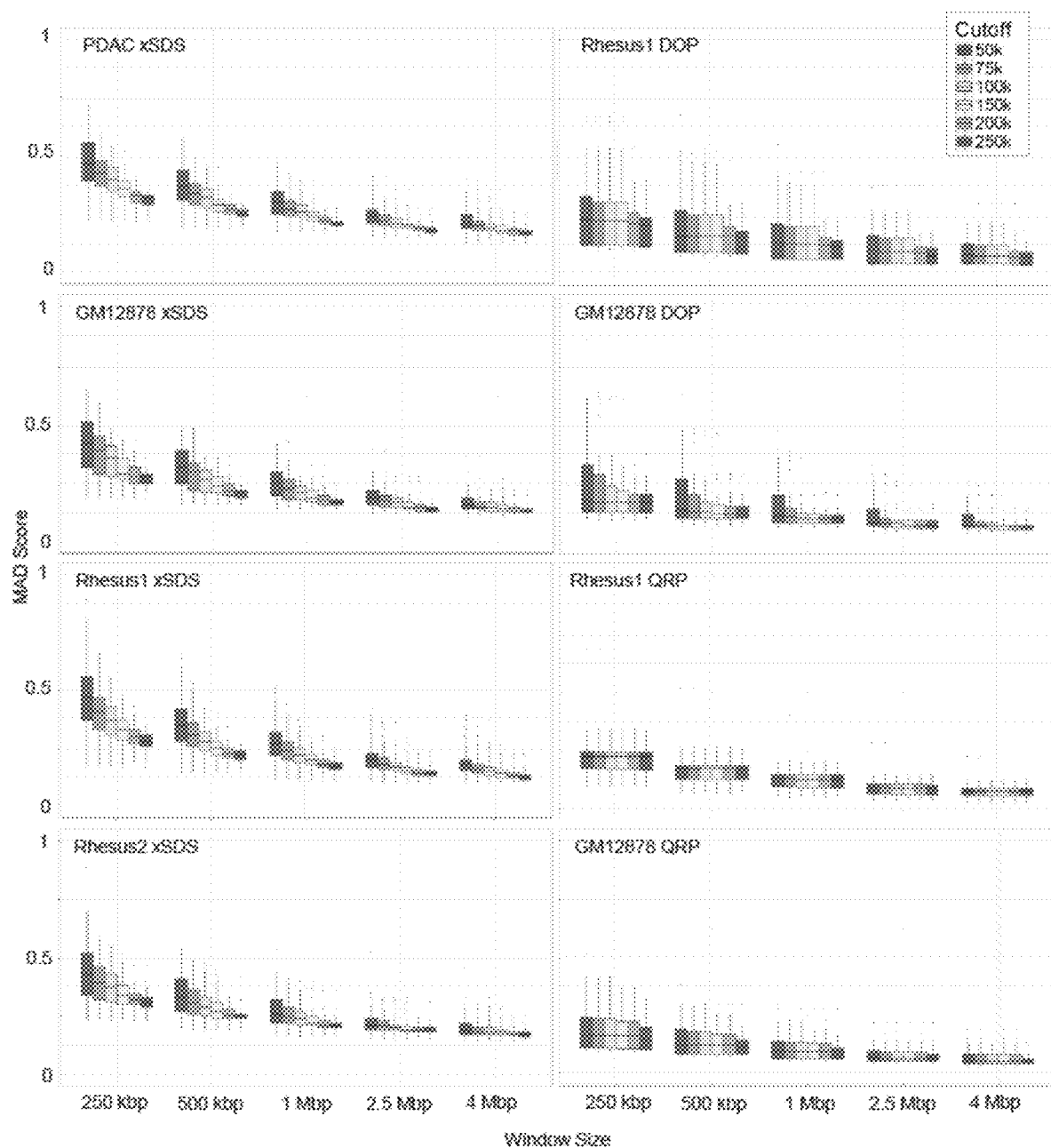
Figures 2, 14:
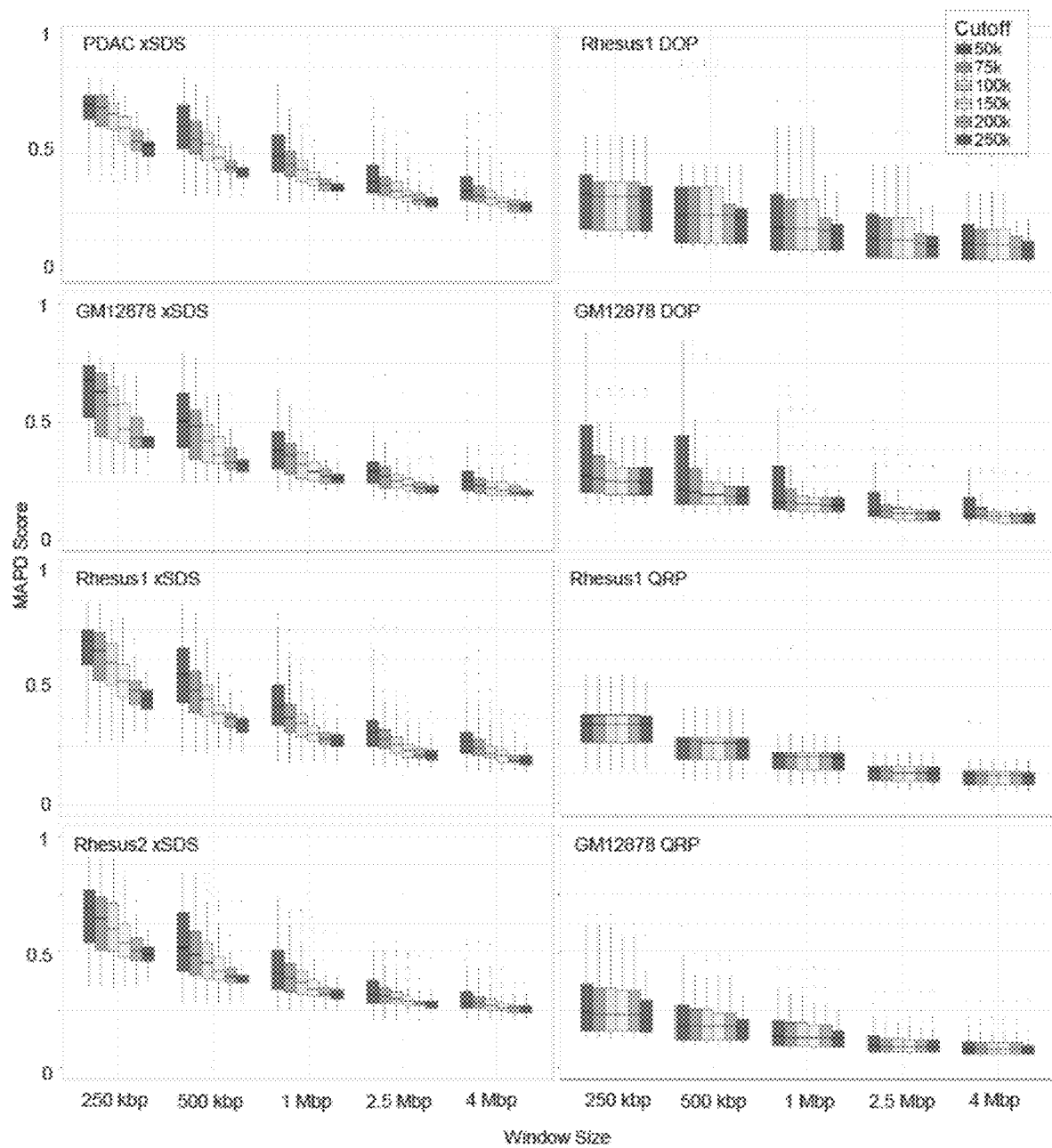
Figures 1, 15:
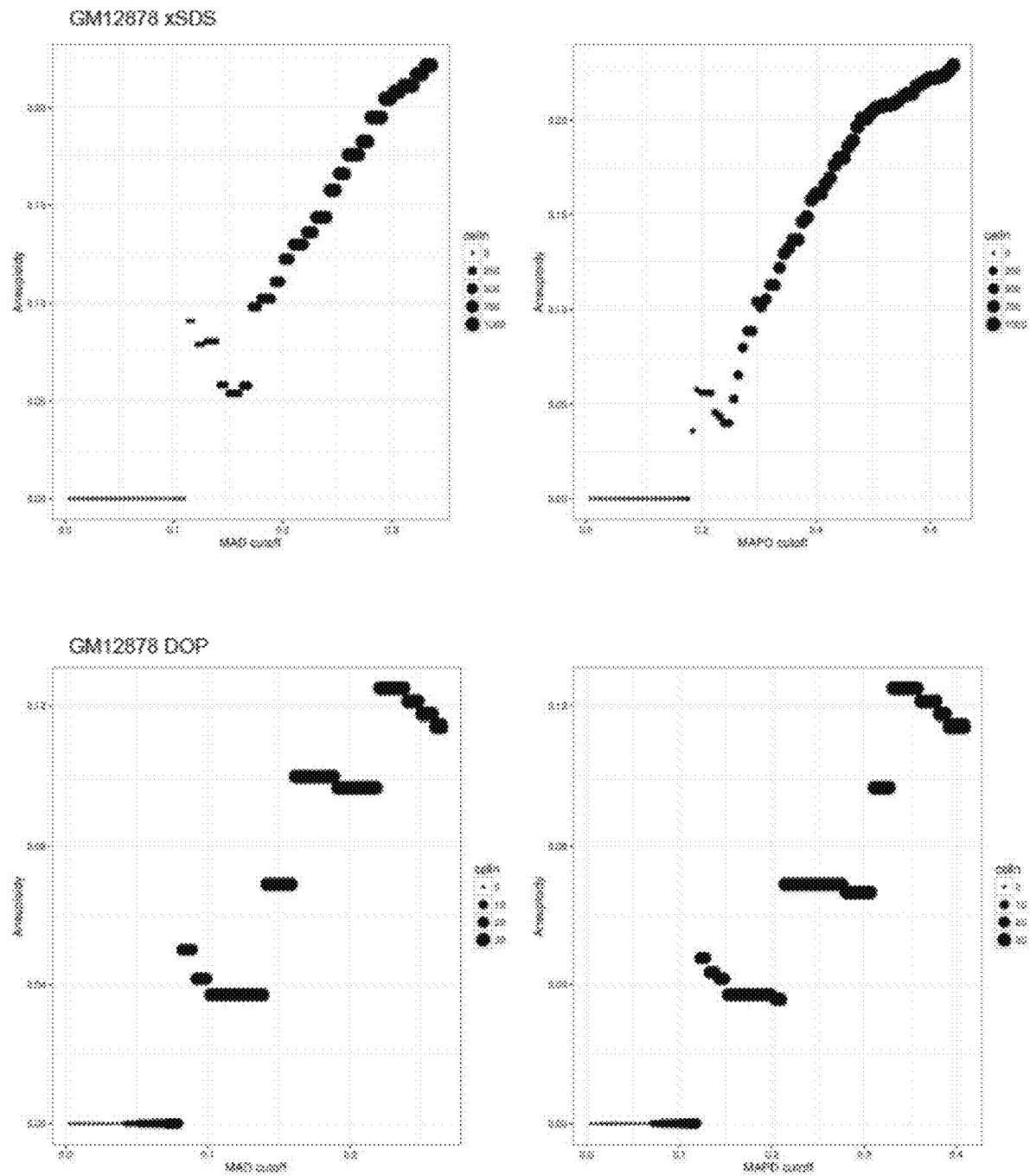
Figures 2, 15:
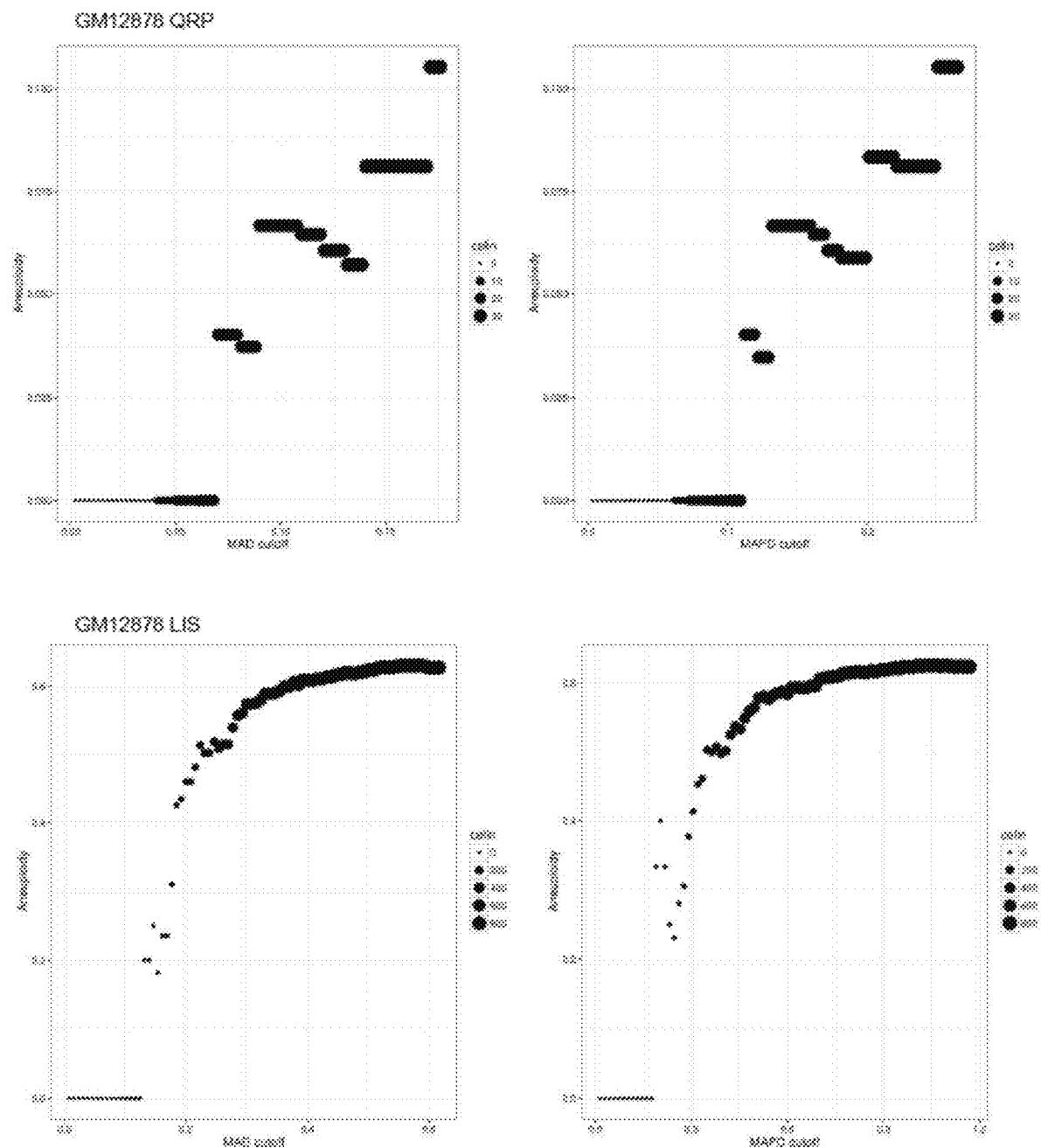
Figure 16:
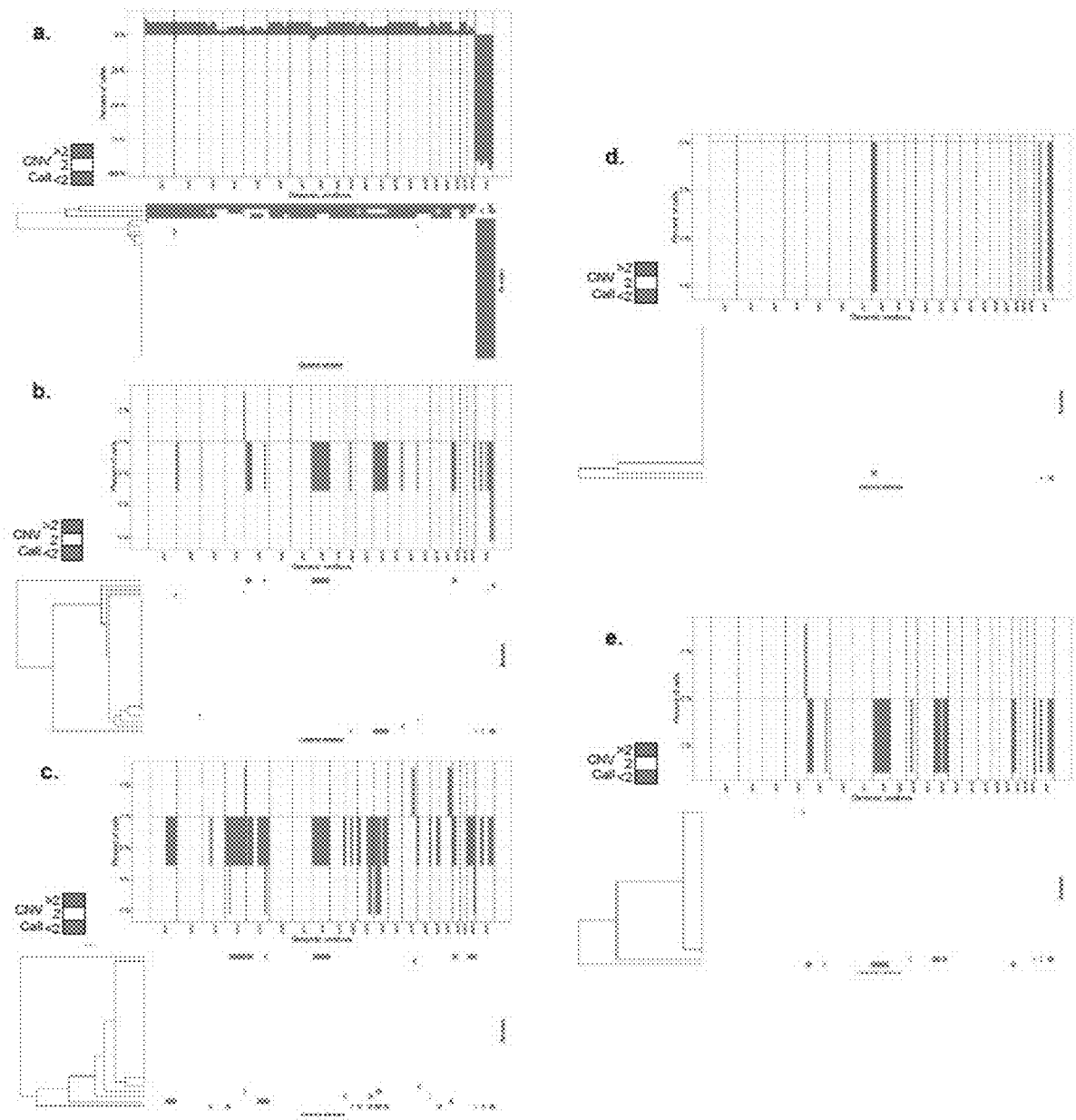
FIG. 16 shows CNV profiles for Rhesus frontal cortex, Individual 1 using quasi-random priming (QRP).
Figure 17:
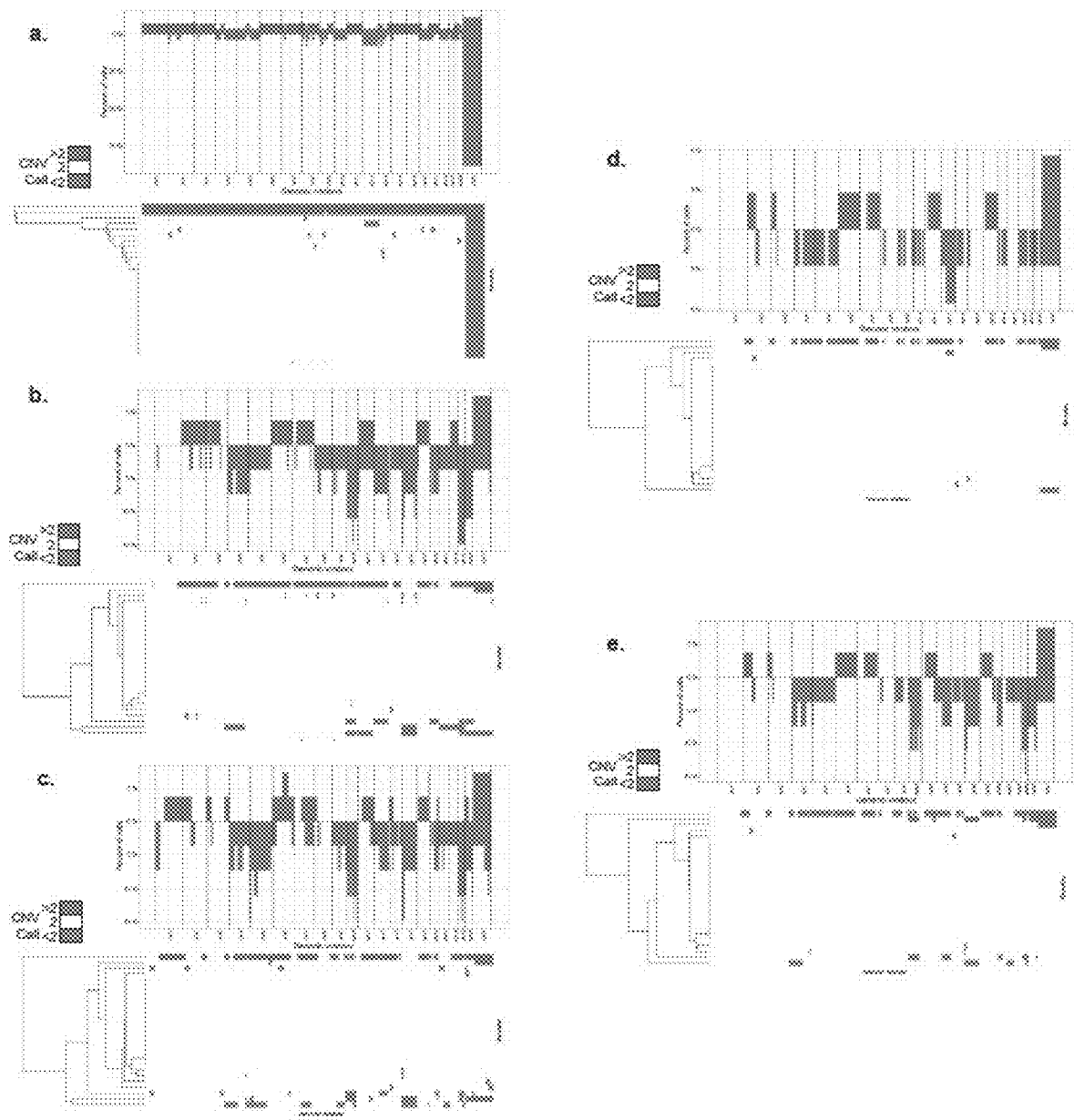
FIG. 17 shows CNV profiles for Rhesus frontal cortex, Individual 1 using degenerate oligonucleotide primed PCR (DOP).
Figure 18:
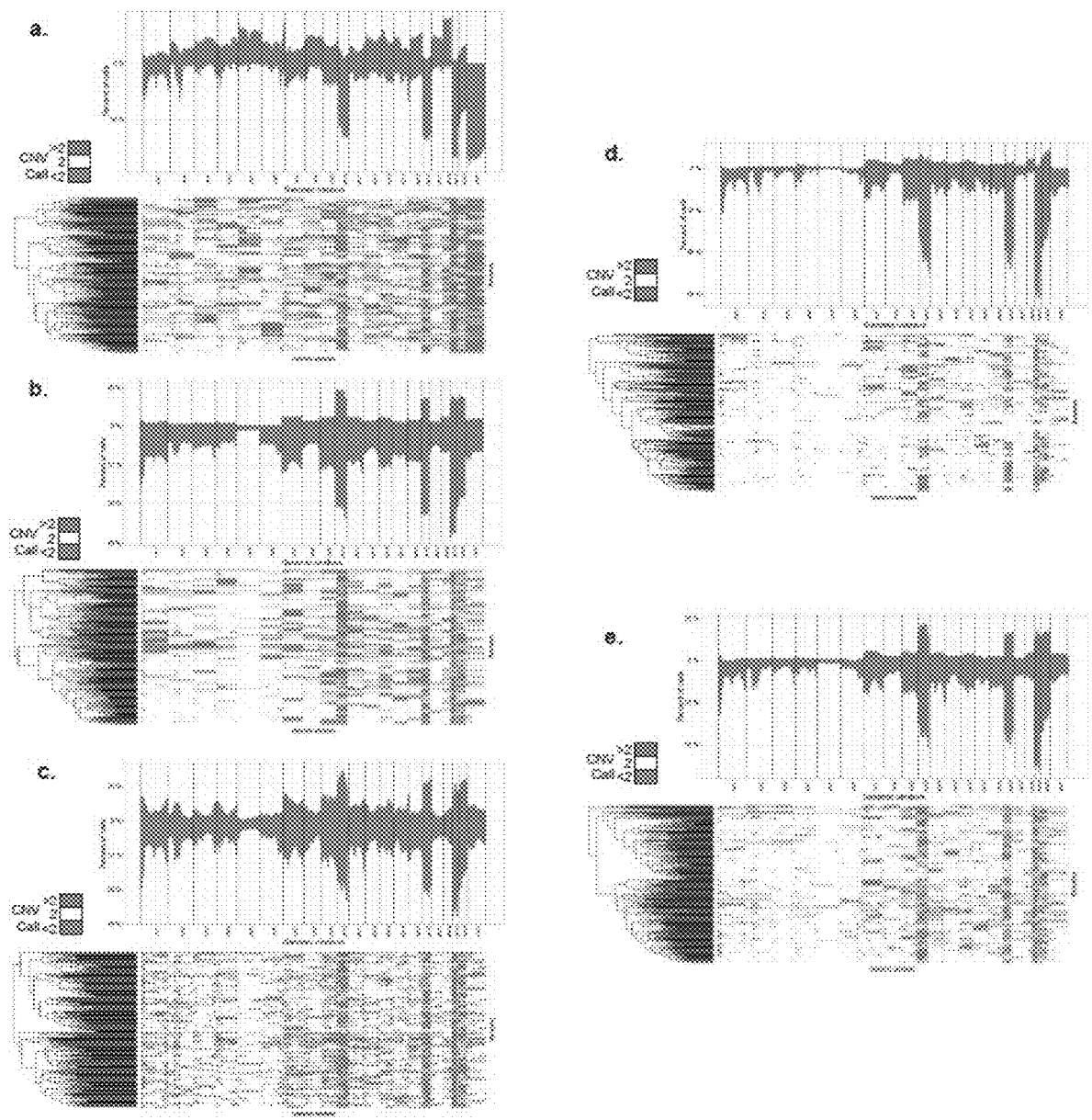
FIG. 18 shows CNV profiles for Rhesus frontal cortex, Individual 1 using SCI-seq with LAND nucleosome depletion.
Figure 19:
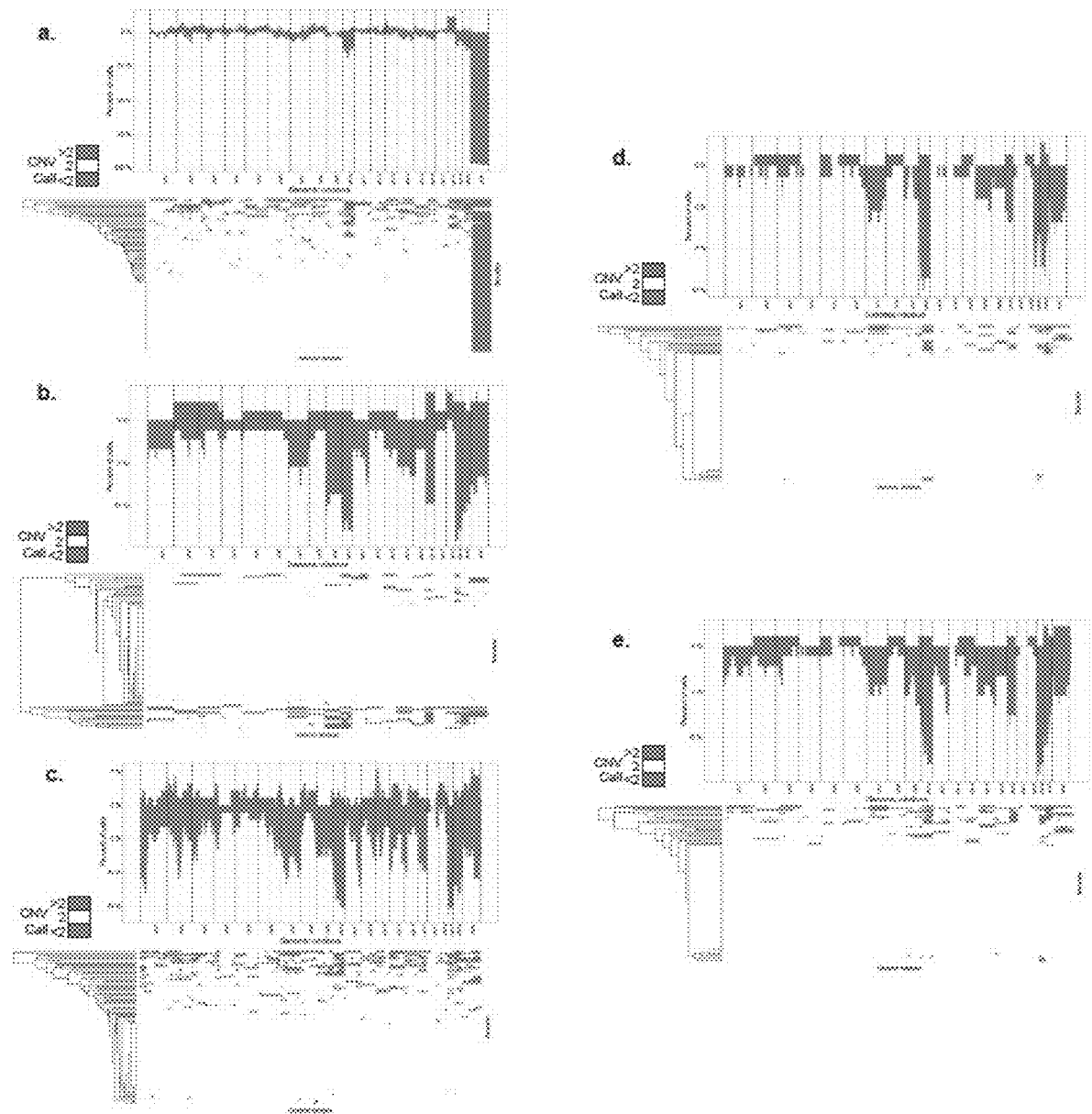
FIG. 19 shows CNV profiles for Rhesus frontal cortex, Individual 1 using SCI-seq with xSDS nucleosome depletion.

We next determined filtering criteria based on MAD and MAPD scores across a variety of resolutions and read count thresholds (FIG. 14). This analysis revealed a greater range of variability in the resolution of our SCI-seq preparations, which is largely driven by the wider range of unique reads per cell when compared to standard methods. By applying a MAD variance filter of 0.2 across all methods, aneuploidy rates for xSDS, DOP and QRP dropped to 12.2%, 9.7% and 10.5% respectively, all below the rate determined by karyotyping, yet closer to one another than prior to filtering (FIG. 15).

Copy Number Variation in the Rhesus Brain

Estimates of aneuploidy and large-scale CNV frequencies in the mammalian brain vary widely, from <5% to 33%[1-4]. This uncertainty largely stems from the inability to profile sufficient numbers of single cells to produce quantitative measurements. The Rhesus macaque is an ideal model for quantifying the abundance of aneuploidy in the brain, as human samples are challenging to acquire and are confounded by high variability in lifetime environmental exposures. Furthermore, the Rhesus brain is phylogenetically, structurally and physiologically more similar to humans than rodents[26].

To demonstrate the versatility of our platform, we applied LAND and xSDS SCI-seq to archived frontal cortex tissue (Individual 1), along with 38 cells using QRP (35 passing QC), and 35 cells using DOP (30 passing QC). Our low-capacity LAND preparation (16 PCR indexes) produced 340 single cell libraries with a median unique read count of 141,449 (248 cells≥50,000 unique reads), and our xSDS preparation generated 171 single cell libraries with a median unique read count of 55,142 (92 cells≥50,000 unique reads). The number of cells produced in our xSDS preparation was lower than expected, largely due to nuclei aggregates during sorting that may be remedied by additional cell dis-aggregation steps.

Figure 20:
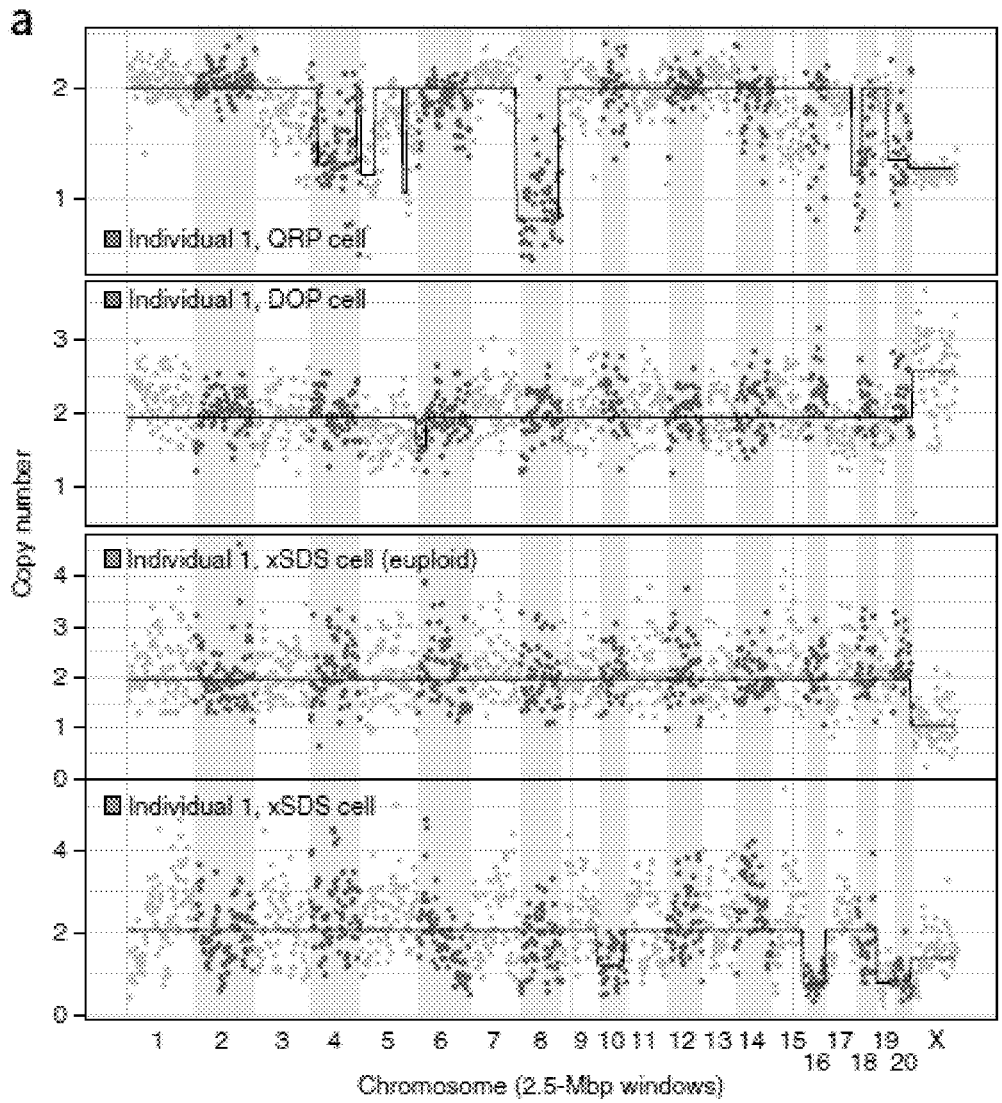
FIG. 20 shows somatic CNVs in the rhesus brain.
Figure 20:
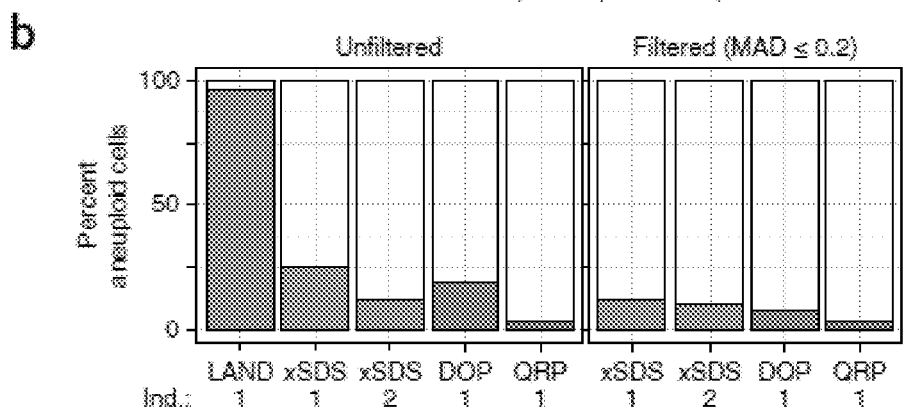
Figure 21:
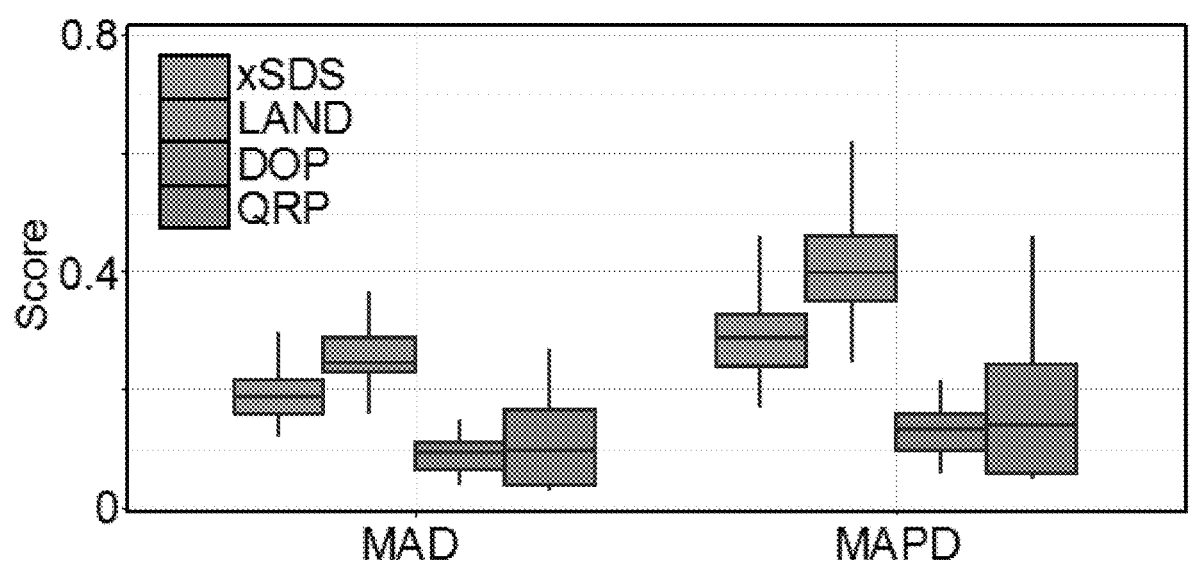
FIG. 21 shows comparison of coverage uniformity for Rhesus frontal cortex individual 1. Uniformity measures are very similar to those of GM12878 preparations (FIG. 7b).
Figures 1, 22:
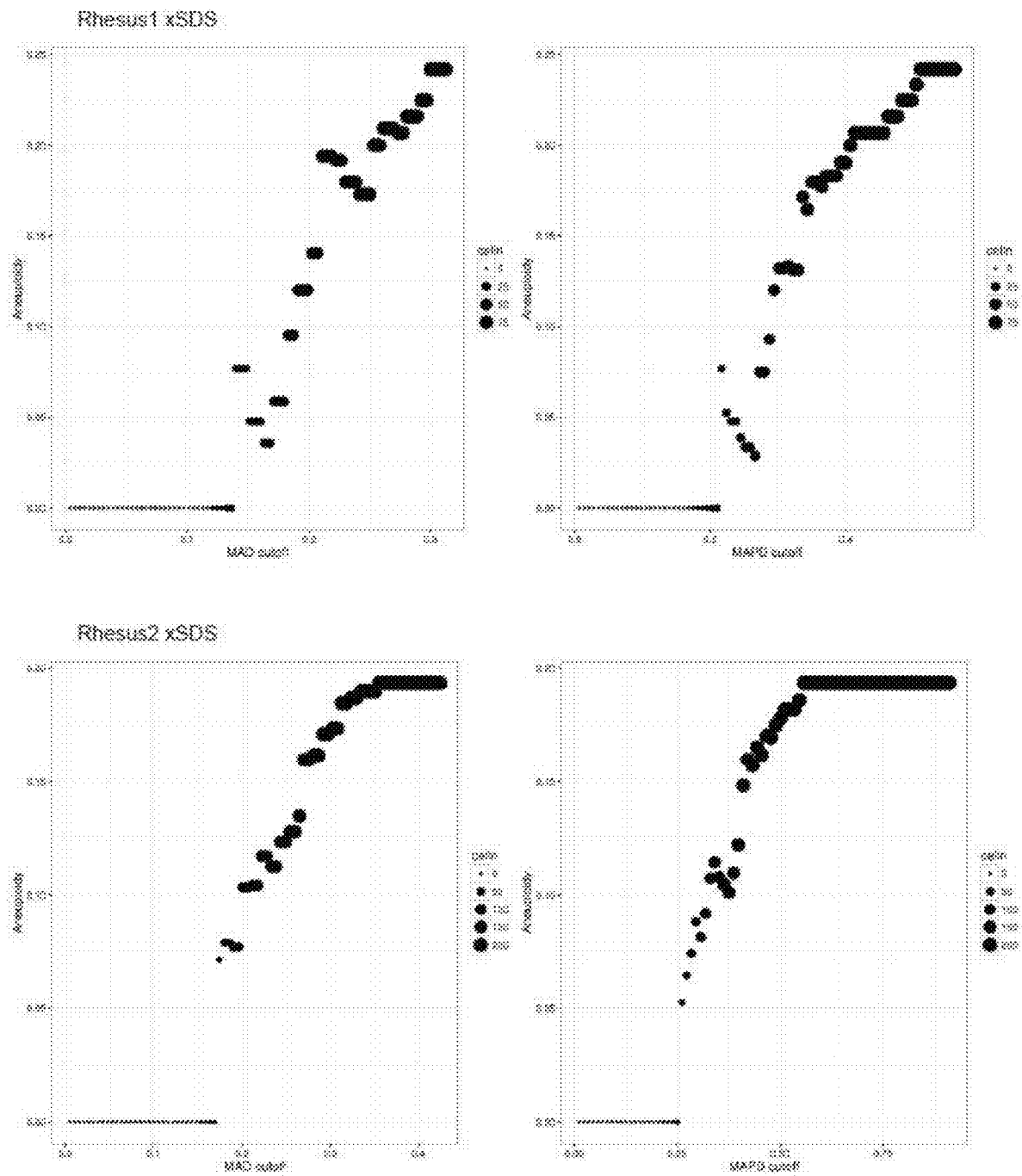
Figures 2, 22:
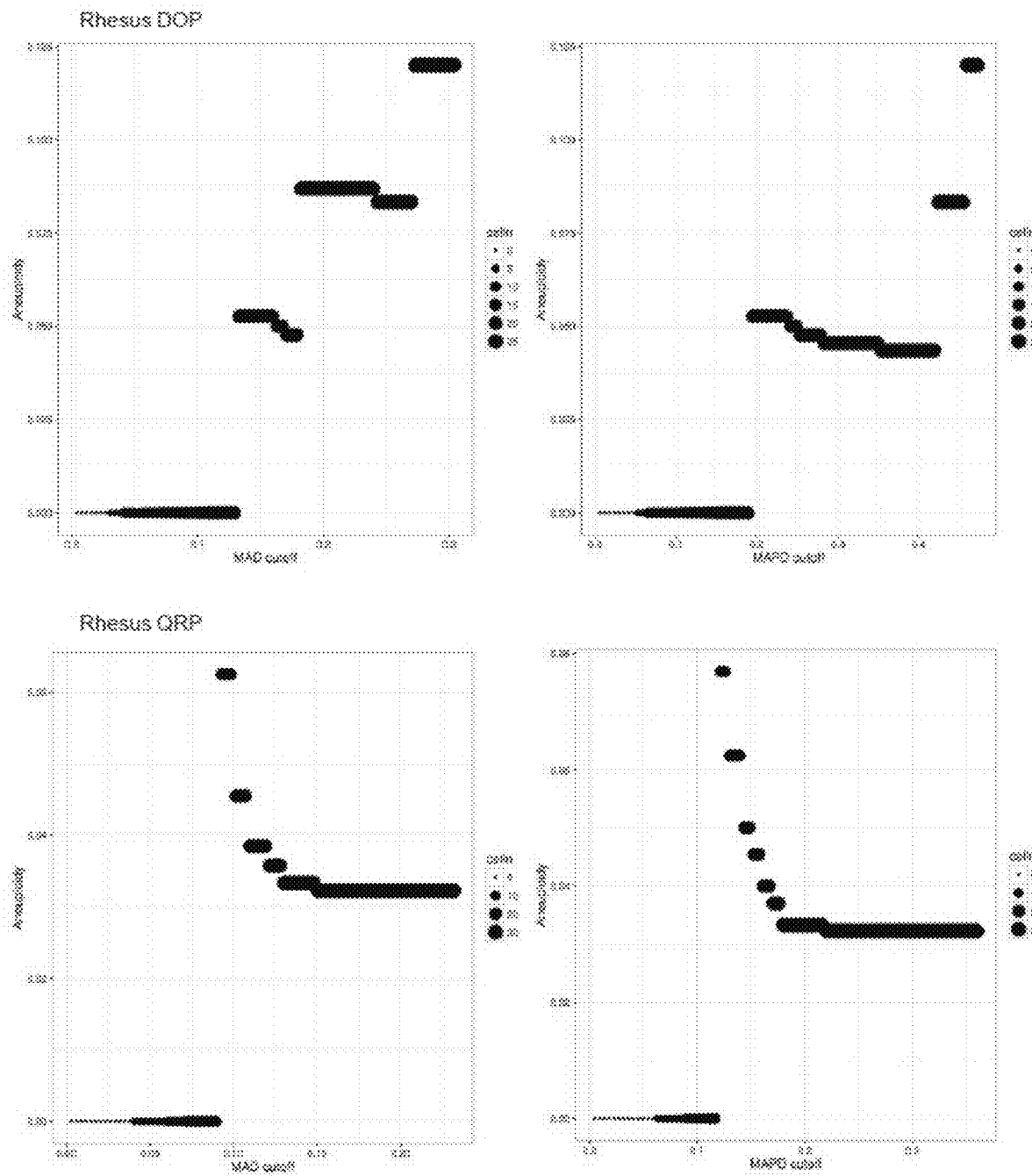
Figure 23:
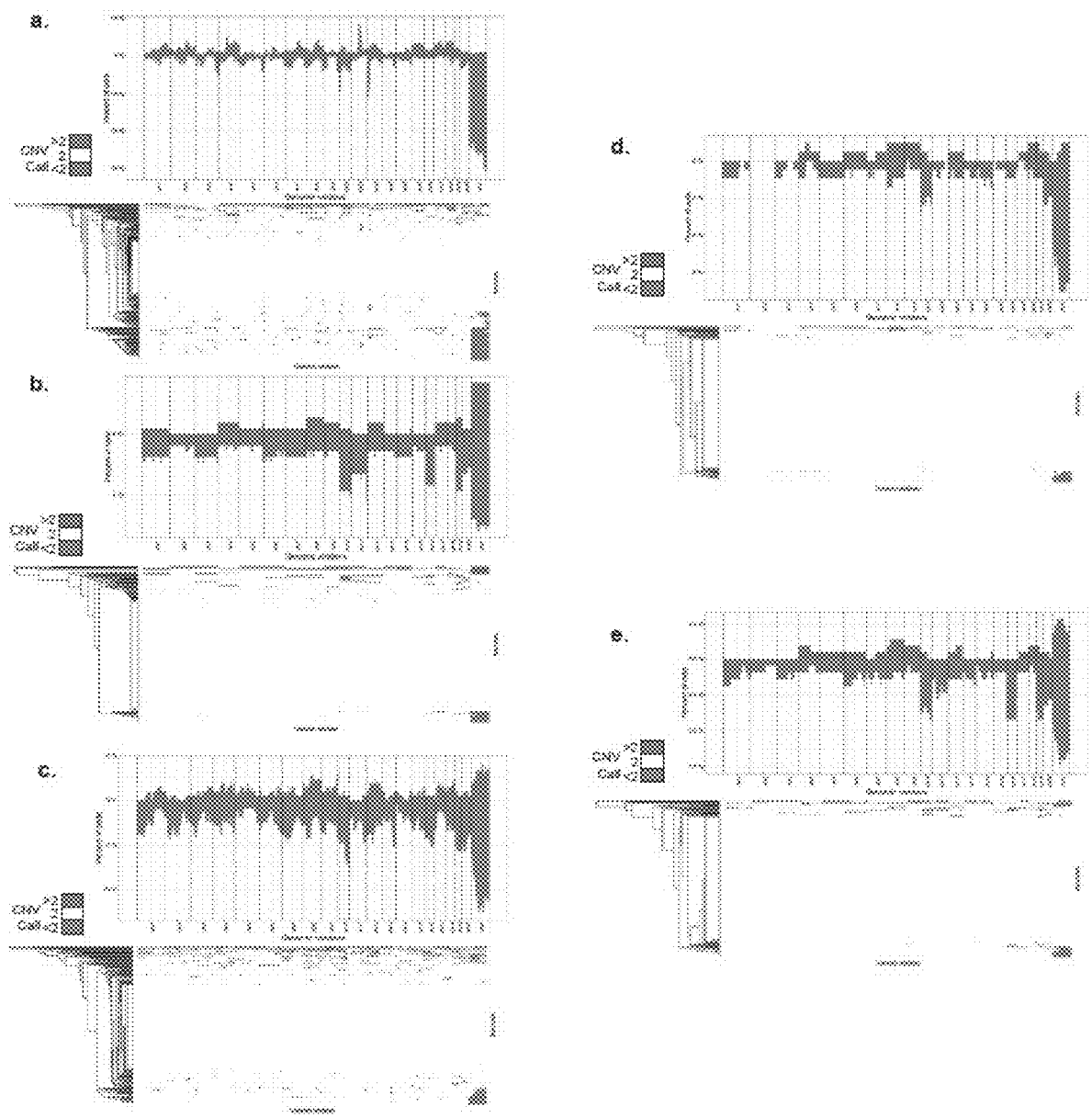
FIG. 23 shows CNV profiles for Rhesus frontal cortex, Individual 2 using SCI-seq with xSDS nucleosome depletion.

Across all methods of library construction we observed greater discrepancies between the three CNV calling approaches than in the human analyses (FIG. 16-19), likely due to the lower quality of the Rhesus reference genome (284,705 contigs<1 Mbp), emphasizing the need for "platinum" quality reference genomes[27]. We therefore focused on the HMM results for sub-chromosomal calls (FIG. 20$a$) and performed aneuploidy analysis using the intersection of CBS and HMM calls. Consistent with our cell line results, the LAND preparation produced a much higher aneuploidy rate (95.1%), suggestive of false positives stemming from coverage nonuniformity (FIG. 21-22). The xSDS SCI-seq unfiltered aneuploidy rate (25.0%) was close to the DOP preparation (18.5%), with QRP producing a much lower rate (3.1%; FIG. 20$b$). After imposing a variance filter for cells with a MAD score of 0.2 or lower, the aneuploidy rates dropped to 12.0% for the xSDS preparation, 8.7% for the DOP, and stayed the same for the QRP preparation at 3.1%. These rates were similar to those produced by xSDS SCI-seq on a 200 mm³ section of frontal cortex from a second individual (381 single cells, median read count of 62,731, 213 cells≥50,000 unique reads) which produced unfiltered and filtered aneuploidy rates of 12.1% and 10.3% respectively (FIG. 23).

SCI-Seq on Primary Tumor Samples Reveals Clonal Populations

Figure 24:
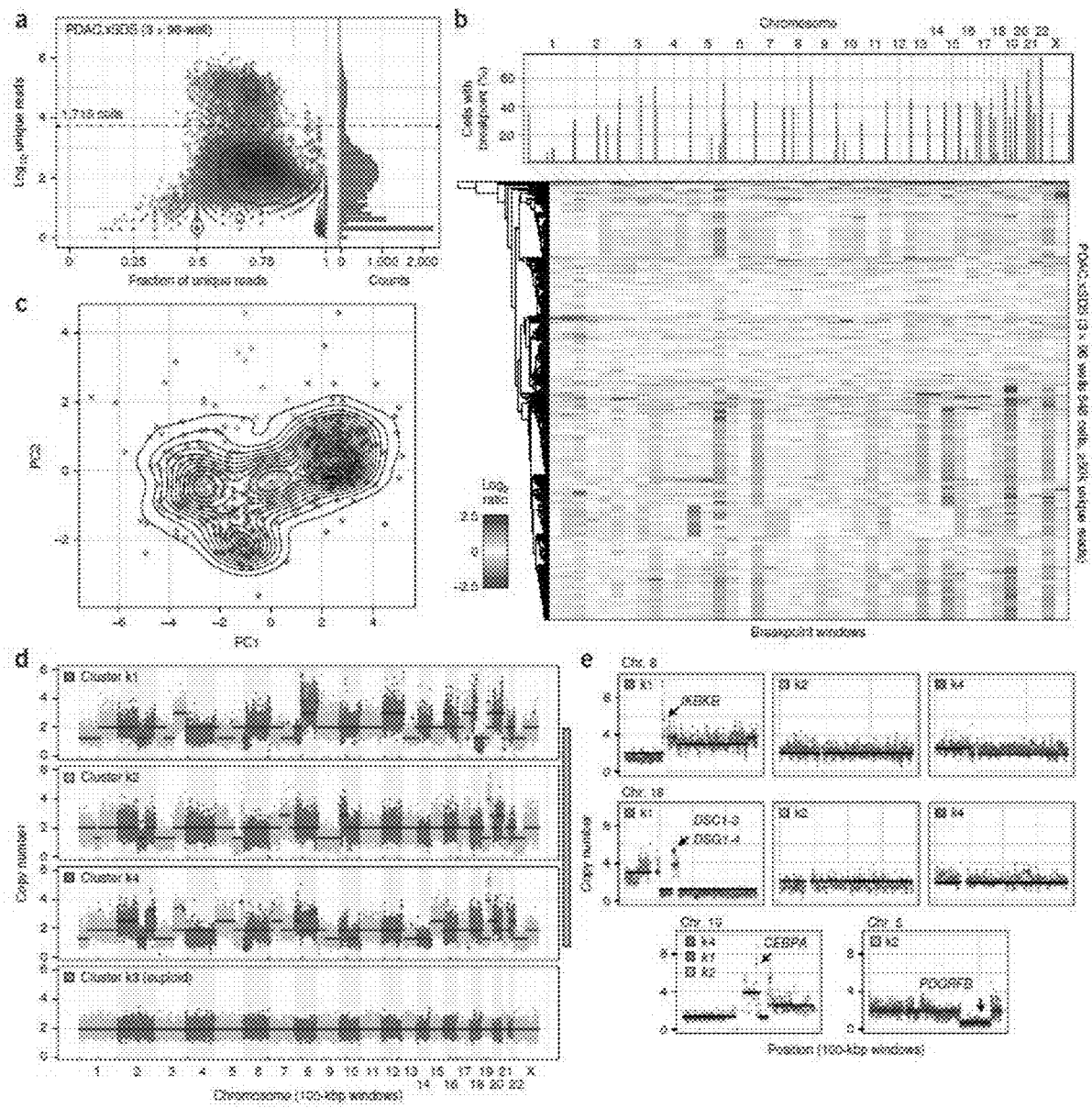
FIG. 24 shows SCI-seq analysis of a stage III human Pancreatic Ductal Adenocarcinoma (PDAC).
Figures 1, 25:
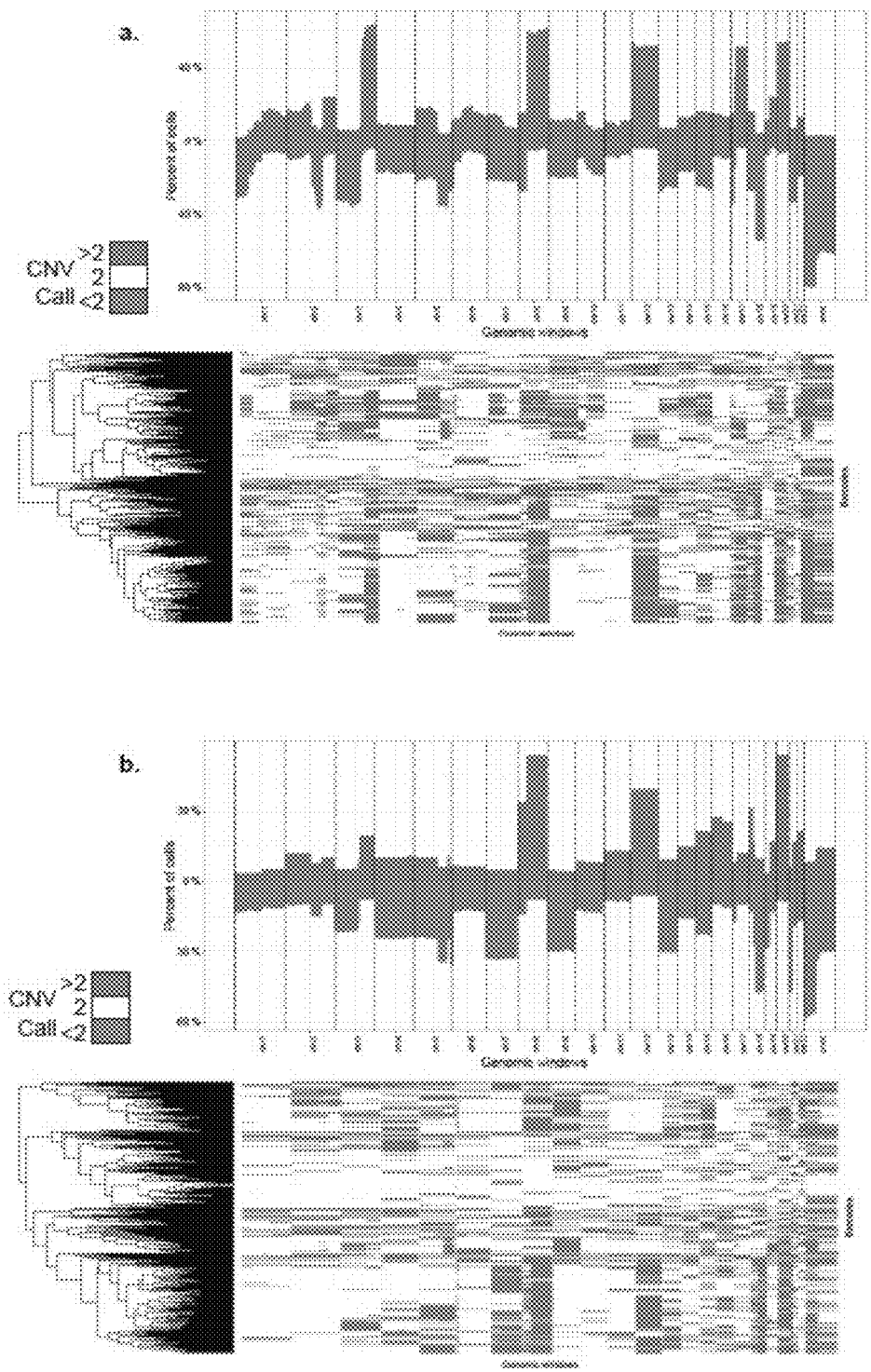
Figures 2, 25:
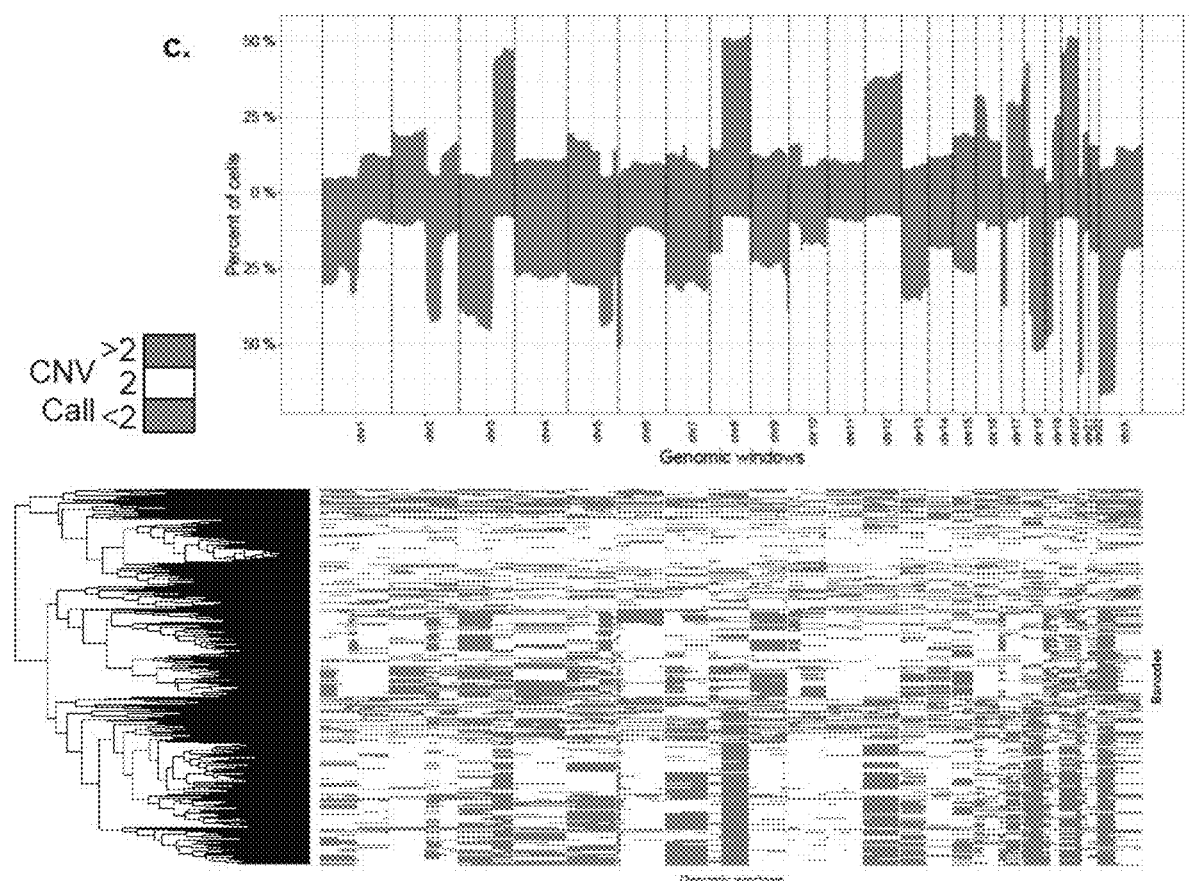
Figure 26:
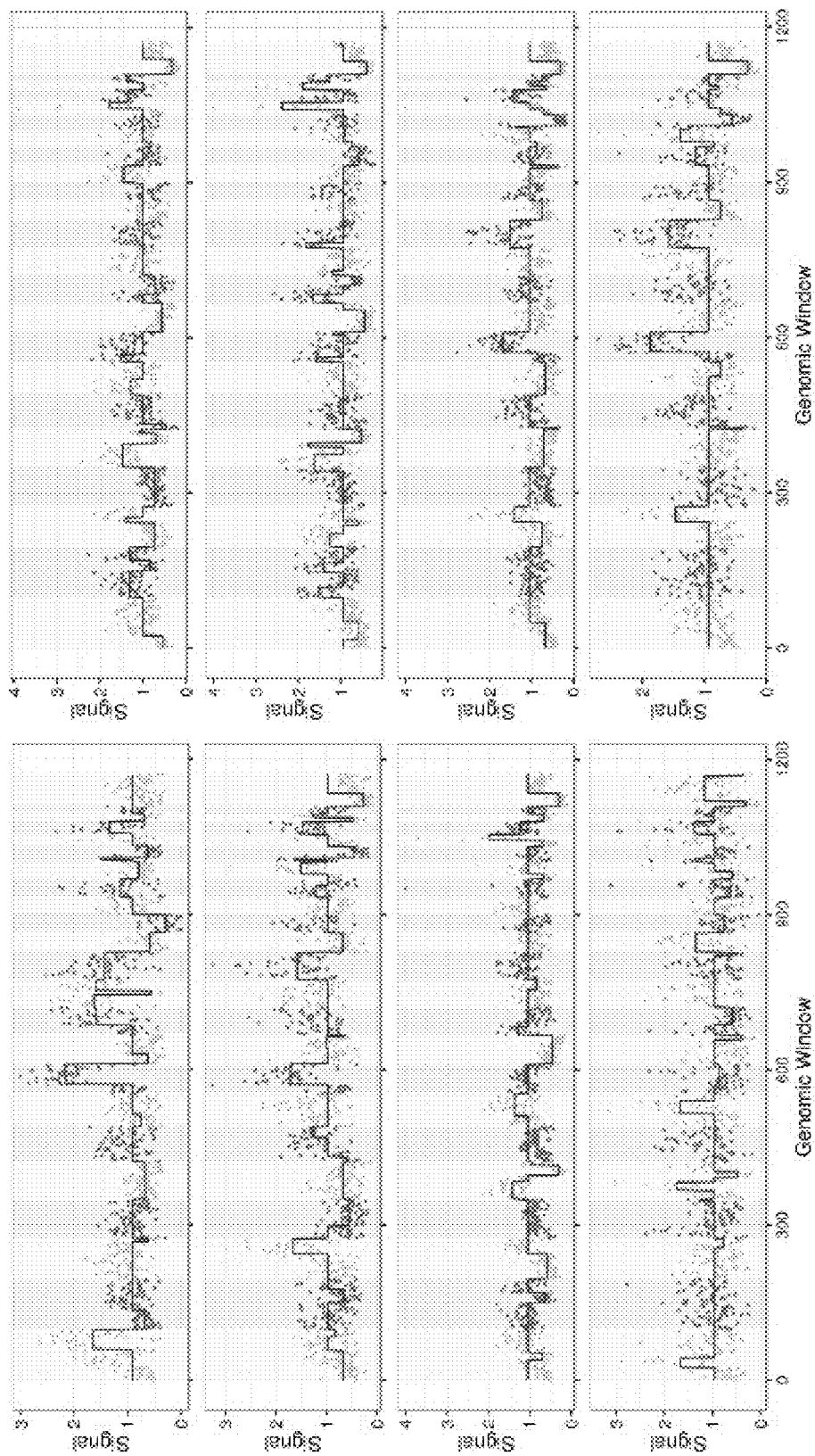
FIG. 26 shows single cell CNV calls on primary PDAC using xSDS SCI-seq. Representative single cell signal plots.
Figure 27:
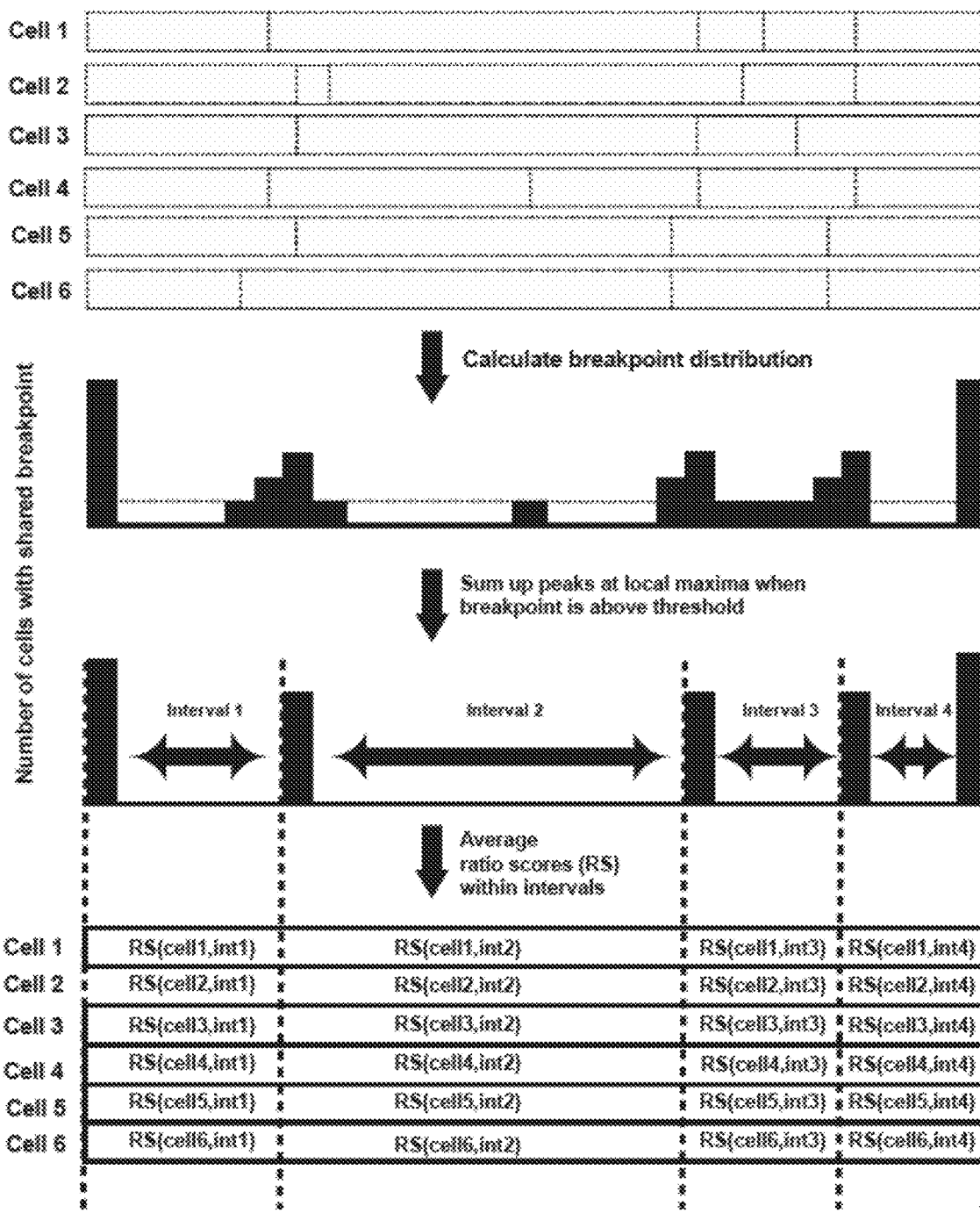
FIG. 27 shows schematic of breakpoint analysis workflow. First, individual cells are analyzed for breakpoints. Breakpoints from all cells are merged and locally summed when above threshold. Intervals are defined between local shared breakpoints and average ratio scores are found within each interval.
Figure 28:
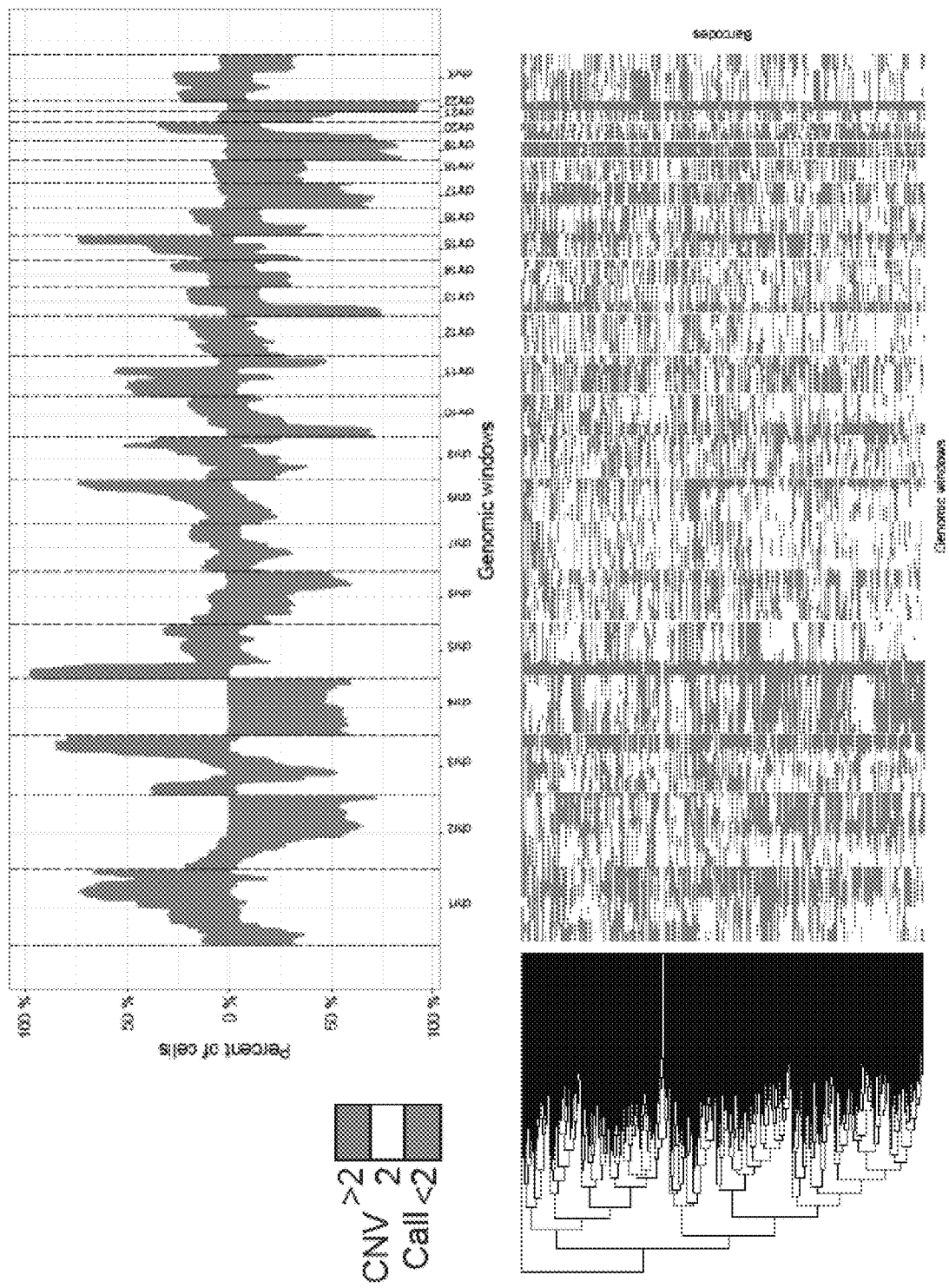
FIG. 28 shows SCI-seq using LAND-based nucleosome depletion on HeLavS3 using the Hidden Markov Model method for copy number variant calling. Summary of windowed (2.5 Mbp) calls and hierarchical clustering of cells. CBC copy number calling resulted in a heavy bias against sub-chromosomal calls and Ginkgo failed to properly identify the ploidy in a number of cells resulting in a majority of cells called as entirely amplified.
Figure 29:
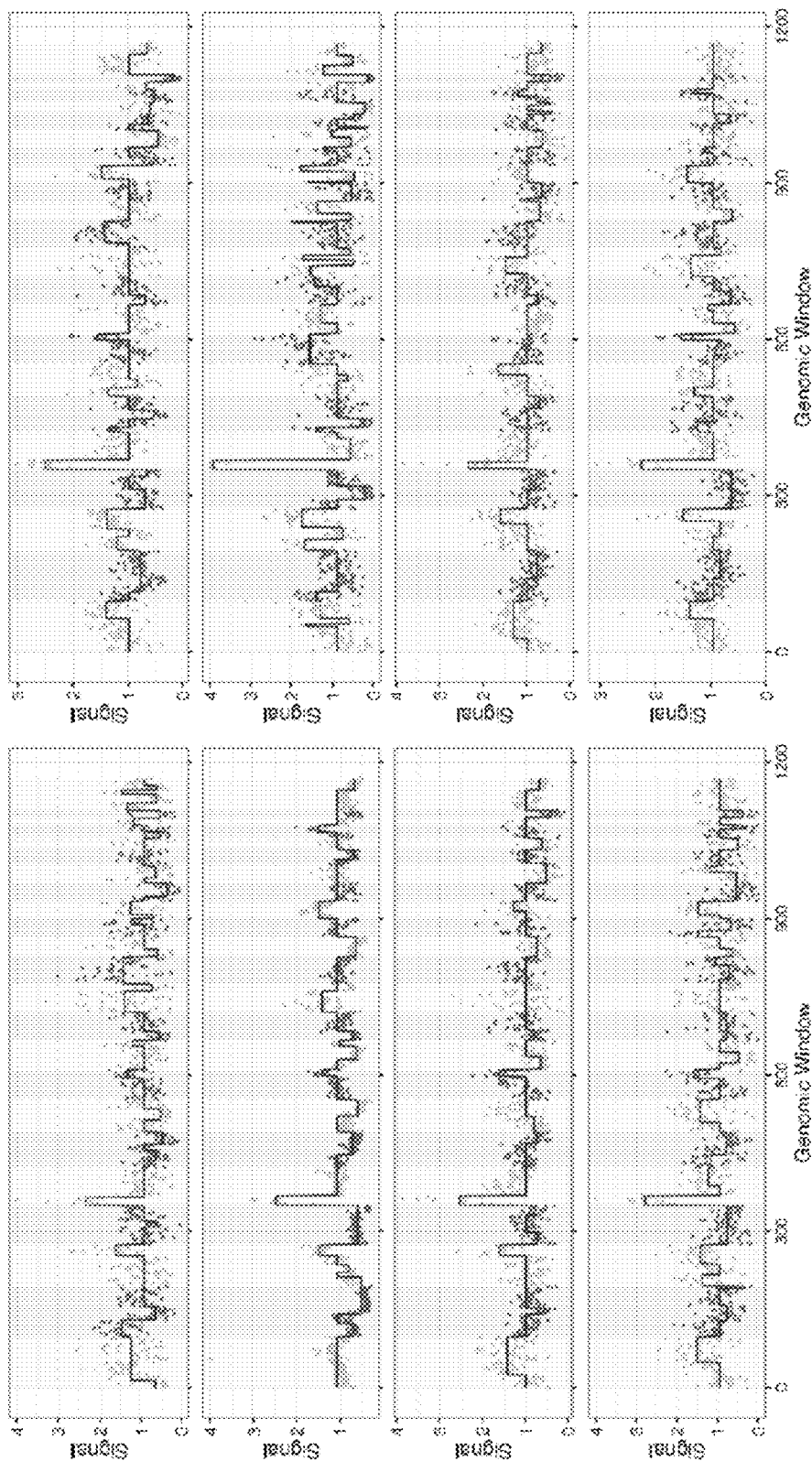
FIG. 29 shows SCI-seq using LAND-based nucleosome depletion on HeLa S3 copy number variant calling in single cells using the Hidden Markov Model method. Representative single cell signal plots. A signal of 1 corresponds to the mean ploidy of 2.98.
Figure 30:
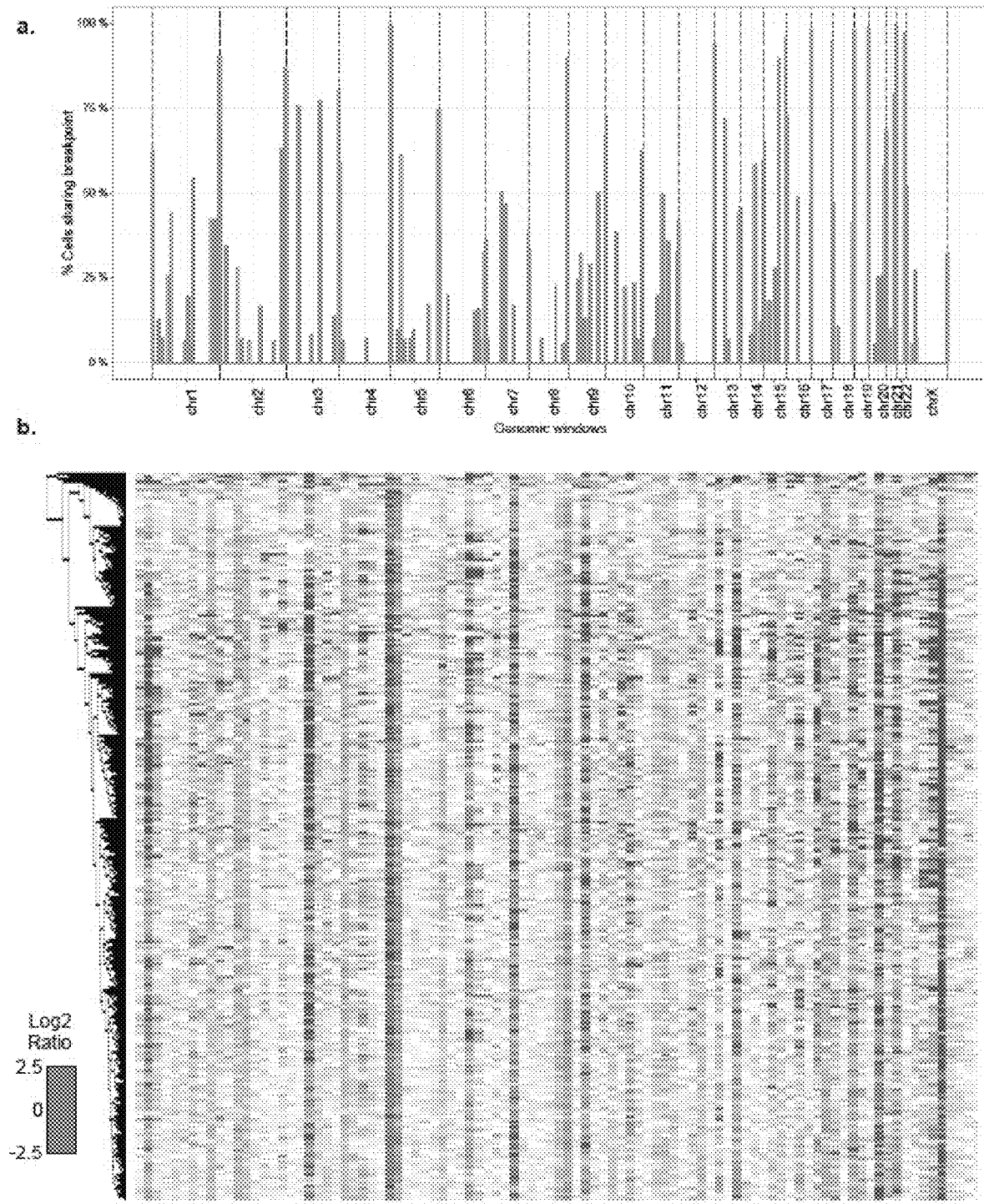
FIG. 30 shows breakpoint analysis of HeLa.
Figure 31:
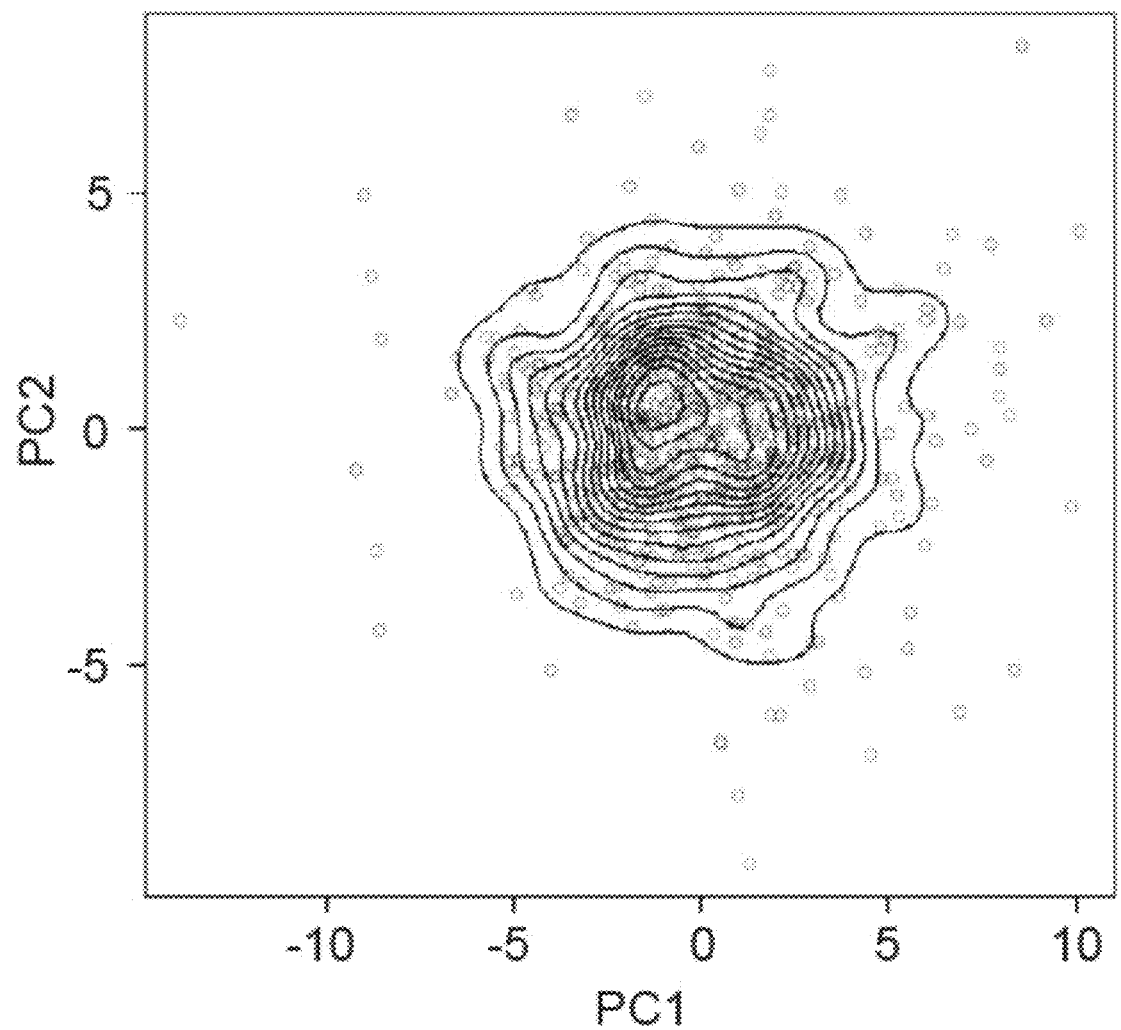
FIG. 31 shows PCA on HeLa breakpoint windows. HeLa produces a single population as expected based on the stability of the cell line. Red and blue points indicate different preparations.

One of the primary applications of single cell genome sequencing is in the profiling of tumor heterogeneity and understanding clonal evolution in cancer as it relates to treatment resistance[5-8]. We carried out a single xSDS SCI-seq preparation on a freshly acquired stage III pancreatic ductal adenocarcinoma (PDAC) sample measuring approximately 250 mm³ which resulted in 1,715 single cell libraries sequenced to a median unique read count of 49,272 per cell (M50 of 71,378; 846 cells≥50,000 unique reads at the depth the library was sequenced; FIG. 24$a$). We first performed CNV calling using our GM12878 library as a euploid baseline for comparison to identify a set of high-confidence euploid cells (298, 35.2%) which were then used as a new baseline specific to the individual and preparation (FIG. 23, 25, 26). Assuming that subchromosomal copy number alterations (caused by genome instability) are more informative for identifying subclonal populations than whole chromosome aneuploidy (due to errors during cell division), we developed a strategy to identify putative copy number breakpoints at low resolution to be used as new window boundaries (Methods, FIG. 27) followed by stratification via principle components analysis (PCA) and k-means clustering. We initially applied this method to our HeLa libraries (2,361 single cells in total), revealing no distinct heterogeneity and further supporting the stability of the HeLa cell line[20] (FIG. 28-31), and then on our primary PDAC sample, which revealed an optimum cluster count of 4 by silhouette analysis (FIG. 24$b,c$).

The first of these clusters (k3) is a population of euploid cells that were not considered high confidence euploid in the initial analysis, and thus not removed. When including these, the euploid population rises to 389 for a final tumor cell purity of 46.0%, within the expected range for PDAC28. For the remaining clusters k1 (199 cells), k2 (115 cells) and k4 (91 cells), we aggregated all reads from cells proximal to each centroid (Methods) and carried out CNV calling using 100 kbp windows, a 25-fold greater resolution than the initial analysis, and then determined absolute copy number states[20] (FIG. 24$d$).

Across the three tumor clusters, a substantial portion of copy number segments were shared (44.8%), suggesting that they arose from a common progenitor population. This includes a highly rearranged chromosome 19 which harbors a focal amplification of CEBPA, which encodes an enhancer binding protein, at copy number 7 which is frequently mutated in AML[29], and has recently been shown to have altered epigenetic regulation in pancreatic tumors[30] (FIG. 24$e$). An all-by-all pairwise comparison revealed clusters k2 and k4 as the most similar, sharing 65.9% of copy number segments, followed by k1 and k4 at 58.3%, and k1 and k2 at 55.0%. Several cluster-specific CNVs contain genes of potential functional relevance (FIG. 24$e$). These include a focal amplification to copy number 6 of IKBKB in cluster k1, which encodes a serine kinase important in the NF-κB signaling pathway[31]; another focal amplification to copy number 5 in cluster k1 containing genes DSCJ,2,3 and DSGJ,2,3,4 all of which encode proteins involved in cell-cell adhesion and cell positioning and are often mis-regulated in cancer[32]; and the deletion of a region containing PDGRFB specific to cluster k2, which encodes a tyrosine kinase cell surface receptor involved in cell proliferation signaling, and is frequently mutated in cancer[33].

Figure 32:
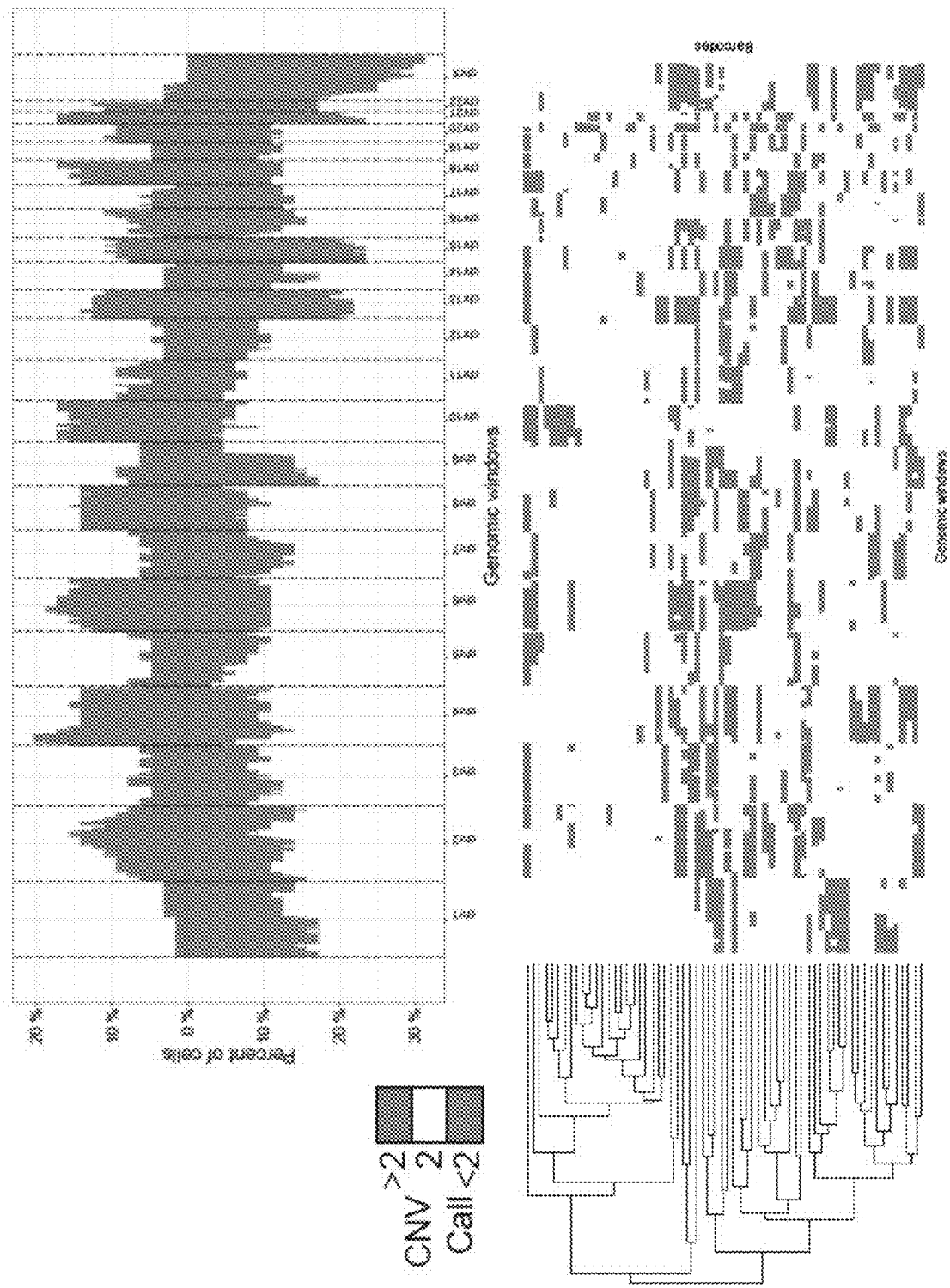
FIG. 32 shows SCI-seq using xSDS-based nucleosome depletion on a banked stage II rectal cancer sample. Intersected copy number call summary for 2.5 Mbp windows.

Lastly, we applied xSDS SCI-seq to a frozen stage II rectal adenocarcinoma measuring 500 mm$^3$. During preparation we noticed a high abundance of nuclear debris and ruptured nuclei which likely attributed to the decreased yield of the preparation (16 PCR indexes) of 146 single cell libraries (median unique read count of 71,378; M50 of 352,168; 111 cells≥50,000 unique reads). We carried out the same CNV calling approach as with the PDAC sample; however high frequency breakpoints were not observed and subclonal populations could not be identified (FIG. 32). This may be a result of nuclear deterioration due to irradiation, a common treatment for rectal cancers, underscoring the challenge of producing high-quality single cell or nuclei suspensions shared by all single cell methods[12].

DISCUSSION

We developed SCI-seq, a method which utilizes nucleosome depletion in a combinatorial indexing workflow to produce thousands of single cell genome sequencing libraries. Using SCI-seq, we produced 16,698 single cell libraries (of which 5,395 were sequenced to a depth sufficient for CNV calling) from myriad samples, including primary tissue isolates representative of the two major areas of single cell genome research: somatic aneuploidy and cancer. In addition to the advantages of throughput, the platform does not require specialized microfluidics equipment or droplet emulsification techniques. Using our more uniform nucleosome depletion strategy, xSDS, we were able to achieve resolution on the order of 250 kbp, though we suspect further optimization, such as alternative crosslinking agents, may provide sufficient depth for improved resolution. We also demonstrate the ability to identify clonal populations that can be aggregated to facilitate high resolution CNV calling by applying this strategy to a pancreatic ductal adenocarcinoma which revealed subclone-specific CNVs that may impact proliferation, migration, or possibly drive other molecular subtypes[34].

It may be possible to use this technology to include in situ pre-amplification within the nuclear scaffold prior to SCI-seq or the incorporation of T4 in vitro transcription, such as in THS-seq[35], an ATAC-seq variant, to boost the resulting coverage and facilitate single nucleotide variant detection. While optimization is possible, as with any new method, we believe that the throughput provided by SCI-seq will open the door to deep quantification of mammalian somatic genome stability as well as serve as a platform to assess other properties of single cells including DNA methylation and chromatin architecture.

Accession Codes
  NCBI BioProject ID: PRJNA326698
  HeLa dbGaP Accession: phs000640
Data Availability
  GM12878 and Rhesus sequence data are accessible through the NCBI Sequence Read Archive (SRA) under BioProject ID: PRJNA326698 for unrestricted access. HeLa sequence data are accessible through the database of Genotypes and Phenotypes (dbGaP), as a substudy under accession number phs000640. Human tumor samples are undergoing submission to dbGaP and are awaiting study accession assignment. Software developed specifically for this project is available on the World Wide Web at sci-seq.sourceforge.net.

REFERENCES CITED IN EXAMPLE 1

1. McConnell, M. J. et al. Mosaic Copy Number Variation in Human Neurons. *Science* (80.). 342, 632-637 (2013).
2. Cai, X. et al. Single-Cell, Genome-wide Sequencing Identifies Clonal Somatic Copy-Number Variation in the Human Brain. *Cell Rep.* 8, 1280-1289 (2014).
3. Knouse, K. A., Wu, J., Whittaker, C. A. & Amon, A. Single cell sequencing reveals low levels of aneuploidy across mammalian tissues. *Proc Natl Acad Sci USA* 111, 13409-13414 (2014).
4. Rehen, S. K. et al. Chromosomal variation in neurons of the developing and adult mammalian nervous system. *Proc. Natl. Acad. Sci. U.S.A* 98, 13361-6 (2001).
5. Navin, N. et al. Tumour evolution inferred by single-cell sequencing. *Nature* 472, 90-94 (2011).
6. Eirew, P. et al. Dynamics of genomic clones in breast cancer patient xenografts at single-cell resolution. *Nature* 518, 422-6 (2014).
7. Gawad, C., Koh, W. & Quake, S. R. Dissecting the clonal origins of childhood acute lymphoblastic leukemia by single-cell genomics. *Proc. Natl. Acad. Sci. U.S.A* 111, 17947-52 (2014).
8. Gao, R. et al. Punctuated copy number evolution and clonal stasis in triple-negative breast cancer. *Nat. Genet.* 1-15 (2016). doi:10.1038/ng.3641
9. Zong, C., Lu, S., Chapman, A. R. & Xie, X. S. Genome-Wide Detection of Single Nucleotide and Copy Number Variations of a Single Human Cell. *Science* (80-.). 338, 1622-1626 (2012).
10. Baslan, T. et al. Optimizing sparse sequencing of single cells for highly multiplex copy number profiling. *Genome Res.* 125, 714-724 (2015).
11. Knouse, K. A., Wu, J. & Amon, A. Assessment of megabase-scale somatic copy number variation using single cell sequencing. *Genome Res.* gr. 198937.115- (2016). doi:10.1101/gr.198937.115
12. Gawad, C., Koh, W. & Quake, S. R. Single-cell genome sequencing: current state of the science. *Nat. Rev. Genet.* 17, 175-88 (2016).
13. Adey, A. et al. Rapid, low-input, low-bias construction of shotgun fragment libraries by high-density in vitro transposition. *Genome Biol.* 11, R119 (2010).
14. Amini, S. et al. Haplotype-resolved whole-genome sequencing by contiguity-preserving transposition and combinatorial indexing. *Nat. Genet.* 46, 1343-9 (2014).
15. Adey, A. et al. In vitro, long-range sequence information for de novo genome assembly via transposase contiguity. *Genome Res.* 24, 2041-2049 (2014).
16. Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. *Nat. Methods* 10, 1213-8 (2013).
17. Cusanovich, D. a et al. Epigenetics. Multiplex single-cell profiling of chromatin accessibility by combinatorial cellular indexing. *Science* 348, 910-4 (2015).
18. Stergachis, A. B. et al. Developmental fate and cellular maturity encoded in human regulatory DNA landscapes. *Cell* 154, 888-903 (2013).
19. The ENCODE Project Consortium. An integrated encyclopedia of DNA elements in the human genome. *Nature* 489, 57-74 (2012).

20. Adey, A. et al. The haplotype-resolved genome and epigenome of the aneuploid HeLa cancer cell line. *Nature* 500, 207-211 (2013).
21. Macosko, E. Z. et al. Highly Parallel Genome-wide Expression Profiling of Individual Cells Using Nanoliter Droplets. *Cell* 161, 1202-1214 (2015).
22. Garvin, T. et al. Interactive analysis and quality assessment of single-cell copy-number variations. *bioRxiv* 11346 (2014). doi:10.1101/011346
23. GORYSHIN, I. Y., MILLER, J. A., KIL, Y. V., LANZOV, V. A. & REZNIKOFF, W. S. Tn5/IS50 target recognition. *Proc. Natl. Acad. Sci. USA* 95, 10716-10721 (1998).
24. Olshen, A. B., Venkatraman, E. S., Lucito, R. & Wigler, M. Circular binary segmentation for the analysis of array-based DNA copy number data. *Biostatistics* 5, 557-572 (2004).
25. Ha, G. et al. Integrative analysis of genome-wide loss of heterozygosity and monoallelic expression at nucleotide resolution reveals disrupted pathways in triple-negative breast cancer. *Genome Res.* 22, 1995-2007 (2012).
26. Rosenkrantz, J. & Carbone, L. Investigating somatic aneuploidy in the brain: why we need a new model. *Chromosoma* (2016).
27. Callaway, E. 'Platinum' genome takes on disease. *Nat. News* 515, 323 (2014).
28. Waddell, N. et al. Whole genomes redefine the mutational landscape of pancreatic cancer. *Nature* 518, 495-501 (2015).
29. De Kouchkovsky, I. & Abdul-Hay, M. 'Acute myeloid leukemia: a comprehensive review and 2016 update'. *Blood Cancer J.* 6, e441 (2016).
30. Kumagai, T. et al. Epigenetic regulation and molecular characterization of C/EBPalpha in pancreatic cancer cells. *Int J Cancer* 124, 827-833 (2009).
31. Perkins, N. D. Integrating cell-signalling pathways with NF-kappaB and IKK function. *Nat. Rev. Mol. Cell Biol.* 8, 49-62 (2007).
32. Stahley, S. N. & Kowalczyk, A. P. Desmosomes in acquired disease. *Cell Tissue Res.* 360, 439-56 (2015).
33. Forbes, S. A. et al. COSMIC: Exploring the world's knowledge of somatic mutations in human cancer. *Nucleic Acids Res.* 43, D805-D811 (2015).
34. Bailey, P. et al. Genomic analyses identify molecular subtypes of pancreatic cancer. *Nature* 531, 47-52 (2016).
35. Sos, B. et al. Characterization of chromatin accessibility with a transposome hypersensitive sites sequencing (THS-seq) assay. *Genome Biol* 17, 20 (2016).

Example 2

Reagents Used in Example 2
  Phosphate Buffer Saline (PBS, Thermo Fisher, Cat. 10010023)
  0.25% Trypsin (Thermo Fisher, Cat. 15050057)
  Tris (Fisher, Cat. T1503)
  HCl(Fisher, Cat. A144)
  NaCl (Fisher, Cat. M-11624)
  MgCl2 (Sigma, Cat. M8226)
  Igepal® CA-630 (Sigma, 18896)
  Protease Inhibitors (Roche, Cat. 11873580001)
  Lithium 3,5-diiodosalicylic acid (Sigma, Cat. D3635)—LAND Only
  Formaldehyde (Sigma, Cat. F8775)—xSDS Only
  Glycine (Sigma, Cat. G8898)—xSDS Only
  HEPES (Fisher, Cat. BP310)—xSDS Only
  NEBuffer 2.1 (NEB, Cat. B7202)—xSDS Only
  SDS (Sigma, Cat. L3771)—xSDS Only
  Triton™-X100 (Sigma, Cat. 9002-93-1)—xSDS Only
  DAPI (Thermo Fisher, Cat. D1306)
  TD buffer and NPM from Nextera® kit (Illumina, Cat. FC-121-1031)
  96 Indexed Transposomes (either assembled using published methods or obtained from Illumina, oligos shown in Table 4)
  Indexed i5 and i7 PCR primers (Table 5)
  SYBR Green (FMC BioProducts, Cat. 50513)
  Qiaquick® PCR purification kit (Qiagen, Cat. 28104)
  dsDNA High Sensitivity qubit (Thermo Fisher, Cat. Q32851)
  High Sensitivity Bioanalyzer kit (Agilent, Cat. 5067-4626)
  NextSeq sequencing kit (High or Mid 150-cycle)
  Sequencing primers (Table 6)
Equipment Used in the Examples
  Dounce Homogenizer
  35 µM Cell Strainer (BD Biosciences, Cat. 352235)
  Sony SH800 cell sorter (Sony Biotechnology, Cat. SH800) or other FACS instrument capable of DAPI-based single nuclei sorting
  CFX Connect RT Thermal Cycler (Bio-Rad, Cat. 1855200) or other real time thermocycler
  Qubit® 2.0 Flourometer (Thermo Fisher, Cat. Q32866)
  2100 Bioanalyzer (Agilent, Cat. G2939A)
  NextSeq® 500 (Illumina, Cat. SY-415-1001)

TABLE 4

Tagmentation Oligos

| Name NO | Sequence (5'→3') | SEQ ID |
|---|---|---|
| Mosaic End Sequence | /5Phos/CTGTCTCTTATACACATCT | 1 |
| CPT_TS_i5_1 | TCGTCGGCAGCGTCTCCACGCTATAGCCTGCGATCGAGGACGGCAGATGTGTATAAGAGACAG | 2 |
| CPT_TS_i5_2 | TCGTCGGCAGCGTCTCCACGCATAGAGGCGCGATCGAGGACGGCAGATGTGTATAAGAGACAG | 3 |
| CPT_TS_i5_3 | TCGTCGGCAGCGTCTCCACGCCCTATCCTGCGATCGAGGACGGCAGATGTGTATAAGAGACAG | 4 |
| CPT_TS_i5_4 | TCGTCGGCAGCGTCTCCACGCGGCTCTGAGCGATCGAGGACGGCAGATGTGTATAAGAGACAG | 5 |
| CPT_TS_i5_5 | TCGTCGGCAGCGTCTCCACGCAGGCGAAGGCGATCGAGGACGGCAGATGTGTATAAGAGACAG | 6 |
| CPT_TS_i5_6 | TCGTCGGCAGCGTCTCCACGCTAATCTTAGCGATCGAGGACGGCAGATGTGTATAAGAGACAG | 7 |

TABLE 4-continued

Tagmentation Oligos

| Name NO | Sequence (5'→3') | SEQ ID |
|---|---|---|
| CPT_TS_i5_7 | TCGTCGGCAGCGTCTCCACGCCAGGACGTGCGATCGAGGACGGCAGATGTGTATAAGAGACAG | 8 |
| CPT_TS_i5_8 | TCGTCGGCAGCGTCTCCACGCGTACTGACGCGATCGAGGACGGCAGATGTGTATAAGAGACAG | 9 |
| CPT_TS_i7_1 | GTCTCGTGGGCTCGGCTGTCCCTGTCCCGAGTAATCACCGTCTCCGCCTCAGATGTGTATAAGAGACAG | 10 |
| CPT_TS_i7_2 | GTCTCGTGGGCTCGGCTGTCCCTGTCCTCTCCGGACACCGTCTCCGCCTCAGATGTGTATAAGAGACAG | 11 |
| CPT_TS_i7_3 | GTCTCGTGGGCTCGGCTGTCCCTGTCCAATGAGCGCACCGTCTCCGCCTCAGATGTGTATAAGAGACAG | 12 |
| CPT_TS_i7_4 | GTCTCGTGGGCTCGGCTGTCCCTGTCCGGAATCTCCACCGTCTCCGCCTCAGATGTGTATAAGAGACAG | 13 |
| CPT_TS_i7_5 | GTCTCGTGGGCTCGGCTGTCCCTGTCCTTCTGAATCACCGTCTCCGCCTCAGATGTGTATAAGAGACAG | 14 |
| CPT_TS_i7_6 | GTCTCGTGGGCTCGGCTGTCCCTGTCCACGAATTCCACCGTCTCCGCCTCAGATGTGTATAAGAGACAG | 15 |
| CPT_TS_i7_7 | GTCTCGTGGGCTCGGCTGTCCCTGTCCAGCTTCAGCACCGTCTCCGCCTCAGATGTGTATAAGAGACAG | 16 |
| CPT_TS_i7_8 | GTCTCGTGGGCTCGGCTGTCCCTGTCCGCGCATTACACCGTCTCCGCCTCAGATGTGTATAAGAGACAG | 17 |
| CPT_TS_i7_9 | GTCTCGTGGGCTCGGCTGTCCCTGTCCCATAGCCGCACCGTCTCCGCCTCAGATGTGTATAAGAGACAG | 18 |
| CPT_TS_i7_10 | GTCTCGTGGGCTCGGCTGTCCCTGTCCTTCGCGGACACCGTCTCCGCCTCAGATGTGTATAAGAGACAG | 19 |
| CPT_TS_i7_11 | GTCTCGTGGGCTCGGCTGTCCCTGTCCGCGCGAGACACCGTCTCCGCCTCAGATGTGTATAAGAGACAG | 20 |
| CPT_TS_i7_12 | GTCTCGTGGGCTCGGCTGTCCCTGTCCCTATCGCTCACCGTCTCCGCCTCAGATGTGTATAAGAGACAG | 21 |

TABLE 5

PCR Primers

| Name | Sequence (5'→3') | SEQ ID NO |
|---|---|---|
| i7-T119-NEX2cpt-A | CAAGCAGAAGACGGCATACGAGATaatgccgcttGTCTCGTGGGCTCGG | 22 |
| i7-T120-NEX2cpt-A | CAAGCAGAAGACGGCATACGAGATtatagacgcaGTCTCGTGGGCTCGG | 23 |
| i7-T121-NEX2cpt-A | CAAGCAGAAGACGGCATACGAGATcaatcgcatGTCTCGTGGGCTCGG | 24 |
| i7-T122-NEX2cpt-A | CAAGCAGAAGACGGCATACGAGATtttcttaataaGTCTCGTGGGCTCGG | 25 |
| i7-T123-NEX2cpt-A | CAAGCAGAAGACGGCATACGAGATgtcctagaggGTCTCGTGGGCTCGG | 26 |
| i7-T124-NEX2cpt-A | CAAGCAGAAGACGGCATACGAGATatattgatacGTCTCGTGGGCTCGG | 27 |
| i7-T125-NEX2cpt-A | CAAGCAGAAGACGGCATACGAGATccgctgccagGTCTCGTGGGCTCGG | 28 |
| i7-T126-NEX2cpt-A | CAAGCAGAAGACGGCATACGAGATcctagtacgtGTCTCGTGGGCTCGG | 29 |
| i7-T127-NEX2cpt-A | CAAGCAGAAGACGGCATACGAGATcaattaccgtGTCTCGTGGGCTCGG | 30 |

TABLE 5-continued

PCR Primers

| Name | Sequence (5'→3') | SEQ ID NO |
|---|---|---|
| i7-T128-NEX2cpt-A | CAAGCAGAAGACGGCATACGAGATggccgtagtcGTCTCGTGGGCTCGG | 31 |
| i7-T129-NEX2cpt-A | CAAGCAGAAGACGGCATACGAGATcgattacggcGTCTCGTGGGCTCGG | 32 |
| i7-T130-NEX2cpt-A | CAAGCAGAAGACGGCATACGAGATtaatgaacgaGTCTCGTGGGCTCGG | 33 |
| i7-T131-NEX2cpt-B | CAAGCAGAAGACGGCATACGAGATccgttccttaGTCTCGTGGGCTCGG | 34 |
| i7-T132-NEX2cpt-B | CAAGCAGAAGACGGCATACGAGATggtaccatatGTCTCGTGGGCTCGG | 35 |
| i7-T133-NEX2cpt-B | CAAGCAGAAGACGGCATACGAGATccgattcgcaGTCTCGTGGGCTCGG | 36 |
| i7-T134-NEX2cpt-B | CAAGCAGAAGACGGCATACGAGATatggctctgcGTCTCGTGGGCTCGG | 37 |
| i7-T135-NEX2cpt-B | CAAGCAGAAGACGGCATACGAGATgtataatacgGTCTCGTGGGCTCGG | 38 |
| i7-T136-NEX2cpt-B | CAAGCAGAAGACGGCATACGAGATatcagcaagtGTCTCGTGGGCTCGG | 39 |
| i7-T137-NEX2cpt-B | CAAGCAGAAGACGGCATACGAGATggcgaactcgGTCTCGTGGGCTCGG | 40 |
| i7-T138-NEX2cpt-B | CAAGCAGAAGACGGCATACGAGATttaattgaatGTCTCGTGGGCTCGG | 41 |
| i7-T139-NEX2cpt-B | CAAGCAGAAGACGGCATACGAGATttaggaccggGTCTCGTGGGCTCGG | 42 |
| i7-T140-NEX2cpt-B | CAAGCAGAAGACGGCATACGAGATaagtaagagcGTCTCGTGGGCTCGG | 43 |
| i7-T141-NEX2cpt-B | CAAGCAGAAGACGGCATACGAGATccttggtccaGTCTCGTGGGCTCGG | 44 |
| i7-T142-NEX2cpt-B | CAAGCAGAAGACGGCATACGAGATcatcagaatgGTCTCGTGGGCTCGG | 45 |
| i7-T143-NEX2cpt-C | CAAGCAGAAGACGGCATACGAGATttatagcagaGTCTCGTGGGCTCGG | 46 |
| i7-T144-NEX2cpt-C | CAAGCAGAAGACGGCATACGAGATttacttggaaGTCTCGTGGGCTCGG | 47 |
| i7-T145-NEX2cpt-C | CAAGCAGAAGACGGCATACGAGATgctcagccggGTCTCGTGGGCTCGG | 48 |

TABLE 5-continued

PCR Primers

| Name | Sequence (5'→3') | SEQ ID NO |
|---|---|---|
| i7-T146-NEX2cpt-C | CAAGCAGAAGACGGCATACGAGATacgtccgcagGTCTCGTGGGCTCGG | 49 |
| i7-T147-NEX2cpt-C | CAAGCAGAAGACGGCATACGAGATttgactgacgGTCTCGTGGGCTCGG | 50 |
| i7-T148-NEX2cpt-C | CAAGCAGAAGACGGCATACGAGATttgcgaggcaGTCTCGTGGGCTCGG | 51 |
| i7-T149-NEX2cpt-C | CAAGCAGAAGACGGCATACGAGATttccaaccgcGTCTCGTGGGCTCGG | 52 |
| i7-T150-NEX2cpt-C | CAAGCAGAAGACGGCATACGAGATtaaccttcggGTCTCGTGGGCTCGG | 53 |
| i7-T151-NEX2cpt-C | CAAGCAGAAGACGGCATACGAGATtcaagccgatGTCTCGTGGGCTCGG | 54 |
| i7-T152-NEX2cpt-C | CAAGCAGAAGACGGCATACGAGATcttgcaacctGTCTCGTGGGCTCGG | 55 |
| i7-T153-NEX2cpt-C | CAAGCAGAAGACGGCATACGAGATccatcgcgaaGTCTCGTGGGCTCGG | 56 |
| i7-T154-NEX2cpt-C | CAAGCAGAAGACGGCATACGAGATtagacttcttGTCTCGTGGGCTCGG | 57 |
| i7-T231-NEX2cpt-D | CAAGCAGAAGACGGCATACGAGATtgcgcgatgcGTCTCGTGGGCTCGG | 58 |
| i7-T232-NEX2cpt-D | CAAGCAGAAGACGGCATACGAGATattgagattgGTCTCGTGGGCTCGG | 59 |
| i7-T233-NEX2cpt-D | CAAGCAGAAGACGGCATACGAGATttgatatattGTCTCGTGGGCTCGG | 60 |
| i7-T234-NEX2cpt-D | CAAGCAGAAGACGGCATACGAGATcggtaggaatGTCTCGTGGGCTCGG | 61 |
| i7-T235-NEX2cpt-D | CAAGCAGAAGACGGCATACGAGATaccagcgcagGTCTCGTGGGCTCGG | 62 |
| i7-T236-NEX2cpt-D | CAAGCAGAAGACGGCATACGAGATcgaatgagctGTCTCGTGGGCTCGG | 63 |
| i7-T237-NEX2cpt-D | CAAGCAGAAGACGGCATACGAGATagttcgagtaGTCTCGTGGGCTCGG | 64 |
| i7-T238-NEX2cpt-D | CAAGCAGAAGACGGCATACGAGATttggacgctgGTCTCGTGGGCTCGG | 65 |
| i7-T239-NEX2cpt-D | CAAGCAGAAGACGGCATACGAGATatagactaggGTCTCGTGGGCTCGG | 66 |

TABLE 5-continued

PCR Primers

| Name | Sequence (5'→3') | SEQ ID NO |
|---|---|---|
| i7-T240-NEX2cpt-D | CAAGCAGAAGACGGCATACGAGATtatagtaagcGTCTCGTGGGCTCGG | 67 |
| i7-T241-NEX2cpt-D | CAAGCAGAAGACGGCATACGAGATcggtcgttaaGTCTCGTGGGCTCGG | 68 |
| i7-T242-NEX2cpt-D | CAAGCAGAAGACGGCATACGAGATtggcggatcGTCTCGTGGGCTCGG | 69 |
| i7-T243-NEX2cpt-E | CAAGCAGAAGACGGCATACGAGATctctgatcagGTCTCGTGGGCTCGG | 70 |
| i7-T244-NEX2cpt-E | CAAGCAGAAGACGGCATACGAGATggccagtccgGTCTCGTGGGCTCGG | 71 |
| i7-T245-NEX2cpt-E | CAAGCAGAAGACGGCATACGAGATcggaagatatGTCTCGTGGGCTCGG | 72 |
| i7-T246-NEX2cpt-E | CAAGCAGAAGACGGCATACGAGATtggctgatgaGTCTCGTGGGCTCGG | 73 |
| i7-T247-NEX2cpt-E | CAAGCAGAAGACGGCATACGAGATgaaggttgccGTCTCGTGGGCTCGG | 74 |
| i7-T248-NEX2cpt-E | CAAGCAGAAGACGGCATACGAGATgttgaaggatGTCTCGTGGGCTCGG | 75 |
| i7-T249-NEX2cpt-E | CAAGCAGAAGACGGCATACGAGATccattcgtaaGTCTCGTGGGCTCGG | 76 |
| i7-T250-NEX2cpt-E | CAAGCAGAAGACGGCATACGAGATgcgccagaaGTCTCGTGGGCTCGG | 77 |
| i7-T251-NEX2cpt-E | CAAGCAGAAGACGGCATACGAGATcgaataattcGTCTCGTGGGCTCGG | 78 |
| i7-T252-NEX2cpt-E | CAAGCAGAAGACGGCATACGAGATgcgacgccttGTCTCGTGGGCTCGG | 79 |
| i7-T253-NEX2cpt-E | CAAGCAGAAGACGGCATACGAGATatcaacgattGTCTCGTGGGCTCGG | 80 |
| i7-T254-NEX2cpt-E | CAAGCAGAAGACGGCATACGAGATgttctgaattGTCTCGTGGGCTCGG | 81 |
| i7-T255-NEX2cpt-F | CAAGCAGAAGACGGCATACGAGATgctaacctcaGTCTCGTGGGCTCGG | 82 |
| i7-T256-NEX2cpt-F | CAAGCAGAAGACGGCATACGAGATcaagcaactgGTCTCGTGGGCTCGG | 83 |
| i7-T257-NEX2cpt-F | CAAGCAGAAGACGGCATACGAGATggagcggccgGTCTCGTGGGCTCGG | 84 |

TABLE 5-continued

PCR Primers

| Name | Sequence (5'→3') | SEQ ID NO |
|---|---|---|
| i7-T258-NEX2cpt-F | CAAGCAGAAGACGGCATACGAGATcgcgtacgacGTCTCGTGGGCTCGG | 85 |
| i7-T259-NEX2cpt-F | CAAGCAGAAGACGGCATACGAGATcgatggcgccGTCTCGTGGGCTCGG | 86 |
| i7-T260-NEX2cpt-F | CAAGCAGAAGACGGCATACGAGATtggtattcatGTCTCGTGGGCTCGG | 87 |
| i7-T261-NEX2cpt-F | CAAGCAGAAGACGGCATACGAGATgataaggcaaGTCTCGTGGGCTCGG | 88 |
| i7-T262-NEX2cpt-F | CAAGCAGAAGACGGCATACGAGATgccggtcgagGTCTCGTGGGCTCGG | 89 |
| i7-T263-NEX2cpt-F | CAAGCAGAAGACGGCATACGAGATgcgccatctGTCTCGTGGGCTCGG | 90 |
| i7-T264-NEX2cpt-F | CAAGCAGAAGACGGCATACGAGATaagtcttccgGTCTCGTGGGCTCGG | 91 |
| i7-T265-NEX2cpt-F | CAAGCAGAAGACGGCATACGAGATagactcaagcGTCTCGTGGGCTCGG | 92 |
| i7-T266-NEX2cpt-F | CAAGCAGAAGACGGCATACGAGATgcaggcgacgGTCTCGTGGGCTCGG | 93 |
| i5-T155-NEX1cpt-A | AATGATACGGCGACCACCGAGATCTACACgtccttaagaTCGTCGGCAGCGTC | 94 |
| i5-T156-NEX1cpt-A | AATGATACGGCGACCACCGAGATCTACACagtaacggtcTCGTCGGCAGCGTC | 95 |
| i5-T157-NEX1cpt-A | AATGATACGGCGACCACCGAGATCTACACgttcgtcagaTCGTCGGCAGCGTC | 96 |
| i5-T158-NEX1cpt-A | AATGATACGGCGACCACCGAGATCTACACcgcctaatgcTCGTCGGCAGCGTC | 97 |
| i5-T159-NEX1cpt-A | AATGATACGGCGACCACCGAGATCTACACaccggaattaTCGTCGGCAGCGTC | 98 |
| i5-T160-NEX1cpt-A | AATGATACGGCGACCACCGAGATCTACACtaggccatagTCGTCGGCAGCGTC | 99 |
| i5-T161-NEX1cpt-A | AATGATACGGCGACCACCGAGATCTACACtaactcttagTCGTCGGCAGCGTC | 100 |
| i5-T162-NEX1cpt-A | AATGATACGGCGACCACCGAGATCTACACtatgagttaaTCGTCGGCAGCGTC | 101 |
| i5-T163-NEX1cpt-B | AATGATACGGCGACCACCGAGATCTACACtatcatgatcTCGTCGGCAGCGTC | 102 |

TABLE 5-continued

PCR Primers

| Name | Sequence (5'→3') | SEQ ID NO |
|---|---|---|
| i5-T164-NEX1cpt-B | AATGATACGGCGACCACCGAGATCTACACgagcatatggTCGTCGGCAGCGTC | 103 |
| i5-T165-NEX1cpt-B | AATGATACGGCGACCACCGAGATCTACACtaacgatccaTCGTCGGCAGCGTC | 104 |
| i5-T166-NEX1cpt-B | AATGATACGGCGACCACCGAGATCTACACggcgtaactTCGTCGGCAGCGTC | 105 |
| i5-T167-NEX1cpt-B | AATGATACGGCGACCACCGAGATCTACACgtcgcagccTCGTCGGCAGCGTC | 106 |
| i5-T168-NEX1cpt-B | AATGATACGGCGACCACCGAGATCTACACgtagctccatTCGTCGGCAGCGTC | 107 |
| i5-T169-NEX1cpt-B | AATGATACGGCGACCACCGAGATCTACACttgccttggcTCGTCGGCAGCGTC | 108 |
| i5-T170-NEX1cpt-B | AATGATACGGCGACCACCGAGATCTACACtgctaattctTCGTCGGCAGCGTC | 109 |
| i5-T171-NEX1cpt-C | AATGATACGGCGACCACCGAGATCTACACgtcctacttgTCGTCGGCAGCGTC | 110 |
| i5-T172-NEX1cpt-C | AATGATACGGCGACCACCGAGATCTACACggtaggttagTCGTCGGCAGCGTC | 111 |
| i5-T173-NEX1cpt-C | AATGATACGGCGACCACCGAGATCTACACgagcatcattTCGTCGGCAGCGTC | 112 |
| i5-T174-NEX1cpt-C | AATGATACGGCGACCACCGAGATCTACACccgctccggcTCGTCGGCAGCGTC | 113 |
| i5-T175-NEX1cpt-C | AATGATACGGCGACCACCGAGATCTACACttcttccggtTCGTCGGCAGCGTC | 114 |
| i5-T176-NEX1cpt-C | AATGATACGGCGACCACCGAGATCTACACaggagagaacTCGTCGGCAGCGTC | 115 |
| i5-T177-NEX1cpt-C | AATGATACGGCGACCACCGAGATCTACACtaactcaattTCGTCGGCAGCGTC | 116 |
| i5-T178-NEX1cpt-C | AATGATACGGCGACCACCGAGATCTACACactataggttTCGTCGGCAGCGTC | 117 |
| i5-T207-NEX1cpt-D | AATGATACGGCGACCACCGAGATCTACACtaacgaattgTCGTCGGCAGCGTC | 118 |
| i5-T208-NEX1cpt-D | AATGATACGGCGACCACCGAGATCTACACtgagaaccaaTCGTCGGCAGCGTC | 119 |
| i5-T209-NEX1cpt-D | AATGATACGGCGACCACCGAGATCTACACttattctgagTCGTCGGCAGCGTC | 120 |

TABLE 5-continued

PCR Primers

| Name | Sequence (5'→3') | SEQ ID NO |
|---|---|---|
| i5-T210-NEX1cpt-D | AATGATACGGCGACCACCGAGATCTACACttattatggtTCGTCGGCAGCGTC | 121 |
| i5-T211-NEX1cpt-D | AATGATACGGCGACCACCGAGATCTACACatatgagccaTCGTCGGCAGCGTC | 122 |
| i5-T212-NEX1cpt-D | AATGATACGGCGACCACCGAGATCTACACcaaccagtacTCGTCGGCAGCGTC | 123 |
| i5-T213-NEX1cpt-D | AATGATACGGCGACCACCGAGATCTACACcatccgactaTCGTCGGCAGCGTC | 124 |
| i5-T214-NEX1cpt-D | AATGATACGGCGACCACCGAGATCTACACatcatggctgTCGTCGGCAGCGTC | 125 |
| i5-T215-NEX1cpt-E | AATGATACGGCGACCACCGAGATCTACACccgcaagttcTCGTCGGCAGCGTC | 126 |
| i5-T216-NEX1cpt-E | AATGATACGGCGACCACCGAGATCTACACcttctcattgTCGTCGGCAGCGTC | 127 |
| i5-T217-NEX1cpt-E | AATGATACGGCGACCACCGAGATCTACACcaggaggagaTCGTCGGCAGCGTC | 128 |
| i5-T218-NEX1cpt-E | AATGATACGGCGACCACCGAGATCTACACgatatcggcgTCGTCGGCAGCGTC | 129 |
| i5-T219-NEX1cpt-E | AATGATACGGCGACCACCGAGATCTACACccagtcctctTCGTCGGCAGCGTC | 130 |
| i5-T220-NEX1cpt-E | AATGATACGGCGACCACCGAGATCTACACcatagttcggTCGTCGGCAGCGTC | 131 |
| i5-T221-NEX1cpt-E | AATGATACGGCGACCACCGAGATCTACACcgtaatgcagTCGTCGGCAGCGTC | 132 |
| i5-T222-NEX1cpt-E | AATGATACGGCGACCACCGAGATCTACACccgttcggatTCGTCGGCAGCGTC | 133 |
| i5-T223-NEX1cpt-F | AATGATACGGCGACCACCGAGATCTACACccataagtccTCGTCGGCAGCGTC | 134 |
| i5-T224-NEX1cpt-F | AATGATACGGCGACCACCGAGATCTACACggcaatgagaTCGTCGGCAGCGTC | 135 |
| i5-T225-NEX1cpt-F | AATGATACGGCGACCACCGAGATCTACACcggttatgccTCGTCGGCAGCGTC | 136 |
| i5-T226-NEX1cpt-F | AATGATACGGCGACCACCGAGATCTACACtggccggcctTCGTCGGCAGCGTC | 137 |
| i5-T227-NEX1cpt-F | AATGATACGGCGACCACCGAGATCTACACagctgcaataTCGTCGGCAGCGTC | 138 |

TABLE 5-continued

PCR Primers

| Name | Sequence (5'→3') | SEQ ID NO |
|---|---|---|
| i5-T228-NEX1cpt-F | AATGATACGGCGACCACCGAGATCTACACtggccatgcaTCGTCGGCAGCGTC | 139 |
| i5-T229-NEX1cpt-F | AATGATACGGCGACCACCGAGATCTACACtgacgctccgTCGTCGGCAGCGTC | 140 |
| i5-T230-NEX1cpt-F | AATGATACGGCGACCACCGAGATCTACACaactgctgccTCGTCGGCAGCGTC | 141 |

TABLE 6

Sequencing Primers

| Name | Sequence (5'→3') | SEQ ID NO |
|---|---|---|
| Read 1 sequencing primer | GCGATCGAGGACGGCAGATGTGTATAAGAGACAG | 142 |
| Read 2 sequencing primer | CACCGTCTCCGCCTCAGATGTGTATAAGAGACAG | 143 |
| Index 1 sequencing primer | CTGTCTCTTATACACATCTGAGGCGGAGACGGTG | 144 |
| Index 2 sequencing primer | CTGTCTCTTATACACATCTGCCGTCCTCGATCGC | 145 |

1. Preparation of Nuclei Using Lithium 3,5-Diiodosalicylic Acid (LAND) or SDS (xSDS)

A. LAND Method of Nuclei Preparation & Nucleosome Depletion

If the cells were in a suspension cell culture, the culture was gently triturated to break up cell clumps, the cells were pelleted by spinning at 500×g for 5 minutes at 4° C., and washed with 500 µL ice cold PBS.

If the cells were in an adherent cell culture, media was aspirated and the cells washed with 10 mL of PBS at 37° C., and then enough 0.25% Trypsin at 37° C. was added to cover the monolayer. After incubating at 37° C. for 5 minutes or until 90% of cells were no longer adhering to the surface, 37° C. media was added at 1:1 ratio to quench Trypsin. The cells were pelleted by spinning at 500×g for 5 minutes at 4° C., and then washed with 500 µL ice cold PBS.

If a tissue was used, the tissue sample was placed in a 2 mL dounce homoginzer on ice. Two mls of NIB buffer (10 mM TrisHCl pH7.4, 10 MM NaCl, 3 mM MgCl$_2$, 0.1% Igepal®, 1× protease inhibitors) were added to the sample and incubated on ice for 5 minutes. The sample was dounced 5 times with loose pestle followed by 15 strokes with tight pestle, and then put through a 35 µM cell strainer, and additional strainers were used as necessary.

The cells from either suspension cell culture, adherent cell culture, or tissue sample were pelleted by spinning at 500×g for 5 minutes and then resuspended in 200 µL 12.5 mM LIS in NIB buffer (2.5 µL 1M LIS+197.5 µL NIB buffer). After incubating on ice for 5 minutes, 800 µL NIB buffer and 5 µL DAPI (5 mg/mL) were added. The cells were gently passed through a 35 µM cell strainer.

B. xSDS Method of Nuclei Preparation & Nucleosome Depletion

If the cells were in a suspension cell culture, the medium was gently triturated to break up cell clumps. To 10 mL of cells in media 406 µL of 37% formaldehyde were added and incubated at room temp for 10 minutes with gentle shaking. Eight hundred microliters of 2.5 M Glycine were added to the cells and incubated on ice for 5 minutes, and then centrifuged at 550×g for 8 minutes at 4° C. After washing with 10 mL of ice cold PBS, the cells were resuspended in 5 mL of ice cold NIB (10 mM TrisHCl pH7.4, 10 mM NaCl, 3 mM MgCl$_2$, 0.1% Igepal®, 1× protease inhibitors), and incubated on ice for 20 minutes with gentle mixing.

If the cells were in an adherent cell culture, media was aspirated and the cells washed with 10 mL of PBS at 37° C., and then enough 0.25% Trypsin at 37° C. was added to cover the monolayer. After incubating at 37° C. for 5 minutes or until 90% of cells were no longer adhering to the surface, 37° C. media was added at 1:1 ratio to quench Trypsin, and the volume brought to 10 ml with media. The cells were resuspended in 10 mL media, and 406 µL of 37% formaldehyde added and incubated at room temp for 10 minutes with gentle shaking. Eight hundred microliters of 2.5 M Glycine were added to the cells and incubated on ice for 5 minutes. The cells were centrifuged at 550×g for 8 minutes at 4° and washed with 10 mL of ice cold PBS. After resuspending the cells in 5 mL of ice cold NIB, they were incubated on ice for 20 minutes with gentle mixing.

If a tissue was used, the tissue sample was placed in a 2 mL Dounce homogenizer on ice. Two mLs of HEPES NIB (20 mM HEPES, 10 MM NaCl, 3 mM MgCl2, 0.1% igepal, 1× protease inhibitors) buffer were added to the sample and incubated on ice for 5 minutes. The sample was dounced 5 times with loose pestle followed by 15 strokes with tight pestle, and then put through a 35 μM cell strainer, and additional strainers were used as necessary. The volume was brought up to 10 ml with HEPES-NIB, and 406 μL of 37% formaldehyde were added to the 10 mL volume. Eight hundred microliters of 2.5 M Glycine were added and incubated on ice 5 minutes.

The cells or nuclei from either suspension cell culture or adherent cell culture were pelleted by spinning at 500×g for 5 minutes and washed with 900 μL of 1×NEBuffer 2.1. After spinning at 500×g for 5 minutes, the pellet was resuspended in 800 μL 1×NEBuffer 2.1 with 12 μL of 20% SDS and incubated at 42° C. with vigorous shaking for 30 minutes, and then 200 μL of 10% Triton™ X-100 was added and incubated at 42° C. with vigorous shaking for 30 minutes. The cells were gently passed through a 35 μM cell strainer, and 5 μL DAPI (5 mg/mL) was added.

II. Nuclei Sorting and Tagmentation

Figure 33:
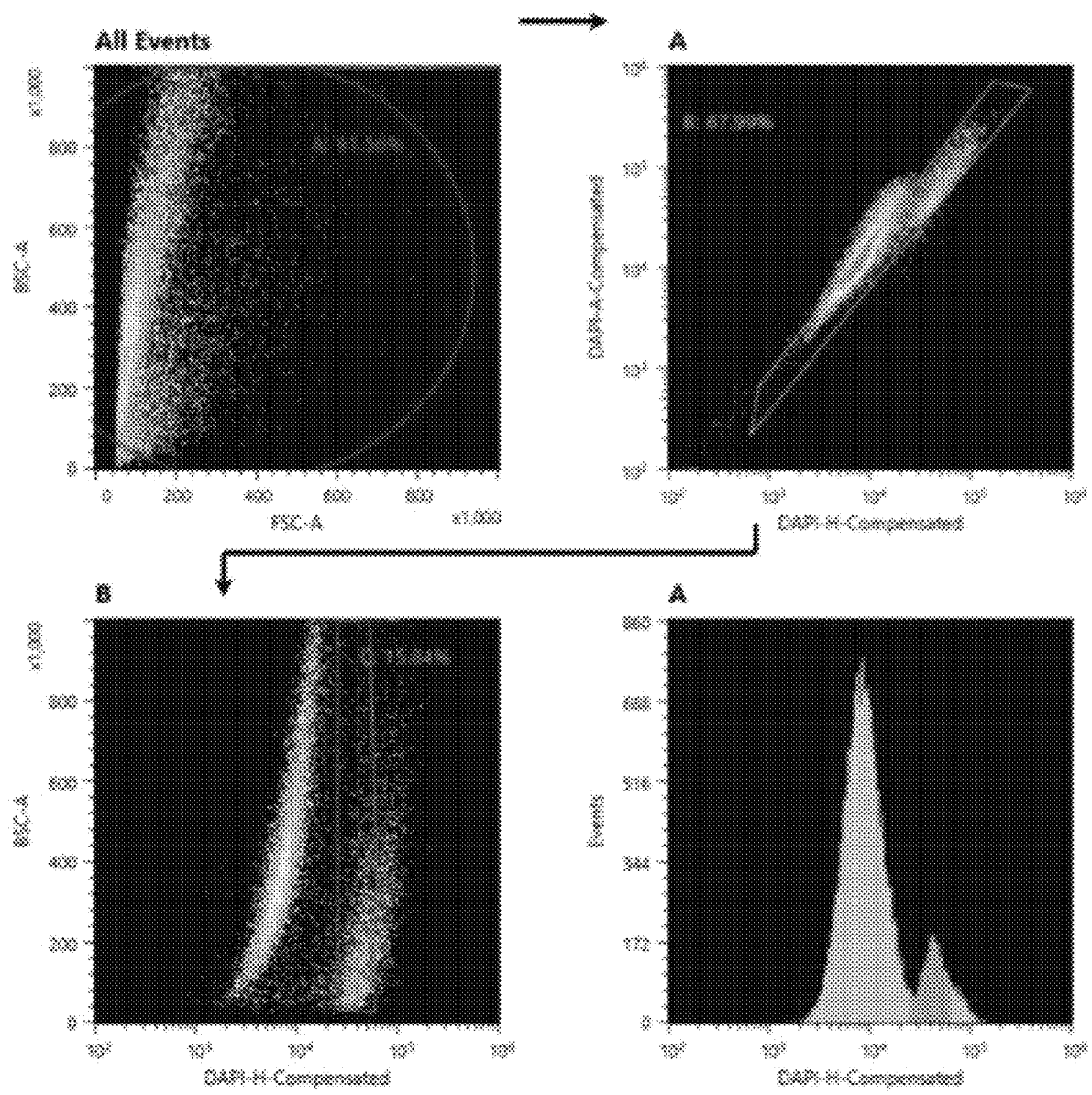
FIG. 33 shows the gating scheme used to isolate single nuclei after treatment with transposase using forward scatter, side scatter, and DAPI intensity parameters.

A tagmentation plate was prepared with 10 μL 1×TD buffer (for 1 plate: 500 μL NIB buffer+500 μL TD buffer), and 2000 single nuclei were sorted into each well of the tagmentation plate. At this step the number of nuclei per well can be varied slightly as long as the number of nuclei per well is consistent for the whole plate. It is also possible to multiplex different samples into different wells of the plate as the transposase index will be preserved. The cells were gated according to FIG. 33. After spinning down the plate, 1 μL 2.5 nM of uniquely indexed transposome were added to each well. After sealing, the plate was incubated at 55° C. for 15 minutes with gentle shaking. The plate was then returned to room temperature and then placed on ice. All the wells were pooled, 5 μl DAPI (5 mg/mL) were added and then the cells were passed through a 35 μM cell strainer.

III. Second Sort of and PCR Indexing

A master mix was prepared for each well with 0.25 μL 20 mg/mL BSA, 0.5 μL 1% SDS, and 7.75 μL H₂O. Master mix (8.5 μL) and 2.5 μL of each (i5 and i7) 10 μM primer was added to each well of a 96 well plate. Single nuclei (15-22) were sorted into each well using the most stringent sort settings. The plate was then spun down. Those nuclei prepared using the LAND method were incubated for 5 minutes at 55° to denature transposase. Those nuclei prepared using the xSDS method were incubated at 68° for 45 minutes to denature transposase and reverse crosslinks.

Buffer was prepared (for 1 plate: 750 μL NPM, 400 μL H₂O, and 50 μL 100×SYBR Green), and 12 μL of the buffer was added to each well of strip tube. The following PCR cycles were performed: 72° C. for 5 minutes, 98° C. for 30 seconds, then continual cycles of (98° C. for 10 seconds, 63° C. for 30 seconds, 72° C. for one minute followed by a plate read and an additional 10 seconds at 72° C.). These cycles were repeated until the majority of wells exhibited exponential amplification as determined by SYBR green fluorescence.

IV. Library Clean Up and Quantification

Libraries were pooled using 5 uL of each well of the PCR plate, then purified using a Qiaquick® PCR Purification column and eluted in 30 μL of 10 mM Tris-Cl, pH 8.5 (EB). Two microliters were used to quantify the concentration of DNA with dsDNA High Sensitivity Qubit® 2.0 Fluorometer, following the manufacturer's protocol. The Qubit® readout was used to dilute library to ~4 ng/uL, and 1 uL was run on a High Sensitivity Bioanalyser 2100, following the manufacturer's protocol. The library was then quantified for the 200 bp-1 kbp range to dilute the pool to 1 nM for Illumina Sequencing.

V. Sequencing

A NextSeq® 500 was set up for a run as per manufacturer's instructions for a 1 nM sample except for the following changes. The library pool was loaded at a concentration of 0.8 μM and a total volume of 1.5 mL and deposited into cartridge position 10; custom primers were setup by diluting 9 μL of 100 μM stock sequencing primer 1 into a total of 1.5 mL of HT1 buffer into cartridge position 7; sequencing primer was setup by diluting 9 μL of 100 μM stock sequencing primer 2 into a total of 1.5 mL of HT1 buffer into cartridge position 8; and custom index sequencing primers were setup by diluting 18 μL of each custom index sequencing primer at 100 μM stock concentrations into a total of 3 mL of HT1 buffer into cartridge position 9 (see Table 7). The NextSeq® 500 was operated in standalone mode; the SCIseq custom chemistry recipe (Amini et al., 2014, Nat. Genet. 46, 1343-1349) was selected; dual index was selected; the appropriate number of read cycles was entered (50 recommended) and 18 cycles for each index; the custom checkbox for all reads and indices was selected.

TABLE 7

| Cartridge position | Reagent | Concentration | Total Volume (dilute in HT1) | Stock oligo (100 uM) | HT1 |
|---|---|---|---|---|---|
| 7 | Custom Read 1 | 0.6 uM | 1.5 mL | 9 μL | 1491 μL |
| 8 | Custom Read 2 | 0.6 uM | 1.5 mL | 9 μL | 1491 μL |
| 9 | Custom Index 1 & 2 | Each 0.6 uM | 3 mL | 18 μL each | 2964 μL |
| 10 | Library | 0.8 pM (<800 bp) | 1.5 mL | | |

Example 3

Single-Cell Combinatorial Indexing and Genome and Chromosome Conformation

Restriction endonuclease digestion of isolated nuclei followed by ligation can be used to acquire information on chromosome structure within a nucleus, such as chromatin folding analysis and detection of genomic rearrangements. Such types of analyses are known in art as chromosome conformation capture (3C) and related methods (4C, 5C, and Hi-C).

The method of single-cell combinatorial indexing and genome and chromosome conformation (sci-GCC) that can be used in conjunction with the method described in Examples 1 and 2 is described in FIG. 34. Specifically, the method of single-cell combinatorial indexing and genome and chromosome conformation includes blocks 12, 13, 14, and 19 as shown in FIG. 34. Unlike other methods of genome and chromosome conformation analysis of single cells (Nagano et al., 2013, Nature, 502:59-64), the method described herein does not require biotin fill-in or biotin pull-down so as to obtain both genome and chromatin conformation sequence data.

Conditions for cross-linking cells were evaluated to determine the minimum concentration of formaldehyde needed to cross-link cells and maintain nuclei integrity. HeLa cells were cross-linked by exposing the cells to formaldehyde at 0.2%, 0.35%, 1.5%, or no formaldehyde, and an abbreviated version of the method described in FIG. 34 was done and the number of nuclei resulting was determined.

No intact nuclei were isolated from cells not exposed to formaldehyde or exposed to 0.2% formaldehyde. Cells exposed to 0.35% formaldehyde yielded $3.8 \times 10^5$ nuclei with normal morphology, and cells exposed to 1.5% formaldehyde yielded $6.4 \times 10^5$ nuclei with normal morphology.

Conditions for reversing cross-linking was also evaluated. HeLa cells were cross-linked by exposing the cells to formaldehyde at 0.35%, 0.75%, 1.5%, or no formaldehyde, and an abbreviated version of the method described in FIG. 34 was performed. Cross-linking was revered by incubating isolated nuclei at 68° C. for with 1 hour or 16 hours (FIG. 35).

The data indicate that the use of 0.35% formaldehyde with reversal conditions of 1 hour incubation at 68° C. was best.

Figure 35:
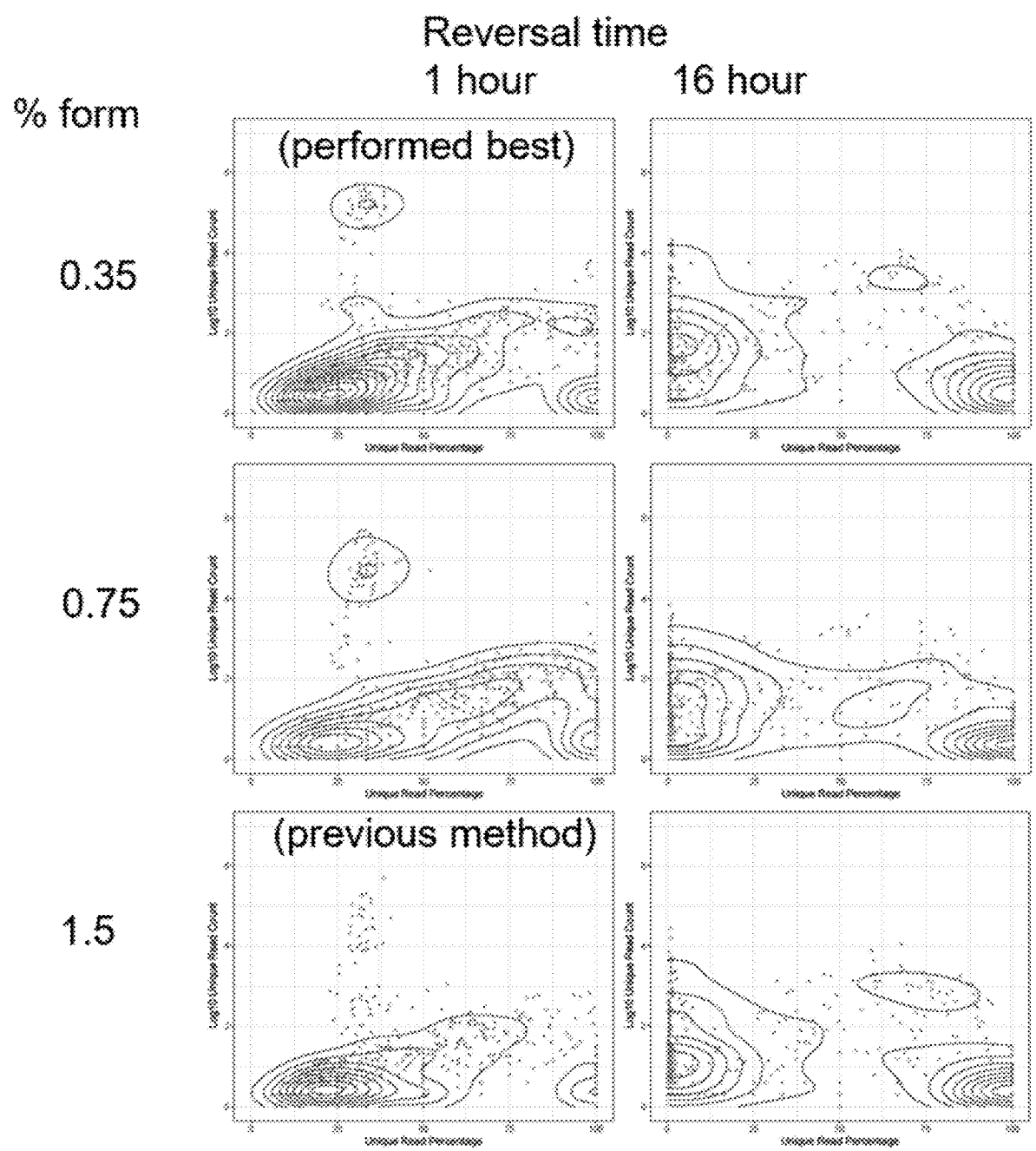
FIG. 35 shows the library complexity and unique read counts obtained from the method using various formaldehyde concentrations and time of crosslink reversal.
Figure 36:
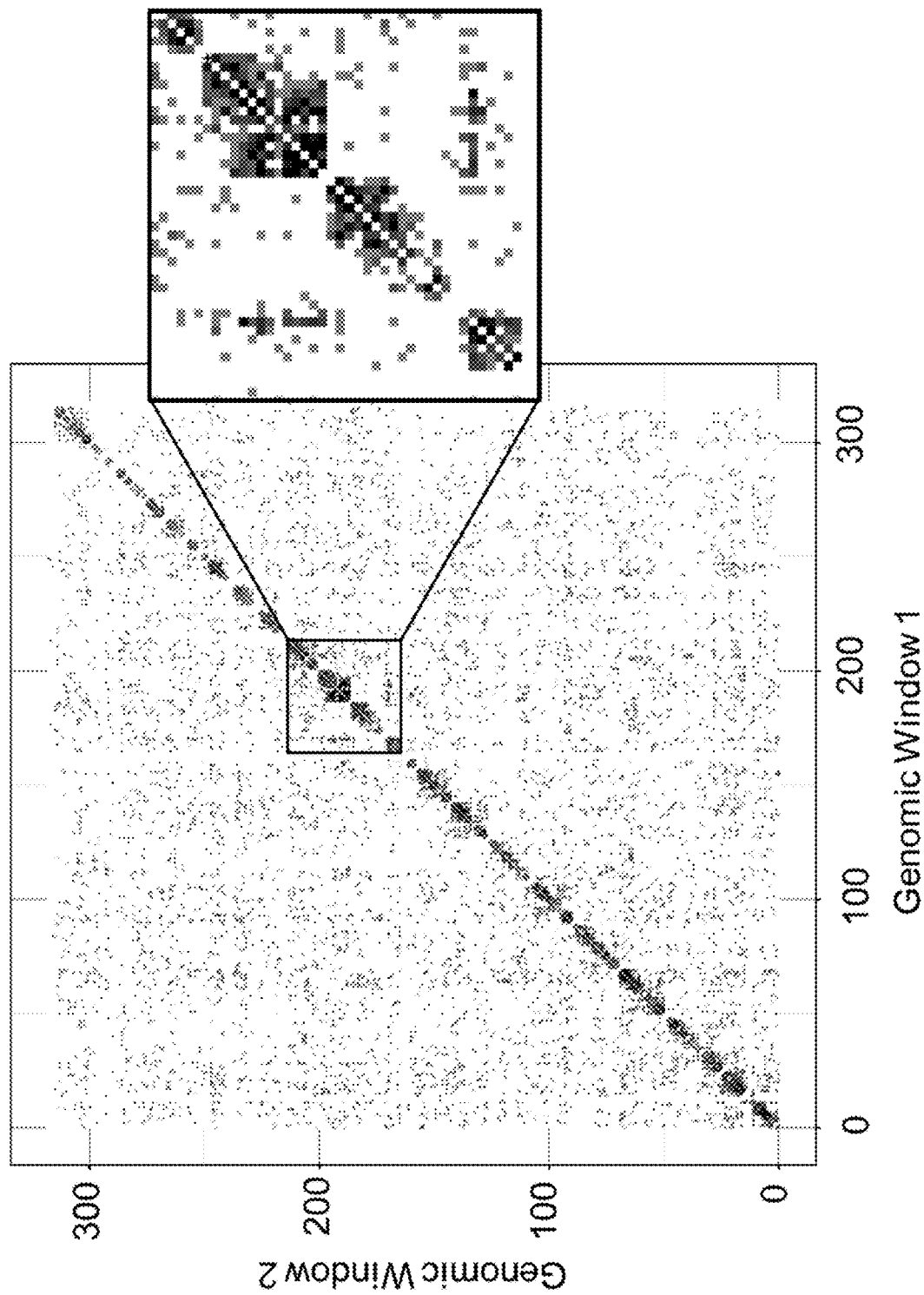
FIG. 36 shows an example of a single cell library using sci-GCC on HeLa. Signal produced from chimeric ligation junction reads is shown between distal regions of the genome over 10 Mbp windows with the first window on the x-axis and linked window on the y-axis. Highlighted is a known translocation present in HeLa where the trans-chromosomal 3C signal is elevated.

From sequenced sci-GCC libraries comparable unique read counts genome wide were obtained as in methods described in Examples 1 and 2 and FIG. 35. In addition to the genomic sequence reads, between 5% and 15% of sequence reads contained chimeric ligation junctions that were characteristic of chromatin conformation signal as described in Nagano et al., (2013, Nature, 502:59-64). On average, we obtained an increased unique chimeric ligation junction read count when compared with existing single cell HiC strategies (see, for instance, Nagano et al., 2013, Nature, 502:59-64) with a mean unique chimeric ligation junction read count of over 40,000 per cell in crosslinking-optimized preparations. On HeLa, these libraries produced sufficient chimeric ligation junction reads to clearly identify chromatin structure, including a known translocation in HeLa (FIG. 36).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of preparing a sequencing library comprising nucleic acids from a plurality of single cells, the method comprising, in the following order:
(a) providing cross-linked isolated nuclei;
(b) subjecting the cross-linked isolated nuclei to a chemical treatment to unbind nucleosomes from genomic DNA to generate nucleosome-depleted nuclei, while maintaining nuclear integrity of the isolated nuclei, wherein the chemical treatment comprises a treatment with a detergent comprising sodium dodecyl sulfate (SDS) which disrupts nucleic acid-protein interactions;
(c) distributing subsets of the nucleosome-depleted nuclei into a first plurality of compartments and contacting each subset with a plurality of transposome complexes, wherein the transposome complexes in each compartment of the first plurality of compartments comprises a transposase and a first index sequence, and
   wherein the first index sequence in each compartment of the first plurality of compartments comprises a nucleotide sequence that is different from the nucleotide sequence of first index sequences in the other compartments of the first plurality of compartments;
(d) fragmenting nucleic acids in the subsets of nucleosome-depleted nuclei into a plurality of nucleic acid fragments and incorporating the first index sequences into at least one strand of the nucleic acid fragments to generate indexed nuclei comprising indexed nucleic acid fragments,
   wherein the indexed nucleic acid fragments remain attached to the transposases,
   wherein the nucleic acid fragments are genomic DNA, and
   wherein the nucleosome depletion within the cross-linked isolated nuclei results in genome-wide uniform incorporation of the first index sequences that is not restricted to sites of chromatin accessibility;
(e) combining the indexed nuclei to generate pooled indexed nuclei;
(f) distributing subsets of the pooled indexed nuclei into a second plurality of compartments;
(g) dissociating the transposases from the indexed nucleic acid fragments;
(h) reversing the cross-links within the isolated nuclei;
(i) incorporating into the indexed nucleic acid fragments in each compartment of the second plurality of compartments a second index sequence to generate dual-index fragments, wherein the second index sequence in each compartment comprises a nucleotide sequence that is different from the nucleotide sequence of second index sequences in the other compartments of the second plurality of compartments; and
(j) combining the dual-index fragments, thereby producing a sequencing library from the plurality of single cells.

2. The method of claim 1, wherein prior to step (a): (i) the isolated nuclei are treated with a cross-linking agent to provide cross-linked isolated nuclei, wherein the cross-linking agent is formaldehyde; or (ii) the plurality of single cells are treated with a cross-linking agent, then the nuclei are isolated from the plurality of single cells to afford cross-linked isolated nuclei, wherein the cross-linking agent is formaldehyde.

3. The method of claim 1, wherein the transposases are disassociated from the indexed nucleic acid fragments using sodium dodecyl sulfate (SDS).

4. The method of claim 1, wherein the nuclei are treated with a restriction enzyme prior to step (d).

5. The method of claim 4, wherein the nuclei are treated with a ligase after treatment with the restriction enzyme.

6. The method of claim 1, wherein the subsets of the pooled indexed nuclei comprise at least 10 times fewer nuclei as compared to the subsets of the nucleosome-depleted nuclei.

7. The method of claim 1, wherein each of the transposome complexes comprises a transposon, each transposon comprising a transferred strand.

8. The method of claim 7, wherein the transferred strand comprises the first index sequence and a first universal sequence.

9. The method of claim 8, wherein the incorporation of the second index sequence in step (i) comprises contacting the indexed nucleic acid fragments in each compartment of the second plurality of compartments with a first universal primer and a second universal primer, each indexed nucleic acid fragment comprising an index sequence and a sequence identical to or complementary to a portion of the first universal sequence.

10. The method of claim 9, wherein the index sequence of the first universal primer is the reverse complement of the index sequence of the second universal primer.

11. The method of claim 9, wherein the first universal primer further comprises a first capture sequence and a first anchor sequence complementary to a universal sequence at the 3' end of the dual-index fragments.

12. The method of claim 9, wherein the second universal primer further comprises a second capture sequence and a second anchor sequence complementary to a universal sequence at the 5' end of the dual-index fragments.

13. The method of claim 1 wherein the treatment with a detergent comprises 0.3% SDS.

14. The method of claim 9 further comprising performing an exponential amplification reaction.

* * * * *